(12) United States Patent
Brower-Toland et al.

(10) Patent No.: US 11,952,578 B2
(45) Date of Patent: Apr. 9, 2024

(54) COMPOSITIONS AND METHODS FOR SITE DIRECTED GENOMIC MODIFICATION

(71) Applicant: Monsanto Technology LLC, St. Louis, MO (US)

(72) Inventors: Brent Brower-Toland, St. Louis, MO (US); Andrei Y. Kouranov, Chesterfield, MO (US); Rosemarie Kuehn, St. Louis, MO (US); Richard J. Lawrence, Kirkwood, MO (US); Ervin D. Nagy, Lake St. Louis, MO (US); Linda Rymarquis, High Ridge, MO (US); Veena Veena, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 18/146,434

(22) Filed: Dec. 26, 2022

(65) Prior Publication Data

US 2023/0212596 A1   Jul. 6, 2023

Related U.S. Application Data

(62) Division of application No. 17/503,235, filed on Oct. 15, 2021, now Pat. No. 11,566,254, which is a division of application No. 15/120,110, filed as application No. PCT/US2015/018104 on Feb. 27, 2015, now Pat. No. 11,186,843.

(60) Provisional application No. 61/945,700, filed on Feb. 27, 2014.

(51) Int. Cl.
   *C12N 15/82* (2006.01)

(52) U.S. Cl.
   CPC ..... *C12N 15/8213* (2013.01); *C12N 15/8216* (2013.01)

(58) Field of Classification Search
   None
   See application file for complete search history.

(56) References Cited

U.S. PATENT DOCUMENTS

| | | | |
|---|---|---|---|
| 8,697,359 B1 | 4/2014 | Zhang | |
| 8,771,945 B1 | 7/2014 | Zhang | |
| 8,795,965 B2 | 8/2014 | Zhang | |
| 8,865,406 B2 | 10/2014 | Zhang et al. | |
| 8,871,445 B2 | 10/2014 | Cong et al. | |
| 8,889,356 B2 | 11/2014 | Zhang | |
| 8,889,418 B2 | 11/2014 | Zhang et al. | |
| 8,895,308 B1 | 11/2014 | Zhang et al. | |
| 8,906,616 B2 | 12/2014 | Zhang et al. | |
| 8,945,839 B2 | 2/2015 | Zhang | |
| 9,840,713 B2 | 12/2017 | Zhang | |
| 10,519,457 B2 * | 12/2019 | Li | C12N 15/63 |
| 2012/0095080 A1 | 4/2012 | Rossi et al. | |
| 2014/0068797 A1 | 3/2014 | Doudna et al. | |
| 2014/0170753 A1 | 6/2014 | Zhang | |
| 2014/0227787 A1 | 8/2014 | Zhang | |
| 2014/0242664 A1 | 8/2014 | Zhang et al. | |
| 2014/0273231 A1 | 9/2014 | Cong et al. | |
| 2014/0273232 A1 | 9/2014 | Zhang et al. | |
| 2014/0273234 A1 | 9/2014 | Zhang et al. | |
| 2014/0302563 A1 | 10/2014 | Doudna et al. | |
| 2015/0082478 A1 | 3/2015 | Cigan et al. | |

FOREIGN PATENT DOCUMENTS

| | | |
|---|---|---|
| WO | 2013176772 | 11/2013 |
| WO | 2014018423 | 1/2014 |
| WO | 2014065596 | 5/2014 |
| WO | 2014150624 | 9/2014 |
| WO | 2014191518 | 12/2014 |
| WO | 2014191521 | 12/2014 |
| WO | 2014194190 | 12/2014 |
| WO | 2015026887 | 2/2015 |

OTHER PUBLICATIONS

Belhaj et al., "Plant genome editing made easy: targeted mutagenesis in model and crop plants using the CRISPR/Cas system," Plant Methods 9:39, 2013.
Cho et al., "Targeted genonne engineering in human cells with the Cas9 RNA-guided endonuclease," Nat Biotechnol, 31:230-232, 2013.
Cong et al., "Multiplex genome engineering using CRISPR/Cas Systems," Science, 339:819-823, 2013.
Connelly et al., "Small nuclear RNA genes transcribed by either RNA polymerase II or RNA polymerase III in monocot plants share three promoter elements and use a strategy to regulate gene expression different from that used by their dicot plant counterparts," Mol Cell Biol, 14(9):5910-5919, 1994.
Doudna et al., "The new frontier of genome engineering with CRISPR-Cas9," Science, 346:1258096, 2014.
EBI Accession No. X51447, dated Mar. 13, 1990.
EBI Accession No. Z17301, dated Oct. 16, 1992.
Esvelt et al., "Concerning RNA-guided gene drives for the alteration of wild populations," Elife, 3:e03401, 2014.
Gaj et al, "ZFN, TALEN, and CRISPR/Cas-based methods for genome engineering," Trends Biotechnol, 31:397-405, 2013.
GenBank CG438579.1 OGTBE38TV ZM_0.7_1.5_KB *Zea mays* genomic clone ZMMBMa0854H03, genomic survey sequence [online] Sep. 17, 2003 [retrieved Jul. 13, 2015]. Available at: http://www.ncbi.nlm.nih.gov/nucgss/CG438579.

(Continued)

*Primary Examiner* — Cynthia E Collins
(74) *Attorney, Agent, or Firm* — Dentons US LLP; Jan Desomer

(57) ABSTRACT

The disclosure provides novel corn, tomato, and soybean U6, U3, U2, U5, and 7SL snRNA promoters which are useful for CRISPR/Cas-mediated targeted gene modifications in plants. The disclosure also provides methods for use for U6, U3, U2, U5, and 7SL promoters in driving expression of sgRNA polynucleotides which function in a CRISPR/Cas system of targeted gene modification in plants. The disclosure also provides methods of genome modification by insertion of blunt-end DNA fragments at a site of genomic cleavage.

14 Claims, 27 Drawing Sheets
Specification includes a Sequence Listing.

(56) References Cited

OTHER PUBLICATIONS

GenBank CP000494.1 *Bradyrhizobium* sp. BTAi1, complete genome [Showing 3.19kb region from base 4149455 to 4152649] [online] Jan. 14, 2014 [retrieved Jul. 13, 2015]. Available at: http://www.ncbi.nlm.nih.gov/nuccore/146403799?from=4149455&to41526498,sat=4&sat_key=105750 108.
Hale et al., "Essential features and rational design of CRISPR RNAs that function with the Cas RAMP module complex to cleave RNAs," Mol Cell, 45:292-302, 2012.
International Search Report and Written Opinion for PCT/US15/18104 dated Jul. 31, 2015.
Jiang et al., "Demonstration of CRISPR/Cas9/sgRNA-mediated targeted gene modification in *Arabidopsis*, tobacco, sorghum and rice," Nucl Acids Res, 41(20):e188, 2013.
Jinek et al., "A programmable dual-RNA-guided DNA endonuclease in adaptive bacterial immunity," Science, 337:816-821, 2012.
Li et al., "Heritable gene targeting in the mouse and rat using a CRISPR-Cas system," Nat Biotechnol, 31:681-683, 2013.
Li et al., "Multiplex and homologous recombination-mediated genome editing in *Arabidopsis* and Nicotiana benthamiana using guide RNA and Cas9," Nat Biotechnol, 31(8):688-691, 2013.
Li et al., "Simultaneous generation and germline transmission of multiple gene mutations in rat using CRISPR-Cas systems," Nature Biotechnol, 31:684-686, 2013.
Liang et al., "Targeted mutagenesis in *Zea mays* using TALENs and the CRISPR/Cas system," J Genet Genomics, 41:63-68, 2014.
Long et al., "Prevention of muscular dystrophy in mice by CRISPR/Cas9-mediated editing of germline DNA," Science, 345:1184-1188, 2014.
Mali et a/., "RNA-guided human genome engineering via Cas9," Science, 339:823-826, 2013.
Marshallsay et al, "Characterization of the U3 and U6 snRNA genes from wheat: U3 snRNA genes in monocot plants are transcribed by RNA polymerase III," Plant Mol Biol, 19:973-983, 1992.
Nekrasov et al., "Targeted mutagenesis in the model plant Nicotiana benthamiana using Cas9 RNA-guided endonuclease," Nat Biotechnol, 31(8):691-693, 2013.

Owor et al., "A rep-based hairpin inhibits replication of diverse maize streak virus isolates in a transient assay", J Gen Virol. Oct. 2011; 92(Pt 10):2458-65. Epub. Jun. 8, 2011. (Year: 2011).
Partial Supplementary European Search Report regarding European Application No. EP 15755923, dated Jun. 21, 2017.
Patron, "How to Knock-Out Plant Genes Using RNA-Guided CAS9," TSL Plasmids & Molecular Tools, <http://synbio.tsl.ac.uk/how-to-assemble-case9crispr-constructs-for-use-in-plants/> Retrieved from the internet on Jun. 1, 2017.
Qi et al., "RNA processing enables predictable programming of gene expression," Nat Biotechnol, 30:1002-1006, 2012.
Qu et al., "Artificial MicroRNA-Mediated Virus Resistance in Plants," Journal of Virology 81(12):6690-6699, 2007.
Sampson et al., "A CRISPR/Cas system mediates bacterial innate immune evasion and virulence," Nature, 497:254-257, 2013.
Shan, et al., "Targeted genome modification of crop plants using a CRISPR-Cas system," Nat Biotechnol, 31(8):686-688, 2013.
Sugano et al., "CRISPR/Cas9-Mediated Targeted Mutagenesis in the Liverwort *Marchantia polymorpha* L.," Plant & Cell Physiology 55(3):475-481, 2014.
Van der Oost, "New tool for genome surgery," Science, 339:768-770, 2013.
Veretnik et al., "Nucleotide sequence of a maize U6 gene," Nucleic Acids Research 18(12):3661, 1990.
Wang et al., "Hairpin RNAs derived from RNA polymerase II and polymerase III promoter-directed transgenes are processed differently in plants", RNA, May 2008;14(5):903-13. Epub. Mar. 26, 2008. (Year: 2008).
Wang et al., "One-step generation of mice carrying mutations in multiple genes by CRISPR/Cas-mediated genome engineering," Cell, 153:910-918, 2013.
Watson et al., "RNA silencing platforms in plants," FESS Letters 579:5982-5987, 2005.
Westra et al., "The CRISPRs, they are a-changin': how prokaryotes generate adaptive immunity," Annu Rev Genet, 46:311-339, 2012.
Xie et al., "RNA-Guided Genome Editing in Plants Using a CRISPR-Cas System," Molecular Plant 6(6):1975-1983, 2013.

\* cited by examiner

L70f

SEQ ID NO:144  CTATCTAGTGAAGATGTAATACTCTATGGTCTGTTTAAGGGATAACAGGGTAATATAGCGTAACTATA
SEQ ID NO:145  CTATCTAGTGAAGATGTAATACTCTATGGTCTGT--------------GGGTAATATAGCGTAACTATA

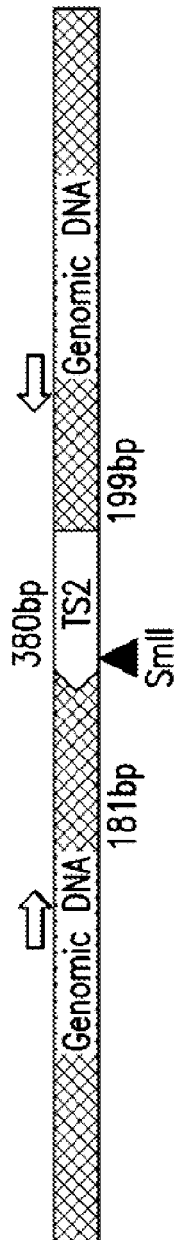
FIG. 17A
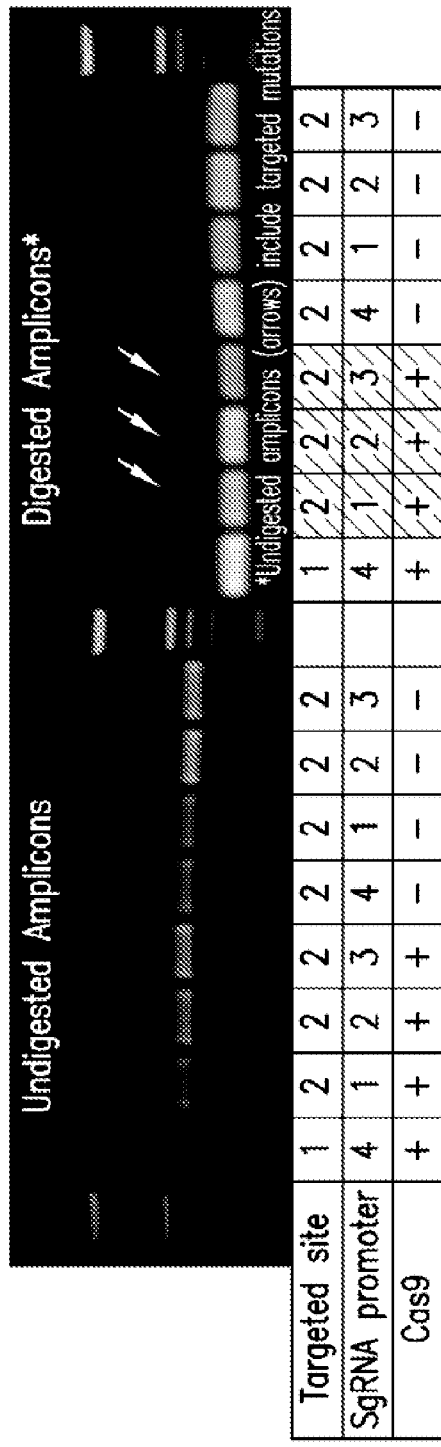
FIG. 17B
FIG. 17C

```
                            SEQUENCE LISTING

Sequence total quantity: 295
SEQ ID NO: 1            moltype = DNA   length = 397
FEATURE                 Location/Qualifiers
source                  1..397
                        mol_type = genomic DNA
                        organism = Zea mays
SEQUENCE: 1
aggaaaagaa gaggtgatta ctgtacctat tcgtctttgt atcggaatat aaatttatca    60
ctattttatg ataaagtaaa tctgtttccc tgtagagtta attaattaat gtaagtataa   120
gcgtaattta tagggcacta gtaggactgt cgactgtgcg ctcggcccgg ataatgcgtc   180
aaaagcgaag acgtgcacgt gggatgggaa aacacgaagc gtggtctgct ttttcgcatg   240
atatctgggc cgcaccaaag aatccagccc acgcggcgtg gcgccgtcgt tacggcttgc   300
gggggaagga aacgagggac gaaccgagat ttagcaccag accggccagc gagcattgca   360
gacaccggct tataagttca gctgcgacta ccactcc                            397

SEQ ID NO: 2            moltype = DNA   length = 200
FEATURE                 Location/Qualifiers
source                  1..200
                        mol_type = genomic DNA
                        organism = Zea mays
SEQUENCE: 2
cgtgggatgg gaaaacacga agcgtggtct gcttttcgc atgatatctg ggccgcacca    60
aagaatccag cccacgcggc gtggcgccgt cgttacggct tgcgggggaa ggaaacgagg   120
gacgaaccga gatttagcac cagaccggcc agcgagcatt gcagacaccg gcttataagt   180
tcagctgcga ctaccactcc                                               200

SEQ ID NO: 3            moltype = DNA   length = 397
FEATURE                 Location/Qualifiers
source                  1..397
                        mol_type = genomic DNA
                        organism = Zea mays
SEQUENCE: 3
ttatatgtta ccgttgcaaa gcacgggcac tcacctagta tataatataa catcagtcgt    60
acgtaatgta ctgatgggcg ggttaacaaa tgtcactcac tatcagcacc agcagcgctt   120
agatgcatcc ggccgggcca agacccagga ccagaaagcg cgcacgttca cagcggatgc   180
tgatgggtta gatcgactga tcgaggaaga ggagagctta attaagaaac gccctgttcc   240
gctttgctag cttgcgccct gactgtccag cccacgcgct tcggtccgat tcacatgcta   300
ggctggtgca agcgagccga gactttttt tagaaccacc ttgctcagca aaccttagga   360
acaccggctt ataagtcgaa gcgaagcgct gtgcact                            397

SEQ ID NO: 4            moltype = DNA   length = 200
FEATURE                 Location/Qualifiers
source                  1..200
                        mol_type = genomic DNA
                        organism = Zea mays
SEQUENCE: 4
tgatcgagga agaggagagc ttaattaaga aacgccctgt tccgctttgc tagcttgcgc    60
cctgactgtc cagcccacgc gcttcggtcc gattcacatg ctaggctggt gcaagcgagc   120
cgagactttt ttttagaacc accttgctca gcaaacctta ggaacaccgg cttataagtc   180
gaagcgaagc gctgtgcact                                               200

SEQ ID NO: 5            moltype = DNA   length = 397
FEATURE                 Location/Qualifiers
source                  1..397
                        mol_type = genomic DNA
                        organism = Zea mays
SEQUENCE: 5
ggattcggtg ttctttatta ggttctcgcc gaatatggtt ctcagttatg acctaacggt    60
gtccacaaga gttcgccagg atttatacaa ctattttctt atttatttct ttaacatttt   120
cccttctacg cacaatagga gataatgtca agcgttgacg gtgcacatat atttgttttt   180
ttaaaggcgt agtggcgtgt gtgcaaaaac atcctcacag gaaagacacg aagaaacatg   240
gtcaatggcc cattatataa agcaccgcca caagcccaa ataccagttc gtcggtggag   300
caagtaacgc gctaggcaac aggcaaacag tttgtcccac ctcgtccagt cacaaaggca   360
aagcgtgact tataagccag agcggaagaa ccatacc                            397

SEQ ID NO: 6            moltype = DNA   length = 200
FEATURE                 Location/Qualifiers
source                  1..200
                        mol_type = genomic DNA
                        organism = Zea mays
SEQUENCE: 6
tgtgtgcaaa aacatcctca caggaaagac acgaagaaac atggtcaatg gcccattata    60
```

```
taaagcaccg ccacaaagcc caaataccag ttcgtcggtg agcaagtaa cgcgctaggc  120
aacaggcaaa cagtttgtcc cacctcgtcc agtcacaaag gcaaagcgtg acttataagc  180
cagagcggaa gaaccatacc                                              200

SEQ ID NO: 7            moltype = DNA   length = 397
FEATURE                 Location/Qualifiers
source                  1..397
                        mol_type = genomic DNA
                        organism = Zea mays
SEQUENCE: 7
tcgtaaaata gtggtgtcca aagaatttcc aggcccagtt gtaaaagcta aaatgctatt   60
cgaatttcta ctagcagtaa gtcgtgttta gaaattattt ttttatatac cttttttcct  120
tctatgtaca gtaggacaca gtgtcagcgc cgcgttgacg gagaatattt gcaaaaaagt  180
aaaagagaaa gtcatagcgg cgtatgtgcc aaaaacttcg tcacagagag ggccataaga  240
aacatggccc acggcccaat cgaagcacc gcgacgaagc ccaaacagca gtccgtaggt   300
ggagcaaagc gctgggtaat acgcaaacgt tttgtcccac cttgactaat cacaagagtg  360
gagcgtacct tataaaccga gccgcaagca ccgaatt                           397

SEQ ID NO: 8            moltype = DNA   length = 200
FEATURE                 Location/Qualifiers
source                  1..200
                        mol_type = genomic DNA
                        organism = Zea mays
SEQUENCE: 8
cggcgtatgt gccaaaaact tcgtcacaga gagggccata agaaacatgg cccacggccc   60
aatacgaagc accgcgacga agcccaaaca gcagtccgta ggtggagcaa agcgctgggt  120
aatacgcaaa cgttttgtcc caccttgact aatcacaaga gtggagcgta ccttataaac  180
cgagccgcaa gcaccgaatt                                              200

SEQ ID NO: 9            moltype = DNA   length = 540
FEATURE                 Location/Qualifiers
source                  1..540
                        mol_type = genomic DNA
                        organism = Solanum lycopersicum
SEQUENCE: 9
gttacgtaat tatatttctt agtcatattt tagttattcc atcttaacca cataggtgat   60
agtcaatatg tctatttcac atgtatggtt ccgtactata attaacaaca tattgatttg  120
aaattctatt tgtgctacat atattagaca aggaaaataa catatgttat tttgaaatca  180
cgtatatatta ctataaatta caatgattaa caacttaaaa ttttaaatg aaaatcatat  240
taatgactct ctaaatttta tctgtgtcac ataaatgaaa aacaaaaaat aacaaatatt  300
gtattcgcac gggcgcatgt gtctagttag ttataaacga agaaataagg ggctgatttc  360
gaaataaacg ttcttagaat tggaagaaat gttcagtttc taaacttgta ggactaaagc  420
aataactttt atttaattta ttttcttta tgtttctccc acatcgatca tacatataac  480
tatacagcag tataagaact ctagcgaagc aataatgctc gtcccgttgg ggacatccga  540

SEQ ID NO: 10           moltype = DNA   length = 600
FEATURE                 Location/Qualifiers
source                  1..600
                        mol_type = genomic DNA
                        organism = Solanum lycopersicum
SEQUENCE: 10
tataataata ctatgttaaa tatgcaacat gtattagaag tgaattaagt atgcaataga   60
tatgtattta aaaatatatt atgcttgttt gataagaagt tgatgcattg tattataagt  120
acgttagaat gtgcaataaa tatattatct atcattagaa cttgaattat aagtgaataa  180
tagattattt tttgtaatat gaattaaaag tgtattaaac atgtattaac ggtgatcaat  240
tggttaaaaa aaagtttatt attaaaatga taaatctttt taatttatag tatatttatg  300
taagttttca cgttgagtaa atagcgaaga agttgggccc aaccaagtaa aataagaagg  360
ccgggccatt acaattaagt cgtcacacaa ctgggcttca ttgaaaaaag cgcaaaaccg  420
attccaggcc cgtgttagca tgaagactca actcaaccag agatttctcc ctcatcgctt  480
acagaaaaaa gctatatgct gtttatattg cgaaatcttaa cagtgtagtt tgtcccttcg  540
gggacatccg ataaaattgg aacgatacag agaagattag catggcccct gcgcaaggat  600

SEQ ID NO: 11           moltype = DNA   length = 540
FEATURE                 Location/Qualifiers
source                  1..540
                        mol_type = genomic DNA
                        organism = Solanum lycopersicum
SEQUENCE: 11
ttctccaaaa aaaaaaagga aagaagaag caaacaaaca aatagaagca tatctcttga    60
tgtggaagga gatcaaaata ttcccaataa atacttatga gaagaagtaa ctgatttaaa  120
attttcacta atagggttcg aaaaatgaaa atgtaatacg tggaacttga atgtaaaacc  180
tcaaggaatt cttgtgttta agaaattcaa atctctcta aatgtataca aaagatgatt   240
tcttttacc ttatatatag taaaataaaa ttgtcggata aattcgagtg aacaccctag   300
cacccctaa atcctccccc gtagtcggcc cattacagtt aaagtccagg tacaacaaaa   360
tgggcttcga ttaagatgga ataaaaggag tccaggccca tgagcccaac aaacaagcta  420
tttctccctc atcggcgcac aaagaagctt tattctctta ttatagctga atattagcat  480
gtgtgtttgt ccccttcgggg acatccgata aaattggaac gatacagaga agattagcat  540

SEQ ID NO: 12           moltype = DNA   length = 540
```

```
FEATURE              Location/Qualifiers
source               1..540
                     mol_type = genomic DNA
                     organism = Glycine max
SEQUENCE: 12
accttttttaa ccgcacaaag ttttaaccag atttatataa tttatttttg aatccccaat    60
acatatcatt ataacatatc aattatcaaa tatttcaata acctcatgat atggcaatga   120
atacatcttc ttctcaatga acagagattt ctgaaaaaga ttaggaaagt gaaagcatac   180
tcgtttgcaa tgtaaaactg atacttcccc aaaatcatca tattccaaat atgccctggt   240
gttactgacc aaaaccagaa aaaagaaacg gaagacatat acgtctaaac ggagaaattt   300
caaaaaacaa aaattggatc atttctcgat ttgtgggtgt catcttgtgc agggcatgct   360
aatcttctct ttacccttc ccacaagact cagcgcatgt tgtctcgtct catccaagtc   420
ccacaccgcc taaacttaac acaatattag tatttataat gacatacaac attcaagatg   480
ttgtcccttc ggggacatcc gataaaattg aacgataca gagaagatta gcatggcccc   540

SEQ ID NO: 13        moltype = DNA   length = 540
FEATURE              Location/Qualifiers
source               1..540
                     mol_type = genomic DNA
                     organism = Glycine max
SEQUENCE: 13
cattataaaa agtaaaatat aactactttg ttttttaata aaaaaaattc aatgggagat    60
actatggatt caattacctt actgatttta tttcatatgt gccagaagta tttcagttta   120
ttttgaaaaa tcagaaaaaa aatgtctgga ataaaatata ataagcgata ctaataaata   180
attgaacaag ataaatggta aaatgtcaaa tcaaaactag gctacagagt gcagagcaga   240
gtcatgatga atgaccagcta gttctactta ctacaccgat tcttgtgtac ataaaaatat   300
tttaaaataa ttgaatcttt ctttagccag ctttgacaac aatgtacacc gttcgtactt   360
cttactggta ggcaatgctt cttgtttgct ttcggtggaa ggtgtatata ctcaacatta   420
cttctttttc agcgtgtttt cttacgggag tcccacaccg cccaaaacta atacagtatt   480
cttgttata aagaagtgca ccacttcaat tgttgtccct tcggggacat ccgataaaat   540

SEQ ID NO: 14        moltype = DNA   length = 540
FEATURE              Location/Qualifiers
source               1..540
                     mol_type = genomic DNA
                     organism = Glycine max
SEQUENCE: 14
atattcataa tttttttttt ttgtttttttt atacaaggac ggctgattca atcatcacac    60
cacacgtcat attaaaaaaa tatagtagat ttattttaaa atagagagaa tcgttaagaa   120
aaaaataaat agtaaagtaa atgaaaaccc aaataatatc attattatgt caataagtcg   180
gagaggatag taatcaaatg gtctatgagg tggtggttca ttcaacatat agcacctatt   240
cattgttcct aaaacataat ttaagaacaa aaacttaaac ttaaataata ataataaag   300
agtacatcga agtatctgtg ttctctatcc ttctgactaa cattcatgtt gtttgtattc   360
agcaaagggc cgtgcaggat ttgtgcgtcg cgctccggtt agttattgca gtgaccgtct   420
ctttagtccc acatcgagta attatgcttc atacagtctg tttatataac agagatggaa   480
caaactggtt gtcccttcgg ggacatccga taaaattgga acgatacaga gaagattagc   540

SEQ ID NO: 15        moltype = DNA   length = 540
FEATURE              Location/Qualifiers
source               1..540
                     mol_type = genomic DNA
                     organism = Glycine max
SEQUENCE: 15
ctttcaggtc atgatttttt gtttctaaat gatactcaca ctcccttcca gtttttttt    60
tttaaactca gctcccttgc ttcctccacc ggttatcata atactgaacc aaatcaaaca   120
ttacagtcaa ggtactatga atatgaaacc tgaaatccta tgaatgtcat aaatttattt   180
taaataataa atttatttag aataatattt ttttgggtaa gagttataaa ataaaataca   240
aaaaaaaaac ctaatatcaa tttttcactg actccgttta tattgagact tgagaaagat   300
ggttcccgtt tgctcccggt ggaggctccg aggctgtgta tatactcgac attactttag   360
cttgttttgt tgtttctttc cctttcccac aagactcagg tctcgttcgc aaacgagtcg   420
cacaccgtct aaacttacca caatattagc gtttataatt agatgcactg catcacttat   480
tgtcccttcg gggacatccg ataaaattgg aacgatacag agaagattag catggcccct   540

SEQ ID NO: 16        moltype = DNA   length = 420
FEATURE              Location/Qualifiers
source               1..420
                     mol_type = genomic DNA
                     organism = Glycine max
SEQUENCE: 16
tgcagagcag agtcatgatg atactactta ctacaccgat tcttgtgtgc agaaaaatat    60
gttaaaataa ttgaatcttt ctctagccaa atttgacaac aatgtacacc gttcatattg   120
agagacgatg cttcttgttt gctttcggtg gaagctgcat atactcaaca ttactccttc   180
agcgagtttt ccaactgagt cccacattgc ccagacctaa cacggtattc ttgtttataa   240
tgaaatgcac caccacatgg attgtccctt cggggacatc cgataaaatt ggaacgatac   300
agagaagatt agcatggccc ctgcgcaagg atgacacgca caaatcgaga atggtccaa   360
attttttttg aaatttctcg tttagataga tgtctttgct tttccgcact atggttctga   420

SEQ ID NO: 17        moltype = DNA   length = 397
FEATURE              Location/Qualifiers
```

| | |
|---|---|
| source | 1..397<br>mol_type = other DNA<br>note = Recombinant<br>organism = synthetic construct |

SEQUENCE: 17

```
aggaaaagaa gaggtgatta ctgtacctat tcgtctttgt atcggaatat aaatttatca    60
ctattttatg ataaagtaaa tctgtttccc tgtagagtta attaattaat gtaagtataa   120
gcgtaattta tagggcacta gtaggactgt cgactgtgcg ctcggccggg ataatgcgtc   180
aaaagcgaag acgtgcacgt gggatgggaa aacacgaagc gtggtctgct ttttcgcatg   240
atatctgggc cgcaccaaag aatccagccc acgcggcgtg gcgccgtcgt tacggcttgc   300
gggggaagga aacagggac gaaccgagat ttagtcccac cttgactaat cacaagagtg   360
gagcgtacct tataaaccga gccgcaagca ccgaatt                           397
```

| SEQ ID NO: 18<br>FEATURE<br>source | moltype = DNA   length = 397<br>Location/Qualifiers<br>1..397<br>mol_type = other DNA<br>note = Recombinant<br>organism = synthetic construct |
|---|---|

SEQUENCE: 18

```
aggaaaagaa gaggtgatta ctgtacctat tcgtctttgt atcggaatat aaatttatca    60
ctattttatg ataaagtaaa tctgtttccc tgtagagtta attaattaat gtaagtataa   120
gcgtaattta tagggcacta gtaggactgt cgactgtgcg ctcggccggg ataatgcgtc   180
aaaagcgaag acgtgcacgt gggatgggaa aacacgaagc gtggtctgct ttttcgcatg   240
atatctgggc cgcaccaaag aatccagccc acgcggaagc caaacagca gtccgtaggt   300
ggagcaaagc gctgggtaat acgcaaacgt tttgtcccac cttgactaat cacaagagtg   360
gagcgtacct tataaaccga gccgcaagca ccgaatt                           397
```

| SEQ ID NO: 19<br>FEATURE<br>source | moltype = DNA   length = 397<br>Location/Qualifiers<br>1..397<br>mol_type = other DNA<br>note = Recombinant<br>organism = synthetic construct |
|---|---|

SEQUENCE: 19

```
aagtcgtaaa atagtggtgt ccaaagaatt tccaggccca gttgtaaaag ctaaatgct    60
attcgaattt ctactagcag taagtcgtgt ttagaaatta ttttatatac cttttttcct   120
tctatgtaca gtaggacaca gtgtcagcgc cgcgttgacg agaatatttt gcaaaaaagt   180
aaaagagaaa gtcatagcgg cgtatgtgcc aaaaacttcg tcacagagag ggccataaga   240
aacatggccc acggcccaat acgaagcacc gcgacgaagc ccaaacagca gtccgtaggt   300
ggagcaaagc gctgggtaat acgcaaacgt tttgcaccag accggccagc gagcattgca   360
gacaccggct tataagttca gctgcgacta ccactcc                           397
```

| SEQ ID NO: 20<br>FEATURE<br>source | moltype = DNA   length = 397<br>Location/Qualifiers<br>1..397<br>mol_type = other DNA<br>note = Recombinant<br>organism = synthetic construct |
|---|---|

SEQUENCE: 20

```
tcgtaaaata gtggtgtcca aagaatttcc aggcccagtt gtaaaagcta aatgctatt    60
cgaatttcta ctagcagtaa gtcgtgttta gaaattattt ttatatac cttttttcct   120
tctatgtaca gtaggacaca gtgtcagcgc cgcgttgacg agaatatttt gcaaaaaagt   180
aaaagagaaa gtcatagcgg cgtatgtgcc aaaaactgtc acagagaggg ccataagaaa   240
catggcccac ggcccaataa gcccaccagc caccggaagc ccaaacagca gtccgtaggt   300
ggagcaaagc gctgggtaat acgcaaacgt tttgtcccac cttgactaat cacaagagtg   360
gagcgtacct tataaaccga gccgcaagca ccgaatt                           397
```

| SEQ ID NO: 21<br>FEATURE<br>source | moltype = DNA   length = 83<br>Location/Qualifiers<br>1..83<br>mol_type = other DNA<br>note = Recombinant<br>organism = synthetic construct |
|---|---|

SEQUENCE: 21

```
gtttagagc tagaaatagc aagtaaaat aaggctagtc cgttatcaac ttgaaaaagt    60
ggcaccgagt cggtgctttt ttt                                          83
```

| SEQ ID NO: 22<br>FEATURE<br>source | moltype = DNA   length = 23<br>Location/Qualifiers<br>1..23<br>mol_type = genomic DNA<br>organism = Zea mays |
|---|---|

SEQUENCE: 22

```
gccggccagc atttgaaaca tgg                                          23
```

| SEQ ID NO: 23<br>FEATURE<br>source | moltype = DNA   length = 20<br>Location/Qualifiers<br>1..20 |
|---|---|

```
                        mol_type = genomic DNA
                        organism = Zea mays
SEQUENCE: 23
gccggccagc atttgaaaca                                                   20

SEQ ID NO: 24           moltype = DNA   length = 20
FEATURE                 Location/Qualifiers
source                  1..20
                        mol_type = unassigned DNA
                        organism = Zea mays
SEQUENCE: 24
gttatcaatt tactttcaat                                                   20

SEQ ID NO: 25           moltype = DNA   length = 20
FEATURE                 Location/Qualifiers
source                  1..20
                        mol_type = unassigned DNA
                        organism = Zea mays
SEQUENCE: 25
gcgcaaggga tcagtaattc                                                   20

SEQ ID NO: 26           moltype = AA    length = 1064
FEATURE                 Location/Qualifiers
source                  1..1064
                        mol_type = protein
                        organism = Bradyrhizobium sp.
SEQUENCE: 26
MKRTSLRAYR LGVDLGANSL GWFVVWLDDH GQPEGLGPGG VRIFPDGRNP QSKQSNAAGR   60
RLARSARRRR DRYLQRRGKL MGLLVKHGLM PADEPARKRL ECLDPYGLRA KALDEVLPLH  120
HVGRALFHLN QRRGLFANRA IEQGDKDASA IKAAAGRLQT SMQACGARTL GEFLNRRHQL  180
RATVRARSPV GGDVQARYEF YPTRAMVDAE FEAIWAAQAP HHPTMTAEAH DTIREAIFSQ  240
RAMKRPSIGK CSLDPATSQD DVDGFRCAWS HPLAQRFRIW QDVRNLAVVE TGPTSSRLGK  300
EDQDKVARAL LQTDQLSFDE IRGLLGLPSD ARFNLESDRR DHLKGDATGA ILSARRHFGP  360
AWHDRSLDRQ IDIVALLESA LDEAAIIASL GTTHSLDEAA AQRALSALLP DGYCRLGLRA  420
IKRVLPLMEA GRTYAEAASA AGYDHALLPG GKLSPTGYLP YYGQWLQNDV VGSDDERDTN  480
ERRWGRLPNP TVHIGIGQLR RVVNELIRWH GPPAEITVEL TRDLKLSPRR LAELEREQAE  540
NQRKNDKRTS LLRKLGLPAS THNLLKLRLW DEQGDVASEC PYTGEAIGLE RLVSDDVDID  600
HLIPFSISWD DSAANKVVCM RYANREKGNR TPFEAFGHRQ GRPYDWADIA ERAARLPRGK  660
RWRFGPGARA QFEELGDFQA RLLNETSWLA RVAKQYLAAV THPHRIHVLP GRLTALLRAT  720
WELNDLLPGS DDRAAKSRKD HRHHAIDALV AALTQDALLR RMANAHDDTR RKIEVLLPWP  780
TFRIDLETRL KAMLVSHKPD HGLQARLHED TAYGTVEHPE TEDGANLVYR KTFVDISEKE  840
IDRIRDRRLR DLVRAHVAGE RQQGKTLKAA VLSFAQRRDI AGHPNGIRHV RLTKSIKPDY  900
LVPIRDKAGR IYKSYNAGEN AFVDILQAES GRWIARATTV FQANQANESH DAPAAQPIMR  960
VFKGDMLRID HAGAEKFVKI VRLSPSNNLL YLVEHHQAGV FQTRHDDPED SFRWLFASFD 1020
KLREWNAELV RIDTLGQPWR RKRGLETGSE DATRIGWTRP KKWP                  1064

SEQ ID NO: 27           moltype = DNA   length = 3195
FEATURE                 Location/Qualifiers
source                  1..3195
                        mol_type = other DNA
                        note = Recombinant
                        organism = synthetic construct
SEQUENCE: 27
atgaagagaa cgagtttacg ggcctaccgt ctgggcgtgg atctcggcgc caattcgctg   60
ggatggttcg tggtctggct cgacgatcac ggacagcccg agggccttgg cccggggcgg  120
gtcaggattt tccccgacgg tcgtaacccg caatccaagc aatccaatgc ggccggtcgc  180
cgcctcgcac gcagtgcacg acgacgacga gaccgctatc tgcagcgacg cggaaagctg  240
atgggcttgc tggtcaagca cggcttgatg cccgccgatg agccggcccg aaagcgattg  300
gaatgcctcg atccctatgg tctccgcgcg aaagcgcttg atgaagtgct gcctttgcat  360
catgtcggcc gggcgctgtt tcacctcaac cagcggcgcg gcctgtttgc caatcgagcg  420
atcgagcaag gcgacaagga cgccagcgcg atcaaggccg cggccggcag actgcagaca  480
tcgatgcagg cgtgcggcgc gcgcacgctc ggcgaattcc tcaaccgccg tcatcagctc  540
cgcgccacag tgcgcgcccg cagccctgtc ggcggcgacg tccaggcgcg gtatgaattc  600
tatccgacac gcgcgatggt tgatgcggag ttcgaagcca tctgcggcca acaggcccgg  660
catcacccaa cgatgacggc cgaagcgcat gacacgatcc gcgaggcgat cttctctcaa  720
cgcgcgatga gcggccgtc gatcgggaaa tgctcgctcg accccgccac cagccaggac  780
gacgtcgacg gcttccgctg cgcctggtcg catcccctgg cgcagcgttt ccgcatctgg  840
caggacgtcc gcaatctagc cgtggtggag actggcccca cgtcttccag gcttggcaag  900
gaggatcagg acaaggtcgc acgggcactg ctacagacg accaactcag cttcgatgag  960
atccgcggcc ttctcggatt gccgtcggac gcgcggttca accttgaaag cgaccggcgt 1020
gatcacctca agggcgacgc gaccggcgcg atcctgtccg ccaggaggca ttttggcccg 1080
gcatggcatg accggtccct ggatcgtcag atcgacatcg tcgcgctgct ggagagcgcg 1140
ctcgatgaag cagcgatcat cgcctcgctc gggacaactc acagccttga tgaagcagct 1200
gcgcagcggg cgttgtccgc cttgctgcct gacggatatt gccggctcgg actgagggcg 1260
atcaagcggg tcctgccgct catggaagct ggcaggacct acgcggaggc cgccagcgcg 1320
gccggctatg atcacgctct gctgccgggc ggcaagctct ctcccaccgg ctacctgccc 1380
tattatggac aatggctgca gaacgatgtc gtgggctcgg acgatgagcg cgacaccaac 1440
gaacggcgct ggggccgctt gccgaatccc accgttcaca tcgggatcgg ccagttcgca 1500
cgcgtcgtca atgagctcat cagatggcat ggaccgccgg ccgagatcac cgtcgagttg 1560
```

-continued

```
acgcgtgacc tgaagctgtc gccccgacgg ctggcggagc tcgaacgcga gcaggccgag   1620
aaccagcgca agaacgacaa gcgtacctcc ctattgcgca agctcggcgt ccccgcgagc   1680
acgcacaatc tcctcaagct tcggctctgg gacgagcaag gcgatgttgc aagcgaatgc   1740
ccctatacgg gcgaggcgat cggcctcgaa cgtctggtct ctgatgatgt ggatatcgat   1800
cacctcatcc cattctcgat cagctgggac gacagcgcgg ccaacaaagt ggtctgcatg   1860
cgctacgcca atcgtgagaa gggcaatcga acgccgttcg aggcctttgg ccatcgccaa   1920
ggcaggcctt acgattgggc ggacattgca gaacgcgcag cgcgcctgcc gcgcggcaag   1980
cgctggcgct tcggtccagg cgcgcgggcg caattcgagg agctcggcga ctttcaggca   2040
cgcctgctca acgagaccag ctggctggcg cgcgtcgtca agcaatatct cgcagcgtc    2100
acccaccccgc acaggatcca cgttctgccg ggccggctga cagcgctgct ccgcgcaaca   2160
tgggagctca acgatttgct gcccggaagc gacgacagag ccgcgaagag ccgcaaggac   2220
caccgtcatc atgccatcga cgcgctggtg cggcactga cagaccaggc gctgctgcgc    2280
cgcatggcga acgcgcatga cgatacgcga cggaagatcg aagttctcct gccctggccg   2340
acgttccgga tcgatctcga gaccaggctg aaggcggatc tcgtatcgca caagcccgat   2400
cacggcctcc aggcccgcct gcatgaagac accgccatg ggaccgtcga acaccccgaa    2460
accgaggatg tgcaaatctc ggtctatcgg aagaccttcg tggacatcag cgaaaaggag   2520
atcgaccgca ttcgcgatcg ccgcttgcgt gacctcgtca gagcccatgt ggccggcgaa   2580
aggcagcagg gcaagacgct caaagcggcc gtgctgtcat tcgcgcagcg cagggacatt   2640
gctggtcacc cgaatggcat tcgccatgtc cgcctgacca aatcgatcaa gccgactat    2700
ctggtaccga tccgcgacaa agccggccga atctacaagt cctacaatgc aggcgagaat   2760
gccttcgtcg acatcctgca agccgagagt ggccgatgga tcgcgcgggc cacgaccgtc   2820
tttcaggcca atcaagccga tgagtcgcat gacgcgcgg tgctgcgaacc gatcatgcgg    2880
gtcttcaagg cgacatgct gcgcatcgat cacgctggcg cggagaagtt cgtgaagatc   2940
gtcaggcttt cgcccctcgaa caacctgctc tacctcgtcg aacatcatca ggcgggcgtg   3000
tttcagaccc gccatgacga cccggaagat tcctttcggt ggctcttcgc cagttttgac   3060
aagcttcgcg aatggaacgc cgagcttgtc cggatcgata cgctgggaca gccctggcgg   3120
cgcaagcgcg gccttgaaac aggaagcgag gacgccactc gcatcggctg gacgcgacca   3180
aaaaaatggc cctga                                                    3195
```

SEQ ID NO: 28          moltype = AA   length = 1378
FEATURE                Location/Qualifiers
source                 1..1378
                       mol_type = protein
                       note = Recombinant
                       organism = synthetic construct
SEQUENCE: 28

```
MDKKYSIGLD IGTNSVGWAV ITDEYKVPSK KFKVLGNTDR HSIKKNLIGA LLFDSGETAE    60
ATRLKRTARR RYTRRKNRIC YLQEIFSNEM AKVDDSFFHR LEESFLVEED KKHERHPIFG   120
NIVDEVAYHE KYPTIYHLRK KLVDSTDKAD LRLIYLALAH MIKFRGHFLI EGDLNPDNSD   180
VDKLFIQLVQ TYNQLFEENP INASGVDAKA ILSARLSKSR RLENLIAQLP GEKKNGLFGN   240
LIALSLGLTP NFKSNFDLAE DAKLQLSKDT YDDDLDNLLA QIGDQYADLF LAAKNLSDAI   300
LLSDILRVNT EITKAPLSAS MIKRYDEHHQ DLTLLKALVR QQLPEKYKEI FFDQSKNGYA   360
GYIDGGASQE EFYKFIKPIL EKMDGTEELL VKLNREDLLR KQRTFDNGSI PHQIHLGELH   420
AILRRQEDFY PFLKDNREKI EKILTFRIPY YVGPLARGNS RFAWMTRKSE ETITPWNFEE   480
VVDKGASAQS FIERMTNFDK NLPNEKVLPK HSLLYEYFTV YNELTKVKYV TEGMRKPAFL   540
SGEQKKAIVD LLFKTNRKVT VKQLKEDYFK KIECFDSVEI SGVEDRFNAS LGTYHDLLKI   600
IKDKDFLDNE ENEDILEDIV LTLTLFEDRE MIEERLKTYA HLFDDKVMKQ LKRRRYTGWG   660
RLSRKLINGI RDKQSGKTIL DFLKSDGFAN RNFMQLIHDD SLTFKEDIQK AQVSGQGDSL   720
HEHIANLAGS PAIKKGILQT VKVVDELVKV MGRHKPENIV IEMARENQTT QKGQKNSRER   780
MKRIEEGIKE LGSQILKEHP VENTQLQNEK LYLYYLQNGR DMYVDQELDI NRLSDYDVDH   840
IVPQSFLKDD SIDNKVLTRS DKNRGKSDNV PSEEVVKKMK NYWRQLLNAK LITQRKFDNL   900
TKAERGGLSE LDKAGFIKRQ LVETRQITKH VAQILDSRMN TKYDENDKLI REVKVITLKS   960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKYLDEII EQISEFSKRV ILADANLDKV LSAYNKHRDK PIREQAENII HLFTLTLNGA  1320
PAAFKYFDTT IDRKRYTSTK EVLDATLIHQ SITGLYETRI DLSQLGGDGS KKRRIKQD   1378
```

SEQ ID NO: 29          moltype = DNA   length = 4137
FEATURE                Location/Qualifiers
source                 1..4137
                       mol_type = other DNA
                       note = Recombinant
                       organism = synthetic construct
SEQUENCE: 29

```
atggacaaga agtacagcat tggtctggac atcggaacga actcggtcgg ctgggccgtg    60
attactgacg agtacaaagt tcccagcaaa aaattcaagg ttctaggcaa cacagaccgc   120
cactcgatta aaaagaatct aatcggcgcg cttctgttcg actctggtga acgggccgag   180
gccacacgct taaagaggac gcgcgccgc cgctacacgc ggcgcaagaa ccgaatctgt    240
tacctccagg agatcttcag taatgagatg gctaaggtcg atgacagctt cttccacagg   300
cttgaagagt cctttctggt cgaagaggac aaaaaacacg aacgtcaccc aatcttcggg   360
aacattgtgg atgaagtggc ataccacgag aagtatccta tcgatcatca tccgcaag    420
aagctcgtgg atagtaccga caaagccgac ctgcgcttaa tctaccttgc gctcgcgcac   480
atgattaagt tccgaggaca cttccttatt gagggtgatc tgaatccgga caattccgat   540
gtggataaac tgttcattca gttggtccag acatacaatc agctattcga ggagaatccg   600
atcaatgctt ccggcgtgga cgcaaaggct attctgtcag caagactttc aaagagcaga   660
aggttggaga atcgatcgc acaacttccc ggagagaaga gaatgggct cttcggcaac   720
```

```
ctcattgcgc tgtctttggg tctgacaccg aactttaagt ctaacttcga ccctcgctgag    780
gatgctaaac ttcagcttag caaagacacc tatgatgatg acctggacaa cctcctcgcc    840
cagattggag accagtacgc ggatctattc ttggctgcca agaacctgtc cgatgcgatt    900
ctgcttagtg acatcctccg agtgaacact gaaattacga agcacccttt gtcggctagt    960
atgattaagc gatacgatga gcaccatcaa gacctgact tgctaaaggc gctcgtaaga   1020
cagcaacttc ctgagaagta caaggagata tttttgatc agtctaagaa tggctacgct   1080
ggttacatcg acggtggagc tagtcaggag gaattctata aattcatcaa gcctatcctg   1140
gaaaaaatgg acggtacgga ggaattgctc gttaaactaa atcgagagga tctgctgaga   1200
aagcagcgga ctttcgacaa tggttctatt ccgcatcaga ttcacctcgg agaacttcac   1260
gccatcctga gacgacagga ggacttctac cctttcctga aagacaaccg ggaaaaaatc   1320
gagaagatcc tgacattcag gattccttac tatgtaggcc ctttagcgag aggcaacagt   1380
agattcgcct ggatgaccag aaagtctgag gaaacaatca caccgtggaa cttcgaggaa   1440
gtggttgata agggtgctag tgcccaatca ttcattgaga gaatgacgaa cttcgacaag   1500
aatctgccta acgagaaggt tctccctaaa catagcctgc tttacgagta tttcacggtg   1560
tacaatgagc taacgaaggt caagtatgtc acagagggaa tgcggaaacc ggctttcctt   1620
tcgggtgaac agaagaaagc aattgtggat ttgctcttca agacaaaccg aaaggtgaca   1680
gtgaagcagc taaaggagga ctacttcaaa aaaatagagt gcttcgactc agttgagatc   1740
agcggagtgg aggaccggtt taacgcttcc ctcggcactt accacgactt gctcaagatc   1800
atcaaggaca aagacttcct tgataacgag gagaacgaag acatccttga ggacattgtg   1860
ctgacattga cgttgttcga ggatcgggag atgatcgagg aacgcctcaa gacgtacgcc   1920
catctgttcg atgataaggt gatgaagcag ttaaagagga gacgttacac tggctggggc   1980
cgtctctctc gcaaactgat aaacgggata agggataaac aaagcggaaa gacaatcctc   2040
gatttcctta aatccgacgg cttcgctaac cggaacttca tgcagctcat ccatgatgac   2100
tcactgacgt tcaaggagga catccagaaa gctcaagtgt ctggccaggg tgacagcttg   2160
cacgagcaca tcgcaaatct agccggttca ccggcgataa gaagggcat tctacaaacg   2220
gtgaaagtgg tggacgagtc atgggtcgcc ataagccaga gaacattgtt   2280
atcgaaatgg cgaggagaa ccagacaacg cagaagggac aaaaaaacag tagggagcgg   2340
atgaagcgca tcgaggaagg cattaaggaa cttggaagcc aaatcctgaa agagcacccg   2400
gtggagaata cgcagttgca gaacgagaaa ctgtacctct actacttgca gaatggacgt   2460
gatatgtatg tggatcaaga gttggacatc aaccgattgt ctgactatga cgtggatcac   2520
atagtaccac agtccttcct caaggatgat agcatagaca acaaggttct tactcgtagc   2580
gacaagaatc gtggcaaatc ggcaatgtt ccatctgagg aagttgtcaa aaagatgaaa   2640
aattattgga ggcaacttct gaacgcgaag ctaattacac aaaggaaatt cgacaatctc   2700
actaaggccg agagaggagg gttaagtgag ttagacaagg ctggcttcat caagcggcag   2760
ttggtcgaga ctcgtcagat tactaagcac gtggctcaga tcctggattc gcgcatgaac   2820
accaaatacg acgagaatga caactcatcc gtgaagtta aggtgattac actgaaatcc   2880
aagctggtct ctgactttag gaaagacttc caattctaca aggtgagaga gattaacaac   2940
taccaccacg cgcatgacgc ctacttgaat gctgtggttg gagtgccct gataaagaaa   3000
tatcctaaac ttgagtctga gttcgtttac ggtgactaca aggtttatga cgttaggaag   3060
atgatcgcca aatccgaaca ggagattggg aaagcaactg ccaaatattt ctttactcc   3120
aacattatga acttttcaa gacagaaatc acactcgcca atggcgagat cggaagagaa   3180
ccactaatcg aaacaaacgg cgaaactggt gaaatcgttt gggataaggg tagggacttc   3240
gcaactgtta ggaaggtctt gtcgatgcct caagtgaaca tagtcaaaaa aacagaggtc   3300
cagaccggtg ggttctcaaa ggagtctatt ctgccaaagc gtaacagcga caaactcatc   3360
gctcgcaaaa aggactggga tcctaaaaag tacggtggat tcgacagccc gaccgttgct   3420
tattctgttc tcgtagttgc taaagtcgag aagggcaagt ccaaaaaact caaatcggtt   3480
aaggaactgc tcggaatcac gataatgaa cgaagcagtt tcgaaaaaa tccaattgac   3540
ttcctggaag ctaaaggtta caggaggtc aagaaggatc ttatcatcaa gctacccaag   3600
tacagtctgt tcgaactgga gaacggtcgc aagagaatgc tggcctcggc tggtgaactc   3660
cagaagggca atgagctggc cctgccgtcc aagtacgtga actttctgta cctggcatct   3720
cattacgaga agtcaagggg ctcaccagag gacaacgagc agaagcagtt gttcgttgaa   3780
cagcacaaac actatcttga tgagatcatt gagcaaatta gcgagttcag taagcgagtt   3840
attctggctg atgctaacct ggataaggtg ctctctgcct acaacaagca ccgggataaa   3900
cctattaggg aacaggcgga gaacataatc caccttctca ctctgacgaa tctcggcgcg   3960
cctgcggcct tcaaatattt tgataccacc atcgacagga agcgctaac aagcactaaa   4020
gaggtgctgg acgccactct cattcaccag tctattaccg ggctctacga gacacggatt   4080
gacctctccc agctaggtgg cgatggatct aagaagagaa gaattaaaca agattaa     4137
SEQ ID NO: 30         moltype = DNA  length = 500
FEATURE               Location/Qualifiers
source                1..500
                      mol_type = other DNA
                      note = Recombinant
                      organism = synthetic construct
SEQUENCE: 30
aggaaaagaa gaggtgatta ctgtacctat tcgtctttgt atcggaatat aaatttatca     60
ctattttatg ataaagtaaa tctgtttccc tgtagagtta attaattaat gtaagtataa    120
gcgtaattta tagggcacta gtaggactgt cgactgtgcg ctcggcccgg ataatgcgtc    180
aaaagcgaag acgtgcacgt gggatggaa aacacgaagc gtgtctgct ttttcgcatg    240
atatctgggc cgcaccaaag aatccagccc acgcggcgtg gcgccgtcgt tacggcttgc    300
gggggaagga aacgagggac gaaccgagat ttagcaccag accggccagc gagcattgca    360
gacaccggct tataagttca gctgcgacta ccactccgcc ggccagcatt tgaaacagtt    420
ttagagctag aaatagcaag ttaaaataag gctagtccgt tatcaacttg aaaaagtggc    480
accgagtcgg tgctttttt                                                  500
SEQ ID NO: 31         moltype = DNA  length = 303
FEATURE               Location/Qualifiers
source                1..303
                      mol_type = other DNA
```

```
                        note = Recombinant
                        organism = synthetic construct
SEQUENCE: 31
cgtgggatgg gaaaacacga agcgtggtct gcttttcgc atgatatctg ggccgcacca    60
aagaatccag cccacgcggc gtggcgccgt cgttacggct tgccggggaa ggaaacgagg   120
gacgaaccga gatttagcac cagaccggcc agcgagcatt gcagacaccg gcttataagt   180
tcagctgcga ctaccactcc gccggccagc atttgaaaca gttttagagc tagaaatagc   240
aagttaaaat aaggctagtc cgttatcaac ttgaaaaagt ggcaccgagt cggtgctttt   300
ttt                                                                 303

SEQ ID NO: 32           moltype = DNA    length = 500
FEATURE                 Location/Qualifiers
source                  1..500
                        mol_type = other DNA
                        note = Recombinant
                        organism = synthetic construct
SEQUENCE: 32
ttatatgtta ccgttgcaaa gcacgggcac tcacctagta tataatataa catcagtcgt    60
acgtaatgta ctgatgggcg ggttaacaaa tgtcactcac tatcagcacc agcagcgctt   120
agatgcatcc ggccgggcca agacccagga ccagaaagcg cgcacgttca cagcggatgc   180
tgatgggtta gatcgactga tcgaggaaga ggagagctta attaagaaac gccctgttcc   240
gctttgctag cttgcgccct gactgtccag cccacgcgct tcggtccgat tcacatgcta   300
ggctggtgca agcgagccga acttttttt tagaaccacc ttgctcagca aaccttagga   360
acaccggctt ataagtcgaa gcgaagcgct gtgcactgcc ggccagcatt tgaaacagtt   420
ttagagctag aaatagcaag ttaaaataag gctagtccgt tatcaacttg aaaaagtggc   480
accgagtcgg tgcttttttt                                               500

SEQ ID NO: 33           moltype = DNA    length = 303
FEATURE                 Location/Qualifiers
source                  1..303
                        mol_type = other DNA
                        note = Recombinant
                        organism = synthetic construct
SEQUENCE: 33
tgatcgagga agaggagagc ttaattaaga aacgccctgt tccgctttgc tagcttgcgc    60
cctgactgtc cagcccacgc gcttcggtcc gattcacatg ctaggctggt gcaagcgagc   120
cgagactttt ttttagaacc accttgctca gcaaaccttag gaacaccgg cttataagtc   180
gaagcgaagc gctgtgcact gccggccagc atttgaaaca gttttagagc tagaaatagc   240
aagttaaaat aaggctagtc cgttatcaac ttgaaaaagt ggcaccgagt cggtgctttt   300
ttt                                                                 303

SEQ ID NO: 34           moltype = DNA    length = 500
FEATURE                 Location/Qualifiers
source                  1..500
                        mol_type = other DNA
                        note = Recombinant
                        organism = synthetic construct
SEQUENCE: 34
ggattcggtg ttctttatta ggttctcgcc gaatatggtt ctcagttatg acctaacggt    60
gtccacaaga gttcgccagg atttatacaa ctatttctt atttatttct ttaacatttt   120
cccttctacg cacaatagga gataatgtca agcgttgacg gtgcacatat atttgttttt   180
ttaaaggcgt agtggcgtgt gtgcaaaaac atcctcacag gaaagacacg aagaaacatg   240
gtcaatggcc cattatataa agcaccgcca caaagcccaa ataccagttc gtcggtggag   300
caagtaacgc gctaggcaac aggcaaacag tttgtcccac ctcgtccagt cacaaaggca   360
aagcgtgact tataagccag agcggaagaa ccataccgcc ggccagcatt tgaaacagtt   420
ttagagctag aaatagcaag ttaaaataag gctagtccgt tatcaacttg aaaaagtggc   480
accgagtcgg tgcttttttt                                               500

SEQ ID NO: 35           moltype = DNA    length = 303
FEATURE                 Location/Qualifiers
source                  1..303
                        mol_type = other DNA
                        note = Recombinant
                        organism = synthetic construct
SEQUENCE: 35
tgtgtgcaaa aacatcctca caggaaagac acgaagaaac atggtcaatg gcccattata    60
taagcaccg ccacaaagcc caaataccag ttcgtcggtg gagcaagtaa cgcgctaggc   120
aacaggcaaa cagtttgtcc cacctcgtcc agtcacaaag gcaaagcgtg acttataagc   180
agagcggaa gaaccatacc gccggccagc atttgaaaca gttttagagc tagaaatagc   240
aagttaaaat aaggctagtc cgttatcaac ttgaaaaagt ggcaccgagt cggtgctttt   300
ttt                                                                 303

SEQ ID NO: 36           moltype = DNA    length = 500
FEATURE                 Location/Qualifiers
source                  1..500
                        mol_type = other DNA
                        note = Recombinant
                        organism = synthetic construct
SEQUENCE: 36
```

```
tcgtaaaata gtggtgtcca aagaatttcc aggcccagtt gtaaaagcta aaatgctatt    60
cgaatttcta ctagcagtaa gtcgtgttta gaaattattt ttttatatac cttttttcct   120
tctatgtaca gtaggacaca gtgtcagcgc cgcgttgacg gagaatattt gcaaaaaagt   180
aaaagagaaa gtcatagcgg cgtatgtgcc aaaaacttcg tcacagagag ggccataaga   240
aacatggccc acggcccaat acgaatgcacc gcgacgaagc ccaaacagca gtccgtaggt   300
ggagcaaagc gctgggtaat acgcaaacgt tttgtcccac cttgactaat cacaagagtg   360
gagcgtacct tataaaccga gccgcaagca ccgaattgcc ggccagcatt tgaaacagtt   420
ttagagctag aaatagcaag ttaaaataag gctagtccgt tatcaacttg aaaaagtggc   480
accgagtcgg tgcttttttt                                                500

SEQ ID NO: 37       moltype = DNA    length = 303
FEATURE             Location/Qualifiers
source              1..303
                    mol_type = other DNA
                    note = Recombinant
                    organism = synthetic construct
SEQUENCE: 37
cggcgtatgt gccaaaaact tcgtcacaga gagggccata agaaacatgg cccacggccc    60
aatacgaagc accgcgacga agcccaaaca gcagtccgta ggtggagcaa agcgctgggt   120
aatacgcaaa cgttttgtcc caccttgact aatcacaaga gtggagcgta ccttataaac   180
cgagccgcaa gcaccgaatt gccggccagc atttgaaaca gttttagagc tagaaatagc   240
aagttaaaat aaggctagtc cgttatcaac ttgaaaaagt ggcaccgagt cggtgctttt   300
ttt                                                                  303

SEQ ID NO: 38       moltype = DNA    length = 500
FEATURE             Location/Qualifiers
source              1..500
                    mol_type = other DNA
                    note = Recombinant
                    organism = synthetic construct
SEQUENCE: 38
aggaaaagaa gaggtgatta ctgtacctat tcgtctttgt atcggaatat aaatttatca    60
ctattttatg ataagtaaa tctgtttccc tgtagagtta attaattaat gtaagtataa   120
gcgtaattta tagggcacta gtaggactgt cgactgtgcg ctcggcccgg ataatgcgtt   180
aaaagcgaag acgtgcacgt gggatgggaa aacacgagct ggtctgctt ttttcgcatg   240
atatctgggc cgcaccaaag aatccagccc acgcggcgtg gcgccgtcgt tacggcttgc   300
ggggggaagga aacgagggac gaaccgagat ttagcaccag accggccagc gagcattgca   360
gacaccggct tataagttca gctgcgacta ccactccgcg caagggatca gtaattcgtt   420
ttagagctag aaatagcaag ttaaaataag gctagtccgt tatcaacttg aaaaagtggc   480
accgagtcgg tgcttttttt                                                500

SEQ ID NO: 39       moltype = DNA    length = 500
FEATURE             Location/Qualifiers
source              1..500
                    mol_type = other DNA
                    note = Recombinant
                    organism = synthetic construct
SEQUENCE: 39
ttatatgtta ccgttgcaaa gcacgggcac tcacctagta tataatataa catcagtcgt    60
acgtaatgta ctgatgggcg ggttaacaaa tgtcactcac tatcagcacc agcagcgctt   120
agatgcatcc ggccgggcca agacccagga tcagaaagcg cgcacgttca cagcggatgc   180
tgatgggtta gatcgactga tcgaggaaga ggagagctta attaagaaac gccctgttcc   240
gctttgctag cttgcgccct gactgtccag cccacgcgct tcggtccgat tcacatgcta   300
ggctggtgca agcgagccga gctttttttt tagaaccacc ttgctcagca aaccttagga   360
acaccggctt ataagtcgaa gcgaagcgct gtgcactgcg caagggatca gtaattcgtt   420
ttagagctag aaatagcaag ttaaaataag gctagtccgt tatcaacttg aaaaagtggc   480
accgagtcgg tgcttttttt                                                500

SEQ ID NO: 40       moltype = DNA    length = 500
FEATURE             Location/Qualifiers
source              1..500
                    mol_type = other DNA
                    note = Recombinant
                    organism = synthetic construct
SEQUENCE: 40
ggattcggtg ttcttattta ggttctcgcc gaatatggtt ctcagttatg acctaacggt    60
gtccacaaga gttcgccagg atttatacaa ctatttctt atttatttct taacattttt   120
cccttctacg cacaatagga gataatgtca agcgttgacg gtgcacatat atttgttttt   180
ttaaaggcgt agtggcgtgt gtgcaaaaac atcctcacag gaaagacacg aagaaacatg   240
gtcaatggcc cattatataa agcaccgcca caaagcccaa ataccagttc gtcggtggag   300
caagtaacgc gctaggcaac aggcaaacag tttgtcccac ctcgtccagt cacaaaggca   360
aagcgtgact tataagccag agcggaagaa ccataccgcg caagggatca gtaattcgtt   420
ttagagctag aaatagcaag ttaaaataag gctagtccgt tatcaacttg aaaaagtggc   480
accgagtcgg tgcttttttt                                                500

SEQ ID NO: 41       moltype = DNA    length = 500
FEATURE             Location/Qualifiers
source              1..500
                    mol_type = other DNA
```

```
                        note = Recombinant
                        organism = synthetic construct
SEQUENCE: 41
tcgtaaaata gtggtgtcca aagaatttcc aggcccagtt gtaaaagcta aaatgctatt    60
cgaatttcta ctagcagtaa gtcgtgttta gaaattattt ttttatatac cttttttcct   120
tctatgtaca gtaggacaca gtgtcagcgc cgcgttgacg gagaatattt gcaaaaaagt   180
aaaagagaaa gtcatagcgg cgtatgtgcc aaaaacttcg tcacagagag ggccataaga   240
aacatggccc acggcccaat acgaagcacc gcgacgaagc ccaaacagca gtccgtaggt   300
ggagcaaagc gctgggtaat acgcaaacgt tttgtcccac cttgactaat cacaagagtg   360
gagcgtacct tataaaccga gccgcaagca ccgaattgcg caagggatca gtaattcgtt   420
ttagagctag aaatagcaag ttaaaataag gctagtccgt tatcaacttg aaaaagtggc   480
accgagtcgg tgcttttttt                                               500

SEQ ID NO: 42           moltype = DNA   length = 500
FEATURE                 Location/Qualifiers
source                  1..500
                        mol_type = other DNA
                        note = Recombinant
                        organism = synthetic construct
SEQUENCE: 42
tcgtaaaata gtggtgtcca aagaatttcc aggcccagtt gtaaaagcta aaatgctatt    60
cgaatttcta ctagcagtaa gtcgtgttta gaaattattt ttttatatac cttttttcct   120
tctatgtaca gtaggacaca gtgtcagcgc cgcgttgacg gagaatattt gcaaaaaagt   180
aaaagagaaa gtcatagcgg cgtatgtgcc aaaaacttcg tcacagagag ggccataaga   240
aacatggccc acggcccaat acgaagcacc gcgacgaagc ccaaacagca gtccgtaggt   300
ggagcaaagc gctgggtaat acgcaaacgt tttgtcccac cttgactaat cacaagagtg   360
gagcgtacct tataaaccga gccgcaagca ccgaattgtt atcaatttac tttcaatcgg   420
ttagagctag aaatagcaag ttaaaataag gctagtccgt tatcaacttg aaaaagtggc   480
accgagtcgg tgcttttttt                                               500

SEQ ID NO: 43           moltype = DNA   length = 23
FEATURE                 Location/Qualifiers
source                  1..23
                        mol_type = genomic DNA
                        organism = Zea mays
SEQUENCE: 43
gttatcaatt tactttcaat cgg                                            23

SEQ ID NO: 44           moltype = DNA   length = 23
FEATURE                 Location/Qualifiers
source                  1..23
                        mol_type = genomic DNA
                        organism = Zea mays
SEQUENCE: 44
gcgcaaggga tcagtaattc agg                                            23

SEQ ID NO: 45           moltype = DNA   length = 86
FEATURE                 Location/Qualifiers
source                  1..86
                        mol_type = other DNA
                        note = Recombinant
                        organism = synthetic construct
SEQUENCE: 45
gggataacag ggtaatatag cgtaactata acggtcctaa ggtagcgaat tacgatacaa    60
ggctacctag cttcgcagtt acgcta                                         86

SEQ ID NO: 46           moltype = DNA   length = 86
FEATURE                 Location/Qualifiers
source                  1..86
                        mol_type = other DNA
                        note = Recombinant
                        organism = synthetic construct
SEQUENCE: 46
tagcgtaact gcgaagctag gtagccttgt atcgtaattc gctaccttag gaccgttata    60
gttacgctat attaccctgt tatccc                                         86

SEQ ID NO: 47           moltype = DNA   length = 23
FEATURE                 Location/Qualifiers
source                  1..23
                        mol_type = genomic DNA
                        organism = Zea mays
SEQUENCE: 47
gatatgccaa acggtacttg agg                                            23

SEQ ID NO: 48           moltype = DNA   length = 500
FEATURE                 Location/Qualifiers
source                  1..500
                        mol_type = other DNA
                        note = Recombinant
```

```
                          organism = synthetic construct
SEQUENCE: 48
tcgtaaaata gtggtgtcca aagaatttcc aggcccagtt gtaaaagcta aaatgctatt    60
cgaatttcta ctagcagtaa gtcgtgttta gaaattattt ttttatatac ctttttttcct  120
tctatgtaca gtaggacaca gtgtcagcgc cgcgttgacg gagaatattt gcaaaaaagt   180
aaaagagaaa gtcatagcgg cgtatgtgcc aaaaacttcg tcacagagag ggccataaga   240
aacatggccc acggcccaat acgaagcacc gcgacgaagc ccaaacagca gtccgtaggt   300
ggagcaaagc gctgggtaat acgcaaacgt tttgtcccac cttgactaat cacaagagtg   360
gagcgtacct tataaaccga gccgcaagca ccgaattgta caaccaact cggcaatgtt    420
ttagagctag aaatagcaag ttaaaataag gctagtccgt tatcaacttg aaaaagtggc   480
accgagtcgg tgcttttttt                                               500

SEQ ID NO: 49             moltype = DNA  length = 20
FEATURE                   Location/Qualifiers
source                    1..20
                          mol_type = other DNA
                          note = Recombinant
                          organism = synthetic construct
SEQUENCE: 49
gcgtaactgc gaagctaggt                                                20

SEQ ID NO: 50             moltype = DNA  length = 20
FEATURE                   Location/Qualifiers
source                    1..20
                          mol_type = other DNA
                          note = Recombinant
                          organism = synthetic construct
SEQUENCE: 50
ctcacgcctt catttcaaag                                                20

SEQ ID NO: 51             moltype = DNA  length = 20
FEATURE                   Location/Qualifiers
source                    1..20
                          mol_type = other DNA
                          note = Recombinant
                          organism = synthetic construct
SEQUENCE: 51
gtaatgggta atcacaaagg                                                20

SEQ ID NO: 52             moltype = DNA  length = 22
FEATURE                   Location/Qualifiers
source                    1..22
                          mol_type = other DNA
                          note = Recombinant
                          organism = synthetic construct
SEQUENCE: 52
ggattatatt agtttaggct tg                                             22

SEQ ID NO: 53             moltype = DNA  length = 20
FEATURE                   Location/Qualifiers
source                    1..20
                          mol_type = other DNA
                          note = Recombinant
                          organism = synthetic construct
SEQUENCE: 53
cgaccaactc tccaccaatc                                                20

SEQ ID NO: 54             moltype = DNA  length = 21
FEATURE                   Location/Qualifiers
source                    1..21
                          mol_type = other DNA
                          note = Recombinant
                          organism = synthetic construct
SEQUENCE: 54
taaggagatg agtttgagac c                                              21

SEQ ID NO: 55             moltype = DNA  length = 20
FEATURE                   Location/Qualifiers
source                    1..20
                          mol_type = other DNA
                          note = Recombinant
                          organism = synthetic construct
SEQUENCE: 55
tagaggtgga agcatcaaag                                                20

SEQ ID NO: 56             moltype = DNA  length = 20
FEATURE                   Location/Qualifiers
source                    1..20
                          mol_type = other DNA
```

```
                        note        = Recombinant
                        organism    = synthetic construct
SEQUENCE: 56
gtaccgtttg gcatatcaac                                                  20

SEQ ID NO: 57           moltype = DNA    length = 20
FEATURE                 Location/Qualifiers
source                  1..20
                        mol_type    = other DNA
                        note        = Recombinant
                        organism    = synthetic construct
SEQUENCE: 57
gagcatctaa ccaccaaaac                                                  20

SEQ ID NO: 58           moltype = DNA    length = 500
FEATURE                 Location/Qualifiers
source                  1..500
                        mol_type    = other DNA
                        note        = Recombinant
                        organism    = synthetic construct
SEQUENCE: 58
tcgtaaaata gtggtgtcca aagaatttcc aggcccagtt gtaaaagcta aaatgctatt       60
cgaatttcta ctagcagtaa gtcgtgttta gaaattattt ttttatatac cttttttcct      120
tctatgtaca gtaggacaca gtgtcagcgc cgcgttgacg gagaatattt gcaaaaaagt      180
aaaagagaaa gtcatagcgg cgtatgtgcc aaaaacttcg tcacagagag ggccataaga      240
aacatggccc acggcccaat acgaagcacc gcgacgaagc ccaaacagca gtccgtaggt      300
ggagcaaagc gctgggtaat acgcaaacgt tttgtcccac cttgactaat cacaagagtg      360
gagcgtacct tataaaccga gccgcaagca ccgaattgat atgccaaacg gtacttggtt      420
ttagagctag aaatagcaag ttaaaataag gctagtccgt tatcaacttg aaaaagtggc      480
accgagtcgg tgcttttttt                                                 500

SEQ ID NO: 59           moltype = DNA    length = 23
FEATURE                 Location/Qualifiers
source                  1..23
                        mol_type    = genomic DNA
                        organism    = Zea mays
SEQUENCE: 59
gatatgccaa acggtacttg agg                                              23

SEQ ID NO: 60           moltype = DNA    length = 500
FEATURE                 Location/Qualifiers
source                  1..500
                        mol_type    = other DNA
                        note        = Recombinant
                        organism    = synthetic construct
SEQUENCE: 60
tcgtaaaata gtggtgtcca aagaatttcc aggcccagtt gtaaaagcta aaatgctatt       60
cgaatttcta ctagcagtaa gtcgtgttta gaaattattt ttttatatac cttttttcct      120
tctatgtaca gtaggacaca gtgtcagcgc cgcgttgacg gagaatattt gcaaaaaagt      180
aaaagagaaa gtcatagcgg cgtatgtgcc aaaaacttcg tcacagagag ggccataaga      240
aacatggccc acggcccaat acgaagcacc gcgacgaagc ccaaacagca gtccgtaggt      300
ggagcaaagc gctgggtaat acgcaaacgt tttgtcccac cttgactaat cacaagagtg      360
gagcgtacct tataaaccga gccgcaagca ccgaattgga tctcctatca taacgttgtt      420
ttagagctag aaatagcaag ttaaaataag gctagtccgt tatcaacttg aaaaagtggc      480
accgagtcgg tgcttttttt                                                 500

SEQ ID NO: 61           moltype = DNA    length = 23
FEATURE                 Location/Qualifiers
source                  1..23
                        mol_type    = genomic DNA
                        organism    = Zea mays
SEQUENCE: 61
ggatctccta tcataacgtt tgg                                              23

SEQ ID NO: 62           moltype = DNA    length = 92
FEATURE                 Location/Qualifiers
source                  1..92
                        mol_type    = other DNA
                        note        = Recombinant
                        organism    = synthetic construct
SEQUENCE: 62
ggcgggataa cagggtaata tagcgtaact ataacggtcc taaggtagcg aattacgata       60
caaggctacc tagcttcgca gttacgctaa at                                    92

SEQ ID NO: 63           moltype = DNA    length = 92
FEATURE                 Location/Qualifiers
source                  1..92
                        mol_type    = other DNA
                        note        = Recombinant
```

```
                        organism = synthetic construct
SEQUENCE: 63
atttagcgta actgcgaagc taggtagcct tgtatcgtaa ttcgctacct taggaccgtt    60
atagttacgc tatattaccc tgttatcccg cc                                  92

SEQ ID NO: 64           moltype = DNA   length = 92
FEATURE                 Location/Qualifiers
source                  1..92
                        mol_type = other DNA
                        note = Recombinant
                        organism = synthetic construct
SEQUENCE: 64
tacgggataa cagggtaata tagcgtaact ataacggtcc taaggtagcg aattacgata    60
caaggctacc tagcttcgca gttacgctat tg                                  92

SEQ ID NO: 65           moltype = DNA   length = 92
FEATURE                 Location/Qualifiers
source                  1..92
                        mol_type = other DNA
                        note = Recombinant
                        organism = synthetic construct
SEQUENCE: 65
caatagcgta actgcgaagc taggtagcct tgtatcgtaa ttcgctacct taggaccgtt    60
atagttacgc tatattaccc tgttatcccg ta                                  92

SEQ ID NO: 66           moltype = DNA   length = 92
FEATURE                 Location/Qualifiers
source                  1..92
                        mol_type = other DNA
                        note = Recombinant
                        organism = synthetic construct
SEQUENCE: 66
aacgggataa cagggtaata tagcgtaact ataacggtcc taaggtagcg aattacgata    60
caaggctacc tagcttcgca gttacgctag tt                                  92

SEQ ID NO: 67           moltype = DNA   length = 92
FEATURE                 Location/Qualifiers
source                  1..92
                        mol_type = other DNA
                        note = Recombinant
                        organism = synthetic construct
SEQUENCE: 67
aactagcgta actgcgaagc taggtagcct tgtatcgtaa ttcgctacct taggaccgtt    60
atagttacgc tatattaccc tgttatcccg tt                                  92

SEQ ID NO: 68           moltype = DNA   length = 3366
FEATURE                 Location/Qualifiers
source                  1..3366
                        mol_type = other DNA
                        note = Recombinant
                        organism = synthetic construct
SEQUENCE: 68
atgagtgacc tggtgctagg gttggatata ggcattggct ccgtgggggt tggcattctt    60
aataaggtga ccggcgaaat aattcataaa aactcacgca tctttccagc agcccaggct   120
gagaacaatc tggtccgtag aaccaaccgg cagggtcgga ggtagccag gcgcaagaag    180
cacagacggg tccggctcaa caggcttttc gaggagtctg gtttgatcac cgatttcact   240
aagatttcta tcaacctgaa tccttatcag ctgcgcgtta aggtctcac agacgaactt    300
agcaacgaag agttgttcat cgccctgaaa aatatggtca agcatcgcgg cattagctac   360
ctggacgacg cttcggatga tggcaacagt agtgtaggtg actacgctca gatcgtgaaa   420
gagaactcga agcaattgga gaccaagacc ccgggccaaa ttcaactcga aggtaccag    480
acgtatggac agttacgagg cgattttacc gttgaaaagg atggtaagaa gcacaggctg   540
attaatgtgt ttccgacctc agcttatcgc tctgaggcgc tgcgtatttt gcagacccaa   600
caggaattta acccgcaaat aacggacgag ttcataaacc gatacttaga gattcttaca   660
ggtaaacgta aatactatca cggcccagga aatgaaaagt ccaggacaga ttatggtcga   720
tatcgcactt ccggagagac tctcgacaat atctttggca ttcttatagg caaatgtacc   780
ttctaccctg acgaatttag agcagcgaag gcttcatata cagcacaaga gtttaatctt   840
ctcaacgacc tcaacaactt gactgtgcct actgaaacca aaaagcttag caaggagcaa   900
aaaaatcaaa tcattaacta tgttaagaat gagaaagcta tggggccgc aaaaattgttc   960
aagtacatag ctaagttact tagctgtgac gttgctgata ttaagggtta ccgtattgac  1020
aagtctggta aagctgaaat tcacaccttt gaggcttata ggaagatgaa gaccccttgag 1080
acacttgaca ttgagcagat ggatagggag actttggaca aactggcata cgtcttgaca  1140
ttgaacaccg aaagggaagg catccaggaa gctctggaac atgaatttgc agatggttcg  1200
ttcagccaaa aacaggttga cgagctggtc caatttagaa aggcaaactc aagcatattc  1260
ggtaaaggtt ggcacaactt cagcgttaag ctgatgatgg aactcattcc agaattatat  1320
gaaacctctg aggaacagat gacgattctc acaagattgg gtaagcagaa acaaccagc   1380
tctagcaata agactaaata cattgacgaa aagctcctca ccgaagagat ttataacccg  1440
gtcgtggcaa agagtgtacg gcaagccatc aagatcgtta atgccgctat caaggagtat  1500
ggtgattttg ataatattgt gattgaaatg gcacgcgaga ctaacgagga cgacgagaag  1560
aaagctatac agaagattca aaaggctaat aaggacgaga aggacgccgc aatgctaaag  1620
```

```
gcggccaatc aatataatgg gaaggctgaa ctacctcata gcgtcttcca tggacataag  1680
caattagcaa ctaaaataag attatgcgcac cagcaaggcg aacgtgtgct ttatacaggt  1740
aaaacgatat ctattcacga cctgattaac aactctaacc agtttgaagt ggatcatatc  1800
ttaccactaa gtatcacctt cgacgattca cttgctaaca aggtgctcgt ttacgccact  1860
gcgaaccaag agaaagggca gaggactcca taccaggccc ttgacagcat ggacgacgcc  1920
tggagtttta gggaattaaa agctttcgta cgtgagtcaa agacgctttc aaataaaaaa  1980
aaggagtact tgctcactga agaagacatc tcaaaattcg acgtgcgcaa aaaattcatt  2040
gagcggaact tagtcgacac tcggtacgca tcaagagtag tgttgaacgc cctccaggag  2100
cacttaggg cacataagat cgacaccaag gtttcagttg ttaggggtca gtttacatcg  2160
cagcttagac gccattgggg tatagaaaaa acacgtgata cctaccatca ccatgcagtt  2220
gacgctctca tcattgcagc atctttctcaa cttaatttgt ggaaaaagca aaagaacact  2280
ctggtctcat atagcgaaga tcagctgctt gatattgaaa ccggcgagct gatttctgac  2340
gacgaataca aagaatctgt gtttaaggca ccatatcaac actttgtaga cacgcttaaa  2400
tctaaagagt ttgaggattc gatccttttc agttaccaag tcgactcaaa atttaaccgt  2460
aagatctctg atgcaacaat ttatgcgacg aggcaggcca aggtaggtaa ggataaggct  2520
gacgaaacct acgtgctcgg aaaaatcaaa gatatttaca ctcaagatgg atatgatgca  2580
ttcatgaaga tatataaaa ggacaaatct aaattcctta tgtatcgtca tgacccacag  2640
acattcgaga aagttattga gcctatcctg gagaactatc cgaacaagca aataaatgag  2700
aagggcaaag aagttccatg taatccgttc ctaaagtaca aggaggaaca cggatatatt  2760
agaaaataca gcaaaaaggg caacggccca gaaatcaaaa gccttaagta ctacgatagt  2820
aaactaggaa accacatcga cattacacca aaagactcta ataataaggt cgtactgcaa  2880
agcgttttccc catggcgcgc cgatgtgtat tttaataaga caacagggaa gtacgaaatc  2940
ttgggggttaa aatatgcgga tctgcaattc gaaaagggaa ccggcacata caaaatttct  3000
caagaaaagt acaacgacat aaagaagaag gaagggggtcg attctgattc tgaattcaag  3060
ttcacactct ataagaatga tcttctgctc gtcaaggaca cagagacaaa ggagcagcag  3120
ttgttcaggt tcttgtctag aactatgcca aaacaaaagc actacgttga actgaagcct  3180
tacgataagc aaaaattcga gggggggcgag gcgcttataa aggtcctagg aaatgttgca  3240
aactctgggc agtgtaagaa gggcctgggc aagagcaaca ttagcatcta taaggttcga  3300
acggatgtgc ttgggaacca gcatatcatc aaaaacgagg gagataaacc aaagctggac  3360
ttctag                                                              3366

SEQ ID NO: 69            moltype = AA  length = 1121
FEATURE                  Location/Qualifiers
source                   1..1121
                         mol_type = protein
                         organism = Streptococcus thermophilus
SEQUENCE: 69
MSDLVLGLDI GIGSVGVGIL NKVTGEIIHK NSRIFPAAQA ENNLVRRTNR QGRRLARRKK   60
HRRVRLNRLF EESGLITDFT KISINLNPYQ LRVKGLTDEL SNEELFIALK NMVKHRGISY  120
LDDASDDGNS SVGDYAQIVK ENSKQLETKT PGQIQLERYQ TYGQLRGDFT VEKDGKKHRL  180
INVFPTSAYR SEALRILQTQ QEFNPQITDE FINRYLEILT GKRKYYHGPG NEKSRTDYGR  240
YRTSGETLDN IFGILIGKCT FYPDEFRAAK ASYTAQEFNL LNDLNNLTVP TEKKLSKEQ   300
KNQIINYVKN EKAMGPAKLF KYIAKLLSCD VADIKGYRID KSGKAEIHTF EAYRKMKTLE  360
TLDIEQMDRE TLDKLAYVLT LNTEREGIQE ALEHEFADGS FSQKQVDELV QFRKANSSIF  420
GKGWHNFSVK LMMELIPELY ETSEEQMTIL TRLGKQKTTS SSNKTKYIDE KLLTEEIYNP  480
VVAKSVRQAI KIVNAAIKEY GDFDNIVIEM ARETNEDDEK KAIQKIQKAN KDEKDAAMLK  540
AANQYNGKAE LPHSVFVHGK QLATKIRLWH QQGERCLYTG KTISIHDLIN NSNQFEVDHI  600
LPLSITFDDS LANKVLVYAT ANQEKGQRTP YQALDSMDDA WSFRELKAFV RESKTLSNKK  660
KEYLLTEEDI SKFDVRKKFI ERNLVDTRYA SRVVLNALQE HFRAHIDTK VSVVRGQFTS   720
QLRRHWGIEK TRDTYHHAV DALIIAASSQ LNLWKKQKNT LVSYSEDQLL DIETGELISD   780
DEYKESVFKA PYQHFVDTLK SKEFEDSILF SYQVDSKFNR KISDATIYAT RQAKVGKDKA  840
DETYVLGKIK DIYTQDGYDA FMKIYKKDKS KFLMYRHDPQ TFEKVIEPIL ENYPNKQINE  900
KGKEVPCNPF LKYKEEHGYI RKYSKKGNGP EIKSLKYYDS KLGNHIDITP KDSNNKVVLQ  960
SVSPWRADVY FNKTTGKYEI LGLKYADLQF EKGTGTYKIS QEKYNDIKKK EGVDSDSEFK 1020
FTLYKNDLLL VKDTETKEQQ LFRFLSRTMP KQKHYVELKP YDKQKFEGGE ALIKVLGNVA 1080
NSGQCKKGLG KSNISIYKVR TDVLGNQHII KNEGDKPKLD F                    1121

SEQ ID NO: 70            moltype = DNA  length = 188
FEATURE                  Location/Qualifiers
source                   1..188
                         mol_type = other DNA
                         note = Recombinant
                         organism = synthetic construct
SEQUENCE: 70
gacattctcc ccaaaatata gttattgtac tctcaagatt tattttttcca aaagggttat   60
tgtactctca agatttattt ttccaaaagg gttacttaaa tcttgcagaa gctacaaaga  120
taaggcttca tgccgaaatc aacaccctgt cattttatgg cagggtgttt tcgttattta  180
atttttt                                                            188

SEQ ID NO: 71            moltype = DNA  length = 20
FEATURE                  Location/Qualifiers
source                   1..20
                         mol_type = unassigned DNA
                         organism = Zea mays
SEQUENCE: 71
gacattctcc caaaatata                                                 20

SEQ ID NO: 72            moltype = DNA  length = 29
FEATURE                  Location/Qualifiers
```

```
source                    1..29
                          mol_type = genomic DNA
                          organism = Zea mays
SEQUENCE: 72
gtttatcttt catgagcttt ttagagaat                                              29

SEQ ID NO: 73             moltype = DNA   length = 29
FEATURE                   Location/Qualifiers
source                    1..29
                          mol_type = genomic DNA
                          organism = Zea mays
SEQUENCE: 73
gtaatactct atggtctgta aggtagaat                                              29

SEQ ID NO: 74             moltype = DNA   length = 28
FEATURE                   Location/Qualifiers
source                    1..28
                          mol_type = genomic DNA
                          organism = Zea mays
SEQUENCE: 74
gagatccaac gtgttgggac tctagaaa                                               28

SEQ ID NO: 75             moltype = DNA   length = 27
FEATURE                   Location/Qualifiers
source                    1..27
                          mol_type = genomic DNA
                          organism = Zea mays
SEQUENCE: 75
gacattctcc ccaaaatata cgagaaa                                                27

SEQ ID NO: 76             moltype = DNA   length = 103
FEATURE                   Location/Qualifiers
source                    1..103
                          mol_type = other DNA
                          note = Recombinant
                          organism = synthetic construct
SEQUENCE: 76
gccggccagc atttgaaaca gttttagagc tagaaatagc aagttaaaat aaggctagtc            60
cgttatcaac ttgaaaaagt ggcaccgagt cggtgctttt ttt                             103

SEQ ID NO: 77             moltype = DNA   length = 103
FEATURE                   Location/Qualifiers
source                    1..103
                          mol_type = other DNA
                          note = Recombinant
                          organism = synthetic construct
SEQUENCE: 77
gcgcaaggga tcagtaattc gttttagagc tagaaatagc aagttaaaat aaggctagtc            60
cgttatcaac ttgaaaaagt ggcaccgagt cggtgctttt ttt                             103

SEQ ID NO: 78             moltype = DNA   length = 103
FEATURE                   Location/Qualifiers
source                    1..103
                          mol_type = other DNA
                          note = Recombinant
                          organism = synthetic construct
SEQUENCE: 78
gttatcaatt tactttcaat gttttagagc tagaaatagc aagttaaaat aaggctagtc            60
cgttatcaac ttgaaaaagt ggcaccgagt cggtgctttt ttt                             103

SEQ ID NO: 79             moltype = RNA   length = 103
FEATURE                   Location/Qualifiers
source                    1..103
                          mol_type = other RNA
                          note = Recombinant
                          organism = synthetic construct
SEQUENCE: 79
gccggccagc atttgaaaca gttttagagc tagaaatagc aagttaaaat aaggctagtc            60
cgttatcaac ttgaaaaagt ggcaccgagt cggtgctttt                                 103

SEQ ID NO: 80             moltype = RNA   length = 103
FEATURE                   Location/Qualifiers
source                    1..103
                          mol_type = other RNA
                          note = Recombinant
                          organism = synthetic construct
SEQUENCE: 80
gcgcaaggga tcagtaattc gttttagagc tagaaatagc aagttaaaat aaggctagtc            60
cgttatcaac ttgaaaaagt ggcaccgagt cggtgctttt                                 103
```

```
SEQ ID NO: 81          moltype = RNA   length = 103
FEATURE                Location/Qualifiers
source                 1..103
                       mol_type = other RNA
                       note = Recombinant
                       organism = synthetic construct
SEQUENCE: 81
gttatcaatt actttcaat gttttagagc tagaaatagc aagttaaaat aaggctagtc    60
cgttatcaac ttgaaaaagt ggcaccgagt cggtgctttt ttt                    103

SEQ ID NO: 82          moltype = DNA   length = 103
FEATURE                Location/Qualifiers
source                 1..103
                       mol_type = other DNA
                       note = Recombinant
                       organism = synthetic construct
SEQUENCE: 82
gtacaaacca actcggcaat gttttagagc tagaaatagc aagttaaaat aaggctagtc    60
cgttatcaac ttgaaaaagt ggcaccgagt cggtgctttt ttt                     103

SEQ ID NO: 83          moltype = DNA   length = 103
FEATURE                Location/Qualifiers
source                 1..103
                       mol_type = other DNA
                       note = Recombinant
                       organism = synthetic construct
SEQUENCE: 83
gatatgccaa acggtacttg gttttagagc tagaaatagc aagttaaaat aaggctagtc    60
cgttatcaac ttgaaaaagt ggcaccgagt cggtgctttt ttt                     103

SEQ ID NO: 84          moltype = DNA   length = 103
FEATURE                Location/Qualifiers
source                 1..103
                       mol_type = other DNA
                       note = Recombinant
                       organism = synthetic construct
SEQUENCE: 84
ggatctccta tcataacgtt gttttagagc tagaaatagc aagttaaaat aaggctagtc    60
cgttatcaac ttgaaaaagt ggcaccgagt cggtgctttt ttt                     103

SEQ ID NO: 85          moltype = RNA   length = 103
FEATURE                Location/Qualifiers
source                 1..103
                       mol_type = other RNA
                       note = Recombinant
                       organism = synthetic construct
SEQUENCE: 85
gtacaaacca actcggcaat gttttagagc tagaaatagc aagttaaaat aaggctagtc    60
cgttatcaac ttgaaaaagt ggcaccgagt cggtgctttt ttt                     103

SEQ ID NO: 86          moltype = RNA   length = 103
FEATURE                Location/Qualifiers
source                 1..103
                       mol_type = other RNA
                       note = Recombinant
                       organism = synthetic construct
SEQUENCE: 86
gatatgccaa acggtacttg gttttagagc tagaaatagc aagttaaaat aaggctagtc    60
cgttatcaac ttgaaaaagt ggcaccgagt cggtgctttt ttt                     103

SEQ ID NO: 87          moltype = RNA   length = 103
FEATURE                Location/Qualifiers
source                 1..103
                       mol_type = other RNA
                       note = Recombinant
                       organism = synthetic construct
SEQUENCE: 87
ggatctccta tcataacgtt gttttagagc tagaaatagc aagttaaaat aaggctagtc    60
cgttatcaac ttgaaaaagt ggcaccgagt cggtgctttt ttt                     103

SEQ ID NO: 88          moltype = DNA   length = 190
FEATURE                Location/Qualifiers
source                 1..190
                       mol_type = other DNA
                       note = Recombinant
                       organism = synthetic construct
SEQUENCE: 88
gtttatctttt catgagcttt ttgttattgt actctcaaga tttatttttc caaaagggtt   60
```

```
attgtactct caagatttat ttttccaaaa gggttactta aatcttgcag aagctacaaa    120
gataaggctt catgccgaaa tcaacaccct gtcatttat ggcagggtgt tttcgttatt    180
taattttttt                                                           190

SEQ ID NO: 89          moltype = DNA   length = 190
FEATURE                Location/Qualifiers
source                 1..190
                       mol_type = other DNA
                       note = Recombinant
                       organism = synthetic construct
SEQUENCE: 89
gtaatactct atggtctgta aggttattgt actctcaaga tttattttc caaagggtt     60
attgtactct caagatttat ttttccaaaa gggttactta aatcttgcag aagctacaaa    120
gataaggctt catgccgaaa tcaacaccct gtcatttat ggcagggtgt tttcgttatt    180
taattttttt                                                           190

SEQ ID NO: 90          moltype = DNA   length = 189
FEATURE                Location/Qualifiers
source                 1..189
                       mol_type = other DNA
                       note = Recombinant
                       organism = synthetic construct
SEQUENCE: 90
gagatccaac gtgttgggac tgttattgta ctctcaagat ttattttcc aaagggtta      60
ttgtactctc aagattatt tttccaaaag ggttacttaa atcttgcaga agctacaaag    120
ataaggcttc atgccgaaat caacaccctg tcatttatg gcagggtgtt ttcgttattt    180
aatttttt                                                            189

SEQ ID NO: 91          moltype = DNA   length = 188
FEATURE                Location/Qualifiers
source                 1..188
                       mol_type = other DNA
                       note = Recombinant
                       organism = synthetic construct
SEQUENCE: 91
gacattctcc ccaaaatata gttattgtac tctcaagatt tattttcca aagggttat     60
tgtactctca agatttatt ttccaaaagg gttacttaaa tcttgcagaa gctacaaaga    120
taaggcttca tgccgaaatc aacaccctgt catttatgg cagggtgttt tcgttattta    180
atttttt                                                             188

SEQ ID NO: 92          moltype = RNA   length = 190
FEATURE                Location/Qualifiers
source                 1..190
                       mol_type = other RNA
                       note = Recombinant
                       organism = synthetic construct
SEQUENCE: 92
gtttatcttt catgagcttt tgttattgt actctcaaga tttattttc caaagggtt      60
attgtactct caagatttat ttttccaaaa gggttactta aatcttgcag aagctacaaa    120
gataaggctt catgccgaaa tcaacaccct gtcatttat ggcagggtgt tttcgttatt    180
taattttttt                                                           190

SEQ ID NO: 93          moltype = RNA   length = 190
FEATURE                Location/Qualifiers
source                 1..190
                       mol_type = other RNA
                       note = Recombinant
                       organism = synthetic construct
SEQUENCE: 93
gtaatactct atggtctgta aggttattgt actctcaaga tttattttc caaagggtt     60
attgtactct caagatttat ttttccaaaa gggttactta aatcttgcag aagctacaaa    120
gataaggctt catgccgaaa tcaacaccct gtcatttat ggcagggtgt tttcgttatt    180
taattttttt                                                           190

SEQ ID NO: 94          moltype = RNA   length = 189
FEATURE                Location/Qualifiers
source                 1..189
                       mol_type = other RNA
                       note = Recombinant
                       organism = synthetic construct
SEQUENCE: 94
gagatccaac gtgttgggac tgttattgta ctctcaagat ttattttcc aaagggtta      60
ttgtactctc aagattatt tttccaaaag ggttacttaa atcttgcaga agctacaaag    120
ataaggcttc atgccgaaat caacaccctg tcatttatg gcagggtgtt ttcgttattt    180
aatttttt                                                            189

SEQ ID NO: 95          moltype = RNA   length = 188
FEATURE                Location/Qualifiers
source                 1..188
```

```
                         mol_type = other RNA
                         note = Recombinant
                         organism = synthetic construct
SEQUENCE: 95
gacattctcc ccaaaatata gttattgtac tctcaagatt tattttccca aaagggttat    60
tgtactctca agatttattt ttccaaaagg gttacttaaa tcttgcagaa gctacaaaga   120
taaggcttca tgccgaaatc aacaccctgt cattttatgg cagggtgttt tcgttattta   180
atttttttt                                                           188

SEQ ID NO: 96            moltype = AA  length = 1368
FEATURE                  Location/Qualifiers
source                   1..1368
                         mol_type = protein
                         organism = Streptococcus pyogenes
SEQUENCE: 96
MDKKYSIGLD IGTNSVGWAV ITDEYKVPSK KFKVLGNTDR HSIKKNLIGA LLFDSGETAE    60
ATRLKRTARR RYTRRKNRIC YLQEIFSNEM AKVDDSFFHR LEESFLVEED KKHERHPIFG   120
NIVDEVAYHE KYPTIYHLRK KLVDSTDKAD LRLIYLALAH MIKFRGHFLI EGDLNPDNSD   180
VDKLFIQLVQ TYNQLFEENP INASGVDAKA ILSARLSKSR RLENLIAQLP GEKKNGLFGN   240
LIALSLGLTP NFKSNFDLAE DAKLQLSKDT YDDDLDNLLA QIGDQYADLF LAAKNLSDAI   300
LLSDILRVNT EITKAPLSAS MIKRYDEHHQ DLTLLKALVR QQLPEKYKEI FFDQSKNGYA   360
GYIDGGASQE EFYKFIKPIL EKMDGTEELL VKLNREDLLR KQRTFDNGSI PHQIHLGELH   420
AILRRQEDFY PFLKDNREKI EKILTFRIPY YVGPLARGNS RFAWMTRKSE ETITPWNFEE   480
VVDKGASAQS FIERMTNFDK NLPNEKVLPK HSLLYEYFTV YNELTKVKYV TEGMRKPAFL   540
SGEQKKAIVD LLFKTNRKVT VKQLKEDYFK KIECFDSVEI SGVEDRFNAS LGTYHDLLKI   600
IKDKDFLDNE ENEDILEDIV LTLTLFEDRE MIEERLKTYA HLFDDKVMKQ LKRRRYTGWG   660
RLSRKLINGI RDKQSGKTIL DFLKSDGFAN RNFMQLIHDD SLTFKEDIQK AQVSGQGDSL   720
HEHIANLAGS PAIKKGILQT VKVVDELVKV MGRHKPENIV IEMARENQTT QKGQKNSRER   780
MKRIEEGIKE LGSQILKEHP VENTQLQNEK LYLYYLQNGR DMYVDQELDI NRLSDYDVDH   840
IVPQSFLKDD SIDNKVLTRS DKNRGKSDNV PSEEVVKKMK NYWRQLLNAK LITQRKFDNL   900
TKAERGGLSE LDKAGFIKRQ LVETRQITKH VAQILDSRMN TKYDENDKLI REVKVITLKS   960
KLVSDFRKDF QFYKVREINN YHHAHDAYLN AVVGTALIKK YPKLESEFVY GDYKVYDVRK  1020
MIAKSEQEIG KATAKYFFYS NIMNFFKTEI TLANGEIRKR PLIETNGETG EIVWDKGRDF  1080
ATVRKVLSMP QVNIVKKTEV QTGGFSKESI LPKRNSDKLI ARKKDWDPKK YGGFDSPTVA  1140
YSVLVVAKVE KGKSKKLKSV KELLGITIME RSSFEKNPID FLEAKGYKEV KKDLIIKLPK  1200
YSLFELENGR KRMLASAGEL QKGNELALPS KYVNFLYLAS HYEKLKGSPE DNEQKQLFVE  1260
QHKHYLDEII EQISEFSKRV ILADANLDKV LSAYNKHRDK PIREQAENII HLFTLTNLGA  1320
PAAFKYFDTT IDRKRYTSTK EVLDATLIHQ SITGLYETRI DLSQLGGD              1368

SEQ ID NO: 97            moltype = DNA  length = 4107
FEATURE                  Location/Qualifiers
source                   1..4107
                         mol_type = other DNA
                         note = Recombinant
                         organism = synthetic construct
SEQUENCE: 97
atggacaaga agtacagcat tggtctggac atcggaacga actcggtcgg ctgggccgtg    60
attactgacg agtacaaagt tcccagcaaa aaattcaagg ttctaggcaa cacagaccgc   120
cactcgatta aaaagaatct aatcggcgcg cttctgttcg actctggtga aacggccgag   180
gccacacgct taaagaggac cgcgcgccgc cgctacacgc ggcgcaagaa ccgaatctgt   240
tacctccagg agatcttcag taatgagatg gctaaggtcg atgacagctt cttccacagg   300
cttgaagagt cctttctggt cgaagaggac aaaaaacacg aacgtcaccc aatcttcggg   360
aacattgtgg atgaagtcgc ataccacgag aagtatccta cgatctatca cctccgcaag   420
aagctcgtgg atagtaccga caaagccgac ctgcgcttaa tctaccttgc gctcgcgcac   480
atgattaagt tccgaggaca cttccttatt gagggtgatc tgaatccgga caattccgat   540
gtggataaac tgttcattca gttggtccga acatacaatc agctattcga ggagaatccg   600
atcaatgctt ccggcgtgga cgcaaaggct atttctgtca gcagactttc aaagagcaga   660
aggttggaga atctgatcgc acaacttccc ggagagaaga gaatgggct cttcggcaac   720
ctcattgcgc tgtctttggg tctgacaccg aactttaagt ctaacttcga cctcgctgag   780
gatgctaaac ttcagcttag caaagacacc tatgatgatg acctggacaa cctcctcgcg   840
cagattggag accagtacgc ggatctattc ttggctgcca agaacctgtc cgatgcgatt   900
ctgcttagtg acatcctccg agtgaacact gaaattacga agcaccctt gtcggctagt   960
atgattaagc gatacgatga gcaccatcaa gacctgacat tgctaaaggc gctcgtaaga  1020
cagcaacttc ctgagaagta caaggagata ttttttgatc agtctaagaa tggctacgct  1080
ggttacatcg acggtggagc tagtcaggag gaattctata aattcatcaa gcctatcctg  1140
gaaaaaatgg acggtacgga ggaattgctc gttaaactaa atcgagagga tctgctgaga  1200
aagcagcgga ctttcgacaa tggttctatt ccgcatcaga ttcacctcgg agaacttcac  1260
gccatcctga cgacacagga ggacttctac cctttcctga agacaaccg ggaaaaaatc  1320
gagaagatcc tgacattcag gattccttac tatgtaggcc ctttagcgag aggcaacagt  1380
agattcgcct ggatgaccag aaagtctgag gaaacaatca ccgtgaa cttcgaggaa  1440
gtggttgata agggtgctag tgcccaatca ttcattgaga gaatgacgaa cttcgacaag  1500
aatctgccta cgagaaggt tctccctaaa catagcttgc tttacgagta tttcacggtg  1560
tacaatgagc taacgaaggt caagtatgtc acagagggaa tgcggaaacc ggctttcctt  1620
tcgggtgaac agaagaaagc aattgtggat tgctcttcca agacaaaccg aaaggtgaca  1680
gtgaagcagc taaaggagga ctacttcaaa aaaatagagt gcttcgactc agttgagatc  1740
agcggagtgg aggaccggtt taacgcttcc ctcggcactt accacgactt gctcaagatc  1800
atcaaggaca agacttcct tgataacgag gagaacgaag acatccttga ggacattgtg  1860
ctgacattga cgttgttcga ggatcggag atgatcgagg aacgcctcaa gacgtacgcc  1920
catctgttcg atgataaggt gatgaagcag ttaaagagga gacgttacac tggctgggc  1980
```

```
cgtctctctc gcaaactgat aaacgggata agggataaac aaagcggaaa gacaatcctc    2040
gatttcctta aatccgacgg cttcgctaac cggaacttca tgcagctcat ccatgatgac    2100
tcactgacgt tcaaggagga catccagaaa gctcaagtgt ctggccaggg tgacagcttg    2160
cacgagcaca tcgcaaatct agccggttca ccggcgataa agaagggcat tctacaaacg    2220
gtgaaagtgg tggacgagtc tgtgaaggtc atgggtcgcc ataagccaga gaacattgtt    2280
atcgaaatgg cgagggagaa ccagacaacg cagaagggac aaaaaaacag tagggagcgg    2340
atgaagcgca tcgaggaagg cattaaggaa cttggaagcc aaatcctgaa agagcacccg    2400
gtggagaata cgcagttgca gaacgagaaa ctgtacctct actacttgca gaatggacgt    2460
gatatgtatg tggatcaaga gttggacatc aaccgattgt ctgactatga cgtcggatca    2520
atagtaccac agtccttcct caaggatgat agcatagaca acaaggttct tactcgtagc    2580
gacaagaatc gtggcaaatc ggacaatgtt ccatctgagg aagttgtcaa aaagatgaaa    2640
aattattgga ggcaacttct gaacgcgaag ctaattacac aaaggaaatt cgacaatctc    2700
actaaggccg agagaggagg gttaagtgag ttagacaagg ctggcttcat caagcggcag    2760
ttggtcgaga ctcgtcagat tactaagcac gtggctcaga tcctggattc gcgcatgaac    2820
accaaatacg acgagaatga caaactcatc cgtgaagtta aggtgattac actgaaatcc    2880
aagctggtct ctgactttag gaaagacttc caattctaca aggtgagaga gattaacaac    2940
taccaccacg cgcatgacgc ctacttgaat gctgtggttg ggactgccct gataaagaaa    3000
tatcctaaac ttgagtctga gttcgtttac ggtgactaca aggtttatga cgttaggaag    3060
atgatcgcca aatccgaaca ggagattggg aaagcaactg ccaaatattt cttttactcc    3120
aacattatga acttttttcaa gacagaaatc acactcgcca atggcgagat tcggaagaga    3180
ccactaatcg aaacaaacgg cgaaactggt gaaatcgttt gggataaggg tagggacttc    3240
gcaactgtta ggaaggtctt gtcgatgcct caagtgaaca tcgtcaaaaa aacagaggtc    3300
cagaccggtg ggttctcaaa ggagtctatt ctgccaaagc gtaacagcga caaactcatc    3360
gctcgcaaaa aggactggga tcctaaaaag tacggtggat cgacagccc gaccgttgct    3420
tattctgttc tcgtagttgc taaagtcgag aagggcaagt ccaaaaaact caaatcggtt    3480
aaggaactgc tcggaatcac gataatgaca cgaagcgtt tcgaaaaaa tccaattgac    3540
ttcctggaag ctaaggtta caaggaggtc aagaaggatc ttatcatcaa gctacccaag    3600
tacagtctgt tcgaactgga gaacggtcgc aagagaatgc tggcctcggc tggtgaactc    3660
cagaagggca atgagctggc cctgccgtcc aagtacgtga actttctgta cctggcatct    3720
cattacagaa agtcaaggg ctcaccagag gacaacggc agaagcagtt gttcgttgaa    3780
cagcacaaac actatcttga tgagatcatt gagcaaatta gcgagttcag taagcgagtt    3840
attctggctg atgctaacct ggataaggtg ctctctgcct acaacaagca ccgggataaa    3900
cctattaggga acaggcgga gaacataatc cacctcttca ctctgacgaa tctcggcgcg    3960
cctgcggcct tcaaatattt tgataccacc atcgacagga agcgctacac aagcactaaa    4020
gaggtgctgg acgccactct cattccaccag tctattaccg ggctctacga gacacggatt    4080
gacctctccc agctaggtgg cgattaa                                       4107

SEQ ID NO: 98          moltype = DNA  length = 469
FEATURE                Location/Qualifiers
source                 1..469
                       mol_type = other DNA
                       note = Recombinant
                       organism = synthetic construct
SEQUENCE: 98
cgtctttgta tcggaatata aatttatcac tattttatga taaagtaaat ctgtttccct     60
gtagagttaa ttaattaatg taagtataag cgtaatttat agggcactag taggactgtc    120
gactgtcgcg tcggcccgga taatgcgtca aaagcgaaca cgtgcagtcg ggatgggaaa    180
acacgaagcg tggtctgctt tttcgcatga tatctgggcc gcaccaagaa atccagccca    240
cgcggcgtgg cgccgtcgtt acttgcgggg gaaggaaacg agggacgaac cgagatttag    300
caccagaccg gccagcgagc attgcagaca ccggcttata agttcagctg cgactaccac    360
tccgtctctt cggagacatc cgataaaatt ggaacgatac agagaagatt agcatggccc    420
ctgcgcaagg atgacacgca caaatcgaga atggtccaaa atttttttg                469

SEQ ID NO: 99          moltype = DNA  length = 268
FEATURE                Location/Qualifiers
source                 1..268
                       mol_type = other DNA
                       note = Recombinant
                       organism = synthetic construct
SEQUENCE: 99
cctgttccgc tttgctagct tgcgccctga ctgtccagcc cacgcgcttc ggtccgattc     60
tgctaggctg tgtcaagcga gccgagactt ttttttagaa ccaccttgct cagcaaacct    120
taggaacacc ggcttataag tcgaagcgaa gcgctgtgca ctgtctcttc ggagacatcc    180
gataaaattg gaacgataca gagaagatta gcatggcccc tgcgcaagga tgacacgcac    240
aaatcgagaa atggtccaaa ttttttg                                       268

SEQ ID NO: 100         moltype = DNA  length = 426
FEATURE                Location/Qualifiers
source                 1..426
                       mol_type = other DNA
                       note = Recombinant
                       organism = synthetic construct
SEQUENCE: 100
gccaggattt atacaactat tttcttattt atttctttaa catttccct tctacgcaca      60
ataggagata atgtcaagcg ttgacggtgc acatatattt gttttttttaa aggcgtagtg    120
gcgtgtgtgc aaaaacatcc tcacaggaaa gacacgaaga acatggtca atggcccatt    180
atataaagca ccgccacaaa gcccaaatac cagttcgttg gagcaagtaa cgcgctaggc    240
aacaggcaaa cagtttgtcc cacctcgtcc agtcacaaag gcaaagcgtg acttataagc    300
cagagcggaa gaaccatacc gtctcttcgg agacatccga taaaattgga acgatacaga    360
```

```
gaagattagc atggcccctg cgcaaggatg acacgcacaa atcgagaaat ggtccaaatt    420
tttttg                                                              426

SEQ ID NO: 101          moltype = DNA  length = 469
FEATURE                 Location/Qualifiers
source                  1..469
                        mol_type = other DNA
                        note = Recombinant
                        organism = synthetic construct
SEQUENCE: 101
ggcccagttg taaaagctaa aatgctattc gaatttctac tagcagtaag tcgtgtttag     60
aaattatttt tttatatacc ttttttcctt ctatgtacag taggacacag tgtcagcgcc    120
gcgttgacgg agaatatttg caaaaaagta aagagaaag tcatagcggc gtatgtgcca    180
aaaacttcgt cacagagagg gccataagaa acatggccca cggcccaata cgaagcccga    240
cgacgaagcc caaacagcag ttaggtggag caaagcgctg ggtaatacgc aaacgttttg    300
tcccaccttg actaatcaca agagtggagc gtaccttata aaccgagccg caagcaccga    360
attgtctctt cggagacatc cgataaaatt ggaacgatac agagaagatt agcatggccc    420
ctgcgcaagg atgacacgca caaatcgaga aatggtccaa atttttttg              469

SEQ ID NO: 102          moltype = DNA  length = 80
FEATURE                 Location/Qualifiers
source                  1..80
                        mol_type = other DNA
                        note = Recombinant
                        organism = synthetic construct
SEQUENCE: 102
acacttaatc ggctctcaag aagtcctcaa gggataacag ggtaatatag cgtaactata     60
acggtcctaa ggtagcgaat                                                80

SEQ ID NO: 103          moltype = DNA  length = 80
FEATURE                 Location/Qualifiers
source                  1..80
                        mol_type = other DNA
                        note = Recombinant
                        organism = synthetic construct
SEQUENCE: 103
acacttaatc ggctctcaag aagtcctcaa gggataacag ggtaatatag cgtaactata     60
acggtcctaa ggtagcgaat                                                80

SEQ ID NO: 104          moltype = DNA  length = 59
FEATURE                 Location/Qualifiers
source                  1..59
                        mol_type = other DNA
                        note = Recombinant
                        organism = synthetic construct
SEQUENCE: 104
acacttaatc ggctctcaag aagtcctcaa gtaactataa cggtcctaag gtagcgaat      59

SEQ ID NO: 105          moltype =     length =
SEQUENCE: 105
000

SEQ ID NO: 106          moltype =     length =
SEQUENCE: 106
000

SEQ ID NO: 107          moltype = DNA  length = 155
FEATURE                 Location/Qualifiers
source                  1..155
                        mol_type = other DNA
                        note = Recombinant
                        organism = synthetic construct
SEQUENCE: 107
gtttatcttt catgagcttt ttgttattgt actctcaaga tttatttttc caaaagggtt     60
acttaaatct tgcagaagct acaaagataa ggcttcatgc cgaaatcaac accctgtcat    120
tttatggcag ggtgttttcg ttatttaatt ttttt                              155

SEQ ID NO: 108          moltype = DNA  length = 155
FEATURE                 Location/Qualifiers
source                  1..155
                        mol_type = other DNA
                        note = Recombinant
                        organism = synthetic construct
SEQUENCE: 108
gtaatactct atggtctgta aggttattgt actctcaaga tttatttttc caaaagggtt     60
acttaaatct tgcagaagct acaaagataa ggcttcatgc cgaaatcaac accctgtcat    120
tttatggcag ggtgttttcg ttatttaatt ttttt                              155

SEQ ID NO: 109          moltype = DNA  length = 154
```

| | |
|---|---|
| FEATURE | Location/Qualifiers |
| source | 1..154<br>mol_type = other DNA<br>note = Recombinant<br>organism = synthetic construct |

SEQUENCE: 109

```
gagatccaac gtgttgggac tgttattgta ctctcaagat ttattttcc aaaagggtta    60
cttaaatctt gcagaagcta caaagataag gcttcatgcc gaaatcaaca ccctgtcatt   120
ttatggcagg gtgttttcgt tatttaattt tttt                               154
```

| | |
|---|---|
| SEQ ID NO: 110 | moltype = DNA length = 153 |
| FEATURE | Location/Qualifiers |
| source | 1..153<br>mol_type = other DNA<br>note = Recombinant<br>organism = synthetic construct |

SEQUENCE: 110

```
gacattctcc ccaaaatata gttattgtac tctcaagatt tatttttcca aaagggttac    60
ttaaatcttg cagaagctac aaagataagg cttcatgccg aaatcaacac cctgtcattt   120
tatggcaggg tgttttcgtt atttaatttt ttt                                153
```

| | |
|---|---|
| SEQ ID NO: 111 | moltype = RNA length = 155 |
| FEATURE | Location/Qualifiers |
| source | 1..155<br>mol_type = other RNA<br>note = Recombinant<br>organism = synthetic construct |

SEQUENCE: 111

```
gtttatcttt catgagcttt tgttattgt actctcaaga tttattttc caaagggtt      60
acttaaatct tgcagaagct acaaagataa ggcttcatgc cgaaatcaac accctgtcat   120
tttatggcag ggtgttttcg ttatttaatt ttttt                              155
```

| | |
|---|---|
| SEQ ID NO: 112 | moltype = RNA length = 155 |
| FEATURE | Location/Qualifiers |
| source | 1..155<br>mol_type = other RNA<br>note = Recombinant<br>organism = synthetic construct |

SEQUENCE: 112

```
gtaatactct atggtctgta aggttattgt actctcaaga tttattttc caaagggtt      60
acttaaatct tgcagaagct acaaagataa ggcttcatgc cgaaatcaac accctgtcat   120
tttatggcag ggtgttttcg ttatttaatt ttttt                              155
```

| | |
|---|---|
| SEQ ID NO: 113 | moltype = RNA length = 154 |
| FEATURE | Location/Qualifiers |
| source | 1..154<br>mol_type = other RNA<br>note = Recombinant<br>organism = synthetic construct |

SEQUENCE: 113

```
gagatccaac gtgttgggac tgttattgta ctctcaagat ttattttcc aaaagggtta    60
cttaaatctt gcagaagcta caaagataag gcttcatgcc gaaatcaaca ccctgtcatt   120
ttatggcagg gtgttttcgt tatttaattt tttt                               154
```

| | |
|---|---|
| SEQ ID NO: 114 | moltype = RNA length = 153 |
| FEATURE | Location/Qualifiers |
| source | 1..153<br>mol_type = other RNA<br>note = Recombinant<br>organism = synthetic construct |

SEQUENCE: 114

```
gacattctcc ccaaaatata gttattgtac tctcaagatt tatttttcca aaagggttac    60
ttaaatcttg cagaagctac aaagataagg cttcatgccg aaatcaacac cctgtcattt   120
tatggcaggg tgttttcgtt atttaatttt ttt                                153
```

| | |
|---|---|
| SEQ ID NO: 115 | moltype = DNA length = 90 |
| FEATURE | Location/Qualifiers |
| source | 1..90<br>mol_type = other DNA<br>note = Recombinant<br>organism = synthetic construct |

SEQUENCE: 115

```
ttaagggata acagggtaat atagcgtaac tataacggtc ctaaggtagc gaattacgat    60
acaaggctac ctagcttcgc agttacgcta                                    90
```

| | |
|---|---|
| SEQ ID NO: 116 | moltype = DNA length = 90 |
| FEATURE | Location/Qualifiers |
| source | 1..90<br>mol_type = other DNA |

```
                        note = Recombinant
                        organism = synthetic construct
SEQUENCE: 116
tagcgtaact gcgaagctag gtagccttgt atcgtaattc gctaccttag gaccgttata     60
gttacgctat attaccctgt tatcccttaa                                      90

SEQ ID NO: 117          moltype = DNA   length = 20
FEATURE                 Location/Qualifiers
source                  1..20
                        mol_type = other DNA
                        note = Recombinant
                        organism = synthetic construct
SEQUENCE: 117
ctatattacc ctgttatccc                                                 20

SEQ ID NO: 118          moltype = AA   length = 1388
FEATURE                 Location/Qualifiers
source                  1..1388
                        mol_type = protein
                        note = Recombinant
                        organism = synthetic construct
SEQUENCE: 118
MGSKKRRIKQ DDKKYSIGLD IGTNSVGWAV ITDEYKVPSK KFKVLGNTDR HSIKKNLIGA     60
LLFDSGETAE ATRLKRTARR RYTRRKNRIC YLQEIFSNEM AKVDDSFFHR LEESFLVEED    120
KKHERHPIFG NIVDEVAYHE KYPTIYHLRK KLVDSTDKAD LRLIYLALAH MIKFRGHFLI    180
EGDLNPDNSD VDKLFIQLVQ TYNQLFEENP INASGVDAKA ILSARLSKSR RLENLIAQLP    240
GEKKNGLFGN LIALSLGLTP NFKSNFDLAE DAKLQLSKDT YDDDLDNLLA QIGDQYADLF    300
LAAKNLSDAI LLSDILRVNT EITKAPLSAS MIKRYDEHHQ DLTLLKALVR QQLPEKYKEI    360
FFDQSKNGYA GYIDGGASQE EFYKFIKPIL EKMDGTEELL VKLNREDLLR KQRTFDNGSI    420
PHQIHLGELH AILRRQEDFY PFLKDNREKI EKILTFRIPY YVGPLARGNS RFAWMTRKSE    480
ETITPWNFEE VVDKGASAQS FIERMTNFDK NLPNEKVLPK HSLLYEYFTV YNELTKVKYV    540
TEGMRKPAFL SGEQKKAIVD LLFKTNRKVT VKQLKEDYFK KIECFDSVEI SGVEDRFNAS    600
LGTYHDLLKI IKDKDFLDNE ENEDILEDIV LTLTLFEDRE MIEEERLKTYA HLFDDKVMKQ    660
LKRRRYTGWG RLSRKLINGI RDKQSGKTIL DFLKSDGFAN RNFMQLIHDD SLTFKEDIQK    720
AQVSGQGDSL HEHIANLAGS PAIKKGILQT VKVVDELVKV MGRHKPENIV IEMARENQTT    780
QKGQKNSRER MKRIEEGIKE LGSQILKEHP VENTQLQNEK LYLYYLQNGR DMYVDQELDI    840
NRLSDYDVDH IVPQSFLKDD SIDNKVLTRS DKNRGKSDNV PSEEVVKKMK NYWRQLLNAK    900
LITQRKFDNL TKAERGGLSE LDKAGFIKRQ LVETRQITKH VAQILDSRMN TKYDENDKLI    960
REVKVITLKS KLVSDFRKDF QFYKVREINN YHHAHDAYLN AVVGTALIKK YPKLESEFVY   1020
GDYKVYDVRK MIAKSEQEIG KATAKYFFYS NIMNFFKTEI TLANGEIRKR PLIETNGETG   1080
EIVWDKGRDF ATVRKVLSMP QVNIVKKTEV QTGGFSKESI LPKRNSDKLI ARKKDWDPKK   1140
YGGFDSPTVA YSVLVVAKVE KGKSKKLKSV KELLGITIME RSSFEKNPID FLEAKGYKEV   1200
KKDLIIKLPK YSLFELENGR KRMLASAGEL QKGNELALPS KYVNFLYLAS HYEKLKGSPE   1260
DNEQKQLFVE QHKHYLDEII EQISEFSKRV ILADANLDKV LSAYNKHRDK PIREQAENII   1320
HLFTLTNLGA PAAFKYFDTT IDRKRYTSTK EVLDATLIHQ SITGLYETRI DLSQLGGDGS   1380
KKRRIKQD                                                           1388

SEQ ID NO: 119          moltype = DNA   length = 4542
FEATURE                 Location/Qualifiers
source                  1..4542
                        mol_type = other DNA
                        note = Recombinant
                        organism = synthetic construct
SEQUENCE: 119
atgggatcta agaagagaag aattaaacaa gatgacaaga agtacagcat tggtctggac     60
atcggaacga actcggtcgg ctgggccgtg attactgacg agtacaaagt tcccagcaaa    120
aaattcaagg ttctaggcaa cacagaccgc cactcgatta aaaagaatct aatcggtgcg    180
cttctgttcg actctggtga aacggccgag gccacacgct taaagaggac cgcgcgccgc    240
cgctacacgc ggcgcaagaa ccgaatctgt acctccagg taagtttctg cttctaccttt   300
tgatatatat ataataatta tcattaatta gtagtaatat aatatttcaa atatttttt    360
caaaataaaa gaatgtagta tatagcaatt gcttttctgt agtttataag tgtgtatatt    420
ttaatttata acttttctaa tatatgacca aaatttgttg atgtgcaggt aagtttctgc    480
ttctaccttt gatatatata taataattat cattaattag tagtaatata atatttcaaa    540
tattttttc aaaataaaag aatgtagtat atagcaattg cttttctgta gtttataagt    600
gtgtatattt taatttataa cttttctaat atatgaccaa aatttgttga tgtgcaggag    660
atcttcagta atgagatggc taaggtcgat gacagcttct tccacaggct tgaagagtcc    720
tttctggtcg aagaggacaa aaaacacgaa cgtcacccaa tcttcgggaa cattgtggat    780
gaagtcgcat accacgagaa gtatcctacg atctatcacc tccgcaagaa gctcgtggat    840
agtaccgaca aagccgacct gcgcttaatc taccttgcgc tcgcgcacat gattaagttc    900
cgaggacact tccttattga gggtgatctg aatccggaca attccgatgt ggataaactg    960
ttcattcagt tggtccagac atacaatcag ctattcgagg agaatccgat caatgcttcc   1020
ggcgtggacg caaaggctat tctgtcagca agactttcaa agagcagaag gttggagaat   1080
ctgatcgcac aacttcccgg agaagaagaa tgggctctct cggcaacctc attgcgctg    1140
tcttttgggtc tgcaccgaa ctttaagtct aacttcgacc ttgcagaagc tgacaaactt   1200
cagcttagca aagacctta tgatgatgac ctggacaacc tcctcgccca gattggagac   1260
cagtacgcgg atcattcttg gctgccaag aacctgtccg atgcgattct gcttagtgac   1320
atcctccgag tgaacactga aattacgaaa gcacccttgt cggctagtat gattaagcga   1380
tacgatgagc accatcaaga cctgacattg ctaaaggcgc tcgtaagaca gcaacttcct   1440
gagaagtaca aggagatatt ttttgatcag tctaagaatg gctacgctgg ttacatcgac   1500
```

```
ggtggagcta gtcaggagga attctataaa ttcatcaagc ctatcctgga aaaaatggac  1560
ggtacggagg aattgctcgt taaactaaat cgagaggatc tgctgagaaa gcagcggact  1620
ttcgacaatg gttctattcc gcatcagatt cacctcggag aacttcacgc catcctgaga  1680
cgacaggagg acttctaccc tttcctgaaa gacaaccggg aaaaaatcga gaagatcctg  1740
acattcagga ttccttacta tgtaggccct ttagcgagga gcaacagtag attcgcctgg  1800
atgaccagaa agtctgagga aacaatcaca ccgtggaact tcgaggaagt ggttgataag  1860
ggtgctagtg cccaatcatt cattgagaga atgacgaact tcgacaagaa tctgcctaac  1920
gagaaggttc tccctaaaca tagcttgctt tacgagtatt tcacggtgta caatgagcta  1980
acgaaggtca agtatgtcac agagggaatg cggaaaccgg ctttcctttc gggtgaacag  2040
aagaaagcaa ttgtggattt gctcttcaag acaaaccgaa aggtgacagt gaagcagcta  2100
aaggaggact acttcaaaaa aatagagtgc ttcgactcag ttgagatcag cggagtggag  2160
gaccggttta acgcttccct cggcacttac cacgacttgc tcaagatcat caaggacaaa  2220
gacttccttg ataacgagga gaacgaagac atccttgagg acattgtgct gacattgacg  2280
ttgttcgagg atcgggagat gatcgaggaa cgcctcagaa cgtacgccca tctgttcgat  2340
gataaggtga tgaagcagtt aaagaggaga cgttacactg gctggggccg tctctctcgc  2400
aaactgataa acgggataag ggataaacaa agcggaaaga caatcctcga tttccttaaa  2460
tccgacggct tcgctaaccg gaacttcatg cagctcatcc atgatgactc actgacgttc  2520
aaggaggaca tccagaaagc tcaagtgtct ggccagggtg acagcttgca cgagcacatc  2580
gcaaatctag ccggttcacc ggcgataaag aagggcattc tacaaacggt gaaagtggtg  2640
gacgagcttg tgaaggtcat gggtcgccat aagccagaga acattgttat cgaaatggcg  2700
agggagaacc agacaacgca gaaggacaaa aaaacagta gggagcggat gaagcgcatc  2760
gaggaaggca ttaaggaact tggaagccaa atcctgaaga agcacccggt ggagaatacg  2820
cagttgcaga acgagaaact gtacctctac tacttgcaga atggacgtga tatgtatgtg  2880
gatcaagagt tggacatcaa ccgattgtct gactatgacg tggatcacat agtaccacag  2940
tccttcctca aggatgatag catagacaac aaggttctta ctcgtagcga caagaatcgt  3000
ggcaaatcgg acaatgttcc atctgaggaa gttgtcaaaa agatgaaaaa ttattgaact  3060
caacttctga acgcgaagct aattacacaa aggaaattcg acaatctcac taaggccgag  3120
agaggagggt taagtgagtt agacaaggct ggcttcatca agcggcagtt ggtcgagact  3180
cgtcagatta ctaagcacgt ggctcagatc ctggattcgc gcatgaacac caaatacgac  3240
gagaatgaca aactcatccg tgaagttaag gtgattacac tgaaatccaa gctggtctct  3300
gactttagga aagacttcca attctacaag gtgagagaga ttaacaacta ccaccacgcg  3360
catgacgcct acttgaatgc tgtggttggg actgccctga taaagaaata tcctaaactt  3420
gagtctgagt tcgtttacgg tgactacaag gtttatgacg ttaggaagat gatcgccaaa  3480
tccgaacagg agatttggga agcaactgcc aaatatttct tttactccaa cattatgaac  3540
ttttcaaga cagaaatcac actcgccaat ggcgagattc ggaagagacc actaatcgaa  3600
acaaacggcg aaactggtga atcgttggg gataagggta gggacttcgc aactgttagg  3660
aaggtcttgt cgatgcctca agtgaacata gtcaaaaaaa cagaggtcca gaccggtggg  3720
ttctcaaagg agtctattct gccaaagcgt aacagcgaca aactcatcgc tcgcaaaaag  3780
gactgggatc ctaaaaagta cggtggattc gacagcccga ccgttgctta ttctgttctc  3840
gtagttgcta aagtcgagaa gggcaagtcc aaaaaactca aatcggttaa ggaactgctc  3900
ggaatcacga taatggaacg aagcagtttc gaaaaaaatc caattgactt cctggaagct  3960
aaaggttaca aggaggtcaa gaaggatctt atcatcaagc tacccaagta cagtctgttc  4020
gaactggaga acgtcgcaa gagaatgctg gcctcggctg gtgaactcca gaagggcaat  4080
gagctggccc tgccgtccaa gtacgtgaac tttctgtacc tggcatctca ttacgagaag  4140
ctcaagggct caccgaggga caacgagcag aagcagttgt tcgttgaaca gcacaaacac  4200
tatcttgatg agatcattga gcaaattagc gagttcagta gcgagttat tctggctgat  4260
gctaacctgg ataaggtgct ctctgcctac aacaagcacc gggataaacc tattagggaa  4320
caggcggaga acataatcca cctcttcact ctgacgaatc tcggcgcgcc tgcggccttc  4380
aaatattttg ataccaccat cgacaggaag cgctacacaa gcactaaaga ggtgctggac  4440
gccactctca ttcaccagtc tattaccggg ctctacgaga cacggattga cctctcccag  4500
ctaggtggcg atggatctaa gaagagaaga attaaacaag at                     4542

SEQ ID NO: 120         moltype = AA  length = 10
FEATURE                Location/Qualifiers
source                 1..10
                       mol_type = protein
                       note = Recombinant
                       organism = synthetic construct
SEQUENCE: 120
GSKKRRIKQD                                                          10

SEQ ID NO: 121         moltype = DNA  length = 92
FEATURE                Location/Qualifiers
source                 1..92
                       mol_type = other DNA
                       note = Recombinant
                       organism = synthetic construct
SEQUENCE: 121
caagggataa cagggtaata tagcgtaact ataacggtcc taaggtagcg aattacgata  60
caaggctacc tagcttcgca gttacgctag ta                                 92

SEQ ID NO: 122         moltype = DNA  length = 92
FEATURE                Location/Qualifiers
source                 1..92
                       mol_type = other DNA
                       note = Recombinant
                       organism = synthetic construct
SEQUENCE: 122
tactagcgta actgcgaagc taggtagcct tgtatcgtaa ttcgctacct taggaccgtt  60
```

```
atagttacgc tatattaccc tgttatccct tg                                    92

SEQ ID NO: 123         moltype = DNA   length = 73
FEATURE                Location/Qualifiers
source                 1..73
                       mol_type = other DNA
                       note = Recombinant
                       organism = synthetic construct
SEQUENCE: 123
catgccctct taggcagtag ccggccagca tttgaattaa gggataacag ggtaatatag      60
cgtaactata acg                                                         73

SEQ ID NO: 124         moltype = DNA   length = 73
FEATURE                Location/Qualifiers
source                 1..73
                       mol_type = other DNA
                       note = Recombinant
                       organism = synthetic construct
SEQUENCE: 124
catgccctct taggcagtag ccggccagca tttgaattaa gggataacag ggtaatatag      60
cgtaactata acg                                                         73

SEQ ID NO: 125         moltype = DNA   length = 68
FEATURE                Location/Qualifiers
source                 1..68
                       mol_type = other DNA
                       note = Recombinant
                       organism = synthetic construct
SEQUENCE: 125
catgccctct taggcagtag ccggccagca tttaagggat aacagggtaa tatagcgtaa      60
ctataacg                                                               68

SEQ ID NO: 126         moltype = DNA   length = 73
FEATURE                Location/Qualifiers
source                 1..73
                       mol_type = other DNA
                       note = Recombinant
                       organism = synthetic construct
SEQUENCE: 126
aaagcaacac ttaatcggct ctcaagaagt cctcaaggga taacagggta atatagcgta      60
actataacgg tcc                                                         73

SEQ ID NO: 127         moltype = DNA   length = 73
FEATURE                Location/Qualifiers
source                 1..73
                       mol_type = other DNA
                       note = Recombinant
                       organism = synthetic construct
SEQUENCE: 127
aaagcaacac ttaatcggct ctcaagaagt cctcaaggga taacagggta atatagcgta      60
actataacgg tcc                                                         73

SEQ ID NO: 128         moltype = DNA   length = 52
FEATURE                Location/Qualifiers
source                 1..52
                       mol_type = other DNA
                       note = Recombinant
                       organism = synthetic construct
SEQUENCE: 128
aaagcaacac ttaatcggct ctcaagaagt cctcaagtaa ctataacggt cc              52

SEQ ID NO: 129         moltype = DNA   length = 73
FEATURE                Location/Qualifiers
source                 1..73
                       mol_type = other DNA
                       note = Recombinant
                       organism = synthetic construct
SEQUENCE: 129
aaagcaacac ttaatcggct ctcaagaagt cctcaaggga taacagggta atatagcgta      60
actataacgg tcc                                                         73

SEQ ID NO: 130         moltype = DNA   length = 71
FEATURE                Location/Qualifiers
source                 1..71
                       mol_type = other DNA
                       note = Recombinant
                       organism = synthetic construct
SEQUENCE: 130
aaagcaacac ttaatcggct ctcaagaagt cctcaaggga taacagggta atatagcgta      60
```

```
actataagtc c                                                          71

SEQ ID NO: 131          moltype = DNA  length = 69
FEATURE                 Location/Qualifiers
source                  1..69
                        mol_type = other DNA
                        note = Recombinant
                        organism = synthetic construct
SEQUENCE: 131
aaagcaacac ttaatcggct ctcaagaagt cctcaagata acagggtaat atagcgtaac      60
tataagtcc                                                             69

SEQ ID NO: 132          moltype = DNA  length = 18
FEATURE                 Location/Qualifiers
source                  1..18
                        mol_type = other DNA
                        note = Recombinant
                        organism = synthetic construct
SEQUENCE: 132
gaaacggttc ggcatgca                                                   18

SEQ ID NO: 133          moltype = DNA  length = 15
FEATURE                 Location/Qualifiers
source                  1..15
                        mol_type = other DNA
                        note = Recombinant
                        organism = synthetic construct
SEQUENCE: 133
tgagctggca cgaac                                                      15

SEQ ID NO: 134          moltype = DNA  length = 20
FEATURE                 Location/Qualifiers
source                  1..20
                        mol_type = other DNA
                        note = Recombinant
                        organism = synthetic construct
SEQUENCE: 134
ccctgtcgtc cgtccaagta                                                 20

SEQ ID NO: 135          moltype = AA  length = 1142
FEATURE                 Location/Qualifiers
source                  1..1142
                        mol_type = protein
                        note = Recombinant
                        organism = synthetic construct
SEQUENCE: 135
MGSKKRRIKQ DMSDLVLGLD IGIGSVGVGI LNKVTGEIIH KNSRIFPAAQ AENNLVRRTN      60
RQGRRLARRK KHRRVRLNRL FEESGLITDF TKISINLNPY QLRVKGLTDE LSNEELFIAL     120
KNMVKHRGIS YLDDASDDGN SSVGDYAQIV KENSKQLETK TPGQIQLERY QTYGQLRGDF     180
TVEKDGKKHR LINVFPTSAY RSEALRILQT QQEFNPQITD EFINRYLEIL TGKRKYYHGP     240
GNEKSRTDYG RYRTSGETLD NIFGILIGKC TFYPDEFRAA KASYTAQEFN LLNDLNNLTV     300
PTETKKLSKE QKNQIINYVK NEKAMGPAKL FKYIAKLLSC DVADIKGYRI DKSGKAEIHT     360
FEAYRKMKTL ETLDIEQMDR ETLDKLAYVL TLNTEREGIQ EALEHEFADG SFSQKQVDEL     420
VQFRKANSSI FGKGWHNFSV KLMMELIPEL YETSEEQMTI LTRLGKQKTT SSSNKTKYID     480
EKLLTEEIYN PVVAKSVRQA IKIVNAAIKE YGDFDNIVIE MARETNEDDE KKAIQKIQKA     540
NKDEKDAAML KAANQYNGKA ELPHSVFHGH KQLATKIRLW HQQGERCLYT GKTISIHDLI     600
NNSNQFEVDH ILPLSITFDD SLANKVLVYA TANQEKGQRT PYQALDSMDD AWSFRELKAF     660
VRESKTLSNK KKEYLLTEED ISKFDVRKKF IERNLVDTRY ASRVVLNALQ EHFRAHKIDT     720
KVSVVRGQFT SQLRRHWGIE KTRDTYHHHA VDALIIAASS QLNLWKKQKN TLVSYSEDQL     780
LDIETGELIS DDEYKESVFK APYQHFVDTL KSKEFEDSIL FSYQVDSKFN RKISDATIYA     840
TRQAKVGKDK ADETYVLGKI KDIYTQDGYD AFMKIYKKDK SKFLMYRHDP QTFEKVIEPI     900
LENYPNKQIN EKGKEVPCNP FLKYKEEHGY IRKYSKKGNG PEIKSLKYYD SKLGNHIDIT     960
PKDSNNKVVL QSVSPWRADV YFNKTTGKYE ILGLKYADLQ FEKGTGTYKI SQEKYNDIKK    1020
KEGVDSDSEF KFTLYKNDLL LVKDTETKEQ QLFRFLSRTM PKQHYVELKK PYDKQKFEGG    1080
EALIKVLGNV ANSGQCKKGL GKSNISIYKV RTDVLGNQHI IKNEGDKPKL DFGSKKRRIK    1140
QD                                                                  1142

SEQ ID NO: 136          moltype = DNA  length = 3618
FEATURE                 Location/Qualifiers
source                  1..3618
                        mol_type = other DNA
                        note = Recombinant
                        organism = synthetic construct
SEQUENCE: 136
atgggatcta agaagagaag aattaaacaa gatatgagtg acctggtgct agggttggat      60
ataggcattg gctccgtggg ggttggcatt cttaataagg tgaccggcga ataattcat     120
aaaaactcac gcatctttcc agcagcccag gctgagaaca atctggtccg tagaaccaac     180
cggcagggtc gaaggttagc caggcgcaag aagcacagac gggtccggct caacaggctt     240
ttcgaggagt ctggtttgat caccgatttc actaagattt ctatcaacct gaatccttat     300
```

```
cagctgcgcg ttaaaggtct cacagacgaa cttagcaacg aagagttgtt catcgccctg    360
aaaaatatgg tcaagcatcg cggcattagc tacctggacg acgcttcgga tgatggcaac    420
agtagtgtag gtgactacgc tcagatcgtg aaagagaact cgaagcaatt ggagaccaag    480
accccgggcc aaattcaact cgaaaggtaa gtttctgctt ctacctttga tatatatata    540
ataattatca ttaattagta gtaatataat atttcaaata tttttttcaa aataaaagaa    600
tgtagtatat agcaattgct tttctgtagt ttataagtgt gtatatttta atttataact    660
tttctaatat atgaccaaaa tttgttgatg tgcaggtacc agacgtatgg acagttacga    720
ggcgatttta ccgttgaaaa ggatggtaag aagcacaggc tgattaatgt gtttccgacc    780
tcagcttatc gctctgaggc gctgcgtatt ttgcagaccc aacaggaatt taacccgcaa    840
ataacggacg agttcataaa ccgatactta gagattctta caggtaaacg taaatactat    900
cacgcccag gaaatgaaaa gtccaggaca gattatggtc gatatcgcac ttccggagag    960
actctcgaca atatctttgg cattcttata ggcaaatgta ccttctaccc tgacgaattt   1020
agagcagcga aggcttcata tacagcacaa gagtttaatc ttctcaacga cctcaacaac   1080
ttgactgtgc ctactgaaac caaaaagctt agcaaggagc aaaaaaatca aatcattaac   1140
tatgttaaga atgagaaagc tatggggccc gcaaaattgt tcaagtacat agctaagtta   1200
cttagctgtg acgttgctga tattaagggt taccgtattg acaagtctgg taaagctgaa   1260
attcacacct tgaggctta taggaagatg aagacccttg agacacttga cattgagcag   1320
atggataggg agactttgga caaactggca tacgtcttga cattgaacac cgaaagggaa   1380
ggcatccagg aagctctgga acatgaattt gcagatggtt cgttcagcca aaaacaggtt   1440
gacgagctgg tccaatttag aaaggcaaac tcaagcatat tcggtaaagg ttggcacaac   1500
ttcagcgtta agctgatgat ggaactcatt ccagaattat atgaaacctc tgaggaacag   1560
atgacgattc tcacaagatt gggtaagcag aaaacaacca gctctagcaa taagactaaa   1620
tacattgacg aaaagctcct caccgaagag atttataacc cggtcgtggc aaagagtgta   1680
cggcaagcca tcaagatcgt taatgccgct atcaaggagt atggtgattt tgataatatt   1740
gtgattgaaa tggcacgcga gactaacgag gacgacgaga agaaagctat acagaagatt   1800
caaaaggcta ataaggacga gaaggacgcc gcaatgctaa aggcggccaa tcaatataat   1860
gggaaggctg aactacctca tagcgtcttc catggacata agcaattagc aactaaaata   1920
agattatggc accagcaagg cgaacggtgt ctttatacag gtaaaacgat atctattcac   1980
gacctgatta acaactctaa ccagtttgaa gtggatcata tcttaccact aagtatcacc   2040
ttcgacgatt cacttgctaa caaggtgctc gtttacgcca ctgcgaacca agagaaaggg   2100
cagaggactc cataccaggc ccttgacagc atggcgacg cctggagttt taggaattaa   2160
aaagctttcg tacgtgagtc aaagacgctt tcaaataaaa aaaaggagta cttgctcact   2220
gaagaagaca tctcaaaatt cgacgtgcgc aaaaaattca ttgagcggaa cttagtcgac   2280
actcggtacg catcaagagt agtgttgaac gccctccagg agcactttag ggcacataag   2340
atcgacacca aggtttcagt tgttaggggt cagtttacat cgcagcttag acgccattgg   2400
ggtatagaaa aaacacgtga tacctaccat caccatgcag ttgacgctct catcattgca   2460
gcatcttctc aacttaattt gtggaaaaag caaaagaaca ctctggtctc atatagcgaa   2520
gatcagctgc ttgatattga aaccggcgag ctgatttctg acgacgaata caaagaatct   2580
gtgtttaagg caccatatca acactttgta gacacgctta aatctaaaga gtttgaggat   2640
tcgatccttt tcagttacca agtcgactca aaatttaacc gtaagatctc tgatgcaaca   2700
atttatgcga cgaggcaggc caaggtaggg aaggataagg ctgacgaaac ctacgtgctc   2760
ggaaaaatca aagatattta cactcaagat ggatatgatg cattcatgaa gatatataaa   2820
aaggacaaat ctaaattcct tatgtatcgt catgacccac agacattgga gaagttatt   2880
gagcctatcc tggagaacta tccgaacaag caaataaatg agaagggcaa agaagttcca   2940
tgtaatccgt tcctaaagta caaggaggaa cacggatata ttagaaaata cagcaaaaag   3000
ggcaacggcc cagaaatcaa aagccttaag tactacgata gtaaactagg aaaccacatc   3060
gacattacac caaaagactc taataataag gtcgtactgc aaagcgtttc cccatggcgc   3120
gccgatgtgt atttaataa gacaacaggg aagtacgaaa tcttgggggtt aaaatatgcg   3180
gatctgcaat tcgaaaaggg aaccggcaca tacaaaattt ctcaagaaaa gtacaacgac   3240
ataaagaaga aggaagggt cgattctgat tctgaattca gttcacact ctataagaat   3300
gatcttctgc tcgtcaagga cacagagaca aaggagcagc agttgttcag gttcttgtct   3360
agaactatgc caaaacaaaa gcactacgtt gaactgaagc cttacgataa gcaaaaattc   3420
gagggggggcg aggcgcttat aaaggtccta ggaaatgttg caaactctgg gcagtgtaag   3480
aagggcctgg gcaagagcaa cattagcatc tataaggttc gaacggatgt gcttgggaac   3540
cagcatatca tcaaaaacga gggagataaa ccaaagctgg acttcggatc taagaagaga   3600
agaattaaac aagattag                                                3618

SEQ ID NO: 137          moltype = DNA   length = 26
FEATURE                 Location/Qualifiers
source                  1..26
                        mol_type = other DNA
                        note = Recombinant
                        organism = synthetic construct
SEQUENCE: 137
ccttgtatcg taattcgcta ccttag                                       26

SEQ ID NO: 138          moltype = DNA   length = 20
FEATURE                 Location/Qualifiers
source                  1..20
                        mol_type = other DNA
                        note = Recombinant
                        organism = synthetic construct
SEQUENCE: 138
ctatattacc ctgttatccc                                              20

SEQ ID NO: 139          moltype = DNA   length = 20
FEATURE                 Location/Qualifiers
source                  1..20
                        mol_type = other DNA
```

```
                            note = Recombinant
                            organism = synthetic construct
SEQUENCE: 139
taatcggctc tcaagaagtc                                                 20

SEQ ID NO: 140              moltype = DNA   length = 20
FEATURE                     Location/Qualifiers
source                      1..20
                            mol_type = other DNA
                            note = Recombinant
                            organism = synthetic construct
SEQUENCE: 140
gggactctag aaaaaacttg                                                 20

SEQ ID NO: 141              moltype = DNA   length = 21
FEATURE                     Location/Qualifiers
source                      1..21
                            mol_type = other DNA
                            note = Recombinant
                            organism = synthetic construct
SEQUENCE: 141
taaggagatg agtttgagac c                                               21

SEQ ID NO: 142              moltype = DNA   length = 20
FEATURE                     Location/Qualifiers
source                      1..20
                            mol_type = other DNA
                            note = Recombinant
                            organism = synthetic construct
SEQUENCE: 142
aacatttcag taatcacgag                                                 20

SEQ ID NO: 143              moltype = DNA   length = 20
FEATURE                     Location/Qualifiers
source                      1..20
                            mol_type = other DNA
                            note = Recombinant
                            organism = synthetic construct
SEQUENCE: 143
taatatgatg gcatgccctc                                                 20

SEQ ID NO: 144              moltype = DNA   length = 68
FEATURE                     Location/Qualifiers
source                      1..68
                            mol_type = other DNA
                            note = Recombinant
                            organism = synthetic construct
SEQUENCE: 144
ctatctagtg aagatgtaat actctatggt ctgtttaagg gataacaggg taatatagcg     60
taactata                                                              68

SEQ ID NO: 145              moltype = DNA   length = 55
FEATURE                     Location/Qualifiers
source                      1..55
                            mol_type = other DNA
                            note = Recombinant
                            organism = synthetic construct
SEQUENCE: 145
ctatctagtg aagatgtaat actctatggt ctgtgggtaa tatagcgtaa ctata          55

SEQ ID NO: 146              moltype = DNA   length = 397
FEATURE                     Location/Qualifiers
source                      1..397
                            mol_type = genomic DNA
                            organism = Solanum lycopersicum
SEQUENCE: 146
aataaatata ttatctatca ttagaacttg aattataagt gaataataga ttatttttg      60
taatatgaat taaagtgta ttaaacatgt attaacggtg atcaattggt taaaaaaaag     120
tttattatta aaatgataaa tctttttaat ttatagtata tttatgtaag ttttcacgtt    180
gagtaaatag cgaagaagtt gggcccaacc aagtaaaata agaaggccgg gccattacaa    240
ttaagtcgtc acacaactgg gcttcattga aaaaagcgca aaaccgattc caggcccgtg    300
ttagcatgaa gactcaactc aaccagagat ttctccctca tcgcttacag aaaaaagcta    360
tatgctgttt atattgcgaa atctaacagt gtagttt                             397

SEQ ID NO: 147              moltype = DNA   length = 397
FEATURE                     Location/Qualifiers
source                      1..397
                            mol_type = genomic DNA
                            organism = Solanum lycopersicum
```

```
SEQUENCE: 147
tacttatgag aagaagtaac tgatttaaaa ttttcactaa tagggttcga aaaatgaaaa        60
tgtaatacgt ggaacttgaa tgtaaaacct caaggaattc ttgtgtttaa gaaattcaaa       120
atctctctaa atgtatacaa aagatgattt ctttttacct tatatatagt aaaataaaat       180
tgtcggataa attcgagtga acaccctagc acccccctaaa tcctcccccg tagtcggccc      240
attacagtta aagtccaggt acaacaaaat gggcttcgat taagatggaa taaaaggagt       300
ccaggcccat gagcccaaca aacaagctat ttctccctca tcggcgcaca aagaagcttt       360
attctcttat tatagctgaa tattagcatg tgtgttt                                397

SEQ ID NO: 148         moltype = DNA   length = 397
FEATURE                Location/Qualifiers
source                 1..397
                       mol_type = genomic DNA
                       organism = Solanum lycopersicum
SEQUENCE: 148
ttctatttgt gctacatata ttagacaagg aaaataacat atgttatttt gaaatcacgt        60
atatttacta taaattacaa tgattaacaa cttaaaatat ttaaatgaaa atcatattaa       120
tgactctcta aattttatct gtgtcacata aatgaaaaac aaaaaataac aaatattgta       180
ttcgcacggg cgcatgtgtc tagttagtta taaacgaaga aataagggc tgatttcgaa        240
ataaacgttc ttagaattgg aagaaatgtt cagtttctaa acttgtagga ctaaagcaat       300
aacttttatt taatttattt tcttttatgt ttctcccaca tcgatcatac atataactat       360
acagcagtat aagaactcta gcgaagcaat aatgctc                                397

SEQ ID NO: 149         moltype = DNA   length = 261
FEATURE                Location/Qualifiers
source                 1..261
                       mol_type = genomic DNA
                       organism = Solanum lycopersicum
SEQUENCE: 149
ataaatcttt ttaatttata gtatatttat gtaagttttc acgttgagta aatagcgaag        60
aagttgggcc caaccaagta aaataagaag gccgggccat tacaattaag tcgtcacaca       120
actgggcttc attgaaaaaa gcgcaaaacc gattccaggc ccgtgttagc atgaagactc       180
aactcaacca gagatttctc cctcatcgct tacagaaaaa agctatatgc tgtttatatt       240
gcgaatctaa cagtgtagtt t                                                 261

SEQ ID NO: 150         moltype = DNA   length = 103
FEATURE                Location/Qualifiers
source                 1..103
                       mol_type = unassigned DNA
                       organism = Solanum lycopersicum
SEQUENCE: 150
ggatctttcc aagcttgagg gttttagagc tagaaatagc aagttaaaat aaggctagtc        60
cgttatcaac ttgaaaaagt ggcaccgagt cggtgctttt ttt                         103

SEQ ID NO: 151         moltype = DNA   length = 119
FEATURE                Location/Qualifiers
source                 1..119
                       mol_type = other DNA
                       organism = Solanum lycopersicum
SEQUENCE: 151
aagctaatca agctgctaat actatttcaa aacttaggca ttctaatcct cctcaagctt        60
ggaaagatcc tttgaagaat tgtgcctttt cgtataaggt aatgtttatt cgttcgtcg        119

SEQ ID NO: 152         moltype = DNA   length = 120
FEATURE                Location/Qualifiers
source                 1..120
                       mol_type = other DNA
                       note = Recombinant
                       organism = synthetic construct
SEQUENCE: 152
aagctaatca agctgctaat actatttcaa aacttaggca ttctaatcct cctacaagct        60
tggaaagatc ctttgaagaa ttgtgccttt cgtataagg taatgtttat tcgttcgtcg       120

SEQ ID NO: 153         moltype = DNA   length = 120
FEATURE                Location/Qualifiers
source                 1..120
                       mol_type = other DNA
                       note = Recombinant
                       organism = synthetic construct
SEQUENCE: 153
aagctaatca agctgctaat actatttcaa aacttaggca ttctaatcct cctgcaagct        60
tggaaagatc ctttgaagaa ttgtgccttt cgtataagg taatgtttat tcgttcgtcg       120

SEQ ID NO: 154         moltype = DNA   length = 117
FEATURE                Location/Qualifiers
source                 1..117
                       mol_type = other DNA
                       note = Recombinant
                       organism = synthetic construct
```

```
SEQUENCE: 154
aagctaatca agctgctaat actatttcaa aacttaggca ttctaatcct cctagcttgg    60
aaagatcctt tgaagaattg tgccttttcg tataaggtaa tgtttattcg ttcgtcg      117

SEQ ID NO: 155           moltype = DNA  length = 116
FEATURE                  Location/Qualifiers
source                   1..116
                         mol_type = other DNA
                         note = Recombinant
                         organism = synthetic construct
SEQUENCE: 155
aagctaatca agctgctaat actatttcaa aacttaggca ttctaatcct cctgcttgga    60
agatcctttg aagaattgtg ccttttcgta taaggtaatg tttattcgtt cgtcg        116

SEQ ID NO: 156           moltype = DNA  length = 114
FEATURE                  Location/Qualifiers
source                   1..114
                         mol_type = other DNA
                         note = Recombinant
                         organism = synthetic construct
SEQUENCE: 156
aagctaatca agctgctaat actatttcaa aacttaggca ttctaatcct cctttggaaa    60
gatcctttga agaattgtgc cttttcgtat aaggtaatgt ttattcgttc gtcg         114

SEQ ID NO: 157           moltype = DNA  length = 20
FEATURE                  Location/Qualifiers
source                   1..20
                         mol_type = other DNA
                         note = Recombinant
                         organism = synthetic construct
SEQUENCE: 157
tagagacaac atgcaagaac                                                20

SEQ ID NO: 158           moltype = DNA  length = 20
FEATURE                  Location/Qualifiers
source                   1..20
                         mol_type = other DNA
                         note = Recombinant
                         organism = synthetic construct
SEQUENCE: 158
taagcaacca gtaagatagg                                                20

SEQ ID NO: 159           moltype = DNA  length = 380
FEATURE                  Location/Qualifiers
source                   1..380
                         mol_type = other DNA
                         note = Recombinant
                         organism = synthetic construct
SEQUENCE: 159
tagagacaac atgcaagaac acaccaaatt ataatttgtg tgtgaaaact ttgtctttag    60
acaaaagaag tgaaaaagca ggagatatta caacattagc attaattatg gttgatgcta   120
ttaaatctaa agctaatcaa gctgctaata ctatttcaaa acttaggcat tctaatcctc   180
ctcaagcttg gaaagatcct ttgaagaatt gtgccttttc gtataaggta atgtttattc   240
gttcgtcgtt tcaatttgtt tgtcctaaca aaactcgact atgatgaatt aggatttat    300
gtttattttt tctgtctcaa tttgcttgtc ttacttcttt ttttggctaa aagtttcgac   360
cctatcttac tggttgctta                                               380

SEQ ID NO: 160           moltype = DNA  length = 246
FEATURE                  Location/Qualifiers
source                   1..246
                         mol_type = genomic DNA
                         organism = Glycine max
SEQUENCE: 160
ggaaacttct gtttgtcccc atactccaaa aacaaaacca ttttttttt atcttcgttt     60
ttgtttgctt tgactgtgag ttgaggccca actttctgct tctgtccgac tctatttgat   120
gaatttgtt tgcctcctgt gatgtgaagg atgtatcatt gaaagggaac gtgtctcaat    180
gatcccacat cggccaaata tgctcattac attgcgttta tatgtccca ggaaaacata    240
tggatt                                                              246

SEQ ID NO: 161           moltype = DNA  length = 493
FEATURE                  Location/Qualifiers
source                   1..493
                         mol_type = genomic DNA
                         organism = Glycine max
SEQUENCE: 161
tctacaaaac attataaaaa gtaagatata acaactttt ttttaaaaaa atcaatagga     60
aatattatcg gttcagttaa tttacagaga gatatttatt tcatatgtgc cagaagtatt   120
tcagttcctt atgaaaaatc agaaaaatgt atggaataaa atataataat cgatactaat   180
aatagaacaa aataaatggt aaaatgtcaa atcaaaaacta ggctgcagta tgcagagcag   240
```

```
agtcatgatg atactactta ctacaccgat tcttgtgtgc agaaaaatat gttaaaataa   300
ttgaatcttt ctctagccaa atttgacaac aatgtacacc gttcatattg agagacgatg   360
cttcttgttt gctttcggtg gaagctgcat atactcaaca ttactccttc agcgagtttt   420
ccaactgagt cccacattgc ccagacctaa cacggtattc ttgtttataa tgaaatgtgc   480
caccacatgg att                                                     493

SEQ ID NO: 162          moltype = DNA   length = 559
FEATURE                 Location/Qualifiers
source                  1..559
                        mol_type = genomic DNA
                        organism = Glycine max
SEQUENCE: 162
aggtggagtt gttccagatt tagttttcga cttagatgat gcatggaact ggctagtgac    60
gtggatggtg gtaggttact ttcaggtcat gatttttttgt ttctaaatga tactcacact   120
cccttccagt ttttttttttt taaactcagc tcccttgctt cctccaccgg ttatcataat   180
actgaaccaa atcaaacatt acagtcaagg tactatgaat atgaaacctg aaatcctatg   240
aatgtcataa atttattttta aataataaat ttatttagaa taatattttt ttgggtaaga   300
gttataaaat aaaatacaaa aaaaaaacct aatatcaatt tttcactgac tccgtttata   360
ttgagacttg agaaagatgg ttcccgtttt ctcccggtgg aggctccgag gctgtgtata   420
tactcgacat tactttagct tgttttgttg tttctttccc tttccacaa gactcaggtc    480
tcgttcgcaa acgagtccca caccgtctaa acttaccaca atattagcgt ttataattag   540
atgcactgca tcacttatt                                                559

SEQ ID NO: 163          moltype = DNA   length = 596
FEATURE                 Location/Qualifiers
source                  1..596
                        mol_type = genomic DNA
                        organism = Glycine max
SEQUENCE: 163
aaattacacg gtagtacatc ctattataga tcgatgaatt cttaactact cgtgtccctt    60
aggccaggcc tgttttcttg cacaatttct gaaatgtata cggtttccac ttcaaccttt   120
ttaaccgcac aaagttttaa ccagatttat ataatttatt tttgaatccc aatacatat    180
cattataaca tatcaattat caaatatttc ataacctca tgatatggca atgaatacat    240
cttcttctca atgaacagag attttctgaaa aagattagga aagtgaaagc atactcgttt   300
gcaatgtaaa actgatactt cccccaaaatc atcatattcc aaatatgcc tggtgttact    360
gaccaaaacc agaaaaaaga aacggaagac atatacgtct aaacggagaa atttcaaaaa   420
acaaaaattg gatcatttct cgatttgtgg gtgtcatctt gtgcagggca tgctaatctt   480
ctctttaccc tttcccacaa gactcagcgc atgttgtctc gtctcatcca agtcccacac   540
cgcctaaact taacacaata ttagtattta taatgacata caacattcaa gatgtt       596

SEQ ID NO: 164          moltype = DNA   length = 737
FEATURE                 Location/Qualifiers
source                  1..737
                        mol_type = genomic DNA
                        organism = Glycine max
SEQUENCE: 164
aattatttaa tcctaaaaat caatcttaca aggaaccact ataaaactag ttgaacccat    60
cgaaaactaa ctacagttga caaaatctat ttggttggtt gatttttttt aattaaaaac   120
atccaatctt aatgatataa ttatagctta atattataag attttttataa aaattatatt   180
tattttgttt ctaattatgc taagagatat tattatttgt tatttaactt aaatattatc   240
acaaacttga ttgaaactta tgtttaattt aaaatattat atgtcatgag ttatgactcc   300
aataatcaca attataaagt gaagtttaat ttttagtatt acaaatattt ttttgttgtt   360
taattttaat tacttaatgt attatgttaa taattaaaaa tacaaattat ttattattaa   420
tgcaatcaca gtttgtggat ttgacaaaag aaataggggga tctaaaattg tagataagcc   480
aaagttaaaa cttgaattga ctatttttttg ctctttactc tgcaccaact ttactattcc   540
ttcttttagt gtgagcttca tgcatccttgt tcaccgcaat tccgctcggt gaaagttgca   600
caattcactc acaatctgtt tctggtctgt taggttttgtt acttggagtg acacgatgac   660
gcaacagtac aagtccccaca tcgtttgagt atacagttttt caagcagttt atattcccat   720
agccttagca agagctt                                                  737

SEQ ID NO: 165          moltype = DNA   length = 484
FEATURE                 Location/Qualifiers
source                  1..484
                        mol_type = genomic DNA
                        organism = Glycine max
SEQUENCE: 165
tttttttaata aaaaaaattc aatgggagat actatggatt caattaccctt actgattta    60
tttcatatgt gccagaagta tttcagttta ttttgaaaaa tcagaaaaaa aatgtctgga   120
ataaaatata ataagcgata ctaatcaaata attgaacaag ataaatggta aaatgtcaaa   180
tcaaaactag gctacagagt gcagagcaga gtcatgatga atgacagcta gttctactta   240
ctacaccgat tcttgtgtac ataaaaatat tttaaaataa ttgaatcttt ctttagccag   300
ctttgacaac aatgtacacc gttcgtactt cttactggta ggcaatgctt cttgtttgct   360
ttcggtggaa ggtgtatata ctcaacatta cttcttttttc agcgtgtttt cttacgggag   420
tcccacaccg cccaaaacta atacagtatt cttgtttata aagaagtgca ccacttcaat   480
tgtt                                                               484

SEQ ID NO: 166          moltype = DNA   length = 427
FEATURE                 Location/Qualifiers
source                  1..427
```

```
                        mol_type = genomic DNA
                        organism = Glycine max
SEQUENCE: 166
cgataaaaat gttttaaacg atatatatta taaaaaaaaa cgtttcaaaa ataaatacaa    60
aaatgttttt aaatatatat aatttaactc attaaagaaa ataaaaatgc aagtgcggtg   120
acaagacaag ctaaaagttg caaaagaaat ggcagggcta taaggctcac ctactcctgg   180
atttaccaaa ttttggttcg tccctatact cgaaaaataa aacaaaataa atttcagtat   240
cttcgttttt gtatgctttg actgtgaggc gaggccaact ttcttcttct gtctgagatg   300
aattttgttt gcctcctgtg aaggatgtat cattcaaagt gaatgttttg caactgccag   360
tagtcccaca tcgaccaaat attccttatta cagtgtgttt atatagcacc tggagaagga   420
atgggtt                                                             427

SEQ ID NO: 167          moltype = DNA  length = 400
FEATURE                 Location/Qualifiers
source                  1..400
                        mol_type = genomic DNA
                        organism = Glycine max
SEQUENCE: 167
gaaaagcatt cagaatattt gagcctctaa aaactttct tctttttctt tgaggagtgt     60
aatgtggatc ccaagtaacc aagaaaagca atccgaaaat tcaatttcaa gcaaactgtt   120
ctcaagtttt cgagggatat agtaatagca gagcaaaaaa acactggaaa aagcttgtac   180
ctattgaaac aaaggataat taaaaatcca aaatgtatca aaagcctaga caattttaat   240
cactattgcc tcttaacaat ttgcgcacta tgcaatcat gctctcataa tgtaacaaaa    300
gacacattag gatactagta ctgacactga caccaaggtt acatagtccc acatcgaagg   360
agtttaggta gagacatcgg tttatataac taagcgtgac                         400

SEQ ID NO: 168          moltype = DNA  length = 434
FEATURE                 Location/Qualifiers
source                  1..434
                        mol_type = genomic DNA
                        organism = Glycine max
SEQUENCE: 168
ttgccaacaa gatataacaa gaagcctaat atttcaaaag gccttttggt ccttaaaaac    60
taaggaatgc atctccagaa agaagtacaa tcataatgt tgctaagaat gcacaaaat    120
tgataaaatta atcgagaaac cacaccacaa atcacacatg gccattagag aaaaagaaag   180
gtttcaggaa aataaagaa aagaaaaagt caattactgc ttagctacct ctctatattc    240
ccatgtgccc cttgcttgaa attggaacca ctaccaggca acagagttgt tcccttttcaa   300
gcaataagag ttagaaatat ttttatatca accgaagtgc aaaaagtca gaaaccatga    360
catacgttta ctttgttagt cccacattgg atagtttag taaaacacag gtcattatat    420
agctaaacgc taac                                                     434

SEQ ID NO: 169          moltype = DNA  length = 436
FEATURE                 Location/Qualifiers
source                  1..436
                        mol_type = genomic DNA
                        organism = Glycine max
SEQUENCE: 169
aatatttcaa agcacactta ggtccttaaa aatgcaatgt tacaattcca aaaggaagta    60
taatcatagt agaagccaag aatgcagaaa aattaacaaa gtgatcgagg aatcattgcc   120
acaaatcact catggctatt agagaaaaaa aaaagtttca agaaaagaaa agaaaaagtt   180
aattactact tagctacttc tttgtaaact caggtgcccc ttgcatgcaa ttgataccac   240
accaggcacc agagctgttc cttttcatgc aataagagta agagacattt ttttatgaac   300
tcagatggcg aagtgtttga aaccatgaca ggcgttactc tggtagtccg acatagagag   360
ttttaataaa acacaaatgt agtcccacat tgaacagttt taataaaaca cagtctttat   420
ataactaaac gctgag                                                   436

SEQ ID NO: 170          moltype = DNA  length = 428
FEATURE                 Location/Qualifiers
source                  1..428
                        mol_type = genomic DNA
                        organism = Glycine max
SEQUENCE: 170
cttaggtggc tcttgcttga aatgggtact gtactggaat tagagtttat cttttcatgc    60
acaaagtttt ggccctcgtt ctactacagt atacagcagt atggtatatg ttcacattaa   120
ttctccgaaa gtaatctatc cctgcgggct agcctgagaa agggtgttta taatcttgta   180
gtgatagaat caagcatcat aagagctttc aaagcctcta atgagtattt ctttttctag   240
aaaagatgaa tatttgggat caatgctgct gctgttatgt aggaaacacc gtggcaggaa   300
gattgtattt gtatccttgt gcaatactca gaccaattct gttagaaaaa tgacacaaag   360
gccgtgatgc tagtcccaca tcgagtgttt ttaacaaaac aggcgcatat atattactgg   420
acgctgag                                                            428

SEQ ID NO: 171          moltype = DNA  length = 432
FEATURE                 Location/Qualifiers
source                  1..432
                        mol_type = genomic DNA
                        organism = Glycine max
SEQUENCE: 171
catgctgtgt agtgaaagac atagacagtc aaaaggcctg agaagggtat atattgtaaa    60
gatgatgatt tttcttacag atggtttata ccgctttatg cttcttcagc gtagaactta   120
```

```
tcaaagagaa cactatccat agctgaatca agttggttca ggcttttgtt ataatcacag  180
tctaggagtc taggacactt ttattttgca ttcattttcg gattgttgac gcctttgtat  240
aaattttaca atctctcagt aaaagatcga acacttctga taatgtttta ggaatttaac  300
tctcattcta taagctttga ccaagtctga accctagaca attgcctctt taacaacttg  360
acacagaaat aataatagtc ccacatcgag agcgtttagc tacaaacatg tgtttatata  420
attaagcata ac                                                      432

SEQ ID NO: 172          moltype = DNA   length = 434
FEATURE                 Location/Qualifiers
source                  1..434
                        mol_type = genomic DNA
                        organism = Glycine max
SEQUENCE: 172
gtttatgttt ggcattcttt aatctttagt atcagaataa ttgatcacat tttgaaatgc  60
caatagaaag acactcctta aacaaaagct atcgtgtatg aaaagctgca gagaaaaatc  120
aaatgtacaa gattttaaat aaagacatgc taaactgtcc aatatgtaac tagttgaaca  180
ggctgcattt ctctgtgttt ttgcttccgc agggaggaat acaaacatct aacaacttat  240
accaaagcat atagtacaaa ttacaatctt ttgttttccc caaattaatc caatttatct  300
ttcatttcat ccagaaagaa gctctttgag attgttagtg ttaaactgca aacttttcttc  360
ttacttatgt cccacatagg aaagaaaagg agacaacaaa atctttatat gccctctgac  420
aaagttgtct gaat                                                    434

SEQ ID NO: 173          moltype = DNA   length = 417
FEATURE                 Location/Qualifiers
source                  1..417
                        mol_type = genomic DNA
                        organism = Glycine max
SEQUENCE: 173
catttaaaat aatgaatgac taatccatta actaataact atagttgatt acttttagt   60
taattaggat gttaggaata cctgaatcca ccgacttaac tattatcata atcagttcat  120
tcaatttgaa tttgtaggat gcacctctat gttttcctct tcactttcta gtggacacaa  180
gaccctgtgt cacacacagt taatagagaa agatcattta catgtaagcg gaacccattg  240
cattctacag caatatttg gggttggtgt tataatacaa gacggataaa atagctagag  300
agaatccaat caaatcccac attccaaatt agactatcca ttgtaggcca agtcccacat  360
tggttagaat attaggcaac gaaacctttta taaatcttct gacaagcact tcagcat    417

SEQ ID NO: 174          moltype = DNA   length = 439
FEATURE                 Location/Qualifiers
source                  1..439
                        mol_type = genomic DNA
                        organism = Glycine max
SEQUENCE: 174
ggcatgtgac ttttattta aattattctc agaaatatta aaatataatc aaatatattt  60
ttttataaga tactggaaat aacattttta ggaatgtaac gaaagcccca ttacaaacac  120
ttgaactcag ggatcgatcc aacttaatta ttatctgcta cttcaaattc aaatttatag  180
gccctacctt tatgttttgc tctgcacttt cttaaatgga aacaagtaac acaatagagt  240
aagtcatttt acttgtaagc ggaaactgtt gcatcatca caatttttc gggttagttt  300
tataatataa caatgaagag aattgccgag aagatcatat caagtcccat attccatta  360
ttggccttta caagtcccac atcggtccaa atattagaca agaaacatt tatatatcgt  420
ctgacaaacc tgtaagatt                                               439

SEQ ID NO: 175          moltype = DNA   length = 169
FEATURE                 Location/Qualifiers
source                  1..169
                        mol_type = genomic DNA
                        organism = Zea mays
SEQUENCE: 175
ggattgtgcg ggcaaagtat tttcgtcgaa agagaagcaa cgaaaaagcc cactgctccg  60
agacaccgtt ccacgaaacc tgtccgcact catctcatcg tttagcacca cctcgccagt  120
ccgcagtcct ctatacctgc ttaaatattc gtccagaccc ccacccctc                169

SEQ ID NO: 176          moltype = DNA   length = 200
FEATURE                 Location/Qualifiers
source                  1..200
                        mol_type = genomic DNA
                        organism = Zea mays
SEQUENCE: 176
ctgttttcat ccggcctgtg atggaaattg tgctgcaaag tgcgcagggc cgttggcccg  60
acgacaagta tttttcgtcg agagaagcaa cgaaagccca ctcctccaag ccaccccttcg  120
ctcaagtcat atttagcacc acctcggcag tcgacactgc agcacaccaa cttaaatatt  180
catcccgatc tccctcactc                                              200

SEQ ID NO: 177          moltype = DNA   length = 200
FEATURE                 Location/Qualifiers
source                  1..200
                        mol_type = genomic DNA
                        organism = Zea mays
SEQUENCE: 177
aaactgtgct tgtgcagggc cgttgggcca cgtgcccacg tcaaagtatt ctagtcgaaa  60
```

```
gagaagcaac gaaagcccac tactactcct aggcaccgtt gccacgagac ctgtccgcac   120
tcatctcatc gtttagcacc aatgcgccag tccgcagtcc gctgtaccag cttaaatatt   180
cgtccctacc gcgctccatc                                               200

SEQ ID NO: 178         moltype = DNA  length = 200
FEATURE                Location/Qualifiers
source                 1..200
                       mol_type = genomic DNA
                       organism = Zea mays
SEQUENCE: 178
catataggga tcagctaagc ttatcatacc ttccttttt tttctcattc agccactact    60
gcagcctaca aaggatatca taatgggccg acccagtcac ccaggacgca atatgttggt   120
caatcccacc agttagtacc acctcggtag ctcagatgag tagaagatac cttaaaagtt   180
cagctcaggc aacttgcagc                                               200

SEQ ID NO: 179         moltype = DNA  length = 200
FEATURE                Location/Qualifiers
source                 1..200
                       mol_type = genomic DNA
                       organism = Zea mays
SEQUENCE: 179
catggtccat aggtatcaag atccagcatt gcacttgggc caaagattga gctctgcgaa   60
gtgtcaacta caatcatcta gatgggctcg acctgaaagg ccacacgatt tgccagaact   120
cccaccaatt aattagtacc acctcggttg ctcgatttag tagaagccag cttaaaagtt   180
cagctctggg gtccggtagc                                               200

SEQ ID NO: 180         moltype = DNA  length = 181
FEATURE                Location/Qualifiers
source                 1..181
                       mol_type = genomic DNA
                       organism = Zea mays
SEQUENCE: 180
catccaggtg aggcatcaag ctactactgc ctcgattggc tggacccgaa gcccacatgt   60
aggataccag aatgggccga cccaggacgc agtatgttgg ccagtcccac cggttagtgc   120
catctcggtt gctcacatgc gtagaagcca gcttaaaaat ttagctttgg taactcacag   180
c                                                                   181

SEQ ID NO: 181         moltype = DNA  length = 200
FEATURE                Location/Qualifiers
source                 1..200
                       mol_type = genomic DNA
                       organism = Zea mays
SEQUENCE: 181
catcaataag ataaagctgg tgcaggctct cgacctgaag cccacacact ggagagcaac   60
gatataccag aatggagcgg cccagtacac gatctgctgg gattgctggc cagtggccag   120
tcccgcagcc gattagcacc acctcggtgg cacagacgaa cgaacgctaa tttaaaagct   180
tagctctgga gcttggcacc                                               200

SEQ ID NO: 182         moltype = DNA  length = 200
FEATURE                Location/Qualifiers
source                 1..200
                       mol_type = genomic DNA
                       organism = Zea mays
SEQUENCE: 182
gcgaggcatc aacaagataa agctggtgca ggctctcgac ctgaagccca cacacaggag   60
agcaacaata taccaggaat gggagcggcc cagtacgcgat ctgctgggat tgctggctag   120
tcccgcaccc gattagcacc acctcgcttg ctcatacgag cgaacgcaaa tttaaaaggt   180
tagctctgga gtttggcagc                                               200

SEQ ID NO: 183         moltype = DNA  length = 200
FEATURE                Location/Qualifiers
source                 1..200
                       mol_type = genomic DNA
                       organism = Zea mays
SEQUENCE: 183
cctaactaat aagtatcgga ggcaacaacg cccgctgggc tgcggcccat taacatagca   60
ctagacggac accgccgcag tcagcgttca gccggatgca gtgcgatcgg cttcatccgt   120
ttagtcccac ctcgcccagc caaagcagcg gggaggcccg gactcgctac aaaaggagac   180
ggaggttggc tgtttagagc                                               200

SEQ ID NO: 184         moltype = DNA  length = 200
FEATURE                Location/Qualifiers
source                 1..200
                       mol_type = genomic DNA
                       organism = Zea mays
SEQUENCE: 184
gccagctgcg gtggaaacga ctgcggaccg ggctagcatc gacgtattgc cgtattagta   60
gcccagaaag cccacgcaac cagatagagg tctgaatgcc tgtactttgt ggtgcttcag   120
tttagtccca cctcggtggc tttcagcggg agagagcaga gaaggcttat aaaagcagac   180
```

```
ctcagtcaac ataacaattc                                                   200

SEQ ID NO: 185          moltype = DNA  length = 200
FEATURE                 Location/Qualifiers
source                  1..200
                        mol_type = genomic DNA
                        organism = Zea mays
SEQUENCE: 185
tcaataaaca attggagcga gagagactct gctgaccggg ccatcattga cgtattggta        60
gcccagaaag cccacacagt catacagagg tctgaatgtc tgtgctttat ggtgcttgag       120
tttagtccca cctcggtggc tttcagcggg agagagcaga gaaggcttat aaaagcagac       180
ctcagtcaac ataacaattc                                                   200

SEQ ID NO: 186          moltype = DNA  length = 200
FEATURE                 Location/Qualifiers
source                  1..200
                        mol_type = genomic DNA
                        organism = Zea mays
SEQUENCE: 186
gaccccatct atgccgtaat tctggcttca ccctgatca agctatcgta ccttaaatgc         60
gtcgtttcac gttttcacc ttgttggagg tctgaatgtc tgtgctttgt ggtgcttcaa       120
tttagtccca cctgtcggc tttcaacggg agggagcgga gaaggcttat aaaagcagac       180
cctagtcaac ataacaattc                                                   200

SEQ ID NO: 187          moltype = DNA  length = 200
FEATURE                 Location/Qualifiers
source                  1..200
                        mol_type = genomic DNA
                        organism = Zea mays
SEQUENCE: 187
ggtggaaacg gactcgagcg agagagactc tgcggaccgg gccagcatcg atgtattggt        60
agcccagaaa gcccacgcaa ccagacagag gtatgaatgt tgtgctttgt ggtgcttcag       120
tttagtccca cctcggcggt tttcagcgga agggagcaga gaaggcttat aaaagcagac       180
ctcagtcaac ataacaattc                                                   200

SEQ ID NO: 188          moltype = DNA  length = 200
FEATURE                 Location/Qualifiers
source                  1..200
                        mol_type = genomic DNA
                        organism = Zea mays
SEQUENCE: 188
tcccttttgtc gccttgctgt tcgctccgtt tgttgggccg gacatgtggc tttctgggcc        60
gcgcacgtag agtcctcctg gccagtgtcg ggctctggct ggctgcctgc tcttttttct       120
gtagtcccaa accgcttgct gaggctaata tcagcccggga acaacgctat ttaggattga       180
ctgaactctg tgtaagaggc                                                   200

SEQ ID NO: 189          moltype = DNA  length = 200
FEATURE                 Location/Qualifiers
source                  1..200
                        mol_type = genomic DNA
                        organism = Zea mays
SEQUENCE: 189
cctttgtggc ttcgcttcat tctcttcatc cgtttgtgac cggagtcagc ggctgtcgac        60
cgcggcgcat cctctgacta gcactgcgtc tggctggctc tggctgcttc agcttgcttt       120
agttcccaaa cccgcttgct gtagctaata ccagcaggga gcgctgctat ttaggatgga       180
ctgggcgctg cgagagaagc                                                   200

SEQ ID NO: 190          moltype = DNA  length = 200
FEATURE                 Location/Qualifiers
source                  1..200
                        mol_type = genomic DNA
                        organism = Zea mays
SEQUENCE: 190
ggccttcgct tcctcgctct tcgctccttt gttgggccgg acaacaagcg gctgtctggg        60
ccgcgcacgc agtcctctgg tccagtggga aactgcctct ggctgcttgc tcttttcctt       120
aatcccaaac cgctcgatga agctaatacc agctgggggg cgctgctatt taggagagac       180
taagcgccac ccgtagatgc                                                   200

SEQ ID NO: 191          moltype = DNA  length = 200
FEATURE                 Location/Qualifiers
source                  1..200
                        mol_type = genomic DNA
                        organism = Zea mays
SEQUENCE: 191
ttcgcttcat ttctcttcac tccgtttgtt gggccggaca tcaagcggct gtctgggccg        60
cgcacgcagt cctcttgact agcactgcgt ctggctggct ctggctgctt cagcttttgct       120
ttagttccaa accgcttgct gtagctaata ccagcaggga gcgctgctat ttaggatgga       180
ctgggcgctg cgagagaagc                                                   200
```

```
SEQ ID NO: 192              moltype = DNA   length = 200
FEATURE                     Location/Qualifiers
source                      1..200
                            mol_type = genomic DNA
                            organism = Zea mays
SEQUENCE: 192
tcaataaaca attggagcaa gagagactct gctgaccggg ccatcatcga cgtattggta    60
gcccagaaag cccacgcagt catacagagg tctgaatgtc tgtgctttgt ggtgcttgag   120
tttagtccca cctcgacggc tttcagcggg agagagcaga gaaggcttat aaaagcagac   180
ctcagtcaac ataacaattc                                               200

SEQ ID NO: 193              moltype = DNA   length = 200
FEATURE                     Location/Qualifiers
source                      1..200
                            mol_type = genomic DNA
                            organism = Zea mays
SEQUENCE: 193
gactcgagaa cttagagcta gagagactct gcggaccggg ccagcatcga cgtattggta    60
gcccagaaag cccacgcaac cagacagagg tctgaatgca tgtgctttgt ggtgcttcag   120
tttagtccca cctcggcggc tttcagcggg agagagcaga gaaggcttat aaaagcagac   180
ctcagttaac ataacaattc                                               200

SEQ ID NO: 194              moltype = DNA   length = 200
FEATURE                     Location/Qualifiers
source                      1..200
                            mol_type = genomic DNA
                            organism = Zea mays
SEQUENCE: 194
ggcccttct atgtcgtaaa tctaggtcca cccccaatca agcaatccta ccttaaatac     60
atctttcac gttttgagc ttgttggagg tgtgaaagtt tgtgctttgt ggtgcttcag    120
tttagtccca cctcggtggc tttcagtgag agggagcgaa gaaggcttat aaaagcacac   180
cccaatcaac ataacaattc                                               200

SEQ ID NO: 195              moltype = DNA   length = 200
FEATURE                     Location/Qualifiers
source                      1..200
                            mol_type = genomic DNA
                            organism = Zea mays
SEQUENCE: 195
tcaatataca attggagcga gagagactct gctgaccggg ccagcatcga cgtattggta    60
gcccagaaag cccacgcagt catacagagg tctgaatgta tgtgctttgt ggtgcttgag   120
tttagtccca cctcggaggc tttcagcggg agagagcaaa gaaggcttat aaaagcagac   180
ctcagtcagc ataacaattc                                               200

SEQ ID NO: 196              moltype = DNA   length = 200
FEATURE                     Location/Qualifiers
source                      1..200
                            mol_type = genomic DNA
                            organism = Zea mays
SEQUENCE: 196
gccagctgcg gtggaaacga ctgcggaccg agccagcatc gacgtattgc cgtattggta    60
gcccagaaag cccacgcaac cggacagagg tctgaatgcc tgtactttgt ggtgcttcag   120
tttagtccca cctcggtggc tttcagcggg agagagcaga gaaggcttat aaaagcagac   180
ctcagtcaat ataacaattc                                               200

SEQ ID NO: 197              moltype = DNA   length = 200
FEATURE                     Location/Qualifiers
source                      1..200
                            mol_type = genomic DNA
                            organism = Zea mays
SEQUENCE: 197
gagtccagaa cttggagcga gagagactct gctgaccggg ccagcatgga cgtattggta    60
gcccagaaag cccacgcaac cagatagagg tcttaatgcc ctttctttgt ggtgctttag   120
tttagtccca cctcgacggc tttcagcggg agggagcaga gaaggcttat aaaagaagat   180
ctcaatcaaa ttaacaattc                                               200

SEQ ID NO: 198              moltype = DNA   length = 200
FEATURE                     Location/Qualifiers
source                      1..200
                            mol_type = genomic DNA
                            organism = Zea mays
SEQUENCE: 198
gactcgagaa cttggagcga gagagactct gctgaccggg ccagcatgga cgtattggta    60
gcccagaaag cccacgctac cagacagagg tctgaatgac tgttctttgt ggtgcttcag   120
tttagtccca cctcgacggc tttcagcggg aggaagcaga gaaggcttat aaaagcagat   180
cctagtcaac ataacaattc                                               200

SEQ ID NO: 199              moltype = DNA   length = 192
FEATURE                     Location/Qualifiers
```

```
source                  1..192
                        mol_type = genomic DNA
                        organism = Zea mays
SEQUENCE: 199
aacggactcg agcgagagag actctgcgga ccgggccagc atcgatgtat ttggtagccc   60
agagcccacg caaccagaca gaggtatgaa tgttgtgctt tgtggtgctt cagtttagtc  120
ccacctcggc ggttttcagc ggaagggagc agagaaggct tataaaagca gacctcagtc  180
aacataacaa tt                                                      192

SEQ ID NO: 200          moltype = DNA   length = 199
FEATURE                 Location/Qualifiers
source                  1..199
                        mol_type = genomic DNA
                        organism = Zea mays
SEQUENCE: 200
ggcgtatgtg ccaaaaactt cgtcacagag agggccataa gaaacatggc ccacggccca   60
atacgaagca ccgcgacgaa gcccaaacag cagtcctag gtggagcaaa gcgctgggta  120
atacgcaaac gttttgtccc accttgacta atcacaagag tggagcgtac cttataaacc  180
gagccgcaag caccgaatt                                               199

SEQ ID NO: 201          moltype = DNA   length = 418
FEATURE                 Location/Qualifiers
source                  1..418
                        mol_type = genomic DNA
                        organism = Zea mays
SEQUENCE: 201
aggaaaagaa gaggtgatta ctgtaccat tcgtctttgt atcggaatat aaatttatca   60
ctattttatg ataaagtaaa tctgtttccc tgtagagtta attaattaat gtaagtataa  120
gcgtaattta tagggcacta gtaggactgt cgactgtgcg ctcggccgg ataatgcgtc  180
aaaagcgaag acgtgcacgt gggatgggaa aacacgaagc gtgtctgct ttttcgcatg  240
atatctgggc cgcaccaaag aatccagccc acgcggcgtg gcgccgtcgt tacggcttgc  300
ggggaagga acgagggac gaaccgagat ttagcaccag accggccagc gagcattgca  360
gacaccggct tataagttca gctgcgacta ccactccggg aggtccgagt tccactcg   418

SEQ ID NO: 202          moltype = DNA   length = 625
FEATURE                 Location/Qualifiers
source                  1..625
                        mol_type = other DNA
                        note = Recombinant
                        organism = synthetic construct
SEQUENCE: 202
ttctatttgt gctacatata ttagacaagg aaaataacat atgttatttt gaaatcacgt   60
atatttacta taaattacaa tgattaacaa cttaaaatat ttaaatgaaa atcatattaa  120
tgactctcta aattttatct gtgtcacata aatgaaaaac aaaaaataac aaatattgta  180
ttcgcacggg cgcatgtgtc tagttagtta taaacgaaga aataaggggc tgatttcgaa  240
ataaacgttt ttagaattgg aagaaatgtt cagtttctaa acttgtagga ctaaagcaat  300
aacttttatt taattatttt tcttttatgt ttctcccaca tcgatcatac atataactat  360
acagcagtat aagaactcta gcgaagcaat aatgctccaa gctgactcta gcagatctcc  420
atgacggcag agaaggtact ggaaaaagaa cttctggcct ggcaggagaa actgcatcag  480
ccgattatca tcaccgaata cggcgtggat acgttagccg gctgcactc aatgtacacc  540
gacatgtgga gtgaagagta tcagtgtgca tggctggata tgtatcaccg cgtctttgat  600
cgcgtcagcg ccgtcgtctt ttttt                                        625

SEQ ID NO: 203          moltype = DNA   length = 474
FEATURE                 Location/Qualifiers
source                  1..474
                        mol_type = other DNA
                        note = Recombinant
                        organism = synthetic construct
SEQUENCE: 203
ggaaacttct gtttgtcccc atactccaaa aacaaaacca ttttttttt atcttcgttt   60
ttgtttgctt tgactgtgag ttgaggccca actttctgct tctgtccgac tctatttgat  120
gaattttgtt tgcctcctgt gatgtgaagg atgtatcatt gaaagggaac gtgtctcaat  180
gatcccacat cggccaaata tgctcattac attgcgttta tatgtccca ggaaaacata  240
tggattcaag ctgactctag cagatctcca tgacggcaga gaaggtactg gaaaaagaac  300
ttctggcctg gcaggagaaa ctgcatcagc cgattatcat caccgaatac ggcgtggata  360
cgttagccgg gctgcactca atgtacaccg acatgtggag tgaagagtat cagtgtgcat  420
ggctggatat gtatcaccgc gtctttgatc gcgtcagcgc cgtcgtcttt tttt        474

SEQ ID NO: 204          moltype = DNA   length = 721
FEATURE                 Location/Qualifiers
source                  1..721
                        mol_type = other DNA
                        note = Recombinant
                        organism = synthetic construct
SEQUENCE: 204
tctacaaaac attataaaaa gtaagatata acaacttttt ttttaaaaaa atcaatagga   60
aatattatcg gttcagttaa tttacagaga gatatttatt tcatatgtgc cagaagtatt  120
tcagttcctt atgaaaaatc agaaaaatgt atggaataaa atataataat cgatactaat  180
```

```
aatagaacaa ataaatggt aaaatgtcaa atcaaaacta ggctgcagta tgcagagcag   240
agtcatgatg atactactta ctacaccgat tcttgtgtgc agaaaaatat gttaaaataa   300
ttgaatcttt ctctagccaa atttgacaac aatgtcacc gttcatattg agagacgatg    360
cttcttgttt gctttcggtg gaagctgcat atactcaaca ttactccttc agcgagtttt   420
ccaactgagt cccacattgc ccagacctaa cacggtactc ttgtttataa tgaaatgtgc   480
caccacatgg attcaagctg actctagcag atctccatga cggcagagaa ggtactggaa   540
aaagaacttc tggcctggca ggagaaactg catcagccga ttatcatcac cgaatacggc   600
gtggatacgt tagccgggct gcactcaatg tacaccgaca tgtggagtga agagtatcag   660
tgtgcatggc tggatatgta tcaccgcgtc tttgatcgcg tcagcgccgt cgtcttttt    720
t                                                                  721

SEQ ID NO: 205          moltype = DNA  length = 787
FEATURE                 Location/Qualifiers
source                  1..787
                        mol_type = other DNA
                        note = Recombinant
                        organism = synthetic construct
SEQUENCE: 205
aggtggagtt gttccagatt tagttttcga cttagatgat gcatggaact ggctagtgac    60
gtggatggtg gtaggttact ttcaggtcat gatttttgt ttctaaatga tactcacact    120
cccttccagt ttttttttt taaactcagc tcccttgctt cctccaccgg ttatcataat   180
actgaaccaa atcaaacatt acagtcaagg tactatgaat gtgaaacctg aaatcctatg   240
aatgtcataa atttatttta aataataaat ttatttagaa taatattttt ttgggtaaga   300
gttataaaat aaaatacaaa aaaaaaacct aatatcaatt tttcactgac tccgtttata   360
ttgagacttg agaagatgg ttcccgtttg ctcccggtgg aggctccgag gctgtgtata    420
tactcgacat tactttagct tgttttgttg tttctttccc ttcccacaa gactcaggtc    480
tcgttcgcaa acgagtccca caccgtctaa acttaccaca atattagcgt ttataattag   540
atgcactgca tcacttattc aagctgactc tagcagatct ccatgacggc agagaaggta   600
ctggaaaaag aacttctggc ctggcaggag aaactgcatc agccgattat catcaccgaa   660
tacggcgtgg atacgttagc cgggctgcac tcaatgtaca ccgacatgtg gagtgaagag   720
tatcagtgtg catggctgga tatgtatcac cgcgtctttg atcgcgtcag cgccgtcgtc   780
ttttttt                                                            787

SEQ ID NO: 206          moltype = DNA  length = 824
FEATURE                 Location/Qualifiers
source                  1..824
                        mol_type = other DNA
                        note = Recombinant
                        organism = synthetic construct
SEQUENCE: 206
aaattacacg gtagtacatc ctattataga tcgatgaatt cttaactact cgtgtccctt    60
aggccaggc tgttttcttg cacaatttct gaaatgtata cggtttccac ttcaaccttt    120
ttaaccgcac aaagttttaa ccagatttat ataatttatt tttgaatccc caatacatat   180
cattataaca tatcaattat caaatatttc ataaccctca tgatatggca atgaatacat   240
cttcttctca atgaacagag atttctgaaa aagattagga aagtgaaagc atactcgttt   300
gcaatgtaaa actgatactt cccccaaaatc atcatattcc aaatatgccc tggtgttact   360
gaccaaaacc agaaaaaaga aacggaagac atatacgtct aaatttcaaaaa             420
acaaaaattg gatcatttct cgatttgtgg gtgtcatctt gtgcagggca tgctaatctt   480
ctctttaccc tttcccacaa gactcagcgc atgttgtctc gtctcatcca agtcccacac   540
cgcctaaaact taacacaata ttagtattta taatgacata caacattcaa gatgttcaag   600
ctgactctag cagatctcca tgacggcaga aaggtactg gaaaaagaac ttctggcctg   660
gcaggagaaa ctgcatcagc cgattatcat caccgaatac ggcgtggata cgttagccgg   720
gctgcactca atgtacaccg acatgtggag tgaagagtat cagtgtgcat ggctggatat   780
gtatcaccgc gtctttgatc gcgtcagcgc cgtcgtcttt tttt                   824

SEQ ID NO: 207          moltype = DNA  length = 965
FEATURE                 Location/Qualifiers
source                  1..965
                        mol_type = other DNA
                        note = Recombinant
                        organism = synthetic construct
SEQUENCE: 207
aattatttaa tcctaaaaat caatcttaca aggaaccact ataaaactag ttgaacccat     60
cgaaaactaa ctacagttga caaaatctat ttggttggtt gatttttttt aattaaaaac   120
atccaatctt aatgatataa ttatagctta atattataag attttataaa aaattatatt   180
tattttgttt ctaattatgc taagagatat tattatttgt tatttaactt aaatattatc   240
acaaacttga ttgaaactta tgtttaattt aaaatattat atgtcatgag ttatgactcc   300
aataatcaca attataaagt gaagtttaat ttttagtatt acaaatattt ttttgttgtt   360
taattttaat tacttaatgt attatgttaa taattaaaaa tacaaattat ttattattaa   420
tgcaatcaca gtttgtggat ttgacaaaag aaataggga tctaaaattg tagataagcc    480
aaagttaaaa cttgaattga ctattttttg ctctttactc tgcaccaact ttactattcc   540
ttctttagt gtgagcttca tgcatcttgt tcaccgcaat tccgctcggt gaagttgca    600
caattcactc acaatctgtt tctggtctgt taggtttgtt acttggagtg acacgatgac   660
gcaacagtac aagtcccaca tcgtttgagt atacagtttt caagcagttt atattcccat   720
agccttagca agagcttcaa gctgactcta gcagatctcc atgacggcag agaaggtact   780
ggaaaaagaa cttctggcct ggcaggagaa actgcatcag ccgattatca tcaccgaata   840
cggcgtggat acgttagccg ggctgcactc aatgtacacc gacatgtgga gtgaagagta   900
tcagtgtgca tggctggata tgtatcaccg cgtctttgat cgcgtcagcg ccgtcgtctt   960
ttttt                                                              965
```

```
SEQ ID NO: 208          moltype = DNA  length = 712
FEATURE                 Location/Qualifiers
source                  1..712
                        mol_type = other DNA
                        note = Recombinant
                        organism = synthetic construct
SEQUENCE: 208
ttttttaata aaaaaaattc aatgggagat actatggatt caattacctt actgatttta    60
tttcatatgt gccagaagta tttcagttta ttttgaaaaa tcagaaaaaa aatgtctgga   120
ataaaatata ataagcgata ctaataaata attgaacaag ataaatggta aaatgtcaaa   180
tcaaaactag gctacagagt gcagagcaga gtcatgatga atgacagcta gttctactta   240
ctacaccgat tcttgtgtac ataaaaatat tttaaaataa ttgaatcttt ctttagccag   300
ctttgacaac aatgtacacc gttcgtactt cttactggta ggcaatgctt cttgtttgct   360
ttcggtggaa ggtgtatata ctcaacatta cttcttttc agcgtgtttt cttacgggag   420
tcccacaccg cccaaaacta atacagtatt cttgtttata aagaagtgca ccacttcaat   480
tgttcaagct gactctagca gatctccatg acggcagaga aggtactgga aaaagaactt   540
ctggccctggc aggagaaact gcatcagccg attatcatca ccgaatacg cgtggatacg   600
ttagccgggc tgcactcaat gtacaccgac atgtggagtg aagagtatca gtgtgcatgg   660
ctggatatgt atcaccgcgt ctttgatcgc gtcagcgccg tcgtcttttt tt           712

SEQ ID NO: 209          moltype = DNA  length = 655
FEATURE                 Location/Qualifiers
source                  1..655
                        mol_type = other DNA
                        note = Recombinant
                        organism = synthetic construct
SEQUENCE: 209
cgataaaaat gttttaaacg atatatatta taaaaaaaaa cgtttcaaaa ataaatacaa    60
aaatgttttt aaatatatat aatttaactc attaaagaaa ataaaatgc aagtgcggtg   120
acaagacaag ctaaaagttg caaaagaaat ggcagggcta taaggctcac ctactcctgg   180
atttaccaaa ttttggttcg tccctatact cgaaaaataa aacaaataa atttcagtat   240
cttcgttttt gtatgctttg actgtgaggc gaggccaact ttcttcttct gtctgagatg   300
aattttgttt gcctcctgtg aaggatgtat cattcaaagt gaatgttttg caactgccag   360
tagtcccaca tcgaccaaat attcttatta cagtgtgttt atatagcacc tggagaagga   420
atgggttcaa gctgactcta gcagatctcc atgacggcag agaaggtact ggaaaaagaa   480
cttctggcct ggcaggagaa actgcatcag ccgattatca tcaccgaata cggcgtggat   540
acgttagccg ggctgcactc aatgtacacc gacatgtgga gtgaagagta tcagtgtgca   600
tggctggata tgtatcaccg cgtctttgat cgcgtcagc ccgtcgtctt ttttt         655

SEQ ID NO: 210          moltype = DNA  length = 628
FEATURE                 Location/Qualifiers
source                  1..628
                        mol_type = other DNA
                        note = Recombinant
                        organism = synthetic construct
SEQUENCE: 210
gaaaagcatt cagaatattt gagcctctaa aaacttttct tctttttctt tgaggagtgt    60
aatgtggatc ccaagtaacc aagaaaagca atccgaaaat tcaatttcaa gcaaactgtt   120
ctcaagtttt cgagggatat agtaaatagca gagcaaaaaa acactggaaa aagcttgtac   180
ctattgaaac aaaggataat taaaaatcca aaatgtaaaa aaagcctaga caattttaat   240
cactattgcc tcttaacaat ttgcgcacta tgacaatcat gctctcataa tgtaacaaaa   300
gacacattag gatactagta ctgacactga caccaaggtt acatagtccc acatcgaagg   360
agtttaggta gagacatcgg tttatataac taagcgtgac caagctgact ctagcagatc   420
tccatgacgg cagagaaggt actggaaaaa gaacttctgg cctggcagga gaaactgcat   480
cagccgatta tcatcaccga atacggcgt gatacgttag ccgggctgca ctcaatgtac   540
accgacatgt ggagtgaaga gtatcagtgt gcatggctgg atatgtatca ccgcgtcttt   600
gatcgcgtca gcgccgtcgt cttttttt                                      628

SEQ ID NO: 211          moltype = DNA  length = 662
FEATURE                 Location/Qualifiers
source                  1..662
                        mol_type = other DNA
                        note = Recombinant
                        organism = synthetic construct
SEQUENCE: 211
ttgccaacaa gatataacaa gaagcctaat atttcaaaag gccttttggt ccttaaaaac    60
taaggaatgc atctccagaa agaagtacaa tcataatagt tgctaagaat gcagcaaaat   120
tgataaatta atcgagaaac cacaccacaa atcacacatg gccattagag aaaaagaaag   180
gtttcaggaa aataaaagaa aagaaaaagt caattactgc ttagctacct ctctatattc   240
ccatgtgccc cttgcttgaa attggaacca ctaccaggca acagagttgt tcccttcaa    300
gcaataagag ttagaaatat ttttatatca accgaagtgg caaaaagtca gaaaccatga   360
catacgttta cttgttagt cccacattgg atagttttag taaaacacag gtcattatat   420
agctaaacgc taaccaagct gactctagca gatctccatg acggcagaga aggtactgga   480
aaaagaactt ctggcctggc aggagaaact gcatcagccg attatcatca ccgaatacg   540
cgtggatacg ttagccgggc tgcactcaat gtacaccgac atgtggagtg aagagtatca   600
gtgtgcatgg ctggatatgt atcaccgcgt ctttgatcgc gtcagcgccg tcgtcttttt   660
tt                                                                  662
```

```
SEQ ID NO: 212            moltype = DNA   length = 664
FEATURE                   Location/Qualifiers
source                    1..664
                          mol_type = other DNA
                          note = Recombinant
                          organism = synthetic construct
SEQUENCE: 212
aatatttcaa agcacactta ggtccttaaa aatgcaatgt tacaattcca aaaggaagta    60
taatcatagt agaagccaag aatgcagaaa aattaacaaa gtgatcgagg aatcattgcc   120
acaaatcact catggctatt agagaaaaaa aaaagtttca gaaaaagaaa agaaaaagtt   180
aattactact tagctacttc tttgtaaact caggtgcccc ttgcatgcaa ttgataccac   240
accaggcacc agagctgttc cttttcatgc aataagagta agagacattt ttttatgaac   300
tcagatggcg aagtgtttga aaccatgaca ggcgttactc tggtagtccg acatagagag   360
ttttaataaa acacaaatgt agtcccacat tgaacagttt taataaaaca cagtctttat   420
ataactaaac gctgagcaag ctgactctag cagatctcca tgacggcaga gaaggtactg   480
gaaaaagaac ttctggcctg gcaggagaaa ctgcatcagc cgattatcat caccgaatac   540
ggcgtggata cgttagccgg gctgcactca atgtacaccg acatgtggag tgaagagtat   600
cagtgtgcat ggctggatat gtatcaccgc gtctttgatc gcgtcagcgc cgtcgtcttt   660
tttt                                                                664

SEQ ID NO: 213            moltype = DNA   length = 656
FEATURE                   Location/Qualifiers
source                    1..656
                          mol_type = other DNA
                          note = Recombinant
                          organism = synthetic construct
SEQUENCE: 213
cttaggtggc tcttgcttga aatgggtact gtactggaat tagagtttat cttttcatgc    60
acaaagtttt ggccctcgtt ctactacagt atacagcagt atggatatgg ttcacattaa   120
ttctccgaaa gtaatctatc cctgcgggct agcctgagaa aggtgttta taatcttgta   180
gtgatagaat caagcatcat aagagctttc aaagcctcta atgagtattt ctttttctag   240
aaaagatgaa tatttgggat caatgctgct gctgttatgt aggaaacacc gtggcaggaa   300
gattgtattt gtatccttgt gcaatactca gaccaattct gttagaaaaa tgacacaaag   360
gccgtgatgc tagtcccaca tcgagtgttt ttaacaaaac aggcgcatat atattactgg   420
acgctgagca agctgactct agcagatctc catgacggca gaaggtac tggaaaaaga   480
acttctggcc tggcaggaga aactgcatca gccgattatc atcaccgaat acggcgtgga   540
tacgttagcc gggctgcact caatgtacac cgacatgtgg agtgaagagt atcagtgtgc   600
atggctggat atgtatcacc gcgtctttga tcgcgtcagc gccgtcgtct tttttt       656

SEQ ID NO: 214            moltype = DNA   length = 660
FEATURE                   Location/Qualifiers
source                    1..660
                          mol_type = other DNA
                          note = Recombinant
                          organism = synthetic construct
SEQUENCE: 214
catgctgtgt agtgaaagac atagacagtc aaaaggcctg agaagggtat atattgtaaa    60
gatgatgatt tttcttacag atggtttata ccgcttatg cttcttcagc gtagaactta   120
tcaaagagaa cactatccat agctgaatca agttggttca ggcttttgtt ataatcacag   180
tctaggagtc taggacactt ttattttgca ttcattttcg gattgttgac gcctttgtat   240
aaattttaca atctctcagt aaaagatcga acacttctga taatgtttta ggaatttaac   300
tctcattcta taagctttga ccaagtctga accctagaca attgcctctt taacaacttg   360
acacagaaat aataatagtc ccacatcgag agcgtttagc tacaaacatg tgtttatata   420
attaagcata accaagctga ctctagcaga tctccatgac ggcagagaag gtactggaaa   480
aagaacttct ggcctggcag gagaaactgc atcagccgat tatcatcacc gaatacggcg   540
tggatacgtt agccgggctg cactcaatgt acaccgacat gtggagtgaa gagtatcagt   600
gtgcatggct ggatatgtat caccgcgtct ttgatcgcgt cagcgccgtc gtcttttttt   660

SEQ ID NO: 215            moltype = DNA   length = 662
FEATURE                   Location/Qualifiers
source                    1..662
                          mol_type = other DNA
                          note = Recombinant
                          organism = synthetic construct
SEQUENCE: 215
gtttatgttt ggcattcttt aatctttagt atcagaataa ttgatcacat tttgaaatgc    60
caatagaaag cacactcctta aacaaaagct atcgtgtatg aaaagctgca gagaaaaatc   120
aaatgtacaa gatttttaaat aaagacatgc taaactgtcc aatatgtaac tagttgaaca   180
ggctgcattt ctctgtgttt ttgcttccgc agggaggaat acaaacatct aacaacttat   240
accaaagcat atagtacaaa ttacaatctt ttgttttccc caaattaatc caatttatct   300
ttcatttcat ccagaaagaa gctctttgag attgttagtg ttaaactgca aacttttcttc   360
ttacttatgt cccacatagg aaagaaaagg agacaacaaa atctttatat gccctctgac   420
aaagttgtct gaatcaagct gactctagca gatctccatg acggcagaga aggtactgga   480
aaaagaactt ctggcctggc aggagaaact gcatcagcg attatcatca ccgaatacgg   540
cgtggatacg ttagccgggc tgcactcaat gtacaccgac atgtggagtg aagagtatca   600
gtgtgcatgg ctggatatgt atcaccgcgt ctttgatcgc gtcagcgccg tcgtcttttt   660
tt                                                                  662

SEQ ID NO: 216            moltype = DNA   length = 645
```

```
FEATURE                 Location/Qualifiers
source                  1..645
                        mol_type = other DNA
                        note = Recombinant
                        organism = synthetic construct
SEQUENCE: 216
catttaaaat aatgaatgac taatccatta actaataact atagttgatt acttttagt    60
taattaggat gttaggaata cctgaatcca ccgacttaac tattatcata atcagttcat  120
tcaatttgaa tttgtaggat gcacctctat gttttcctct tcactttcta gtggacacaa  180
gaccctgtgt cacacacagt taatagaaga agatcattta catgtaagcg gaacccattg  240
cattctacag caatattttg gggttggtgt tataatacaa gacggataaa atagctagag  300
agaatccaat caaatcccac attccaaatt agactatcca ttgtaggcca agtcccacat  360
tggttagaat attaggcaac gaaaccttta taaatcttct gacaagcact tcagcatcaa  420
gctgactcta gcagatctcc atgacggcag agaaggtact ggaaaaagaa cttctggcct  480
ggcaggagaa actgcatcag ccgattatca tcaccgaata cggcgtggat acgttagccg  540
ggctgcactc aatgtacacc gacatgtgga gtgaagagta tcagtgtgca tggctggata  600
tgtatcaccg cgtctttgat cgcgtcagcg ccgtcgtctt ttttt             645

SEQ ID NO: 217          moltype = DNA   length = 667
FEATURE                 Location/Qualifiers
source                  1..667
                        mol_type = other DNA
                        note = Recombinant
                        organism = synthetic construct
SEQUENCE: 217
ggcatgtgac ttttattta aattattctc agaaatatta aaatataatc aaatatattt    60
ttttataaga tactggaaat aacatttta ggaatgtaac gaaagcccca ttacaaacac  120
ttgaactcag ggatcgatcc aacttaatta ttatctgcta cttcaaattc aaatttatag  180
gccctacctt tatgttttgc tctgcacttt cttaaatgga aacaagtaac acaatagagt  240
aagatcattt acttgtaagc ggaaactgtt gcatcaactg caatattttc gggttagttt  300
tataatataa caatgaagag aattgccgag aagatcatat caagtcccat attccattta  360
ttggcccttta caagtcccac atcggtccaa atattagaca aagaaacatt tatatatcgt  420
ctgacaaacc tgtaagattc aagctgactc tagcagatct ccatgacggc agagaaggta  480
ctggaaaaag aacttctggc ctggcaggag aaactgcatc agccgattat catcaccgaa  540
tacggcgtgg atacgttagc cgggctgcac tcaatgtaca ccgacatgtg gagtgaagag  600
tatcagtgtg catggctgga tatgtatcac cgcgtctttg atcgcgtcag cgccgtcgtc  660
tttttt                                                            667

SEQ ID NO: 218          moltype = DNA   length = 398
FEATURE                 Location/Qualifiers
source                  1..398
                        mol_type = other DNA
                        note = Recombinant
                        organism = synthetic construct
SEQUENCE: 218
ggattgtgcg ggcaaagtat tttcgtcgaa agagaagcaa cgaaaaagcc cactgctccg    60
agacaccgtt ccacgaaacc tgtccgcact catctcatcg tttagcacca cctcgccagt  120
ccgcagtcct ctatacctgc ttaaatattc gtccagaccg cccaccctcc aagctgactc  180
tagcagatct ccatgacggc agagaaggta ctggaaaaag aacttctggc ctggcaggag  240
aaactgcatc agccgattat catcaccgaa tacggcgtgg atacgttagc cgggctgcac  300
tcaatgtaca ccgacatgtg gagtgaagag tatcagtgtg catggctgga tatgtatcac  360
cgcgtctttg atcgcgtcag cgccgtcgtc tttttttt                          398

SEQ ID NO: 219          moltype = DNA   length = 429
FEATURE                 Location/Qualifiers
source                  1..429
                        mol_type = other DNA
                        note = Recombinant
                        organism = synthetic construct
SEQUENCE: 219
ctgttttcat ccggcctgtg atggaaattg tgctgcaaag tgcgcagggc cgttggcccg    60
acgacaagta ttttttcgtcg agagaagcaa cgaaagccca ctcctccaag ccaccccttcg  120
ctcaagtcat atttagcacc acctcggcag tcgacactgc agcacaccaa cttaaatatt  180
catcccgatc tccctcactc caagctgact ctagcagatc tccatgacgg cagagaaggt  240
actggaaaaa gaacttctgg cctggcagga gaaactgcat cagccgatta tcatcaccga  300
atacggcgtg gatacgttag ccgggctgca ctcaatgtac accgacatgt ggagtgaaga  360
gtatcagtgt gcatggctgg atatgtatca ccgcgtcttt gatcgcgtca gcgccgtcgt  420
ctttttttt                                                         429

SEQ ID NO: 220          moltype = DNA   length = 429
FEATURE                 Location/Qualifiers
source                  1..429
                        mol_type = other DNA
                        note = Recombinant
                        organism = synthetic construct
SEQUENCE: 220
aaactgtgct tgtgcagggc cgttgggcca cgtgcccacg tcaaagtatt ctagtcgaaa    60
gagaagcaac gaaagcccac tactactcct aggcaccgtt gccacgagac ctgtccgcac  120
tcatctcatc gtttagcacc aatgcgccag tccgcagtcc gctgtaccag cttaaatatt  180
```

```
cgtccctacc gcgctccatc caagctgact ctagcagatc tccatgacgg cagagaaggt    240
actggaaaaa gaacttctgg cctggcagga gaaactgcat cagccgatta tcatcaccga    300
atacggcgtg gatacgttag ccgggctgca ctcaatgtac accgacatgt ggagtgaaga    360
gtatcagtgt gcatggctgg atatgtatca ccgcgtcttt gatcgcgtca gcgccgtcgt    420
cttttttttt                                                            429

SEQ ID NO: 221          moltype = DNA  length = 429
FEATURE                 Location/Qualifiers
source                  1..429
                        mol_type = other DNA
                        note = Recombinant
                        organism = synthetic construct
SEQUENCE: 221
catataggga tcagctaagc ttatcatacc ttccttttt tttctcattc agccactact       60
gcagcctaca aaggatatca taatgggccg acccagtcac ccaggacgca atatgttggt    120
caatcccacc agttagtacc acctcggtag ctcagatgag tagaagatac cttaaaagtt    180
cagctcaggc aacttgcagc caagctgact ctagcagatc tccatgacgg cagagaaggt    240
actggaaaaa gaacttctgg cctggcagga gaaactgcat cagccgatta tcatcaccga    300
atacggcgtg gatacgttag ccgggctgca ctcaatgtac accgacatgt ggagtgaaga    360
gtatcagtgt gcatggctgg atatgtatca ccgcgtcttt gatcgcgtca gcgccgtcgt    420
cttttttttt                                                            429

SEQ ID NO: 222          moltype = DNA  length = 429
FEATURE                 Location/Qualifiers
source                  1..429
                        mol_type = other DNA
                        note = Recombinant
                        organism = synthetic construct
SEQUENCE: 222
catggtccat aggtatcaag atccagcatt gcacttgggc caaagattga gctctgcgaa      60
gtgtcaacta caatcatcta gatgggctcg acctgaaagg ccacacgatt tgccagaact    120
cccaccaatt aattagtacc acctcggttg ctcgatttag tagaagccag cttaaaagtt    180
cagctctggg gtccggtagc caagctgact ctagcagatc tccatgacgg cagagaaggt    240
actggaaaaa gaacttctgg cctggcagga gaaactgcat cagccgatta tcatcaccga    300
atacggcgtg gatacgttag ccgggctgca ctcaatgtac accgacatgt ggagtgaaga    360
gtatcagtgt gcatggctgg atatgtatca ccgcgtcttt gatcgcgtca gcgccgtcgt    420
cttttttttt                                                            429

SEQ ID NO: 223          moltype = DNA  length = 410
FEATURE                 Location/Qualifiers
source                  1..410
                        mol_type = other DNA
                        note = Recombinant
                        organism = synthetic construct
SEQUENCE: 223
catccaggtg aggcatcaag ctactactgc ctcgattggc tggacccgaa gcccacatgt      60
aggataccag aatgggccga cccaggacgc agtatgttgg ccagtcccac cggttagtgc    120
catctcggtt gctcacatgc gtagaagcca gcttaaaaat ttagctttgg taactcacag    180
ccaagctgac tctagcagat ctccatgacg gcagagaagg tactggaaaa agaacttctg    240
gcctggcagg agaaactgca tcagccgatt atcatcaccg aatacggcgt ggatacgtta    300
gccgggctgc actcaatgta caccgacatg tggagtgaag agtatcagtg tgcatggctg    360
gatatgtatc accgcgtctt tgatcgcgtc agcgccgtcg tctttttttt                 410

SEQ ID NO: 224          moltype = DNA  length = 429
FEATURE                 Location/Qualifiers
source                  1..429
                        mol_type = other DNA
                        note = Recombinant
                        organism = synthetic construct
SEQUENCE: 224
catcaataag ataaagctgg tgcaggctct cgacctgaag cccacacact ggagagcaac      60
gatataccag aatggagcgg cccagtacac gatctgctgg gattgctggc cagtggccag    120
tcccgcagcc gattagcacc acctcggtgg cacagacgaa cgaacgctaa tttaaaagct    180
tagctctgga gcttggcacc caagctgact ctagcagatc tccatgacgg cagagaaggt    240
actggaaaaa gaacttctgg cctggcagga gaaactgcat cagccgatta tcatcaccga    300
atacggcgtg gatacgttag ccgggctgca ctcaatgtac accgacatgt ggagtgaaga    360
gtatcagtgt gcatggctgg atatgtatca ccgcgtcttt gatcgcgtca gcgccgtcgt    420
cttttttttt                                                            429

SEQ ID NO: 225          moltype = DNA  length = 429
FEATURE                 Location/Qualifiers
source                  1..429
                        mol_type = other DNA
                        note = Recombinant
                        organism = synthetic construct
SEQUENCE: 225
gcgaggcatc aacaagataa agctggtgca ggctctcgac ctgaagccca cacacaggag      60
agcaacaata taccaggaat ggagcggccc agtacgcgat ctgctgggat tgctggctag    120
tcccgcaccc gattagcacc acctcgcttg ctcatacgag cgaacgcaaa tttaaaaggt    180
```

```
tagctctgga gtttggcagc caagctgact ctagcagatc tccatgacgg cagagaaggt    240
actggaaaaa gaacttctgg cctggcagga gaaactgcat cagccgatta tcatcaccga    300
atacggcgtg gatacgttag ccgggctgca ctcaatgtac accgacatgt ggagtgaaga    360
gtatcagtgt gcatggctgg atatgtatca ccgcgtcttt gatcgcgtca gcgccgtcgt    420
cttttttttt                                                           429

SEQ ID NO: 227           moltype = DNA   length = 442
FEATURE                  Location/Qualifiers
source                   1..442
                         mol_type = other DNA
                         note = Recombinant
                         organism = synthetic construct
SEQUENCE: 226
cctaactaat aagtatcgga ggcaacaacg cccgctgggc tgcggcccat taacatagca    60
ctagacggac accgccgcag tcagcgttca gccggatgca gtgcgatcgg cttcatccgt    120
ttagtcccac ctcgcccagc caaagcagcg gggaggcccg gactcgctac aaaaggagac    180
ggaggttggc tgtttagagc caagctgact ctagcagatc tccatgacgg cagagaaggt    240
actggaaaaa gaacttctgg cctggcagga gaaactgcat cagccgatta tcatcaccga    300
atacggcgtg gatacgttag ccgggctgca ctcaatgtac accgacatgt ggagtgaaga    360
gtatcagtgt gcatggctgg atatgtatca ccgcgtcttt gatcgcgtca gcgccgtcgt    420
cacaattcaa aacaagtttt at                                              442

SEQ ID NO: 227           moltype = DNA   length = 442
FEATURE                  Location/Qualifiers
source                   1..442
                         mol_type = other DNA
                         note = Recombinant
                         organism = synthetic construct
SEQUENCE: 227
gccagctgcg gtggaaacga ctgcggaccg ggctagcatc gacgtattgc cgtattagta    60
gcccagaaag cccacgcaac cagatagagg tctgaatgcc tgtactttgt ggtgcttcag    120
tttagtccca cctcggtggc tttcagcggg agagagcaga aaggcttat aaaagcagac    180
ctcagtcaac ataacaattc caagctgact ctagcagatc tccatgacgg cagagaaggt    240
actggaaaaa gaacttctgg cctggcagga gaaactgcat cagccgatta tcatcaccga    300
atacggcgtg gatacgttag ccgggctgca ctcaatgtac accgacatgt ggagtgaaga    360
gtatcagtgt gcatggctgg atatgtatca ccgcgtcttt gatcgcgtca gcgccgtcgt    420
cacaattcaa aacaagtttt at                                              442

SEQ ID NO: 228           moltype = DNA   length = 442
FEATURE                  Location/Qualifiers
source                   1..442
                         mol_type = other DNA
                         note = Recombinant
                         organism = synthetic construct
SEQUENCE: 228
tcaataaaca attggagcga gagagactct gctgaccggg ccatcattga cgtattggta    60
gcccagaaag cccacacagt catacagagg tctgaatgcc tgtgctttat ggtgcttgag    120
tttagtccca cctcggtggc tttcagcggg agagagcaga aaggcttat aaaagcagac    180
ctcagtcaac ataacaattc caagctgact ctagcagatc tccatgacgg cagagaaggt    240
actggaaaaa gaacttctgg cctggcagga gaaactgcat cagccgatta tcatcaccga    300
atacggcgtg gatacgttag ccgggctgca ctcaatgtac accgacatgt ggagtgaaga    360
gtatcagtgt gcatggctgg atatgtatca ccgcgtcttt gatcgcgtca gcgccgtcgt    420
cacaattcaa aacaagtttt at                                              442

SEQ ID NO: 229           moltype = DNA   length = 442
FEATURE                  Location/Qualifiers
source                   1..442
                         mol_type = other DNA
                         note = Recombinant
                         organism = synthetic construct
SEQUENCE: 229
gaccccatct atgccgtaat tctggcttca cccctgatca agctatcgta ccttaaatgc    60
gtcgtttcac gttttttcacc ttgttggagg tctgaatgtc tgtgctttgt ggtgcttcaa    120
tttagtccca ccttgtcggc tttcaacggg agggagcgga gaaggcttat aaaagcagac    180
cctagtcaac ataacaattc caagctgact ctagcagatc tccatgacgg cagagaaggt    240
actggaaaaa gaacttctgg cctggcagga gaaactgcat cagccgatta tcatcaccga    300
atacggcgtg gatacgttag ccgggctgca ctcaatgtac accgacatgt ggagtgaaga    360
gtatcagtgt gcatggctgg atatgtatca ccgcgtcttt gatcgcgtca gcgccgtcgt    420
cacaattcaa aacaagtttt at                                              442

SEQ ID NO: 230           moltype = DNA   length = 442
FEATURE                  Location/Qualifiers
source                   1..442
                         mol_type = other DNA
                         note = Recombinant
                         organism = synthetic construct
SEQUENCE: 230
ggtggaaacg gactcgagcg agagagactc tgcggaccgg gccagcatcg atgtattggt    60
agcccagaaa gcccacgcaa ccagacagag gtatgaatgt tgtgctttgt ggtgcttcag    120
```

```
tttagtccca cctcggcggt tttcagcgga agggagcaga gaaggcttat aaaagcagac    180
ctcagtcaac ataacaattc caagctgact ctagcagatc tccatgacgg cagagaaggt    240
actggaaaaa gaacttctgg cctggcagga gaaactgcat cagccgatta tcatcaccga    300
atacggcgtg gatacgttag ccgggctgca ctcaatgtac accgacatgt ggagtgaaga    360
gtatcagtgt gcatggctgg atatgtatca ccgcgtcttt gatcgcgtca gcgccgtcgt    420
cacaattcaa aacaagtttt at                                             442

SEQ ID NO: 231            moltype = DNA   length = 442
FEATURE                   Location/Qualifiers
source                    1..442
                          mol_type = other DNA
                          note = Recombinant
                          organism = synthetic construct
SEQUENCE: 231
tccctttgtc gccttgctgt tcgctccgtt tgttgggccg gacatgtggc tttctgggcc    60
gcgcacgtag agtcctcctg gccagtgtcg ggctctggct ggctgcctgc tcttttttct    120
gtagtcccaa accgcttgct gaggctaata tcagccggga acaacgctat ttaggattga    180
ctgaactctg tgtaagaggc caagctgact ctagcagatc tccatgacgg cagagaaggt    240
actggaaaaa gaacttctgg cctggcagga gaaactgcat cagccgatta tcatcaccga    300
atacggcgtg gatacgttag ccgggctgca ctcaatgtac accgacatgt ggagtgaaga    360
gtatcagtgt gcatggctgg atatgtatca ccgcgtcttt gatcgcgtca gcgccgtcgt    420
cacaattcaa aacaagtttt at                                             442

SEQ ID NO: 232            moltype = DNA   length = 442
FEATURE                   Location/Qualifiers
source                    1..442
                          mol_type = other DNA
                          note = Recombinant
                          organism = synthetic construct
SEQUENCE: 232
cctttgtggc ttcgcttcat tctcttcatc cgtttgtgac cggagtcagc ggctgtcgac    60
cgcggcgcat cctctgacta gcactgcgtc tggctggctc tggctgcttc agcttgcttt    120
agttcccaaa cccgcttgct gtagctaata ccagcaggga gcgctgctat ttaggatgga    180
ctgggcgctg cgagagaagc caagctgact ctagcagatc tccatgacgg cagagaaggt    240
actggaaaaa gaacttctgg cctggcagga gaaactgcat cagccgatta tcatcaccga    300
atacggcgtg gatacgttag ccgggctgca ctcaatgtac accgacatgt ggagtgaaga    360
gtatcagtgt gcatggctgg atatgtatca ccgcgtcttt gatcgcgtca gcgccgtcgt    420
cacaattcaa aacaagtttt at                                             442

SEQ ID NO: 233            moltype = DNA   length = 442
FEATURE                   Location/Qualifiers
source                    1..442
                          mol_type = other DNA
                          note = Recombinant
                          organism = synthetic construct
SEQUENCE: 233
ggcctttcgct tcctcgctct tcgctccttt gttgggccgg acaacaagcg gctgtctggg    60
ccgcgcacgc agtcctctgg tccagtgggc aactgcctct ggctgcttgc tcttttcctt    120
aatcccaaac cgctcgatga agctaatacc agctggggga cgctgctatt taggagagac    180
taagcgccac ccgtagatgc caagctgact ctagcagatc tccatgacgg cagagaaggt    240
actggaaaaa gaacttctgg cctggcagga gaaactgcat cagccgatta tcatcaccga    300
atacggcgtg gatacgttag ccgggctgca ctcaatgtac accgacatgt ggagtgaaga    360
gtatcagtgt gcatggctgg atatgtatca ccgcgtcttt gatcgcgtca gcgccgtcgt    420
cacaattcaa aacaagtttt at                                             442

SEQ ID NO: 234            moltype = DNA   length = 442
FEATURE                   Location/Qualifiers
source                    1..442
                          mol_type = other DNA
                          note = Recombinant
                          organism = synthetic construct
SEQUENCE: 234
ttcgcttcat ttctcttcac tccgtttgtt gggccggaca tcaagcggct gtctgggccg    60
cgcacgcagt cctcttgact agcactgcgt ctggctgct ctggctgcttc agctttgct    120
ttagttccaa accgcttgct gtagctaata ccagcaggga gcgctgctat ttaggatgga    180
ctgggcgctg cgagagaagc caagctgact ctagcagatc tccatgacgg cagagaaggt    240
actggaaaaa gaacttctgg cctggcagga gaaactgcat cagccgatta tcatcaccga    300
atacggcgtg gatacgttag ccgggctgca ctcaatgtac accgacatgt ggagtgaaga    360
gtatcagtgt gcatggctgg atatgtatca ccgcgtcttt gatcgcgtca gcgccgtcgt    420
cacaattcaa aacaagtttt at                                             442

SEQ ID NO: 235            moltype = DNA   length = 427
FEATURE                   Location/Qualifiers
source                    1..427
                          mol_type = other DNA
                          note = Recombinant
                          organism = synthetic construct
SEQUENCE: 235
ggcgtatgtg ccaaaaactt cgtcacagag agggccataa gaaacatggc ccacggccca    60
```

```
atacgaagca ccgcgacgaa gcccaaacag cagtccgtag gtggagcaaa gcgctgggta   120
atacgcaaac gttttgtccc accttgacta atcacaagag tggagcgtac cttataaacc   180
gagccgcaag caccgaattc aagctgactc tagcagatct ccatgacggc agagaaggta   240
ctggaaaaag aacttctggc ctggcaggag aaactgcatc agccgattat catcaccgaa   300
tacggcgtgg atacgttagc cgggctgcac tcaatgtaca ccgacatgtg gagtgaagag   360
tatcagtgtg catggctgga tatgtatcac cgcgtctttg atcgcgtcag cgccgtcgtc   420
tttttttt                                                            427

SEQ ID NO: 236            moltype = DNA  length = 428
FEATURE                   Location/Qualifiers
source                    1..428
                          mol_type = other DNA
                          note = Recombinant
                          organism = synthetic construct
SEQUENCE: 236
gcgtggtctg cttttccgca tgatatctgg gccgcaccaa agaatccagc ccacgcggcg   60
tggcgccgtc gttacggctt gcggggaag gaaacgaggg acgaaccgag atttagcacc   120
agaccggcca gcgagcattg cagacaccgg cttataagtt cagctgcgac taccactccg   180
ggaggtccga gttccactcg caagctgact ctagcagatc tccatgacgg cagagaaggt   240
actgaaaaaa gaacttctgg cctgcgcagga gaaactgcat cagccgatta tcatcaccga   300
atacggcgtg gatacgttag ccgggctgca ctcaatgtac accgacatgt ggagtgaaga   360
gtatcagtgt gcatggctgg atatgtatca ccgcgtcttt gatcgcgtca gcgccgtcgt   420
ctttttt                                                             428

SEQ ID NO: 237            moltype = DNA  length = 21
FEATURE                   Location/Qualifiers
source                    1..21
                          mol_type = other DNA
                          note = Recombinant
                          organism = synthetic construct
SEQUENCE: 237
acaattcaaa acaagtttta t                                              21

SEQ ID NO: 238            moltype = DNA  length = 4622
FEATURE                   Location/Qualifiers
source                    1..4622
                          mol_type = other DNA
                          note = Recombinant
                          organism = synthetic construct
SEQUENCE: 238
atgggatcta agaagagaag aattaaacaa gatatgagtg acctggtgct agggttggct   60
ataggcattg gctccgtggg ggttggcatt cttaataagg tgaccggcga ataattcat    120
aaaaactcac gcatctttcc agcagcccag gctgagaaca atctggtccg tagaaccaac   180
cggcagggtc gaaggttagc caggcgcaag aagcacagac gggtccggct caacaggctt   240
ttcgaggagt ctggtttgat caccgatttc actaagattt ctatcaacct gaatccttat   300
cagctgcgcg ttaaaggtct cacagacgaa cttagcaacg aagagttgtt catcgccctg   360
aaaaatatgg tcaagcatcg cggcattagc tacctggacg acgcttcgga tgatggcaac   420
agtagtgtag gtgactacgc tcagatcgtg aaagagaact cgaagcaatt ggagaccaag   480
accccgggcc aaaattcaact cgaaaggtaa gtttctgctt ctacctttga tatatatata   540
ataattatca ttaattagta gtaatataat atttcaaata ttttttttcaa aataaaagaa   600
tgtagtatat agcaattgct tttctgtagt ttataagtgt gtatatttta atttataact   660
tttctaatat atgaccaaaa tttgttgatg tgcaggtacc agacgtatgg acagttacga   720
ggcgatttta ccgttgaaaa ggatggtaag aagcacaggc tgattaatgt gtttccgacc   780
tcagcttatc gctctgaggc gctgcgtatt ttgcagaccc aacaggaatt taacccgcaa   840
ataaccggacg agttcataaa ccgatactta gagattctta caggtaaacg taaatactat   900
cacggcccag gaaatgaaaa gtccaggaca gattatggtc gatatcgcac ttccggagag   960
actctcgaca atatctttgg cattcttata ggcaaatgta ccttctaccc tgacgaattt   1020
agagcagcga aggcttcata tacagcacaa gagtttaatc ttctcaacga cctcaacaac   1080
ttgactgtgc ctactgaaac caaaaagctt agcaaggagc aaaaaaatca aatcattaac   1140
tatgttaaga atgagaaagc tatgggccc gcaaaattgt tcaagtacat agctaagtta   1200
cttagctgtg acgttgctga tattaagggt accgtattg acaagtctgg taaagctgaa   1260
attcacacct tgaggcctta taggaagatg aagacccttg agacacttga cattgagcag   1320
atggataggg agactttgga caaactggca tacgtcttga cattgaacac cgaaagggaa   1380
ggcatccagg aagctctgga acatgaattt gcagatgctt cgttcagcca aaaacaggtt   1440
gacgagctgg tccaatttag aaaggcaaac tcaagcatat tcggtaaagg ttggcacaac   1500
ttcagcgtta agctgatgat ggaactcatt ccagaattat atgaacctct gaggaacag   1560
atgacgattc tcacaagatt gggtaagcag aaaacaacca gctctagcaa taagactaaa   1620
tacattgacg aaaagctcct caccgaagag atttataacc cggtcgtggc aaagagtgta   1680
cggcaagcca tcaagatcgt taatgccgct atcaaggagt atggtgattt tgataataat   1740
gtgattgaaa tggcacgcga gactaacgag gacgacgaga agaaagctat acagaagatt   1800
caaaaggcta ataaggacga gaaggacgcc gcaatgctaa agcggccaa tcaatataat   1860
gggaaggctg aactacctca tagcgtcttc catggacata gcaattagc aactaaaata   1920
agattatggc accagcaagg cgaacggtgt ctttatacag gtaaaacgat atctattcac   1980
gacctgatta caactctaa ccagtttgaa gtggatgcta tcttaccact aagtatccaa   2040
ttcgacgatt cacttgctaa caaggtgctc gtttacgcca ctgcgaacca agagaaaggg   2100
cagaggactc cataccaggc ccttgacagc atgacgacg cctggagttt agggaatta    2160
aaagctttcg tacgtgagtc aaagacgctt tcaaataaaa aaaggagta cttgctcact   2220
gaagaagaca tctcaaaatt cgacgtgcgc aaaaaattca ttgagcggaa cttagtcgac   2280
actcggtacg catcaagagt agtgttgaac gccctccagg agcactttag ggcacataag   2340
```

-continued

```
atcgacacca aggtttcagt tgttaggggt cagtttacat cgcagcttag acgccattgg    2400
ggtatagaaa aaacacgtga tacctaccat caccatgcag ttgacgctct catcattgca    2460
gcatcttctc aacttaattt gtggaaaaag caaaagaaca ctctggtctc atatagcgaa    2520
gatcagctgc ttgatattga aaccggcgag ctgatttctg acgacgaata caaagaatct    2580
gtgtttaagg caccatatca acactttgta gacacgctta aatctaaaga gtttgaggat    2640
tcgatccttt tcagttacca agtcgactca aaatttaacc gtaagatctc tgatgcaaca    2700
atttatgcga cgaggcaggc caaggtaggt aaggataagg ctgacgaaac ctacgtgctc    2760
ggaaaaatca aagatattta cactcaagat ggatatgatg cattcatgaa gatatataaa    2820
aaggacaaat ctaaattcct tatgtatcgt catgacccac agacattcga gaagtttatt    2880
gagcctatcc tggagaacta tccgaacaag caaatcaaaaatg agaagggcaa agaagttcca    2940
tgtaatccgt tcctaaagta caaggaggaa cacggatata ttagaaaata cagcaaaaag    3000
ggcaacggcc cagaaatcaa aagccttaag tactacgata gtaaactagg aaaccacatc    3060
gacattacac caaaagactc taataataag gtcgtactgc aaagcgtttc cccatggcgc    3120
gccgatgtgt attttaataa gacaacaggg aagtacgaaa tcttggggtt aaaatatgcg    3180
gatctgcaat tcgaaaaggg aaccggcaca tacaaaattt ctcaagaaaa gtacaacgac    3240
ataaagaaga aggaagggt cgattctgat tctgaattca agttcacact ctataagaat    3300
gatcttctgc tcgtcaagga cacagagaca aggagcagc agttgttcag gttcttgtct    3360
agaactatgc caaaacaaaa cactacgtt gaactgaaca cttacgataa gcaaaaattc    3420
gaggggggcg aggcgcttat aaaggtccta ggaaatgttg caaactctgg gcagtgtaag    3480
aagggcctgg gcaagagcaa cattagcatc tataaggttc gaacggatgt gcttgggaac    3540
cagcatatca tcaaaaacga gggagataaa ccaaagctgg acttcggatc ttctattgtg    3600
gcgcagctct caagaaggga cccggcgcta gcggctctga ctaatgacca tctcgtggct    3660
ctggcttgcc tggggggggcg gcctgctctg gacgctgtga agaaggggct cccacacgcg    3720
ccagagttca tccgcagggt gaacaggagg attgctgagc ggacaagcca cagggtcgct    3780
gactacgctc atgtggtccg cgttctggag ttcttccagt gccactcgca tccggctcac    3840
gccttcgatg aggccatgac ccagtccggc atgtctcggc atggcgtgt cagctcttc    3900
aggcgggttg gcgtgactga gttcgaggct cgctacggga ccctgccacc agcgtcccga    3960
cgctgggaca ggatcctcca ggcgagcggc atgaagaggg ctaagccaag ccctacctcg    4020
gctcagacgc cagaccagac atctctccac gcgttcgctg attcactgga gagggacctc    4080
gatgctccat ccccaatgca tgagggcgac cagaccaggg cgtccagccg caaggagtca    4140
cggtccgata gggctgtgac gggggccatcg gctcagcagg ctgtcgaggt taggggtgcct    4200
gagcagaggg acgctctcca cctgccactc tcctggaggg tcaagcgccc taggacgagg    4260
atctggggcg ggctgccaga ccctggcaca ccgattgccg cggatctcgc tgcctcgtct    4320
actgtttatgt gggagcagga cgctgctcca ttcgctggcg ctgctgacga tttcccagcc    4380
ttcaatgagg aggagctggc ttggctgatg gagctgctgc ctcagtcggg gtcggttggc    4440
gggacaatcg ctgccgacct ggcggcttcg tctaccgtca tgtgggagca ggacgccgcg    4500
ccgttcgctg gcgctgccga cgatttccct gcgttcaacg aggaggagct ggcgtggctg    4560
atggagctgc tgccccagag cgggagcgtc ggcgggacaa tctgaagcag aacacgcgct    4620
ga                                                                  4622
```

SEQ ID NO: 239     moltype = AA   length = 1471
FEATURE            Location/Qualifiers
source             1..1471
                   mol_type = protein
                   note = Recombinant
                   organism = synthetic construct

```
SEQUENCE: 239
MGSKKRRIKQ DMSDLVLGLA IGIGSVGVGI LNKVTGEIIH KNSRIFPAAQ AENNLVRRTN     60
RQGRRLARRK KHRRVRLNRL FEESGLITDF TKISINLNPY QLRVKGLTDE LSNEELFIAL    120
KNMVKHRGIS YLDDASDDGN SSVGDYAQVI KENSKQLETK TPGQIQLERY QTYGQLRGDF    180
TVEKDGKKHR LINVFPTSAY RSEALRILQT QQEFNPQITD EFINRYLEIL TGKRKYYHGP    240
GNEKSRTDYG RYRTSGETLD NIFGILIGKC TFYPDEFRAA KASYTAQEFN LLNDLNNLTV    300
PTETKKLSKE QKNQIINYVK NEKAMGPAKL FKYIAKLLSC DVADIKGYRI DKSGKAEIHT    360
FEAYRKMKTL ETLDIEQMDR ETLDKLAYVL TLNTEREGIQ EALEHEFADG SFSQKQVDEL    420
VQFRKANSSI FGKGWHNFSV KLMMELIPEL YETSEEQMTI LTRLGKQKTT SSSNKTKYID    480
EKLLTEEIYN PVVAKSVRQA IKIVNAAIKE YGDFDNIVIE MARETNEDDE KKAIQKIQKA    540
NKDEKDAAML KAANQYNGKA ELPHSVFHGH KQLATKIRLW HQQGERCLYT GKTISIHDLI    600
NNSNQFEVDA ILPLSITFDD SLANKVLVYA TANQEKGQRT PYQALDSMDD AWSFRELKAF    660
VRESKTLSNK KKEYLLTEED ISKFDVRKKF IERNLVDTRY ASRVVLNALQ EHFRAHKIDT    720
KVSVVRGQFT SQLRRHWGIE KTRDTYHHHA VDALIIAASS QLNLWKKQKN TLVSYSEDQL    780
LDIETGELIS DDEYKESVFK APYQHFVDTL KSKEFEDSIL FSYQVDSKFN RKISDATIYA    840
TRQAKVGKDK ADETYVLGKI KDIYTQDGYD AFMKIYKKDK SKFLMYRHDP QTFEKVIEPI    900
LENYPNKQIN EKGKEVPCNP FLKYKEEHGY IRKYSKKGNG PEIKSLKYYD SKLGNHIDIT    960
PKDSNNKVVL QSVSPWRADV YFNKTTGKYE ILGLKYADLQ FEKGTGTYKI SQEKYNDIKK   1020
KEGVDSDSEF KFTLYKNDLL LVKDTETKEQ QLFRFLSRTM PKQKHYVELK PYDKQKFEGG   1080
EALIKVLGNV ANSGQCKKGL GKSNISIYKV RTDVLGNQHI IKNEGDKPKL DFGSSIVAQL   1140
SRRDPALAAL TNDHLVALAC LGGRPALDAV KKGLPHAPEF IRRVNRRIAE RTSHRVADYA   1200
HVVRVLEFFQ CHSHPAHAFD EAMTQFGMSR HGLVQLFRRV GVTEFEARYG TLPPASQRWD   1260
RILQASGMKR AKPSPTSAQT PDQTSLHAFA DSLERDLDAP SPMHEGDQTR ASSRKRSRSD   1320
RAVTGPSAQQ AVEVRVPEQR DALHLPLSWR VKRPRTRIWG GLPDPGTPIA ADLAASSTVM   1380
WEQDAAPFAG AADDFPAFNE EELAWLMELL PQSGSVGGTI AADLAASSTV MWEQDAAPFA   1440
GAADDFPAFN EELAWLMEL LPQSGSVGGT I                                   1471
```

SEQ ID NO: 240     moltype = DNA   length = 27
FEATURE            Location/Qualifiers
source             1..27
                   mol_type = other DNA
                   note = Recombinant
                   organism = synthetic construct

```
SEQUENCE: 240
ggaggtccga gttccactcg caagaat                                        27

SEQ ID NO: 241           moltype = DNA  length = 353
FEATURE                  Location/Qualifiers
source                   1..353
                         mol_type = other DNA
                         note = Recombinant
                         organism = synthetic construct
SEQUENCE: 241
ggcgtatgtg ccaaaaactt cgtcacagag agggccataa gaaacatggc ccacggccca   60
atacgaagca ccgcgacgaa gcccaaacag cagtccgtag gtggagcaaa gcgctgggta  120
atacgcaaac gttttgtccc accttgacta atcacaagag tggagcgtac cttataaacc  180
gagccgcaag caccgaattg ggaggtccga gttccactcg gttattgtac tctcaagatt  240
tatttttcca aaagggttac ttaaatcttg cagaagctac aaagataagg cttcatgccg  300
aaatcaacac cctgtcattt tatggcaggg tgttttcgtt atttaatttt ttt          353

SEQ ID NO: 242           moltype = DNA  length = 350
FEATURE                  Location/Qualifiers
source                   1..350
                         mol_type = other DNA
                         note = Recombinant
                         organism = synthetic construct
SEQUENCE: 242
tttcatccgg cctgtgatgg aaattgtgct gcaaagtgcg cagggccgtt ggcccgacga   60
caagtatttt tcgtcgagag aagcaacgaa agcccactcc tccaagccac ccttcgctca  120
agtcatattt agcaccacct cggcagtcga cactgcagca caccaactta aatattcatc  180
ccgatctccc tcactcggga ggtccgagtt ccactcggtt attgtactct caagatttat  240
ttttccaaaa gggttactta aatcttgcag aagctacaaa gataaggctt catgccgaaa  300
tcaacaccct gtcattttat ggcagggtgt ttcgttatt taattttttt              350

SEQ ID NO: 243           moltype = DNA  length = 360
FEATURE                  Location/Qualifiers
source                   1..360
                         mol_type = other DNA
                         note = Recombinant
                         organism = synthetic construct
SEQUENCE: 243
aacggactcg agcgagagag actctgcgga ccgggccagc atcgatgtat tggtagccc    60
agagcccacg caaccagaca gaggtatgaa tgttgtgctt tgtggtgctt cagtttagtc  120
ccacctcggc ggttttcagc ggaagggagc agagaaggct tataaaagca gacctcagtc  180
aacataacaa ttaggaggtc cgagttccac tcggttattg tactctcaag atttattttt  240
ccaaaaggt tacttaaatc ttgcagaagc tacaaagata aggcttcatg ccgaaatcaa   300
caccctgtca ttttatggca gggtgttttc gttatttaat caaattcaaa tttttttaa   360

SEQ ID NO: 244           moltype = DNA  length = 373
FEATURE                  Location/Qualifiers
source                   1..373
                         mol_type = other DNA
                         note = Recombinant
                         organism = synthetic construct
SEQUENCE: 244
aggcgttcgc ttcatttctc ttcactccgt ttgttgggcc ggacatcaag cggctgtctg   60
ggccgcgcac gcagtcctct tgactagcac tgcgtctggc tggctctggc tgcttcagct  120
ttgctttagt tccaaaacgc ttgctgtagc taataccagc agggagcgct gctatttagg  180
atggactggg cgctgcgaga gaagcaggag gtccgagttc cactcggtta ttgtactctc  240
aagatttatt ttccaaaag ggttacttaa atcttgcaga agctacaaag ataaggcttc   300
atgccgaaat caacaccctg tcattttatg gcagggtgtt tcgttatttt aatcaaattc  360
aaatttttttt taa                                                     373

SEQ ID NO: 245           moltype = DNA  length = 348
FEATURE                  Location/Qualifiers
source                   1..348
                         mol_type = other DNA
                         note = Recombinant
                         organism = synthetic construct
SEQUENCE: 245
caataagata aagctggtgc aggctctcga cctgaagccc acacactgga gagcaacgat   60
ataccagaat ggagcggccc agtacacgat ctgctgggat tgctggccag tggccagtcc  120
cgcagccgat tagcaccacc tcggtggcac agacgaacga acgctaattt aaaagcttag  180
ctctggagct tggcaggagg tccgagttcc actcggttat tgtactctca agatttattt  240
tccaaaagg gttacttaaa tcttgcagaa gctacaaaga taaggcttca tgccgaaatc   300
aacaccctgt cattttatgg cagggtgttt tcgttattta attttttt                348

SEQ ID NO: 246           moltype = DNA  length = 3131
FEATURE                  Location/Qualifiers
source                   1..3131
                         mol_type = other DNA
                         note = Recombinant
```

```
                        organism = synthetic construct
SEQUENCE: 246
gaattcctat gataaagttg ctctgtaaca gaaaacacca tctaggtcga cttacttgcg    60
gccgcttact tggcgcgccg gaggtccgag ttccactcgc aagaatttgc ttcttgggag   120
gtccgagttc cactcgcaag aatcctctca ttaggaggtc cgagttccac tcgcaagaat   180
attattcgca agaccccttcc tctatataaga gaagttcatt tcatttggag aggacacgct   240
gaaatcacca gtctctctct acaaatctat ctctctctat tttccggacc gaccgtcttc   300
ggtacgcgct cactccgccc tctgcctttg ttactgccac gtttctctga atgctctctt   360
gtgtggtgat tgctgagagt ggtttagctg gatctagaat tacactctga aatcgtgttc   420
tgcctgtgct gattacttgc cgtcctttgt agcagcaaaa tatagggaca tggtagtacg   480
aaacgaagat agaacctaca cagcaatacg agaaatgtgt aatttggtgc ttagcggtat   540
ttatttaagc acatgttggt gttataggc acttggattc agaagtttgc tgttaattta   600
ggcacaggct tcatactaca tgggtcaata gtataggat tcatattata ggcgatacta   660
taataatttg ttcgtctgca gagcttatta tttgccaaaa ttagatattc ctattctgtt   720
tttgtttgtg tgctgttaaa ttgttaacgc ctgaaggaat aaatataaat gacgaaattt   780
tgatgtttat ctctgctcct ttattgtgac cataagtcaa gatcagatgc acttgtttta   840
aatattgttg tctgaagaaa taagtactga cagtatttttg atgcattgat ctgcttgttt   900
gttgtaacaa aatttaaaaa taaagagttt ccttttttgtt gctctcctta cctcctgatg   960
gtatctagta tctaccaact gacactatat tgcttctctt tacatacgta tcttgctcga  1020
tgccttctcc ctagtgttga ccagtgttac tcacatagtc tttgctcatt tcattgtaat  1080
gcagatacca agcggggtac cctcagcgct gtgcctgttg cgatcgcacc atggtccgtc  1140
ctgtagaaac cccaaccgt gaaatcaaaa acctcgtggca ttcagtctgg  1200
atcgcgaaaa ctgtgaatt gatcagcgtt ggtgggaaag cgcgttacaa gaaagccggg  1260
caattgctgt gccaggcagt tttaacgatc agttcgccga tgcagatatt cgtaattatg  1320
cgggcaacgt ctggtatcag cgcgaagtct ttataccgaa aggttgggca ggccagcgta  1380
tcgtgctgcg tttcgatgcg gtcactcatt acggcaaagt gtgggtcaat aatcaggaag  1440
tgatggagca tcagggcggc tatacgccat ttgaagccga tgtcacgccg tatgttattg  1500
ccgggaaaag tgtacgtaag tttctgcttc tacctttgat atatatataa taattatcat  1560
taattagtag taatataata tttcaaatat ttttttcaaa ataaagaat gtagtatata  1620
gcaattgctt ttctgtagtt tataagtgtg tatattttaa tttataactt ttctaatata  1680
tgaccaaaat ttgttgatgt gcaggtatca ccgtttgtgt gaacaacgaa ctgaactggc  1740
agactatccc gccgggaatg gtgattaccg acgaaacgg caagaaaaag cagtcttact  1800
tccatgattt ctttaactat gccggaatcc atcgcagcgt aatgctctac accacgccga  1860
acacctgggt ggacgatatc accgtggtga cgcatgtcgc gcaagactgt gcaacacgcg  1920
ctgttgactg gcaggtggtg gccaatggtg atgtcagcgt tgaactgcgt gatgcggatc  1980
aacaggtggt tgcaactgga caaggcacta gcgggacttt gcaagtggtg aatccgcacc  2040
tctggcaacc gggtgaaggt tatctctatg aactgtgcgt cacagccaaa agccagacag  2100
agtgtgatat ctacccgctt cgcgtcggca tccggtcagt ggcagtgaag ggcgaacagt  2160
tcctgattaa ccacaaaccg ttctactta ctggcttttgg tcgtcatgaa gatcggaact  2220
tgcgtggcaa aggattcgat aacgtgctga tggtgcacga ccacgcatta atggactgga  2280
ttggggccaa ctcctaccgt acctcgcatt accttacgc tgaagagatg ctcgactggg  2340
cagatgaaca tggcatcgtg gtgattgatg aaactgctgc tgtcggcttt aacctctctt  2400
taggcattgg tttcgaagcg ggcaacaagc cgaaagaact atacagcgaa gaggcagtca  2460
acggggaaac tcagcaagcg cacttacagg cgattaaaga agctgatacg cgtgacaaaa  2520
accacccaag cgtggtgatg tggagtattg ccaacgaacc ggataccgt ccgcaaggtg  2580
cacgggaata tttcgcgcca ctggcggaag caacgcgtaa actcgacccg acgcgtccga  2640
tcacctgcgt caatgtaatg ttctgcgacg ctcacaccga taccatcagc gatctctttg  2700
atgtgctgtg cctgaaccgt tattacggat ggtatgtcca aagcggcgat ttggaaacgg  2760
cagagaaggt actggaaaaa gaacttctcg cctggcagga gaaactgcat cagccgatta  2820
tcatcaccga atacggcgtg gatacgttag ccgggctgca ctcaatgtac accgacatgt  2880
ggagtgaaga atatcagtgt gcatggctgg atatgtatca ccgcgtcttt gatcgcgtca  2940
gcgccgtcgt cggtaacag gtatggaatt cgccgatttt gcgacctcg caaggcatat  3000
tgcgcgttgg cggtaacaag aaagggatct tcactcgcga ccgcaaaccg aagtcggcgg  3060
ctttttctgct gcaaaaacgc tggactggca tgaacttcgg tgaaaaaccg cagcagggag  3120
gcaaacaatg a                                                       3131

SEQ ID NO: 247           moltype = DNA   length = 200
FEATURE                  Location/Qualifiers
source                   1..200
                         mol_type = genomic DNA
                         organism = Glycine max
SEQUENCE: 247
atccaagcaa aatacttgga agatacgaaa gtgtttgaaa tcagttatta gtttcacgtt    60
tgataaaatt gctgatttaa atttttgact gttgctctcg gctaggaatg ttgcaagcga   120
agaagtccca catttgtcag aacattggca ggcagctgaa gctcactgta taaaaatgga   180
gtacttggat agttgaaagc                                               200

SEQ ID NO: 248           moltype = DNA   length = 200
FEATURE                  Location/Qualifiers
source                   1..200
                         mol_type = genomic DNA
                         organism = Glycine max
SEQUENCE: 248
acttgtttga actcaattat tagtctcaag ttcgaagaat attggataaa ctcaactgcc    60
gatttaaatt tgaaaatgtt gttcttgtgt agagatttta ggagcatctg acaccagtga   120
caaagtccca catttgtcag aacactgaca atcagctaat gctgacagta taaaagtgga   180
gtacttggaa ggttgaaagc                                               200

SEQ ID NO: 249           moltype = DNA   length = 200
```

| FEATURE | Location/Qualifiers |
|---|---|
| source | 1..200 |
| | mol_type = genomic DNA |
| | organism = Glycine max |

SEQUENCE: 249
```
aacgtgtttg aactcaatta ttagtctcaa gtttgaagag tactggataa actcaactgc   60
tgcattaaat ttgaaactgt tagttcttgt ttggagattt tagaagcatc ttacacaagt  120
cagagcccca cattcgtcag aacactgaca agcagctaat gctcacagta taaaagttga  180
atacttagac gtttcaaagc                                              200
```

| SEQ ID NO: 250 | moltype = DNA  length = 200 |
|---|---|
| FEATURE | Location/Qualifiers |
| source | 1..200 |
| | mol_type = genomic DNA |
| | organism = Glycine max |

SEQUENCE: 250
```
tagttatctg gtttcgttaa ttgtggttga agcctgaagg catccattat ccctaactat   60
cctggatggt tgcaaatact gtcctaagta ctacagaaac aagaagactg acagtgtaac  120
gaagtaccac gtctctcaag agaaataaca agcgttgaag actaaactat aaataaaaac  180
attatttcat tgtacaaagc                                              200
```

| SEQ ID NO: 251 | moltype = DNA  length = 200 |
|---|---|
| FEATURE | Location/Qualifiers |
| source | 1..200 |
| | mol_type = genomic DNA |
| | organism = Glycine max |

SEQUENCE: 251
```
aaataaaccc gttgaatgaa tggaccgaag acaatctgaa tccaaaaaag atagctatca   60
ttgcttgtga ttgaactggc tcatgctctg catccgaaca aaacttggag acacttataa  120
cgaagtccca cattgctgag atgagataac actcgcttca gatttattta taaaaaacgc  180
attacatatt gtggaaactc                                              200
```

| SEQ ID NO: 252 | moltype = DNA  length = 200 |
|---|---|
| FEATURE | Location/Qualifiers |
| source | 1..200 |
| | mol_type = genomic DNA |
| | organism = Glycine max |

SEQUENCE: 252
```
attaattgtg gatgatggca tccattatcc gtggtatttg ttagacttgg atggttgctg   60
gtcgaccaaa caaatactgt cctaaggact acaaaaacaa gaagactgac agtgcaacaa  120
agtatcacat cattcaagag aaataacaag cgctaaagac taaactttta aaaaaaatgc  180
attattccat tgttcaaagc                                              200
```

| SEQ ID NO: 253 | moltype = DNA  length = 200 |
|---|---|
| FEATURE | Location/Qualifiers |
| source | 1..200 |
| | mol_type = genomic DNA |
| | organism = Glycine max |

SEQUENCE: 253
```
tgttaattgt gtttgaggac atccattatc caacattaga acaagatttg ttagacttgg   60
atagttgcta atcgagaagt cccagcaaat actacagaaa ctagaaagct attgatgtaa  120
tgaagtccca catcgctcaa gagaaataac aagcactgaa gactgaagta taaacaagc   180
attatttcat tgtgcaaagc                                              200
```

| SEQ ID NO: 254 | moltype = DNA  length = 200 |
|---|---|
| FEATURE | Location/Qualifiers |
| source | 1..200 |
| | mol_type = genomic DNA |
| | organism = Glycine max |

SEQUENCE: 254
```
atgaatggaa cggcttgagt ttcgctcaac tgcaggaaaa tgtggattgc agacaatctg   60
aatcccaaaa agatagttat ccttgcttgt tatcagaact agacttggac acacttatta  120
cgatggccca tatcgcttag atgagataac actcgcttca gatttattta taaaaaatgc  180
attgtatgtt gtgtaaactc                                              200
```

| SEQ ID NO: 255 | moltype = DNA  length = 200 |
|---|---|
| FEATURE | Location/Qualifiers |
| source | 1..200 |
| | mol_type = genomic DNA |
| | organism = Glycine max |

SEQUENCE: 255
```
gtttcatgat tccgatcaaa gcaagagcat ccagtctcaa ttttgtcttc tcaattcact   60
cattcatcaa aatcagcagt tttatgcatc aacaagcatg gaatgttgaa ccacccatga  120
ttaagcccca tatcgttgtg ttgagataac tatcacctga agttgtctta taaaaaacac  180
atctgaatac ttttataatc                                              200
```

| SEQ ID NO: 256 | moltype = DNA  length = 200 |
|---|---|
| FEATURE | Location/Qualifiers |
| source | 1..200 |

```
                        mol_type = genomic DNA
                        organism = Glycine max
SEQUENCE: 256
agtaaaatat caacgggaag attataatgt gtttgaactt tcattagtct cagatttgaa    60
cttttatgtt gctgatctaa attttttaacc atgttgctct tggctaggat gttgggatga  120
attagtccca catttgtcag aactttgtca ggaagctgaa gctcccagta taaaatttga   180
atacttacat tgtacaaagc                                               200

SEQ ID NO: 257          moltype = DNA   length = 200
FEATURE                 Location/Qualifiers
source                  1..200
                        mol_type = genomic DNA
                        organism = Glycine max
SEQUENCE: 257
attcactcat tttcagaatt atcagtgtgt ctacactcta cactctacac tcagaaacaa    60
gcttgaaaca ttggtgccca ttgtcgaaga ctccatggct aagtcaaatt gtcaccatga   120
ctaagtccca tatcgattag aagagaggac aatcactcca gagcttatta taaaacagac   180
attataacac cgttgtactc                                               200

SEQ ID NO: 258          moltype = DNA   length = 200
FEATURE                 Location/Qualifiers
source                  1..200
                        mol_type = genomic DNA
                        organism = Glycine max
SEQUENCE: 258
tgtggctgaa ggcatcaatt atccatagtt agaacaaaga tttgttagac atggatagtt    60
gctggtcgac caaacaaata ctgtcctaag gactacaaaa caagaagacc ttcagtgtaa   120
cgaagtccca cattgcgcaa gagaaataac aagcactgaa gactgaagta taaaaacaac   180
attatttcat tgaacaaatc                                               200

SEQ ID NO: 259          moltype = DNA   length = 200
FEATURE                 Location/Qualifiers
source                  1..200
                        mol_type = genomic DNA
                        organism = Glycine max
SEQUENCE: 259
agtaaaatat caacgggaag attataatgt gtttgaactt ttattagtct caggtttgaa    60
cttttatgtt gctgatctaa attttttaacc atgttgctct tggctaggat gttgggatga  120
attagtccca catttgtcag aactttgtca ggcagctgaa gctcccagta taaaatttga   180
atacctacaa tgtacaaagc                                               200

SEQ ID NO: 260          moltype = DNA   length = 200
FEATURE                 Location/Qualifiers
source                  1..200
                        mol_type = genomic DNA
                        organism = Glycine max
SEQUENCE: 260
agtaaaatat caacgggaag attataatgt gtttgaactt ttattagtct caggtttgaa    60
cttttatgtt gctgatctaa attttttaacc atgttgctct tggctaggat gttgggatga  120
attagtccca catttgtcag gactttgtca ggcagctgaa gctcccagta taaaatttga   180
atacttacat tgtacaaagc                                               200

SEQ ID NO: 261          moltype = DNA   length = 200
FEATURE                 Location/Qualifiers
source                  1..200
                        mol_type = genomic DNA
                        organism = Glycine max
SEQUENCE: 261
ggtgccccat ctggtggcag cagagtattg taatgtgggt gtttggagac tggagtgtcc    60
atggatttct gtacggagaa atggaagatt taacacataa gggtgcgcgt tgaagtacta   120
atatggccca tatcgtttag aagagataga aataactcta tatcttatta taaaagaaga   180
ttttgaagcc atgtatactc                                               200

SEQ ID NO: 262          moltype = DNA   length = 200
FEATURE                 Location/Qualifiers
source                  1..200
                        mol_type = genomic DNA
                        organism = Glycine max
SEQUENCE: 262
tgttcatgga tttgttctgt gtggagaaat tattgatcgt cacaactaca ttttctagac    60
tctgctttgc cattgtagta gaggaattac tgtttctctg ttccaggcgt tacaagtata   120
aacagtccca tatcgtttag aagagataga aataactcta tatcttatta taaaagaaga   180
ttttgaagca tagcaaactc                                               200

SEQ ID NO: 263          moltype = DNA   length = 200
FEATURE                 Location/Qualifiers
source                  1..200
                        mol_type = genomic DNA
                        organism = Glycine max
```

```
SEQUENCE: 263
gttatagggg tttagcatta atccagatgg gttgtgaaat atgcaagtgt aagtgtaatc    60
taattaggat acgttataga cacaaaggtc acttgatgtt caatgtggaa ccacccatga   120
gtgagtccca catcgctgag ttaagataag aatcacctga agtttattta taaaacaaac   180
gtttcaacag ttaaaaattc                                               200

SEQ ID NO: 264          moltype = DNA   length = 200
FEATURE                 Location/Qualifiers
source                  1..200
                        mol_type = genomic DNA
                        organism = Glycine max
SEQUENCE: 264
tttttgcagga atcaggataa tggaagaatg aagaaaagat atagagacgt agaggttgaa    60
gagaaggtag tagcagaaaa tccaagttct tatgtatgtt ggcgcttaac tccttattgc   120
ccaagtccca caccggcgat gagaaagaat ctgcgccaaa gacttggcta taaaacaaac   180
aatccttgaa attcttaagc                                               200

SEQ ID NO: 265          moltype = DNA   length = 200
FEATURE                 Location/Qualifiers
source                  1..200
                        mol_type = genomic DNA
                        organism = Glycine max
SEQUENCE: 265
ggtttggact ctgtacgcac tgtcacatcc taaataagaa aacacatttc gaagaaagac    60
cggatattag aagaattaac atttcaaatt gttactattg caacagcaac gtagtcgcca   120
aagagtccca catcagtcag tcaagaaagc agtagaacta gtaacagaaa taaaagcaac   180
aacaatatac tgatcaaagc                                               200

SEQ ID NO: 266          moltype = DNA   length = 200
FEATURE                 Location/Qualifiers
source                  1..200
                        mol_type = genomic DNA
                        organism = Glycine max
SEQUENCE: 266
ctatgtaaca agtacaattt cacagacccg gtgttgttct ggtcttttga gaagtggtat    60
tgtattgtgc agaatgcatg agttatgtag aaacaagctt gccctgaaga gctatcctac   120
ctaagtccca cactggtaag gagaaagaat atgcaaaaat agtttgacta taaaagaaac   180
agtctatgat agaacaaatc                                               200

SEQ ID NO: 267          moltype = DNA   length = 200
FEATURE                 Location/Qualifiers
source                  1..200
                        mol_type = genomic DNA
                        organism = Glycine max
SEQUENCE: 267
gtagcttcag attactcgtg tgttaactgg gtcatgaatc cgtgatccaa cgttagaaca    60
agaacaaaac ctgaatagaa gagaaaggct atttggtgga tgttgcagaa atactagcga   120
tgaagtctca cattgctgag aagagaaaac aatgacctga tatttattta taaaagcaa   180
ctctggagcc ttaaaagctc                                               200

SEQ ID NO: 268          moltype = DNA   length = 400
FEATURE                 Location/Qualifiers
source                  1..400
                        mol_type = genomic DNA
                        organism = Glycine max
SEQUENCE: 268
aagaatgtcc actctcaatc actaagttgt gtttcctttt taattcact cattttaga     60
attatcagtt ttatactgaa tctagattga acatttgtg cccgaagact ccatccatga   120
caaagcccca tatcgtctag aagagatgac aatcactcca gggcttatca taaaaagac   180
tttttgcagc tgtaacactc aagaatgtcc actctcaatc actaagttgt gtttccttt   240
ttaattcact cattttaga attatcagtt ttatactgaa tctagattga acatttgtg   300
cccgaagact ccatccatga caaagcccca tatcgtctag aagagatgac aatcactcca   360
gggcttatca taaaaagac tttttgcagc tgtaacactc                           400

SEQ ID NO: 269          moltype = DNA   length = 200
FEATURE                 Location/Qualifiers
source                  1..200
                        mol_type = genomic DNA
                        organism = Glycine max
SEQUENCE: 269
agctgaggaa ggtagcttca gattactcgt gtgttaactg ggtcatgaat ccgtgatcca    60
acgtttgaac aagagcaaaa tctgaataga agagaaaggc tgttgcagaa atactagtga   120
tgaagtctca cattgctgag aagagaaaac aatgacctga tatttattta taaaacacaa   180
ctctggagcc ttaacaactc                                               200

SEQ ID NO: 270          moltype = DNA   length = 200
FEATURE                 Location/Qualifiers
source                  1..200
                        mol_type = genomic DNA
```

```
                        organism = Glycine max
SEQUENCE: 270
gttaatatta ttactcgtgt gttaactggg tcatgaatcc gcgatccaac gttagcacaa    60
gaacaaaatc tgaatagaag agaaaaggcg atttggtgga tatagcagaa gaactagtga   120
gaaagtccca cattgctgag aagagaaaac aataacatga tgtttattta taaaacgcaa   180
ctctggagtg tgaacaactc                                               200

SEQ ID NO: 271          moltype = DNA  length = 200
FEATURE                 Location/Qualifiers
source                  1..200
                        mol_type = genomic DNA
                        organism = Glycine max
SEQUENCE: 271
tctgtggaaa gattgaagat tcaatacaaa ccagaccctg tcttgttttg ttttggaatt    60
atcagttctc tattgcagcc agacccagag caagcgtgga tgttgcggaa gtactagtta   120
tgaagtccca cattgctgag aagagaaaac aatgacctga tgtttattta taaaatgcaa   180
ctctggaaca tgaacaactc                                               200

SEQ ID NO: 272          moltype = DNA  length = 200
FEATURE                 Location/Qualifiers
source                  1..200
                        mol_type = genomic DNA
                        organism = Glycine max
SEQUENCE: 272
agtaaaatat caacgggaag attataatgt gtttgaactt tcattagtct caggtttgaa    60
cttttatgtt gctgatctaa attttttaacc atgttgctct tggctaggat gttgggatga   120
attagtccca catttgtcag aactttgtca ggcagctgaa gctcccagta taaaatttga   180
atacttacat tgtacaaagc                                               200

SEQ ID NO: 273          moltype = DNA  length = 200
FEATURE                 Location/Qualifiers
source                  1..200
                        mol_type = genomic DNA
                        organism = Glycine max
SEQUENCE: 273
agttcttgtt tcttttttaa ttaattcatt ttcagaatta ttatacacaa aaactagctt    60
gaaaaatttg tgcccattgt ccaagactcc atccatgact aggcgtctaa gccgcatcga   120
ttaagtccca tatcgcttag aaaatatgac aatcactcca gagcttatta taaaagagac   180
attttttagac taaggcattc                                              200

SEQ ID NO: 274          moltype = DNA  length = 200
FEATURE                 Location/Qualifiers
source                  1..200
                        mol_type = genomic DNA
                        organism = Glycine max
SEQUENCE: 274
ctaaattctt gtttctttt taattcactc attttcagaa ttattataca caaactagct    60
tgaaaatttt gtgcccattg tcgaagactc caccatgact aagggtctaa gccccatcga   120
ataagtccca tatcacttag aaaagatgaa aatgactcca gagcttatta taaaataaac   180
attttttacac tgttatattc                                              200

SEQ ID NO: 275          moltype = DNA  length = 200
FEATURE                 Location/Qualifiers
source                  1..200
                        mol_type = genomic DNA
                        organism = Glycine max
SEQUENCE: 275
ctggatccaa cttataaatc agttataggg ggtttagcat gactccagat gggttgtgaa    60
atatgcatgt gagtgcaatc acattaggac acttgaagtt taatgttaaa ccacccacga   120
ttaagtcccg tatcgatgag taaagataac aatcatctga agtattttta taaaacgcac   180
gtttcaaagc atagaaattc                                               200

SEQ ID NO: 276          moltype = DNA  length = 200
FEATURE                 Location/Qualifiers
source                  1..200
                        mol_type = genomic DNA
                        organism = Glycine max
SEQUENCE: 276
tgataggtga attaattatt tttaatatac gaatgaggaa gaaagaaaaa ctattataac    60
aatctgctaa gttggggccg aagttgaagt atcaagcgca cgagtgcctc tgtatagtga   120
aaaaagccca catcgagcag cttactaagt tgaagtaaac tctaggctat aaaatgagag   180
agctactcgt cagttcaacc                                               200

SEQ ID NO: 277          moltype = DNA  length = 200
FEATURE                 Location/Qualifiers
source                  1..200
                        mol_type = genomic DNA
                        organism = Glycine max
SEQUENCE: 277
```

```
catgttgaga tgaaagatca agtattcgta ttgcattgat gagtcagatc attgactttg    60
gagatgctct acatagagaa gagaaagtga aggatcaagt gtcattcttt gtttctggcg   120
aaggtccaca tcgagccgca tactgaggga aagtgagctg cttgtactat aaatttcaaa   180
ggtgcatctg taaacaaatc                                               200

SEQ ID NO: 278          moltype = DNA   length = 200
FEATURE                 Location/Qualifiers
source                  1..200
                        mol_type = genomic DNA
                        organism = Glycine max
SEQUENCE: 278
caagctagtt gtcccaagcc tgcatagagt gataacagca tgctaataac tcccaaagaa    60
cacagatgaa aaatcaagta tcaagtgtgt gggtgctaac atttcagatt ctgactaaat   120
aaagcccaca tcgaatggta tacttagagc tagtaagctt cttacgctat aaaatgaaag   180
gctcattgct attgatattc                                               200

SEQ ID NO: 279          moltype = DNA   length = 200
FEATURE                 Location/Qualifiers
source                  1..200
                        mol_type = genomic DNA
                        organism = Glycine max
SEQUENCE: 279
aacaccatca gaagctatga agaagaacaa aaggctcctg agatattcc attttcatt    60
gattccctat cttcatgata ttaacagtgt gggagcttg cctgagttta catttctgac   120
caaagcccac atcgactggt attgtaatag caagtgaact ggttatacaa taaaggaaa   180
gggctgttag ctcattactt                                               200

SEQ ID NO: 280          moltype = DNA   length = 200
FEATURE                 Location/Qualifiers
source                  1..200
                        mol_type = genomic DNA
                        organism = Glycine max
SEQUENCE: 280
caacaataag ttggtacctt tagagaaaag acatgctttc tgtgtatagc attattagcg    60
cacagttgat agaaaatgaa gtattgtata tgggtatgat cgagtgtcta tttcttgagc   120
aaagcccaca ttgagtaata taccaaatag aagtgaactg cttatgctat aaaatggaag   180
agctgcattt agttttaagc                                               200

SEQ ID NO: 281          moltype = DNA   length = 200
FEATURE                 Location/Qualifiers
source                  1..200
                        mol_type = genomic DNA
                        organism = Glycine max
SEQUENCE: 281
atgtgagatg aaaaatcaag tattcataat gggtggacga gactgtgaca acttcattca    60
ggggtattac aggtgactgg aaagaaagta ttaagtgtgc gggtgctaac tttctgact   120
aaagtccaca tcgaagggta taccaagagc aagtaagcag cttatgctat aaaatgaaag   180
ggtcgtttgt tttgttactc                                               200

SEQ ID NO: 282          moltype = DNA   length = 200
FEATURE                 Location/Qualifiers
source                  1..200
                        mol_type = genomic DNA
                        organism = Glycine max
SEQUENCE: 282
aaagatcaag tattcatatt gcattgatga gtgagaccat tgactttgta gatgctaccg    60
ttgataagaa agaaagtgaa ggatcaagta tggtcatttc tttgtttccg tcttctaacg   120
aaggtccaca tcgagccgta ttctgagtga gagtgagctg cttataatat aaaattcgaa   180
ggtgtttact tactaaaaca                                               200

SEQ ID NO: 283          moltype = DNA   length = 389
FEATURE                 Location/Qualifiers
source                  1..389
                        mol_type = genomic DNA
                        organism = Glycine max
SEQUENCE: 283
tagagagaat cgttaagaaa aaataaata gtaaagtaaa tgaaacccca aataatatca    60
ttattatgtc aataagtcgg agaggatagt aatcaaatgg tctatgaggt ggtggttcat   120
tcaacatata gcacctaatt attgttccta aaacataatt taagaacaaa aacttaaact   180
taaataataa taataaaaga gtacatcgaa gtatctgtgt tctctatcct tctgactaac   240
attcatgttg tttgtattca gcaaagggcc gtgcaggatt tgtgcgtcgc gctccggtta   300
gttattgcag tgaccgtctc tttagtccca catcgagtaa ttatgcttca tacagtctgt   360
ttatataaca gagatggaac aaactggtt                                     389

SEQ ID NO: 284          moltype = AA    length = 9
FEATURE                 Location/Qualifiers
source                  1..9
                        mol_type = protein
                        note = Synthetic peptide
```

```
                                     -continued organism = synthetic construct
SEQUENCE: 284
LAGLIDADG                                                            9

SEQ ID NO: 285           moltype = DNA  length = 28
FEATURE                  Location/Qualifiers
source                   1..28
                         mol_type = other DNA
                         note = consensus sequence
                         organism = synthetic construct
SEQUENCE: 285
agctannatg tntacaaat ttctncta                                       28

SEQ ID NO: 286           moltype = DNA  length = 22
FEATURE                  Location/Qualifiers
source                   1..22
                         mol_type = other DNA
                         note = consensus sequence
                         organism = synthetic construct
SEQUENCE: 286
ctatttnntt ctatagcttt tt                                            22

SEQ ID NO: 287           moltype = DNA  length = 16
FEATURE                  Location/Qualifiers
source                   1..16
                         mol_type = other DNA
                         note = consensus sequence
                         organism = synthetic construct
SEQUENCE: 287
atccntctan gnacaa                                                   16

SEQ ID NO: 288           moltype = DNA  length = 20
FEATURE                  Location/Qualifiers
source                   1..20
                         mol_type = other DNA
                         note = consensus sequence
                         organism = synthetic construct
SEQUENCE: 288
naggacanag tgtcancnag                                               20

SEQ ID NO: 289           moltype = DNA  length = 71
FEATURE                  Location/Qualifiers
source                   1..71
                         mol_type = other DNA
                         note = consensus sequence
                         organism = synthetic construct
SEQUENCE: 289
gcgcgttgac cgtgcananT nannggntag ttcacagaa ngncTagng gcgtgtgtga     60
tcnaaaaaca n                                                        71

SEQ ID NO: 290           moltype = DNA  length = 53
FEATURE                  Location/Qualifiers
source                   1..53
                         mol_type = other DNA
                         note = consensus sequence
                         organism = synthetic construct
SEQUENCE: 290
cntnannggc ntngccnnaa gaaacatggg ccanggccca nnatncaang cac          53

SEQ ID NO: 291           moltype = DNA  length = 48
FEATURE                  Location/Qualifiers
source                   1..48
                         mol_type = other DNA
                         note = consensus sequence
                         organism = synthetic construct
SEQUENCE: 291
cgcnnncaag cccanatacc agttcgtngg tggagcaanc gaggcgct                48

SEQ ID NO: 292           moltype = DNA  length = 187
FEATURE                  Location/Qualifiers
source                   1..187
                         mol_type = other DNA
                         note = consensus sequence
                         organism = synthetic construct
SEQUENCE: 292
aacagncaaa catttngtnc cacctngncc agncacnatt gcnnannnng gcttataagn   60
cganncgcaa cgcaccncac ngtctcttcg gagacatccg ataaaattgg aacgatacag  120
agaagattag catggcccct gcgcaaggat gacacgcaca aatcgagaaa tggtccaaat  180
tttttttg                                                          187
```

```
SEQ ID NO: 293         moltype = DNA  length = 24
FEATURE                Location/Qualifiers
source                 1..24
                       mol_type = other DNA
                       note = blunt-end oligonucleotide
                       organism = synthetic construct
SEQUENCE: 293
agaagtcctc aagtaccgtt tggc                                            24

SEQ ID NO: 294         moltype = DNA  length = 14
FEATURE                Location/Qualifiers
source                 1..14
                       mol_type = other DNA
                       note = blunt-end oligonucleotide
                       organism = synthetic construct
SEQUENCE: 294
aagtcctcaa ggga                                                       14

SEQ ID NO: 295         moltype = DNA  length = 14
FEATURE                Location/Qualifiers
source                 1..14
                       mol_type = other DNA
                       note = blunt-end oligonucleotide
                       organism = synthetic construct
SEQUENCE: 295
gctagtaccg tttg                                                       14
```

COMPOSITIONS AND METHODS FOR SITE DIRECTED GENOMIC MODIFICATION

CROSS REFERENCE TO RELATED APPLICATIONS

This application is a divisional of U.S. application Ser. No. 15/120,110, filed Aug. 18, 2016, which is a '371 National Stage application of International Application Serial No. PCT/US2015/018104, filed Feb. 27, 2015, which claims the benefit of priority to U.S. Provisional Application Ser. No. 61/945,700, filed Feb. 27, 2014, the entire disclosures of which are incorporated herein by reference.

INCORPORATION OF SEQUENCE LISTING

The sequence listing that is contained in the file named "MONS350USD2_ST26", which is 383 kilobytes (measured in MS-WINDOWS) and created on Dec. 20, 2022, is filed herewith by electronic submission and incorporated herein by reference.

BACKGROUND

Field

The disclosure relates to the field of biotechnology. More specifically, the disclosure provides a method of introducing recombinant blunt-end double-strand DNA fragments into the genome of a plant by introducing a double-strand break in the genome and novel plant promoters beneficial for the expression of, for instance, non-protein-coding small RNAs for CRISPR-mediated genome modification.

Description of Related Art

Site-specific recombination has potential for application across a wide range of biotechnology-related fields. Meganucleases, zinc finger nucleases (ZFNs), and transcription activator-like effector nucleases (TALENs) containing a DNA-binding domain and a DNA-cleavage domain enable genome modification. While meganucleases, ZFNs, and TALENs, are effective and specific, these technologies require generation through protein engineering of one or more components for each genomic site chosen for modification. Recent advances in application of clustered, regularly interspaced, short palindromic repeats (CRISPR) have illustrated a method of genome modification that may be as robust as the comparable systems (meganucleases, ZFNs, and TALENs), yet has the advantage of being quick to engineer.

The Clustered Regularly Interspersed Short Palindromic Repeats (CRISPRs) system constitutes an adaptive immune system in prokaryotes that targets endonucleolytic cleavage of invading phage. The system is composed of a protein component (Cas) and a guide RNA (gRNA) that targets the protein to a specific locus for endonucleolytic cleavage. This system has been successfully engineered to target specific loci for endonucleolytic cleavage of mammalian, zebrafish, drosophila, nematode, bacteria, yeast, and plant genomes.

SUMMARY

In one aspect the invention provides a recombinant DNA construct comprising a snRNA promoter selected from the group consisting of: a U6 promoter, a U3 promoter, a U2 promoter, a U5 promoter, and a 7SL promoter; operably linked to a sequence encoding a single-guide RNA (sgRNA), wherein the sequence of said snRNA promoter comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NOs:146-149, SEQ ID NOs:160-201, or SEQ ID NOs:247-283; or a fragment thereof, wherein the fragment is at least 140 bp in length.

In one embodiment the sequence of said U6 promoter may comprise any of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NOs:146-149, SEQ ID NOs:160-166, SEQ ID NOs:200-201, or SEQ ID NO:283, or a fragment thereof, wherein the fragment is at least 140 bp in length. In a further embodiment, the sequence of said U6 promoter may comprise SEQ ID NO:7. In another embodiment the sequence of said U6 promoter may comprise a sequence selected from the group consisting of: SEQ ID NO:17, SEQ ID NO:18, SEQ ID NO:19, and SEQ ID NO:20. In yet another embodiment the sequence of said U3 promoter may comprise any of SEQ ID NOs:167-171 or SEQ ID NOs:178-182, or a fragment thereof; wherein the fragment is at least 140 bp in length. In still yet another embodiment the sequence of said U2 promoter comprises any of SEQ ID NOs:183-187, SEQ ID NOs:192-199, or SEQ ID NOs:247-275, or a fragment thereof; wherein the fragment is at least 140 bp in length. In another embodiment the sequence of said U5 promoter comprises any of SEQ ID NOs:188-191, or SEQ ID NOs:276-282, or a fragment thereof; wherein the fragment is at least 140 bp in length. In a further embodiment the sequence of said 7SL promoter comprises any of SEQ ID NOs:172-177, or a fragment thereof; wherein the fragment is at least 140 bp in length. The recombinant DNA construct may further comprise a transcription termination sequence.

The recombinant DNA construct may also further comprise a sequence encoding a promoter operably linked to a sequence encoding a clustered, regularly interspaced, short palindromic repeats (CRISPR)-associated Cas endonuclease gene product. In certain embodiments of the recombinant DNA construct, the Cas endonuclease gene product may be further operably linked to a nuclear localization sequence (NLS). Further, in certain embodiments of the contemplated recombinant DNA construct, the sequence encoding said Cas endonuclease may be selected from the group consisting of SEQ ID NO:27, SEQ ID NO:68, and SEQ ID NO:97, SEQ ID NO:119, and SEQ ID NO:136.

Another aspect of the invention provides a recombinant DNA construct comprising a snRNA promoter selected from the group consisting of: a U6 promoter, a U3 promoter, a U2 promoter, a U5 promoter, and a 7SL promoter; operably linked to a sequence specifying a non-coding RNA, wherein the sequence of said snRNA promoter comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NOs:146-149, SEQ ID NOs:160-201 or SEQ ID NOs:247-283, or a fragment thereof, wherein the fragment is at least 140 bp in length. In some embodiments the non-coding RNA is selected from the group consisting of: a microRNA (miRNA), a miRNA precursor, a small interfering RNA (siRNA), a small RNA (22-26 nt in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), and a naturally occurring antisense siRNA (nat-siRNA).

Certain embodiments if the invention further comprise such a recombinant DNA construct, wherein the sequence of said U3 promoter comprises any of SEQ ID NOs:167-171 and SEQ ID NOs:178-182, or a fragment thereof; wherein the fragment is at least 140 bp in length. In another embodiment of the recombinant DNA construct, the sequence of said U2 promoter comprises any of SEQ ID NOs:183-187, SEQ ID NOs:192-199, or SEQ ID NOs:247-275, or a fragment thereof; wherein the fragment is at least 140 bp in length. In yet another embodiment of the recombinant DNA construct, the sequence of said U5 promoter comprises any of SEQ ID NOs:188-191, or SEQ ID NOs:276-282, or a fragment thereof; wherein the fragment is at least 140 bp in length. Still further, the invention provides an embodiment wherein the sequence of said U6 promoter may comprise any of SEQ ID NOs:1-20, SEQ ID NOs:146-149, SEQ ID NOs:160-166, SEQ ID NOs:200-201, or SEQ ID NO:283, or a fragment thereof; wherein the fragment is at least 140 bp in length. Another embodiment comprises the recombinant DNA construct wherein the sequence of said 7SL promoter comprises any of SEQ ID NOs:172-177, or a fragment thereof; wherein the fragment is at least 140 bp in length.

Another aspect of the invention provides a cell comprising a recombinant DNA construct as described above. In certain embodiments the cell is a plant cell.

The invention further provides a method of introducing a double-strand break in the genome of a cell, comprising introducing in said cell: a) at least one recombinant DNA construct of claim 1; and b) a second recombinant DNA construct comprising a sequence encoding a promoter operably linked to a sequence encoding a clustered, regularly interspaced, short palindromic repeats (CRISPR)-associated Cas endonuclease gene product operably linked to a nuclear localization sequence (NLS). In one embodiment of such a method, the sequence of the U6 promoter comprises SEQ ID NO:7. In another embodiment of the method, the U6 promoter comprises a sequence selected from the group consisting of: SEQ ID NO:17, SEQ ID NO:18, SEQ ID NO:19, and SEQ ID NO:20. In yet another embodiment of the method, the sequence encoding said Cas endonuclease is selected from the group consisting of SEQ ID NO:27, SEQ ID NO:68, and SEQ ID NO:97, SEQ ID NO:119, and SEQ ID NO:136.

The invention further provides a method of introducing a double-strand break in the genome of a cell, comprising introducing to said cell at least one recombinant DNA construct which comprises a recombinant DNA construct comprising a snRNA promoter selected from the group consisting of: a U6 promoter, a U3 promoter, a U2 promoter, a U5 promoter, and a 7SL promoter; operably linked to a sequence encoding a single-guide RNA (sgRNA), wherein the sequence of said snRNA promoter comprises SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NOs:146-149, SEQ ID NOs:160-201, or SEQ ID NOs:247-283; or a fragment thereof, wherein the fragment is at least 140 bp in length, and also further comprises a sequence encoding a promoter operably linked to a sequence encoding a clustered, regularly interspaced, short palindromic repeats (CRISPR)-associated Cas endonuclease gene product.

In certain embodiments of the method, the sequence of said U6 promoter comprises SEQ ID NO:7. In other embodiments the U6 promoter comprises a sequence selected from the group consisting of: SEQ ID NO:17, SEQ ID NO:18, SEQ ID NO:19, and SEQ ID NO:20. In some embodiments of the method the sequence encoding the Cas endonuclease is selected from the group consisting of SEQ ID NO:27, SEQ ID NO:68, and SEQ ID NO:97, SEQ ID NO:119, and SEQ ID NO:136.

Another aspect of the invention provides a method of genome modification comprising: a) introducing a double-strand break at a selected site in the genome of a plant cell, and b) introducing into said plant cell a recombinant blunt-end double-strand DNA fragment, wherein said recombinant blunt-end double-strand DNA fragment is incorporated into said double strand break by endogenous DNA repair. The method may comprise genome modification such as production of a modified linkage block, linking two or more QTLs, disrupting linkage of two or more QTLs, gene insertion, gene replacement, gene conversion, deleting or disrupting a gene, transgenic event selection, transgenic trait donor selection, transgene replacement, or targeted insertion of at least one nucleic acid of interest. In some embodiments of the method the double stranded break is introduced by an endonuclease. In certain embodiments the endonuclease may be selected from the group consisting of: a TALEN endonuclease; a CRISPR endonuclease; a meganuclease comprising a "LAGLIDADG," (SEQ ID NO:284) "GIY-YIG," "His-Cys box," or HNH sequence motif; and a Zinc finger nuclease. In particular embodiments the endonuclease is a TALEN endonuclease and TALEN expression constructs are introduced into the plant cell, wherein about 0.1 pmol of each TALEN expression construct is introduced into the plant cell.

Further, in the method the plant cell may be a protoplast or may have been, or is being, grown in a plant cell culture. In certain embodiments of the method the plant cell is selected from the group consisting of: a soybean plant cell; a corn plant cell; a rice plant cell; a wheat plant cell; a turfgrass plant cell; a cotton plant cell; and a canola plant cell. In other embodiments of the method the recombinant blunt-end double-strand DNA fragment does not comprise a region of homology to the selected site in the genome.

Embodiments of the method are contemplated wherein about 0.03 to about 0.3 fmol of recombinant blunt-end double-strand DNA fragment is introduced into said plant cell. In particular embodiments about 0.15 fmol of recombinant blunt-end double-strand DNA fragment is introduced into said plant cell. Further, the blunt-end double-strand DNA fragment may comprise on the 5' end, or the 3' end, or both the 5' and 3' ends, a region with microhomology to a sequence comprising one or both ends of said double-strand break in the genome. Some embodiments comprise a method wherein the region of microhomology is selected from a sequence 1 bp, 2 bp, 3 bp, 4, bp, 5 bp, 6 bp, 7 bp, 8 bp, 9 bp, or 10 bp in length. In a particular embodiment of the method the region of microhomology is 3 bp in length.

The method may comprise introduction of a double-strand break in step a) as described above, by providing said cell with an endonuclease designed to target a selected target site in the genome of said cell. Further, the endonuclease may be provided by at least one recombinant DNA construct encoding the endonuclease. In an embodiment, the endonuclease is provided by delivering an mRNA encoding the endonuclease or the endonuclease to the plant cell. In particular embodiments The endonuclease is selected from the group consisting of: a TALEN endonuclease; a Zinc finger endonuclease; a meganuclease; and a CRISPR endonuclease. Additional embodiments may comprise introduction of a double-strand break in step a) by providing said cell with a recombinant DNA construct encoding a promoter operably linked to a sequence encoding a clustered, regularly interspaced, short palindromic repeats (CRISPR)-associated Cas endonuclease gene product and a recombinant DNA construct comprising a U6, U3, U2, U5, or 7SL promoter operably linked to a sequence encoding a single-guide RNA (sgRNA) designed to target a selected target site in the chromosome of said cell. In particular embodiments the Cas endonuclease gene product may be further operably linked to at least one nuclear localization sequence (NLS).

In certain embodiments of the method the sequence of said U6, U3, U2, U5, or 7SL promoter may comprise SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NOs:146-149, SEQ ID NOs:160-201 or SEQ ID NOs:247-283, or a fragment thereof; wherein the fragment is at least 140 bp in length and comprises a transcription termination sequence. In particular embodiments the U6 promoter may comprise a sequence selected from the group consisting of: SEQ ID NOs:1-20, SEQ ID NOs:146-149, SEQ ID NOs:160-166, SEQ ID NOs:200-201, and SEQ ID NO:283, or a fragment thereof; wherein the fragment is at least 140 bp in length comprising a transcription termination sequence. In alternative embodiments the U6 promoter may comprise a sequence selected from the group consisting of: SEQ ID NO:17, SEQ ID NO:18, SEQ ID NO:19, and SEQ ID NO:20. In further embodiments the sequence of said U3 promoter may comprise any of SEQ ID NOs:167-171 or SEQ ID NOs:178-182, or a fragment thereof; wherein the fragment is at least 140 bp in length. In still further embodiments the sequence of said U5 promoter comprises any of SEQ ID NOs:188-191, or SEQ ID NOs:276-282, or a fragment thereof; wherein the fragment is at least 140 bp in length. Additionally, the sequence of said U2 promoter may comprise any of SEQ ID NOs:183-187, SEQ ID NOs:192-199, or SEQ ID NOs:247-275, or a fragment thereof; wherein the fragment is at least 140 bp in length. In yet other embodiments the sequence of said 7SL promoter comprises any of SEQ ID NOs:172-177, or a fragment thereof, wherein the fragment is at least 140 bp in length.

Embodiments are also contemplated wherein the recombinant DNA construct encoding a promoter operably linked to a sequence encoding a clustered, regularly interspaced, short palindromic repeats (CRISPR)-associated Cas endonuclease gene product, and the recombinant DNA construct comprising a U6, U3, U2, U5, or 7SL promoter operably linked to a sequence encoding a single-guide RNA (sgRNA) is designed to target a selected target site in the chromosome of said cell, are on the same construct. Other embodiments of the method may comprise use of a recombinant DNA construct encoding a promoter operably linked to a sequence encoding a clustered, regularly interspaced, short palindromic repeats (CRISPR)-associated Cas endonuclease gene product and the recombinant DNA construct comprising a U6, U3, U2, U5, or 7SL promoter is operably linked to a sequence encoding a single-guide RNA (sgRNA) designed to target a selected target site in the chromosome of said cell are on at least two constructs.

A further aspect of the invention comprises a plant cell comprising a targeted recombinant sited-directed integration of a blunt-end double-strand DNA fragment. Further provided are a plant, plant part, or plant seed comprising a targeted recombinant sited-directed integration of a blunt-end double-strand DNA fragment.

A still further aspect of the invention comprises: a method of genome modification comprising: a) introducing a double-strand break in the genome of a plant cell by introducing a double-strand break in the genome of a cell, comprising introducing in said cell: a) at least one recombinant DNA construct of claim 1; and b) a second recombinant DNA construct comprising a sequence encoding a promoter operably linked to a sequence encoding a clustered, regularly interspaced, short palindromic repeats (CRISPR)-associated Cas endonuclease gene product operably linked to a nuclear localization sequence (NLS); and b) introducing into said plant cell a recombinant blunt-end double-strand DNA fragment, wherein said recombinant blunt-end double-strand DNA fragment is incorporated into said double strand break by endogenous DNA repair.

A further aspect of the invention comprises a method of genome modification comprising: a) introducing a double-strand break in the genome of a plant cell as described above, and b) introducing into said plant cell a recombinant blunt-end double-strand DNA fragment, wherein said recombinant blunt-end double-strand DNA fragment is incorporated into said double strand break by endogenous DNA repair.

Yet another aspect of the invention comprises a recombinant DNA construct comprising at least a first expression cassette comprising a U6, U3, U2, U5, or 7SL promoter operably linked to a sequence encoding a single-guide RNA (sgRNA), wherein the sequence of said promoter comprises any of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NOs:146-149, SEQ ID NOs:160-201, or SEQ ID NOs:247-283, or a fragment thereof; wherein the fragment is at least 140 bp in length. In certain embodiments the recombinant DNA construct further comprises at least a second expression cassette, wherein the sequence encoding the first sgRNA is distinct from the sequence encoding the second sgRNA. The recombinant DNA construct may also comprise a construct wherein the promoter operably linked to the sequence encoding the first sgRNA is distinct from the promoter operably linked to the sequence encoding the second sgRNA. In certain embodiments the construct comprises flanking left and right homology arms (HA) which are each about 200-1200 bp in length. In particular embodiments the homology arms are about 230 to about 1003 bp in length.

Another aspect of the invention provides a method of quantifying the activity of a nuclease by detecting integrated DNA fragments by determining the rate of homologous recombination (HR) mediated targeted integration by use of using digital PCR or quantitative PCR.

Yet another aspect of the invention comprises a recombinant DNA construct comprising: a) a first snRNA promoter selected from the group consisting of: a U6 promoter, a U3 promoter, a U2 promoter, a U5 promoter, and a 7SL promoter; operably linked to a sequence encoding a non-coding RNA, and b) a second snRNA promoter selected from the group consisting of: a U6 promoter, a U3 promoter, a U2 promoter, a U5 promoter, and a 7SL promoter; operably linked to a sequence encoding a non-coding RNA, wherein the first snRNA promoter and the second snRNA promoter are different. In certain embodiments the sequence encoding the first snRNA promoter and the sequence encoding the second snRNA promoter each comprise SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NOs:146-149, SEQ ID NOs:160-201, or SEQ ID NOs:247-283, or a fragment thereof; wherein the fragment is at least 140 bp in length. Further, a recombinant DNA construct, wherein the first and second snRNA promoter are U6 promoters and the sequences encoding the first and second snRNA promoters are each selected from the group consisting of: SEQ ID NOs:1-8, SEQ ID NOs:17-20, and SEQ ID NOs:200-201 is also provided in certain embodiments.

Thus, a recombinant DNA construct wherein the first and second snRNA promoter are U6 promoters and the sequences encoding the first and second snRNA promoters are each selected from the group consisting of: SEQ ID NOs:12-16, SEQ ID NOs:160-166, and SEQ ID NO:283, is also provided. Alternatively, a recombinant DNA construct, wherein the first and second snRNA promoter are U6 promoters and the sequences encoding the first and second snRNA promoters are each selected from the group consisting of: SEQ ID NOs:9-11 and SEQ ID NO:146-149, is provided.

A recombinant DNA construct, wherein the first and second snRNA promoter are U2 promoters and the sequences encoding the first and second snRNA promoters are each selected from the group consisting of SEQ ID NOs:183-187 and SEQ ID NOs:192-199 is also contemplated. Additionally, certain embodiments of the invention comprise a recombinant DNA construct wherein the first and second snRNA promoter are U2 promoters and the sequences encoding the first and second snRNA promoters are each selected from the group consisting of SEQ ID NOs:247-275.

Yet other embodiments comprise a recombinant DNA construct, wherein the first and second snRNA promoter are U3 promoters and the sequences encoding the first and second snRNA promoters are each selected from the group consisting of SEQ ID NOs:178-182. Still other embodiments of the invention comprise a recombinant DNA construct, wherein the first and second snRNA promoter are U3 promoters and the sequences encoding the first and second snRNA promoters are each selected from the group consisting of SEQ ID NOs:167-171.

Alternatively, the recombinant DNA construct may comprise first and second snRNA promoter which are U5 promoters and wherein the sequences encoding the first and second snRNA promoters are each selected from the group consisting of SEQ ID NOs:188-191. Alternatively provided are recombinant DNA constructs wherein the first and second snRNA promoter are U5 promoters and the sequences encoding the first and second snRNA promoters are each selected from the group consisting of SEQ ID NOs:276-282.

Certain embodiments of the invention provide a recombinant DNA construct wherein the first and second snRNA promoter are 7SL promoters and the sequences encoding the first and second snRNA promoters are each selected from the group consisting of SEQ ID NOs:175-177. In other embodiments the recombinant DNA construct wherein the first and second snRNA promoter are 7SL promoters and the sequences encoding the first and second snRNA promoters are each selected from the group consisting of SEQ ID NOs:172-174.

Also contemplated are embodiments wherein the recombinant DNA construct comprises a first snRNA promoter which is a U6 promoter and a second snRNA promoter is also present and is selected from the group consisting of: a U3 promoter, a U2 promoter, a U5 promoter, and a 7SL promoter. Other embodiments include a recombinant DNA construct wherein the first snRNA promoter is a U3 promoter and the second snRNA promoter is selected from the group consisting of: a U6 promoter, a U2 promoter, a U5 promoter, and a 7SL promoter. Alternatively in the recombinant DNA construct, the first snRNA promoter is a U2 promoter and the second snRNA promoter may be selected from the group consisting of: a U6 promoter, a U3 promoter, a U5 promoter, and a 7SL promoter; or the first snRNA promoter is a U5 promoter and the second snRNA promoter is selected from the group consisting of: a U6 promoter, a U2 promoter, a U3 promoter, and a 7SL promoter. Further, the recombinant DNA construct may comprise a first snRNA promoter which is a 7SL promoter and the second snRNA promoter may be selected from the group consisting of: a U6 promoter, a U2 promoter, a U3 promoter, and a U5 promoter.

Other contemplated embodiments of the invention include a recombinant DNA construct as described above, wherein the sequences encoding the first and second snRNA promoters are each selected from the group consisting of: SEQ ID NOs:1-8, SEQ ID NOs:17-20, SEQ ID NOs:200-201, SEQ ID NOs:183-187, SEQ ID NOs:192-199, SEQ ID NOs:178-182, SEQ ID NOs:188-191, and SEQ ID NOs:175-177. In certain embodiments of the recombinant DNA construct, the sequences encoding the first and second snRNA promoters are each selected from the group consisting of: SEQ ID NOs:12-16, SEQ ID NOs:160-166, SEQ ID NO:283, SEQ ID NOs:247-275, SEQ ID NOs:167-171, SEQ ID NOs:276-282, and SEQ ID NOs:172-174.

The recombinant DNA construct may further comprise a sequence specifying one or more additional snRNA promoters selected from the group consisting of: a U6 promoter, a U3 promoter, a U2 promoter, a U5 promoter, and a 7SL promoter; operably linked to a sequence encoding a non-coding RNA, wherein the first snRNA promoter, the second snRNA promoter, and each of the one or more additional snRNA promoters are different. In particular embodiments of the recombinant DNA construct, the sequence specifying said one or more additional snRNA promoters is selected from the group consisting of: SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NOs:146-149, SEQ ID NOs:160-201, or SEQ ID NOs:247-283; or a fragment thereof, wherein the fragment is at least 140 bp in length. Further, the recombinant DNA construct may comprise 3, 4, 5, 6, 7, 8, 9 or 10 snRNA promoters.

In some embodiments of the recombinant DNA construct, the non-coding RNAs are sgRNAs targeting different selected target sites in a chromosome of a plant cell. The recombinant DNA constructs may further comprise a sequence encoding a promoter operably linked to a sequence encoding a clustered, regularly interspaced, short palindromic repeats (CRISPR)-associated Cas endonuclease gene product.

Yet another aspect of the invention provides a method of genome modification comprising: a) introducing double-strand breaks at two or more selected sites in the genome of a plant cell by providing said cell with a clustered, regularly interspaced, short palindromic repeats (CRISPR)-associated Cas endonuclease and a recombinant DNA construct wherein the non-coding RNAs are sgRNAs targeting different selected target sites in a chromosome of a plant cell, and b) introducing into said plant cell one or more exogenous double-strand DNA fragment; wherein said exogenous double-strand DNA fragments are incorporated into said double strand breaks by endogenous DNA repair. In some embodiments said one or more exogenous double-strand DNA fragments are blunt-ended. In certain embodiments of the method, said one or more exogenous double-strand DNA fragments comprise a region of homology to a selected site in the genome. In other embodiments the exogenous double-strand DNA fragments comprise regions of homology to different selected sites in the genome.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

(FIG. 1A) and (FIG. 1B) The sequence consensus, and (SEQ ID NOs:285-292) percent conservation are presented below the alignments. (FIG. 1B) The thick arrow indicates the transcription start site; upstream from the transcriptional start site are a 'TATA Box', an Upstream Sequence Element (USE), and Monocot-Specific Promoter (MSP) elements, each marked with heavy lined boxes; the stretch of seven thymidine bases (poly-T) at the 3' end is the transcription termination signal. The sequences in FIG. 1.A and FIG. 1.B correspond the following: ZmU6_Ch1 represented by SEQ ID NO:98; ZmU6_Ch2 represented by SEQ ID NO:99; ZmU6_Ch3 represented by SEQ ID NO:100; ZmU6_Ch8 represented by SEQ ID NO:101.

(FIG. 5B) blunt-end oligonucleotide without microhomology used for insertion at a corn genomic target site (SEQ ID NO:293 pre-insertion and SEQ ID NOs:294 and 295 after insertion; (FIG. 5C) blunt-end oligonucleotide with microhomology ends used for insertion at a corn genomic target site (SEQ ID NO:293 pre-insertion and SEQ ID NOs:294 and 295 after insertion; (FIG. 5D) fragment analysis profile of PCR amplicons spanning the oligo-chromosome junction in test (upper panel) and negative control samples (bottom panel) of the oligonucleotide integration assay (where the arrow indicates the expected peak); and (FIG. 5E) DNA sequences of oligonucleotide-chromosome junctions (SEQ ID NOs:294 and 295) at the Zm_L70c corn genomic target site confirming integrations of both full-length (integration 1; SEQ ID NO:103) and truncated oligonucleotides (integration 2; SEQ ID NO:104), the expected sequence (template) is presented as SEQ ID NO:102.

(FIG. 7B) a CRISPR/Cas multiplex system to evaluate gene linkage of multiple QTL candidate genes. Where likelihood of odds (LOD) is a statistical measure for genetic linkage; an LOD of 3 means that it is 1000× more likely that a QTL exists in the interval than that there is no QTL.

FIG. 10A. Corn chromosome site Zm7 targeted by CRISPR/Cas9 constructs and with blunt-end double-strand DNA fragment formed by annealed DNA fragments represented by SEQ ID NO:115 and SEQ ID NO:116. FIG. 10B. Corn chromosome site L70c targeted by CRISPR/Cas9 constructs and with blunt-end double-strand DNA fragment without micro-homology sequences formed by annealed DNA fragments represented by SEQ ID NO:45 and SEQ ID NO:46. FIG. 10C. Corn chromosome site L70c targeted by CRISPR/Cas9 constructs and with blunt-end double-strand DNA fragment with 3 bp micro-homology sequences at each end of the DNA fragment formed by annealed DNA fragments represented by SEQ ID NO:121 and SEQ ID NO:122.

FIG. 13A. Schematic for HR-cassette construct for targeting the corn chromosome site Zm7 with LHA and RHA of 240 and 230 bp in length, respectively. FIG. 13B. Schematic for HR-cassette construct for targeting the corn chromosome site Zm7 with LHA and RHA of 240 and 1003 bp in length, respectively.

FIG. 14A. Schematic for HR-cassette construct for targeting the corn chromosome site L70.4 with both the LHA and RHA 230 bp in length. FIG. 14B. Schematic for HR-cassette construct for targeting the corn chromosome site L70.4 with LHA and RHA of 1027 bp and 230 bp in length, respectively.

FIG. 15A. Graphical presentation of data showing percent targeted integration rates in transfected corn protoplasts using StCas9 CRISPR constructs targeting native corn chromosomal target sites L70e, L70f, and L70g. The controls lacked a StCas9 expression cassette construct in the transfection mixture. FIG. 15B. Sequence alignment of expected integration of the blunt-end, double-strand DNA fragment at the L70f target site (SEQ ID NO:144) and one example of target site integration with indel of the DNA fragment sequence (SEQ ID NO:145).

FIG. 16A. Chromosomal integration rates using constructs with the corn chromosome 8 U6 promoter or one of three separate chimeric U6 promoters driving sgRNA expression in CRISPR/Cas9 system to target three different corn chromosomal target sites. Targeted integration was measured by ddPCR assay using MGB TaqMan probes. FIG. 16B. Chromosomal integration rates using constructs with the corn chromosome 8 U6 promoter or one of three separate chimeric U6 promoters driving sgRNA expression in CRISPR/Cas9 system to target three different corn chromosomal target sites. Targeted integration was measured by ddPCR assay using EvaGreen® intercalating dye.

FIGS. 17A-17C. FIG. 17A. Schematic of PCR screening strategy to detect CRISPR/Cas9 induced mutation by NHEJ at tomato invertase inhibitor target site 2 (TS2), resulting in mutation of restriction endonuclease site Sm1I. FIG. 17B. Photograph of PCR amplicons run on an agarose gel showing undigested amplicons and Sm1I digested amplicons to detect CRISPR/Cas9 induced mutation at tomato invertase inhibitor target site 2. FIG. 17C. Multiple sequence alignment of sequences of PCR amplicons from CRISPR/Cas9 induced mutation by NHEJ at the tomato invertase inhibitor target site 2.

FIG. 18A. Graphical representation of data showing normalized GUS mRNA levels from soybean cotyledon protoplast assays with recombinant expression constructs with U6, U3, and 7SL promoters. FIG. 18B. Graphical representation of data showing normalized GUS mRNA levels from corn leaf protoplast assays with recombinant expression constructs with U6, U3, 7SL, U2, or U5 promoters.

DETAILED DESCRIPTION

Figure 1A:
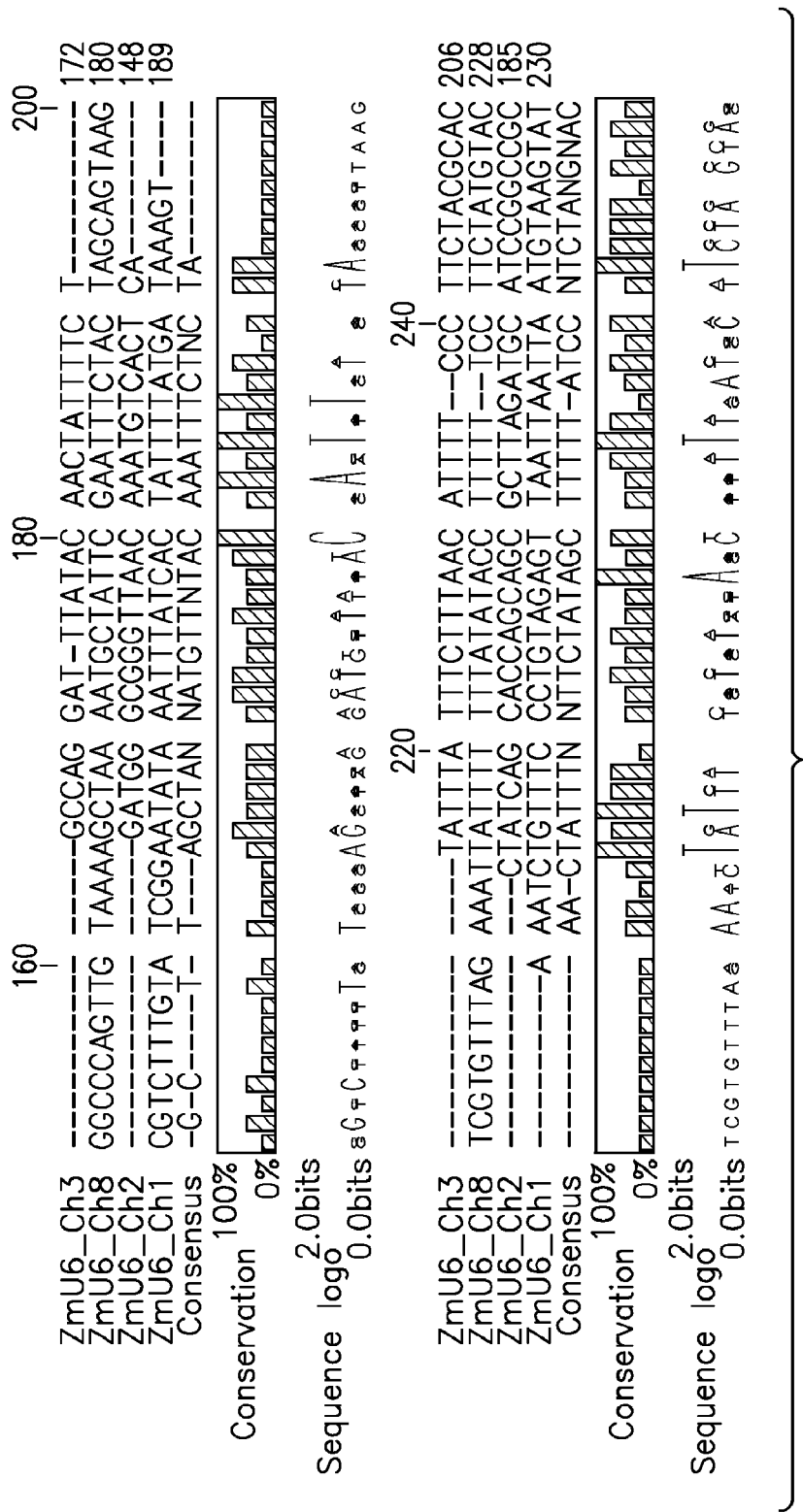
FIGS. 1A-1B: Nucleotide sequence alignment of four native corn U6 small nuclear RNA (snRNA) genes, including their putative promoters from chromosomes 1, 2, 3, and 8.
Figure 1A:
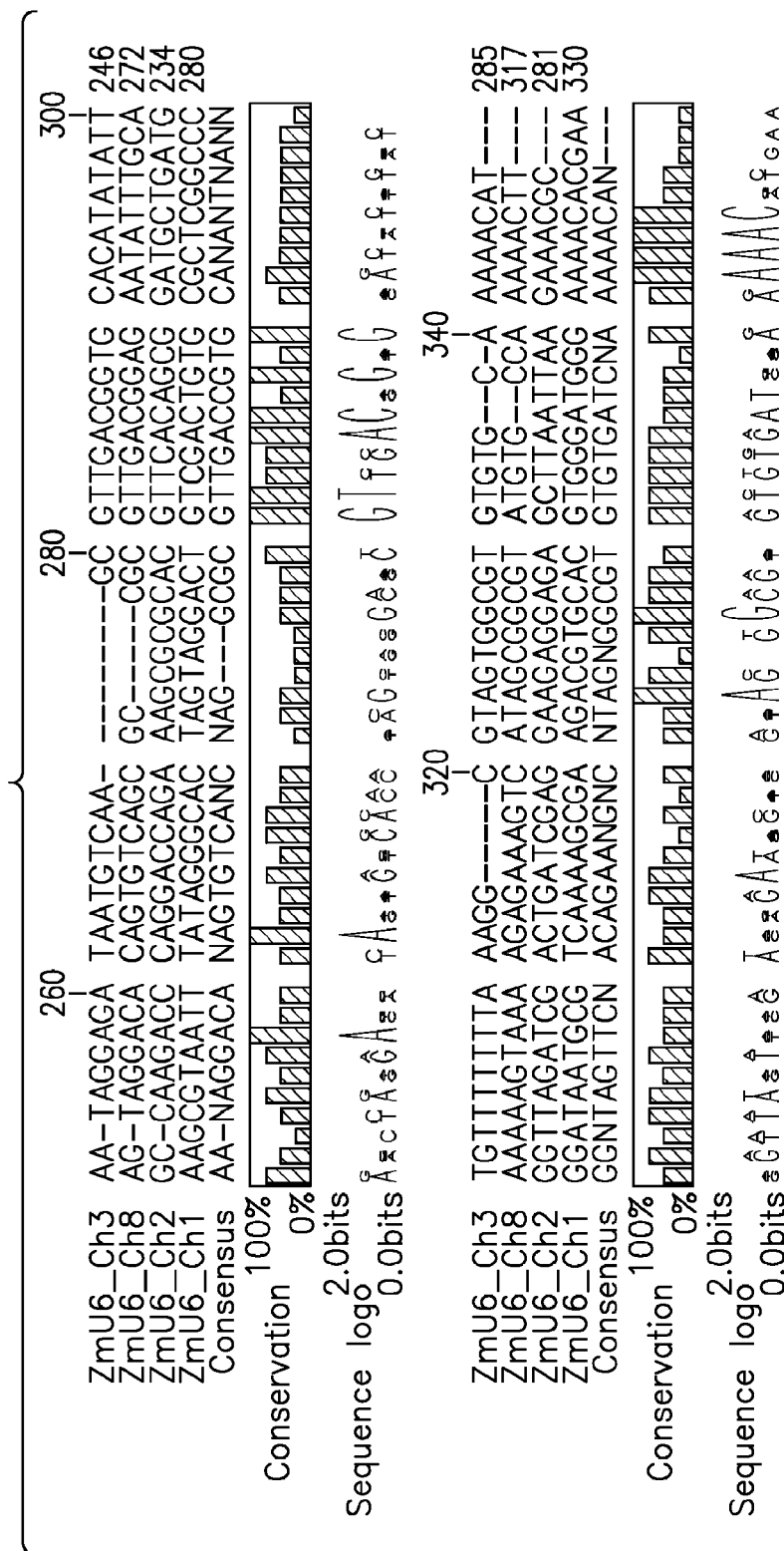

The disclosure provides novel promoters from *Zea mays* and other plants, and methods for their use that include targeted gene modification of a plant genome using transgenic expression of a gene, or genes, involved in the Clustered Regularly Interspersed Short Palindromic Repeats (CRISPR) system found in many bacteria. For instance, the disclosure provides, in one embodiment, DNA constructs encoding at least one expression cassette including a U6 promoter disclosed herein and a sequence encoding a single-guide RNA (sgRNA). Methods for causing a CRISPR system to modify a target genome are also provided, as are the genomic complements of a plant modified by the use of such a system. The disclosure thus provides tools and methods that allow one to insert, remove, or modify genes, loci, linkage blocks, and chromosomes within a plant. Also disclosed are U3, U2, U5 and 7SL promoters and methods for their use that include targeted gene modification of a plant genome.

The disclosure provides, in another embodiment, DNA constructs encoding at least one expression cassette including a promoter disclosed herein and a sequence encoding a non-protein-coding small RNA (npcRNA). These constructs are useful for targeting nuclear expression of the npcRNA molecules.

The CRISPR system constitutes an adaptive immune system in prokaryotes that targets endonucleolytic cleavage of the DNA and RNA of invading phage (reviewed in Westra et al., *Annu Rev Genet*, 46:311-39, 2012). There are three known types of CRISPR systems, Type I, Type II, and Type III. The CRISPR systems rely on small RNAs for sequence-specific detection and targeting of foreign nucleic acids for destruction. The components of the bacterial CRISPR systems are CRISPR-associated (Cas) genes and CRISPR array(s) consisting of genome-target sequences (protospacers) interspersed with short palindromic repeats. Transcription of the protospacer/repeat elements into precursor CRISPR RNA (pre-crRNA) molecules is followed by enzymatic cleavage triggered by hybridization between a trans-acting CRISPR RNA (tracrRNA) molecule and a pre-crRNA palindromic repeat. The resulting crRNA:tracrRNA molecules, consisting of one copy of the spacer and one repeat, complex with a Cas nuclease. The CRISPR/Cas complex is then directed to DNA sequences (protospacer) complementary to the crRNA spacer sequence, where this RNA-Cas protein complex silences the target DNA through enzymatic cleavage of both strands (double-strand break; DSB).

The native bacterial type II CRISPR system requires four molecular components for targeted cleavage of exogenous DNAs: a Cas endonuclease (e.g., Cas9), the house-keeping RNaseIII, CRISPR RNA (crRNA) and trans-acting CRISPR RNA (tracrRNA). The latter two components form a dsRNA complex and bind to Cas9 resulting in an RNA-guided DNA endonuclease complex. For targeted genome modifications in eukaryotes, this system was simplified to two components: the Cas9 endonuclease and a chimeric crRNA-tracrRNA, called guide-RNA (gRNA) or, alternatively, single-guide RNA (sgRNA). Experiments initially conducted in eukaryotic systems determined that the RNaseIII component was not necessary to achieve targeted DNA cleavage. The minimal two component system of Cas9 with the sgRNA, as the only unique component, enables this CRISPR system of targeted genome modification to be more cost effective and flexible than other targeting platforms such as meganucleases, Zn-finger nucleases, or TALE-nucleases which require protein engineering for modification at each targeted DNA site. Additionally, the ease of design and production of sgRNAs provides the CRISPR system with several advantages for application of targeted genome modification. For example, the CRISPR/Cas complex components (Cas endonuclease, sgRNA, and, optionally, exogenous DNA for integration into the genome) designed for one or more genomic target sites can be multiplexed in one transformation, or the introduction of the CRISPR/Cas complex components can be spatially and/or temporally separated.

Expression Strategies for sgRNAs

The disclosure provides, in certain embodiments, novel combinations of promoters and a sequence encoding a sgRNA, to allow for specifically introducing a double-stranded DNA cleavage event into endogenous DNA (i.e., a genome). In one embodiment, a U6 promoter from corn is operably linked to a sgRNA-encoding gene, in order to constitutively express the sgRNA in transformed cells. This may be desirable, for example, when the resulting sgRNA transcripts are retained in the nucleus and will thus be optimally located within the cell to guide nuclear processes. This may also be desirable, for example, when the activity of the CRISPR is low or the frequency of finding and cleaving the target site is low. It may also be desirable when a promoter for a specific cell type, such as the germ line, is not known for a given species of interest. In another embodiment, a U3, U2, U5, or 7SL promoter is operably linked to a sgRNA-encoding gene, for expression of an sgRNA in transformed cells.

In another embodiment, a chimeric promoter comprising all or a portion of any of the U6 promoters provided herein can be used to express a sgRNA. Alternatively, a U3, U2, U5, or 7SL chimeric promoter comprising all or a portion of any of these promoters, may be utilized. For example, the 5' portion of the U6 promoter from corn chromosome 1 (SEQ ID NO:1), including one MSP element, operably linked to the 3' portion of the U6 promoter from corn chromosome 8 (SEQ ID NO:7), including a USE element and a TATA box (SEQ ID NO:17), cloned upstream of a sgRNA, may be used to induce CRISPR-mediated cleavage under different environmental conditions.

Multiple U6 promoters with differing sequence may be utilized to minimize problems in vector stability, which is typically associated with sequence repeats. Further, highly repetitive regions in chromosomes may lead to genetic instability and silencing. Therefore, use of multiple U6 (or other disclosed) promoters in the CRISPR/Cas system of targeted gene modification may facilitate vector stacking of multiple sgRNA cassettes in the same transformation construct, wherein the differing sgRNA transcript levels are to be optimized for efficient targeting of a single target site. Chimeric U6 promoters can result in new, functional versions with improved or otherwise modified expression levels, and four representative chimeric corn U6 promoters have been designed (SEQ ID NO:17, SEQ ID NO:18, SEQ ID NO:19, and SEQ ID NO:20).

The disclosed U6 promoters may also drive expression of other non-protein-coding RNA (npcRNA). Non-limiting examples of non-protein-coding small RNA include a microRNA (miRNA), a miRNA precursor, a small interfering RNA (siRNA), a small RNA (22-26 nt in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), and a naturally occurring antisense siRNA (nat-siRNA).

Promoters and transcriptional elements for additional small nuclear RNA (snRNA) genes, similar to U6 promoters and which may be transcribed by RNA polymerase II or RNA polymerase III, can also be identified, such as U3, U2, U5, and 7SL promoters. These alternate promoters can be useful in cassette design, especially where these additional elements may facilitate nuclear retention of the CRISPR system transcripts. Additional gene transcription elements that can be useful in CRISPR cassette design include intron-embedded elements and transcriptional elements of plant specific RNA polymerase IV and V promoters.

Expression Strategies for Cas-Associated Genes

The disclosure provides novel promoters for use in sequence-specific or sequence-directed CRISPR-mediated cleavage for molecular breeding by providing transcription of, for example, a sgRNA including a spacer sequence used to target a protospacer sequence within a genomic target site for endonuclease cleavage by at least one Cas protein, wherein the genomic target site is native or transgenic. In addition, CRISPR systems can be customized to catalyze cleavage at one or more genomic target sites. In certain embodiments, such a custom CRISPR system would have properties making it amenable to genetic modification such that the system's Cas endonuclease protein(s) recognition, binding and/or catalytic activity could be manipulated.

One aspect of this disclosure is to introduce into a plant cell an expression vector comprising one or more cassettes encoding a U6 corn promoter, or other disclosed promoter such as an U3, U2, U5 or 7SL promoter, operably linked to a sgRNA, including a copy of a spacer sequence complementary to a protospacer sequence within a genomic target site, and an expression vector encoding a Cas-associated gene to modify the plant cell in such a way that the plant cell, or a plant comprised of such cells, will subsequently exhibit a beneficial trait. In one non-limiting example, the trait is a trait such as improved yield, resistance to biotic or abiotic stress, herbicide tolerance, or other improvements in agronomic performance. The ability to generate such a plant cell derived therefrom depends on introducing the CRISPR system using transformation vectors and cassettes described herein.

The expression vector encoding a Cas-associated gene may comprise a promoter. In certain embodiments, the promoter is a constitutive promoter, a tissue specific promoter, a developmentally regulated promoter, or a cell cycle regulated promoter. Certain contemplated promoters include ones that only express in the germline or reproductive cells, among others. Such developmentally regulated promoters have the advantage of limiting the expression of the CRISPR system to only those cells in which DNA is inherited in subsequent generations. Therefore, a CRISPR-mediated genetic modification (i.e., chromosomal or episomal dsDNA cleavage) is limited only to cells that are involved in transmitting their genome from one generation to the next. This might be useful if broader expression of the CRISPR system were genotoxic or had other unwanted effects. Examples of such promoters include the promoters of genes encoding DNA ligases, recombinases, replicases, and so on.

Endonucleases are enzymes that cleave the phosphodiester bond within a polynucleotide chain. Examples of endonucleases that cleave only at specific nucleotide sequences are well known in the art and can include, for instance, restriction endonucleases. However, the need for targeted genome engineering as an alternative to classical plant breeding requires highly customizable tools for genome editing. The CRISPR-associated type II prokaryotic adaptive immune system provides such an alternative. As such, the DNA constructs provided herein can recognize a specific nucleotide sequence of interest within a target host genome and allow for mutation or integration at that site. In a particular embodiment, the DNA constructs contain one or more corn U6 promoter, or chimeras thereof, that express high levels of a sequence encoding a sgRNA. A DNA construct that expresses a sgRNA that targets a Cas-associated gene product with endonuclease activity to a specific genomic sequence, such that the specific genomic sequence is cleaved and produces a double-stranded break which is repaired by a double strand break repair pathway, which may include, for example, non-homologous end-joining, homologous recombination, synthesis-dependent strand annealing (SDSA), single-strand annealing (SSA), or a combination thereof thereby disrupting the native locus, may be particularly useful.

In one embodiment, a CRISPR system comprises at least one Cas-associated gene encoding a CRISPR endonuclease and one sgRNA comprising a copy of a spacer sequence complementary to a protospacer sequence within an endogenous genomic target site.

In particular embodiments, a Cas-associated gene can include any type II CRISPR system endonuclease. Such a Cas-associated gene product would have properties making it amenable to genetic modification such that its nuclease activity and its recognition and binding of crRNA, tracrRNA, and/or sgRNA could be manipulated.

The present disclosure also provides for use of CRISPR-mediated double-stranded DNA cleavage to genetically alter expression and/or activity of a gene or gene product of interest in a tissue- or cell-type specific manner to improve productivity or provide another beneficial trait, wherein the nucleic acid of interest may be endogenous or transgenic in nature. Thus, in one embodiment, a CRISPR system is engineered to mediate disruption at specific sites in a gene of interest. Genes of interest include those for which altered expression level/protein activity is desired. These DNA cleavage events can be either in coding sequences or in regulatory elements within the gene.

This disclosure provides for the introduction of a type II CRISPR system into a cell. Exemplary type II Cas-associated genes include natural and engineered (i.e., modified, including codon-optimized) nucleotide sequences encoding polypeptides with nuclease activity such as Cas9 from *Streptococcus pyogenes, Streptococcus thermophilus*, or *Bradyrhizobium* sp.

The catalytically active CRISPR-associate gene (e.g., Cas9 endonuclease) can be introduced into, or produced by, a target cell. Various methods may be used to carry this out, as disclosed herein.

Transient Expression of CRISPRs

In some embodiments, the sgRNA and/or Cas-associated gene is transiently introduced into a cell. In certain embodiments, the introduced sgRNA and/or Cas-associated gene is provided in sufficient quantity to modify the cell but does not persist after a contemplated period of time has passed or after one or more cell divisions. In such embodiments, no further steps are needed to remove or segregate the sgRNA and/or Cas-associated gene from the modified cell. In yet other embodiments of this disclosure, double-stranded DNA fragments are also transiently introduced into a cell along with sgRNA and/or Cas-associated gene. In such embodiments, the introduced double-stranded DNA fragments are provided in sufficient quantity to modify the cell but do not persist after a contemplated period of time has passed or after one or more cell divisions.

In another embodiment, mRNA encoding the Cas-associated gene is introduced into a cell. In such embodiments, the mRNA is translated to produce the type II CRISPR system endonuclease in sufficient quantity to modify the cell (in the presence of at least one sgRNA) but does not persist after a contemplated period of time has passed or after one or more cell divisions. In such embodiments, no further steps are needed to remove or segregate the Cas-associated gene from the modified cell.

In one embodiment of this disclosure, a catalytically active Cas-associated gene product is prepared in vitro prior to introduction to a cell, including a prokaryotic or eukaryotic cell. The method of preparing a Cas-associated gene product depends on its type and properties and would be known by one of skill in the art. For example, if the Cas-associated gene product is a large monomeric DNA nuclease, the active form of the Cas-associated gene product can be produced via bacterial expression, in vitro translation, via yeast cells, in insect cells, or by other protein production techniques described in the art. After expression, the Cas-associated gene product is isolated, refolded if needed, purified and optionally treated to remove any purification tags, such as a His-tag. Once crude, partially purified, or more completely purified Cas-associated gene products are obtained, the protein may be introduced to, for example, a plant cell via electroporation, by bombardment with Cas-associated gene product coated particles, by chemical transfection or by some other means of transport across a cell membrane. Methods for introducing nucleic acids into bacterial and animal cells are similarly well known in the art. The protein can also be delivered using nanoparticles, which can deliver a combination of active protein and nucleic acid. Once a sufficient quantity of the Cas-associated gene product is introduced so that an effective amount of in vivo nuclease activity is present, along with the appropriate sgRNA, the protospacer sequences within the episomal or genomic target sites are cleaved. It is also recognized that one skilled in the art might create a Cas-associated gene product that is inactive but is activated in vivo by native processing machinery; such a Cas-associated gene product is also contemplated by this disclosure.

In another embodiment, a construct that will transiently express a sgRNA and/or Cas-associated gene is created and introduced into a cell. In yet another embodiment, the vector will produce sufficient quantities of the sgRNAs and/or Cas-associated gene in order for the desired episomal or genomic target site or sites to be effectively modified by CRISPR-mediated cleavage. For instance, the disclosure contemplates preparation of a vector that can be bombarded, electroporated, chemically transfected or transported by some other means across the plant cell membrane. Such a vector could have several useful properties. For instance, in one embodiment, the vector can replicate in a bacterial host such that the vector can be produced and purified in sufficient quantities for transient expression. In another embodiment, the vector can encode a drug resistance gene to allow selection for the vector in a host, or the vector can also comprise an expression cassette to provide for the expression of the sgRNA and/or Cas-associated gene in a plant. In a further embodiment, the expression cassette could contain a promoter region, a 5' untranslated region, an optional intron to aid expression, a multiple cloning site to allow facile introduction of a sequence encoding sgRNAs and/or Cas-associated gene, and a 3' UTR. In particular embodiments, the promoters in the expression cassette would be U6 promoters from *Zea mays* In yet other embodiments, the promoters would be chimeric U6 promoters from *Zea mays*. In some embodiments, it can be beneficial to include unique restriction sites at one or at each end of the expression cassette to allow the production and isolation of a linear expression cassette, which can then be free of other vector elements. The untranslated leader regions, in certain embodiments, can be plant-derived untranslated regions. Use of an intron, which can be plant-derived, is contemplated when the expression cassette is being transformed or transfected into a monocot cell.

In other embodiments, one or more elements in the vector include a spacer complementary to a protospacer contained within an episomal or genomic target site. This facilitates CRISPR-mediated modification within the expression cassette, enabling removal and/or insertion of elements such as promoters and transgenes.

In another approach, a transient expression vector may be introduced into a cell using a bacterial or viral vector host. For example, *Agrobacterium* is one such bacterial vector that can be used to introduce a transient expression vector into a host cell. When using a bacterial, viral or other vector host system, the transient expression vector is contained within the host vector system. For example, if the *Agrobacterium* host system is used, the transient expression cassette would be flanked by one or more T-DNA borders and cloned into a binary vector. Many such vector systems have been identified in the art (reviewed in Hellens et al., 2000).

In embodiments whereby the sgRNA and/or Cas-associated gene is transiently introduced in sufficient quantities to modify a cell, a method of selecting the modified cell may be employed. In one such method, a second nucleic acid molecule containing a selectable marker is co-introduced with the transient sgRNA and/or Cas-associated gene. In this embodiment, the co-introduced marker may be part of a molecular strategy to introduce the marker at a target site. For example, the co-introduced marker may be used to disrupt a target gene by inserting between genomic target sites. In another embodiment, the co-introduced nucleic acid may be used to produce a visual marker protein such that transfected cells can be cell-sorted or isolated by some other means. In yet another embodiment, the co-introduced marker may randomly integrate or be directed via a second sgRNA:Cas-protein complex to integrate at a site independent of the primary genomic target site. In still yet another embodiment, the co-introduced molecule may be targeted to a specific locus via a double strand break repair pathway, which may include, for example, non-homologous end-joining, homologous recombination, synthesis-dependent strand annealing (SDSA), single-strand annealing (SSA), or a combination thereof, at the genomic target site(s). In the above embodiments, the co-introduced marker may be used to identify or select for cells that have likely been exposed to the sgRNA and/or Cas-associated gene and therefore are likely to have been modified by the CRISPR.

Stable Expression of CRISPRs

In another embodiment, a CRISPR expression vector is stably transformed into a cell so as to cleave a DNA sequence at or near a genomic target site in the host genome with a sgRNA and Cas-associated gene product encoded within the vector. In this embodiment, the design of the transformation vector provides flexibility for when and under what conditions the sgRNA and/or Cas-associated gene is expressed. Furthermore, the transformation vector can be designed to comprise a selectable or visible marker that will provide a means to isolate or efficiently select cell lines that contain and/or have been modified by the CRISPR.

Cell transformation systems have been described in the art and descriptions include a variety of transformation vectors. For example, for plant transformations, two principal methods include *Agrobacterium*-mediated transformation and particle gun bombardment-mediated (i.e., biolistic) transformation. In both cases, the CRISPR is introduced via an expression cassette. The cassette may contain one or more of the following elements: a promoter element that can be used to express the sgRNA and/or Cas-associated gene; a 5' untranslated region to enhance expression; an intron element to further enhance expression in certain cell types, such as monocot cells; a multiple-cloning site to provide convenient restriction sites for inserting the sgRNA and/or Cas-associated gene sequences and other desired elements; and a 3' untranslated region to provide for efficient termination of the expressed transcript. In particular embodiments, the promoters in the expression cassette would be U6 promoters from *Zea mays*. In yet other embodiments, the promoters would be chimeric U6 promoters from *Zea mays*.

For particle bombardment or with protoplast transformation, the expression cassette can be an isolated linear fragment or may be part of a larger construct that might contain bacterial replication elements, bacterial selectable markers or other elements. The sgRNA and/or Cas-associated gene expression cassette(s) may be physically linked to a marker cassette or may be mixed with a second nucleic acid molecule encoding a marker cassette. The marker cassette is comprised of necessary elements to express a visual or selectable marker that allows for efficient selection of transformed cells. In the case of *Agrobacterium*-mediated transformation, the expression cassette may be adjacent to or between flanking T-DNA borders and contained within a binary vector. In another embodiment, the expression cassette may be outside of the T-DNA. The presence of the expression cassette in a cell may be manipulated by positive or negative selection regime(s). Furthermore, a selectable marker cassette may also be within or adjacent to the same T-DNA borders or may be somewhere else within a second T-DNA on the binary vector (e.g., a 2 T-DNA system).

In another embodiment, cells that have been modified by a CRISPR, either transiently or stably, are carried forward along with unmodified cells. The cells can be sub-divided into independent clonally derived lines or can be used to regenerate independently derived plants. Individual plants or clonal populations regenerated from such cells can be used to generate independently derived lines. At any of these stages a molecular assay can be employed to screen for cells, plants or lines that have been modified. Cells, plants or lines that have been modified continue to be propagated and unmodified cells, plants or lines are discarded. In these embodiments, the presence of an active CRISPR in a cell is essential to ensure the efficiency of the overall process.

Transformation Methods

Methods for transforming or transfecting a cell are well known in the art. Methods for plant transformation using *Agrobacterium* or DNA coated particles are well known in the art and are incorporated herein. Suitable methods for transformation of host cells for use with the current disclosure are believed to include virtually any method by which DNA can be introduced into a cell, for example by *Agrobacterium*-mediated transformation (U.S. Pat. Nos. 5,563, 055; 5,591,616; 5,693,512; 5,824,877; 5,981,840; and 6,384,301) and by acceleration of DNA coated particles (U.S. Pat. Nos. 5,015,580; 5,550,318; 5,538,880; 6,160,208; 6,399,861; and 6,403,865), etc. Through the application of techniques such as these, the cells of virtually any species may be stably transformed.

Various methods for selecting transformed cells have been described. For example, one might utilize a drug resistance marker such as a neomycin phosphotransferase protein to confer resistance to kanamycin or to use 5-enolpyruvyl shikimate phosphate synthase to confer tolerance to glyphosate. In another embodiment, a carotenoid synthase is used to create an orange pigment that can be visually identified. These three exemplary approaches can each be used effectively to isolate a cell or plant or tissue thereof that has been transformed and/or modified by a CRISPR.

When a nucleic acid sequence encoding a selectable or screenable marker is inserted into a genomic target site, the marker can be used to detect the presence or absence of a CRISPR or its activity. This may be useful once a cell has been modified by a CRISPR, and recovery of a genetically modified cell that no longer contains the CRISPR, or a regenerated plant from such a modified cell, is desired. In other embodiments, the marker may be intentionally designed to integrate at the genomic target site, such that it can be used to follow a modified cell independently of the CRISPR. The marker can be a gene that provides a visually detectable phenotype, such as in the seed, to allow rapid identification of seeds that carry or lack a CRISPR expression cassette.

This disclosure provides for a means to regenerate a plant from a cell with a repaired double-stranded break within a protospacer sequence at a genomic target site. The regenerant can then be used to propagate additional plants.

The disclosure additionally provides novel plant transformation vectors and expression cassettes which include novel U6 promoters, and U3, U2, U5 and 7SL promoters, and combinations thereof, with CRISPR-associated gene(s) and sgRNA expression cassettes. The disclosure further provides methods of obtaining a plant cell, a whole plant, and a seed or embryo that have been specifically modified using CRISPR-mediated cleavage. This disclosure also relates to a novel plant cell containing a CRISPR-associated Cas endonuclease expression construct and sgRNA expression cassettes.

Targeting Using Blunt-End Oligonucleotides

In certain embodiments, the CRISPR/Cas9 system can be utilized for targeting insertion of a blunt-end double-stranded DNA fragment into a genomic target site of interest. CRISPR-mediated endonuclease activity can introduce a double stand break (DSB) in the protospacer of the selected genomic target site and DNA repair, such as microhomology-driven non-homologous end-joining DNA repair, results in insertion of the blunt-end double-stranded DNA fragment into the DSB. Blunt-end double-stranded DNA fragments can be designed with 1-10 bp of microhomology, on both the 5' and 3' ends of the DNA fragment, that correspond to the 5' and 3' flanking sequence at the cut site of the protospacer in the genomic target site.

Use of Custom CRISPRs in Molecular Breeding

In some embodiments, genome knowledge is utilized for targeted genetic alteration of a genome. At least one sgRNA can be designed to target at least one region of a genome to disrupt that region from the genome. This aspect of the disclosure may be especially useful for genetic alterations. The resulting plant could have a modified phenotype or other property depending on the gene or genes that have been altered. Previously characterized mutant alleles or introduced transgenes can be targeted for CRISPR-mediated modification, enabling creation of improved mutants or transgenic lines.

In another embodiment, a gene targeted for deletion or disruption may be a transgene that was previously introduced into the target plant or cell. This has the advantage of allowing an improved version of a transgene to be introduced or by allowing disruption of a selectable marker encoding sequence. In yet another embodiment, a gene targeted for disruption via CRISPR is at least one transgene that was introduced on the same vector or expression cassette as (an)other transgene(s) of interest, and resides at the same locus as another transgene. It is understood by those skilled in the art that this type of CRISPR-mediated modification may result in deletion or insertion of additional sequences. Thus it may, in certain embodiments, be preferable to generate a plurality of plants or cells in which a deletion has occurred, and to screen such plants or cells using standard techniques to identify specific plants or cells that have minimal alterations in their genomes following CRISPR-mediated modification. Such screens may utilize genotypic and/or phenotypic information. In such embodiments, a specific transgene may be disrupted while leaving the remaining transgene(s) intact. This avoids having to create a new transgenic line containing the desired transgenes without the undesired transgene.

In another aspect, the present disclosure includes methods for inserting a DNA fragment of interest into a specific site of a plant's genome, wherein the DNA fragment of interest is from the genome of the plant or is heterologous with respect to the plant. This disclosure allows one to select or target a particular region of the genome for nucleic acid (i.e., transgene) stacking (i.e., mega-locus). A targeted region of the genome may thus display linkage of at least one transgene to a haplotype of interest associated with at least one phenotypic trait, and may also result in the development of a linkage block to facilitate transgene stacking and transgenic trait integration, and/or development of a linkage block while also allowing for conventional trait integration.

Use of Custom CRISPRs in Trait Integration

Directed insertion, in at least one genomic protospacer site, of DNA fragments of interest, via CRISPR-mediated cleavage allows for targeted integration of multiple nucleic acids of interest (i.e., a trait stack) to be added to the genome of a plant in either the same site or different sites. Sites for targeted integration can be selected based on knowledge of the underlying breeding value, transgene performance in that location, underlying recombination rate in that location, existing transgenes in that linkage block, or other factors. Once the stacked plant is assembled, it can be used as a trait donor for crosses to germplasm being advanced in a breeding pipeline or be directly advanced in the breeding pipeline.

The present disclosure includes methods for inserting at least one nucleic acid of interest into at least one site, wherein the nucleic acid of interest is from the genome of a plant, such as a QTL or allele, or is transgenic in origin. A targeted region of the genome may thus display linkage of at least one transgene to a haplotype of interest associated with at least one phenotypic trait (as described in U.S. Patent Application Publication No. 2006/0282911), development of a linkage block to facilitate transgene stacking and transgenic trait integration, development of a linkage block to facilitate QTL or haplotype stacking and conventional trait integration, and so on.

In another embodiment of this disclosure, multiple unique sgRNAs can be used to modify multiple alleles at specific loci within one linkage block contained on one chromosome by making use of knowledge of genomic sequence information and the ability to design custom sgRNAs as described in the art. A sgRNA that is specific for, or can be directed to, a genomic target site that is upstream of the locus containing the non-target allele is designed or engineered as necessary. A second sgRNA that is specific for, or can be directed to, a genomic target site that is downstream of the target locus containing the non-target allele is also designed or engineered. The sgRNAs may be designed such that they complement genomic regions where there is no homology to the non-target locus containing the target allele. Both sgRNAs may be introduced into a cell using one of the methods described above.

The ability to execute targeted integration relies on the action of the sgRNA:Cas-protein complex and the endonuclease activity of the Cas-associated gene product. This advantage provides methods for engineering plants of interest, including a plant or cell, comprising at least one genomic modification.

A custom sgRNA can be utilized in a CRISPR system to generate at least one trait donor to create a custom genomic modification event that is then crossed into at least one second plant of interest, including a plant, wherein CRISPR delivery can be coupled with the sgRNA of interest to be used for genome editing. In other aspects one or more plants of interest are directly transformed with the CRISPR system and at least one double-stranded DNA fragment of interest for directed insertion. It is recognized that this method may be executed in various cell, tissue, and developmental types, including gametes of plants. It is further anticipated that one or more of the elements described herein may be combined with use of promoters specific to particular cells, tissues, plant parts and/or developmental stages, such as a meiosis-specific promoter.

In addition, the disclosure contemplates the targeting of a transgenic element already existing within a genome for deletion or disruption. This allows, for instance, an improved version of a transgene to be introduced, or allows selectable marker removal. In yet another embodiment, a gene targeted for disruption via CRISPR-mediated cleavage is at least one transgene that was introduced on the same vector or expression cassette as (an)other transgene(s) of interest, and resides at the same locus as another transgene.

In one aspect, the disclosure thus provides a method for modifying a locus of interest in a cell comprising (a) identifying at least one locus of interest within a DNA sequence; (b) creating a modified nucleotide sequence, in or proximal to the locus of interest, that includes a protospacer sequence within a genomic target site for a first sgRNA according to the disclosure; (c) introducing into at least one cell the sgRNA and Cas-associated gene, wherein the sgRNA and/or Cas-associated gene is expressed transiently or stably; (d) assaying the cell for a CRISPR-mediated modification in the DNA making up or flanking the locus of interest; and (e) identifying the cell or a progeny cell thereof as comprising a modification in said locus of interest.

Another aspect provides a method for modifying multiple loci of interest in a cell comprising (a) identifying multiple loci of interest within a genome; (b) identifying multiple genomic protospacer sites within each locus of interest; (c) introducing into at least one cell multiple sgRNA and at least one Cas-associated gene according to the disclosure, wherein the cell comprises the genomic protospacer sites and the sgRNA and Cas-associated gene is expressed transiently or stably and creates a modified locus, or loci, that includes at least one CRISPR-mediated cleavage event; (d) assaying the cell for CRISPR-mediated modifications in the DNA making up or flanking each locus of interest; and (e) identifying a cell or a progeny cell thereof which comprises a modified nucleotide sequence at said loci of interest.

The disclosure further contemplates sequential modification of a locus of interest, by two or more sgRNAs and Cas-associated gene(s) according to the disclosure. Genes or other sequences added by the action of such a first CRISPR-mediated genomic modification may be retained, further modified, or removed by the action of a second CRISPR-mediated genomic modification.

The present invention thus includes a method for modifying a locus of interest in a crop plant such as maize (corn; *Zea mays*), soybean (*Glycine max*), cotton (*Gossypium hirsutum*; *Gossypium* sp.), peanut (*Arachis hypogaea*), barley (*Hordeum vulgare*); oats (*Avena sativa*); orchard grass (*Dactylis glomerata*); rice (*Oryza sativa*, including indica and japonica varieties); sorghum (*Sorghum bicolor*); sugar cane (*Saccharum* sp.); tall fescue (*Festuca arundinacea*); turfgrass species (e.g. species: *Agrostis stolonifera, Poa pratensis, Stenotaphrum secundatum*); wheat (*Triticum aestivum*); alfalfa (*Medicago sativa*); members of the genus *Brassica*, including broccoli, cabbage, carrot, cauliflower, Chinese cabbage; cucumber, dry bean, eggplant, tobacco, fennel, garden beans, gourd, leek, lettuce, melon, okra, onion, pea, pepper, pumpkin, radish, spinach, squash, sweet corn, tomato, watermelon, ornamental plants, and other fruit, vegetable, tuber, oilseed, and root crops, wherein oilseed crops include soybean, canola, oil seed rape, oil palm, sunflower, olive, corn, cottonseed, peanut, flaxseed, safflower, and coconut.

The genome modification may comprise a modified linkage block, the linking of two or more QTLs, disrupting linkage of two or more QTLs, gene insertion, gene replacement, gene conversion, deleting or disrupting a gene, transgenic event selection, transgenic trait donor selection, transgene replacement, or targeted insertion of at least one nucleic acid of interest.

Definitions

The definitions and methods provided define the present disclosure and guide those of ordinary skill in the art in the practice of the present disclosure. Unless otherwise noted, terms are to be understood according to conventional usage by those of ordinary skill in the relevant art. Definitions of common terms in molecular biology may also be found in Alberts et al., Molecular Biology of The Cell, 5th Edition, Garland Science Publishing, Inc.: New York, 2007; Rieger et al., Glossary of Genetics: Classical and Molecular, 5th edition, Springer-Verlag: New York, 1991; King et al, A Dictionary of Genetics, 6th ed., Oxford University Press: New York, 2247; and Lewin, Genes IX, Oxford University Press: New York, 2007. The nomenclature for DNA bases as set forth at 37 CFR § 1.822 is used.

As used herein, "CRISPR-associated genes" refers to nucleic acid sequences that encode polypeptide components of clustered regularly interspersed short palindromic repeats (CRISPR)-associated systems (Cas). Examples include, but are not limited to, Cas3 and Cas9, which encode endonucleases from the CRISPR type I and type II systems, respectively.

As used herein, "single-guide RNA (sgRNA)" refers to a crRNA:tracrRNA fused hybrid single-stranded RNA molecule encoded by a customizable DNA element that, generally, comprises a copy of a spacer sequence which is complementary to the protospacer sequence of the genomic target site, and a binding domain for an associated-Cas endonuclease of the CRISPR complex.

As used herein, "genomic target site" refers to a protospacer and a protospacer adjacent motif (PAM) located in a host genome selected for targeted mutation and/or double-strand break.

As used herein, "protospacer" refers to a short DNA sequence (12 to 40 bp) that can be targeted for mutation, and/or double-strand break, mediated by enzymatic cleavage with a CRISPR system endonuclease guided by complementary base-pairing with the spacer sequence in the crRNA or sgRNA.

As used herein, "protospacer adjacent motif (PAM)" includes a 3 to 8 bp sequence immediately adjacent to the protospacer sequence in the genomic target site.

As used herein, "microhomology" refers to the presence of the same short sequence (1 to 10 bp) of bases in different polynucleotide molecules.

As used herein, "codon-optimized" refers to a polynucleotide sequence that has been modified to exploit the codon usage bias of a particular plant. The modified polynucleotide sequence still encodes the same, or substantially similar polypeptide as the original sequence but uses codon nucleotide triplets that are found in greater frequency in a particular plant.

As used herein, "non-protein-coding RNA (npcRNA)" refers to a non-coding RNA (ncRNA) which is a precursor small non-protein coding RNA, or a fully processed non-protein coding RNA, which are functional RNA molecules that are not translated into a protein.

As used herein, the term "chimeric" refers to the product of the fusion of portions of two or more different polynucleotide molecules, or to a gene expression element produced through the manipulation of known elements or other polynucleotide molecules. Novel chimeric regulatory elements can be designed or engineered by a number of methods. In one embodiment of the present disclosure, a chimeric promoter may be produced by fusing the 5' portion of a U6 promoter from corn chromosome 1, which includes at least one Monocot-Specific Promoter (MSP) element, to the 3' portion of the U6 promoter from corn chromosome 8, which includes an Upstream Sequence Element (USE) and a TATA Box. The resultant chimeric promoter may have novel expression properties relative to the first or second promoters.

As used herein, "promoter" refers to a nucleic acid sequence located upstream or 5' to a translational start codon of an open reading frame (or protein-coding region) of a gene and that is involved in recognition and binding of RNA polymerase I, II, or III and other proteins (transacting transcription factors) to initiate transcription. A "plant promoter" is a native or non-native promoter that is functional in plant cells. Constitutive promoters are functional in most or all tissues of a plant throughout plant development. Tissue-, organ- or cell-specific promoters are expressed only or predominantly in a particular tissue, organ, or cell type, respectively. Rather than being expressed "specifically" in a given tissue, plant part, or cell type, a promoter may display "enhanced" expression, i.e., a higher level of expression, in one cell type, tissue, or plant part of the plant compared to other parts of the plant. Temporally regulated promoters are functional only or predominantly during certain periods of plant development or at certain times of day, as in the case of genes associated with circadian rhythm, for example. Inducible promoters selectively express an operably linked DNA sequence in response to the presence of an endogenous or exogenous stimulus, for example by chemical compounds (chemical inducers) or in response to environmental, hormonal, chemical, and/or developmental signals. Inducible or regulated promoters include, for example, promoters regulated by light, heat, stress, flooding or drought, phytohormones, wounding, or chemicals such as ethanol, jasmonate, salicylic acid, or safeners.

As used herein, an "expression cassette" refers to a polynucleotide sequence comprising at least a first polynucleotide sequence capable of initiating transcription of an operably linked second polynucleotide sequence and optionally a transcription termination sequence operably linked to the second polynucleotide sequence.

A palindromic sequence is a nucleic acid sequence that is the same whether read 5' to 3' on one strand or 3' to 5' on the complementary strand with which it forms a double helix. A nucleotide sequence is said to be a palindrome if it is equal to its reverse complement. A palindromic sequence can form a hairpin.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein.

In some embodiments, the terms "a" and "an" and "the" and similar references used in the context of describing a particular embodiment (especially in the context of certain of the following claims) can be construed to cover both the singular and the plural, unless specifically noted otherwise. In some embodiments, the term "or" as used herein, including the claims, is used to mean "and/or" unless explicitly indicated to refer to alternatives only or the alternatives are mutually exclusive.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and can also cover other unlisted steps. Similarly, any composition or device that "comprises," "has" or "includes" one or more features is not limited to possessing only those one or more features and can cover other unlisted features.

All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the present disclosure and does not pose a limitation on the scope of the present disclosure otherwise claimed. No language in the specification should be construed as indicating any non-claimed element essential to the practice of the present disclosure.

Groupings of alternative elements or embodiments of the present disclosure disclosed herein are not to be construed as limitations. Each group member can be referred to and claimed individually or in any combination with other members of the group or other elements found herein. One or more members of a group can be included in, or deleted from, a group for reasons of convenience or patentability.

Having described the present disclosure in detail, it will be apparent that modifications, variations, and equivalent embodiments are possible without departing from the scope of the present disclosure defined in the appended claims. Furthermore, it should be appreciated that all examples in the present disclosure are provided as non-limiting examples.

EXAMPLES

The following examples are included to demonstrate embodiments of the disclosure. It should be appreciated by those of skill in the art that many changes can be made in the specific embodiments which are disclosed and still obtain a like or similar result without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

Example 1

Identification of Promoters to Express sgRNA

Figure 1B:
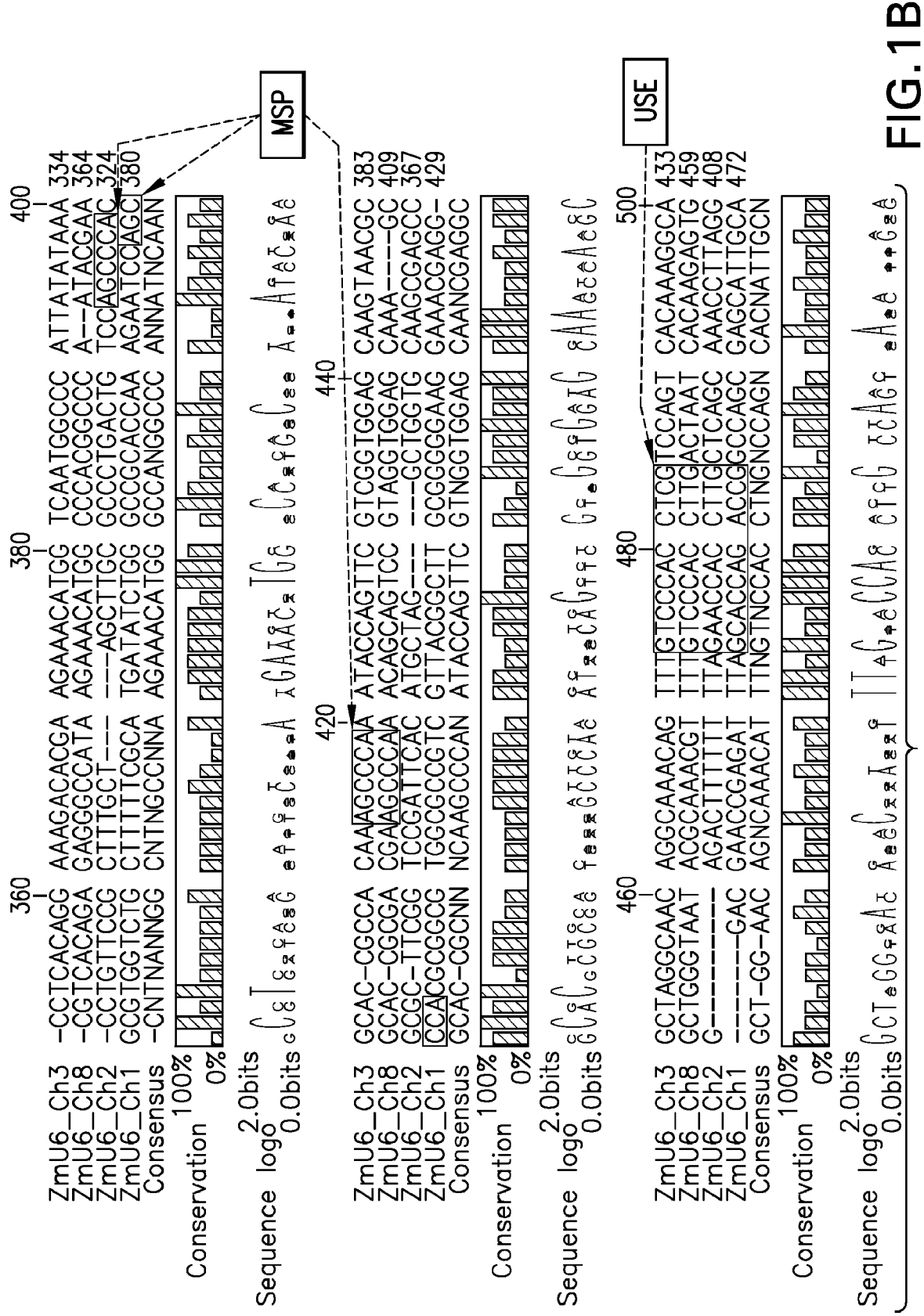
Figure 1B:
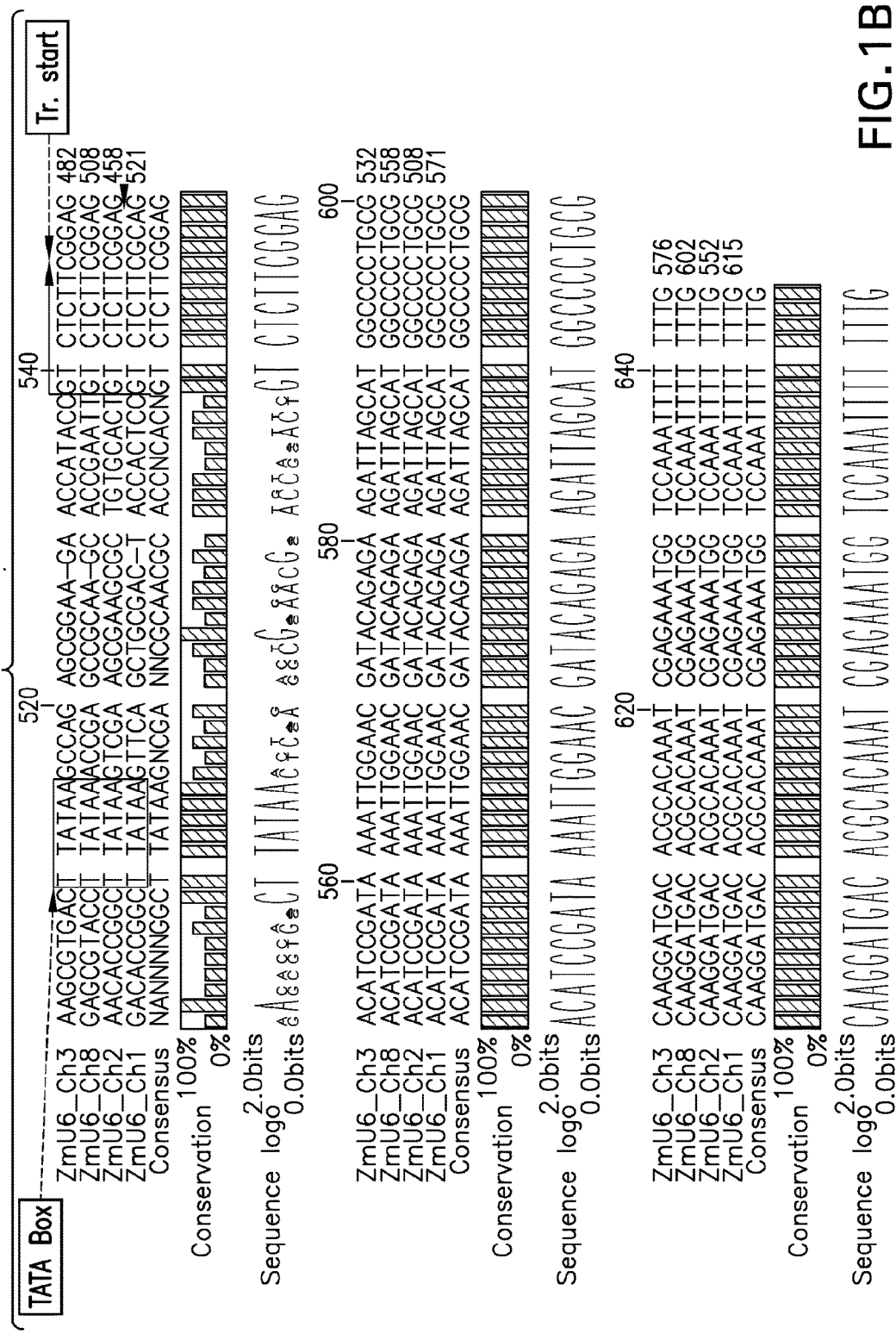

To enable genome engineering in corn, soy, and tomato using the CRISPR-based gene targeting system, novel U6 promoters native to these three genomes were identified. After BLAST searching for the highly conserved U6 gene in corn, soy, and tomato genomes, 200-600 bp of sequence upstream of these putative U6 genes was selected to test for promoter function (Table 1). Four U6 promoters were identified from the corn B73 genome, one each on chromosome 1 (SEQ ID NO:1), chromosome 2 (SEQ ID NO:3), chromosome 3 (SEQ ID NO:5), and chromosome 8 (SEQ ID NO:7). A multiple sequence alignment of these four corn U6 promoters and corresponding U6 genes was compiled as shown in FIGS. 1A and B. For each of these corn U6 promoters, conserved U6 promoter motifs (e.g., TATA Box, Upstream Sequence Element (USE), and Monocot-Specific Promoter (MSP) elements (Connelly, Mol. Cell Biol. 14:5910-5919, 1994) are present (FIG. 1B). A guanine nucleobase following the poly-T tracts was conserved among these four genes, and may have a significant role in transcription. The sequence consensus, and percent conservation are presented below the alignment (FIG. 1). Based on the multiple sequence alignment, the conserved motifs of these U6 promoters were within the 140 bp proximal to the transcription start site. Based on the proximity of these conserved U6 promoter motifs, 200 bp of the proximal upstream sequence from the transcription start site for each of the corn chromosome U6 promoters, chromosome 1 (SEQ ID NO:2), chromosome 2 (SEQ ID NO:4), chromosome 3 (SEQ ID NO:6), and chromosome 8 (SEQ ID NO:8) was selected for testing for efficient promoter activity in sgRNA expression cassettes.

In addition to the four corn U6 promoters, chimeric U6 promoters were designed. Four chimeric corn U6 promoters were designed using differing combinations of the corn U6 promoters from chromosome 1, 2, and 8, with each chimeric promoter being 397 bp in length. The breakpoints of the chimeras were determined so that the conserved elements (e.g., USE, MSP, and TATA box) of different chromosomal origins were mixed in the new chimeric U6 promoters but retained their relative spacing to the native corn U6 promoters. For example, the 5' end of the U6 promoter including MSP and USE were derived from one chromosome, while the 3' end including the TATA box and one or more MSP elements were derived from a second chromosome. Although the corn U6 promoter from chromosome 2 was not a very strong promoter in its native form, it included more than one MSP element. Consequently, chimeras that include mainly chromosome 1 and/or 8 sequence can also include one or more chromosome 2 MSP elements. Specifically, the 5' portion of chimera 1 (SEQ ID NO:17) is derived from the U6 promoter from corn chromosome 1 (SEQ ID NO:1), including one MSP element, and the 3' portion of this chimera is derived from the U6 promoter from corn chromosome 8 (SEQ ID NO:7), including a USE element and a TATA box. Similarly, the 5' portion of chimera 2 (SEQ ID NO:18) is derived from the U6 promoter from corn chromosome 1 (SEQ ID NO:1), including one MSP element, and the 3' portion of this chimera is derived from the U6 promoter from corn chromosome 8 (SEQ ID NO:7), including a second MSP element, a USE element, and a TATA box. The 5' portion of chimera 3 (SEQ ID NO:19) is derived from the U6 promoter from corn chromosome 8 (SEQ ID NO:7), including one MSP element, and the 3' portion of this chimera is derived from the U6 promoter from corn chromosome 1 (SEQ ID NO:1), including a second MSP element, a USE element, and a TATA box. Additionally, for chimera 3, there is a 3 bp deletion beginning at bp 100 of SEQ ID NO:7, and the 5' end of the chimera begins with 5'-AAG-3'. Chimera 4 (SEQ ID NO:20) was derived from the U6 promoter from corn chromosome 8 (SEQ ID NO:7), including the MSP element, the USE element and the TATA box. However, this chimera also includes two additional MSP elements (for a total of 3 MSP elements) derived from the U6 promoter of corn chromosomes 1 and 2.

TABLE 1

U6 promoters from corn (*Zea mays*), tomato (*Solanum lycopersicum*), and soybean (*Glycine max*), their chromosomal source and length.

| SEQ ID NO. | Source | Chromosome | Length (bp) |
|---|---|---|---|
| 1 | Zea mays | 1 | 397 |
| 2 | Zea mays | 1 | 200 |
| 3 | Zea mays | 2 | 397 |
| 4 | Zea mays | 2 | 200 |
| 5 | Zea mays | 3 | 397 |
| 6 | Zea mays | 3 | 200 |
| 7 | Zea mays | 8 | 397 |
| 8 | Zea mays | 8 | 200 |
| 9 | Solanum lycopersicum | 10 | 540 |
| 10 | Solanum lycopersicum | 1 | 600 |
| 11 | Solanum lycopersicum | 7 | 540 |
| 12 | Glycine max | 6 | 540 |
| 13 | Glycine max | 16 | 540 |
| 14 | Glycine max | 19 | 540 |
| 15 | Glycine max | 4 | 540 |
| 16 | Glycine max | 19 | 420 |
| 17 | Zea mays | Chimeric: 1 + 8 | 397 |
| 18 | Zea mays | Chimeric: 1 + 8 | 397 |
| 19 | Zea mays | Chimeric: 8 + 1 | 397 |
| 20 | Zea mays | Chimeric: 8 + 2 + 1 + 8 | 397 |

Example 2

Identification of Cas9 Genes to Enable Genome Engineering in Plants

The *S. pyogenes* Cas9 sequence (SEQ ID NO:28 is the polypeptide sequence of Cas9 with NLS, and SEQ ID NO:96 is the polypeptide sequence of Cas9 without NLS) was used for CRISPR-mediated site-directed targeting of a reporter construct in immature corn embryos. For expression, the codon-optimized nucleotide sequence of Cas9 was designed into an expression vector capable of expression in a plant. This Cas9 expression vector contained a 35S promoter driving expression of the Cas9 open reading frame, a NLS sequence incorporated into the 3' end of the Cas9 coding region, and a Nos transcription termination sequence (SEQ ID NO:29).

A Cas9 protein (SEQ ID NO:26), and a monocot codon-optimized version of the nucleotide sequence encoding the same (SEQ ID NO:27), were identified from the plant-related bacteria *Bradyrhizobium*, and can be useful for increasing the robustness of CRISPR/Cas-mediated genome modification in plants. A Cas9 protein (SEQ ID NO:69) and a monocot codon-optimized version thereof (SEQ ID NO:68), were identified from *Streptococcus thermophilus*, and can be useful for increasing the robustness of CRISPR/Cas-mediated genome modification in plants. Additional Cas9 genes from plant-related bacteria (e.g., symbiotic or pathogenic bacteria) can also be identified.

Example 3

Single-Guide RNA Cassette Design

A set of single-guide RNA (sgRNA) expression cassettes were designed to target a protospacer in a corn genomic target site referred to as Zm7 (5'-GCCGGCCAGCATTT-GAAACATGG-3', SEQ ID NO:22). The different expression cassettes included one of the 397 bp U6 promoters from corn: chromosome 1 (SEQ ID NO:30), chromosome 2 (SEQ ID NO:32), chromosome 3 (SEQ ID NO:34), or chromosome 8 (SEQ ID NO:36); or one of the 200 bp U6 promoter from corn: chromosome 1 (SEQ ID NO:31), chromosome 2 (SEQ ID NO:33), chromosome 3 (SEQ ID NO:35), or chromosome 8 (SEQ ID NO:37). Each expression cassette also contained, i) the U6 poly-T terminator conserved in each of the four corn U6 genes; ii) a sgRNA including a copy of the spacer sequence 5'-GCCGGCCAGCATTT-GAAACA-3' (SEQ ID NO:23) corresponding to the protospacer of the Zm7 genomic target site (SEQ ID NO:22); and iii) the conserved 3' domain of a sgRNA providing the Cas endonuclease binding domain, and ending with the U6 poly-T tract (SEQ ID NO:21).

Similarly, a set of sgRNA cassettes were designed with one of the four corn U6 397 bp promoters (SEQ ID NO:30, SEQ ID NO:32, SEQ ID NO:34, or SEQ ID NO:36; see Table 2), and the spacer sequence of the sgRNA complementary to the protospacer of the corn genomic target site referred to as Zm231 (SEQ ID NO:24). Table 3 lists the corresponding SEQ ID NOs for the DNA and RNA sequences of the sgRNAs containing the Zm7, Zm231, and Zm14 target sites. A negative control sgRNA cassette was designed with the corn U6 397 bp promoter from corn chromosome 8 (SEQ ID NO:36) and spacer sequence of the sgRNA complementary to the protospacer of the corn genomic target site referred to as Zm14 (SEQ ID NO:24). This negative control sgRNA cassette was designed with a spacer sequence of the sgRNA that is non-complementary to the protospacer sequence of the Zm231 corn genomic target site. Inclusion of a sgRNA comprising the spacer sequence complementary to the Zm14 corn genomic target site will not result in CRISPR/Cas-mediated cleavage of the protospacer sequence of the Zm231 corn target protospacer site. These Zm231 and Zm14 sgRNA cassettes are represented by SEQ ID NO:38, SEQ ID NO:39, SEQ ID NO:40, SEQ ID NO:41, and SEQ ID NO:42 (Table 2). Each of these sgRNA cassettes also contains at the 3' end of the sgRNA sequence a U6 poly-T tract.

TABLE 2

Cassettes with the indicated corn (*Zea mays*) U6 promoters and sgRNA containing spacers complementary to the protospacer sequence of the indicated corn genomic target sites.

| SEQ ID NO. | U6 Promoter from Chromosome | U6 Promoter Length (bp) | Genomic target site |
|---|---|---|---|
| 30 | 1 | 397 | Zm7 |
| 31 | 1 | 200 | Zm7 |

TABLE 2-continued

Cassettes with the indicated corn (Zea mays) U6 promoters and sgRNA containing spacers complementary to the protospacer sequence of the indicated corn genomic target sites.

| SEQ ID NO. | U6 Promoter from Chromosome | U6 Promoter Length (bp) | Genomic target site |
|---|---|---|---|
| 32 | 2 | 397 | Zm7 |
| 33 | 2 | 200 | Zm7 |
| 34 | 3 | 397 | Zm7 |
| 35 | 3 | 200 | Zm7 |
| 36 | 8 | 397 | Zm7 |
| 37 | 8 | 200 | Zm7 |
| 38 | 1 | 397 | Zm231 |
| 39 | 2 | 397 | Zm231 |
| 40 | 3 | 397 | Zm231 |
| 41 | 8 | 397 | Zm231 |
| 42 | 8 | 397 | Zm14 |

TABLE 3

DNA and RNA sequences of Streptococcus pyogenes sgRNAs containing spacer sequences complementary to the protospacer sequence of the corn genomic target sites Zm7, Zm231, and Zm14.

| SEQ ID NO. | | Genomic target site |
|---|---|---|
| DNA | RNA | |
| 76 | 79 | Zm7 |
| 77 | 80 | Zm231 |
| 78 | 81 | Zm14 |

Example 4

CRISPR Activity in Corn—Modified GUS Reporter Assay

To determine the activity of CRISPR/Cas-mediated gene-targeting efficiency in corn, a system for the transient expression of a reporter gene in immature corn embryos was used. In addition to the sgRNA cassettes described above, the design incorporated an expression cassette containing the Cas9 endonuclease of Streptococcus pyogenes (SEQ ID NO:28) containing a nuclear localization signal (NLS) sequence and was codon-optimized for expression in corn.

Figure 2:
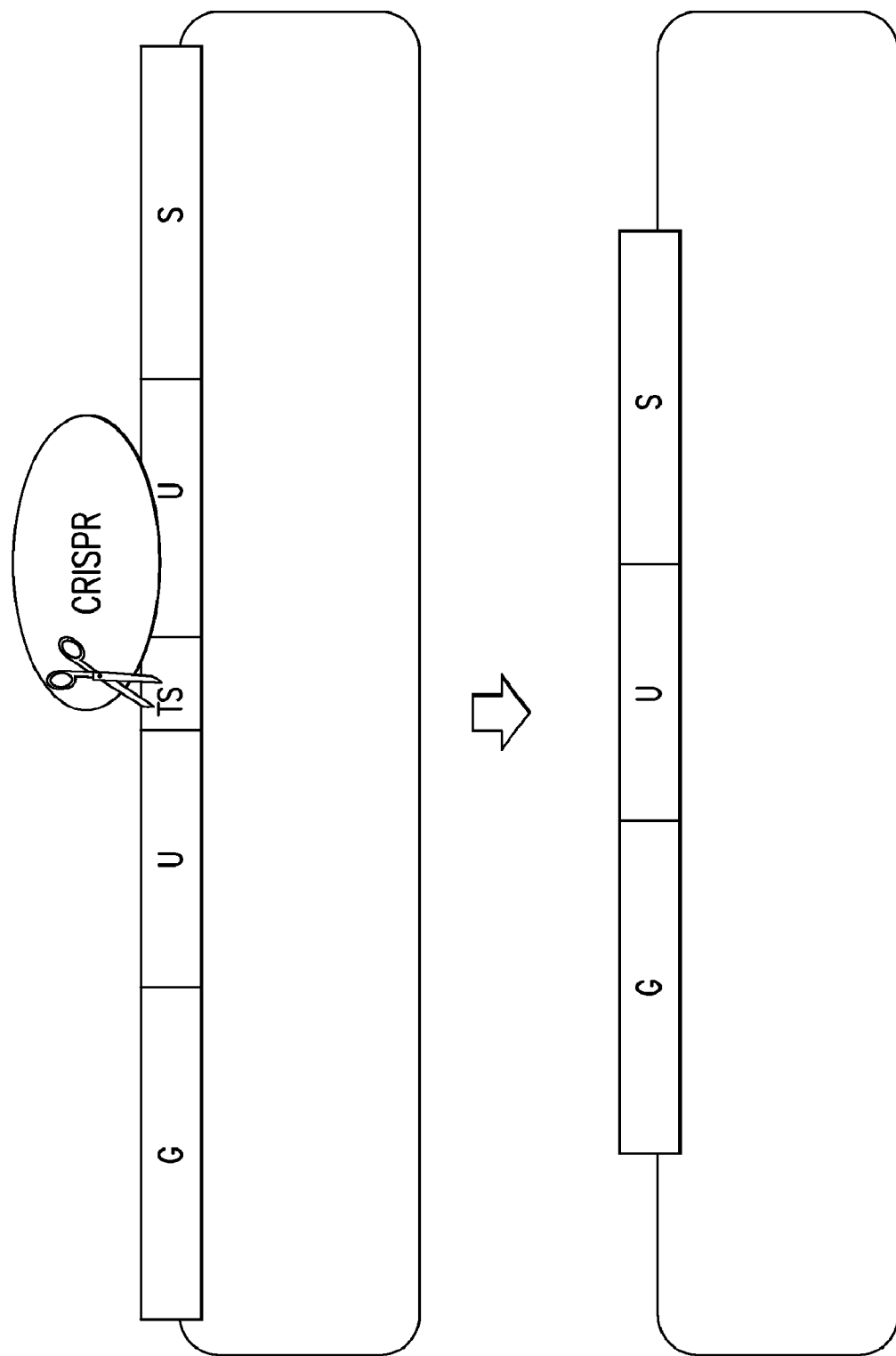
FIG. 2: Illustration of a modified GUS (β-glucuronidase) reporter gene harboring a direct repeat of the coding sequence (GUUS) interrupted by a target site (TS) for CRISPR cleavage.

The reporter gene construct for these experiments was a cassette containing a modified β-glucuronidase (GUS) coding sequence with a corn genomic target site (protospacer and PAM) for targeted CRISPR cleavage (e.g., the Zm7 (SEQ ID NO:22), Zm231 (SEQ ID NO:44), or Zm14 (SEQ ID NO:43)) engineered into the reporter gene and surrounded by an internal direct repeat of the GUS coding sequence (FIG. 2). When co-delivered with expression vectors for CRISPR components, if the CRISPR system cleaves the protospacer sequence, the endogenous plant single-strand annealing (SSA) pathway of homologous recombination DNA repair will reconstitute a functional GUS gene. These modified GUS reporter constructs were named GU-Zm7-US, GU-Zm231-US, or GU-Zm14-US, referring to the corn genomic target site inserted into the GUS gene, Zm7, Zm231, and Zm14, respectively. One of the modified GUS reporter gene cassettes was co-delivered with expression vectors for the other CRISPR components (e.g., one of the sgRNA cassettes) and the expression cassette encoding the Cas9 endonuclease (SEQ ID NO:28). Expression cassettes were mixed and co-coated on 0.6 µM gold particles using standard protocols. 3-day old pre-cultured immature corn embryos were then bombarded with these prepared gold particles. Embryos were maintained in culture for 3-5 days after bombardment and then processed for histochemical staining using X-Gluc (5-bromo-4-chloro-3-indolyl glucuronide) and standard laboratory protocols.

Figure 3:
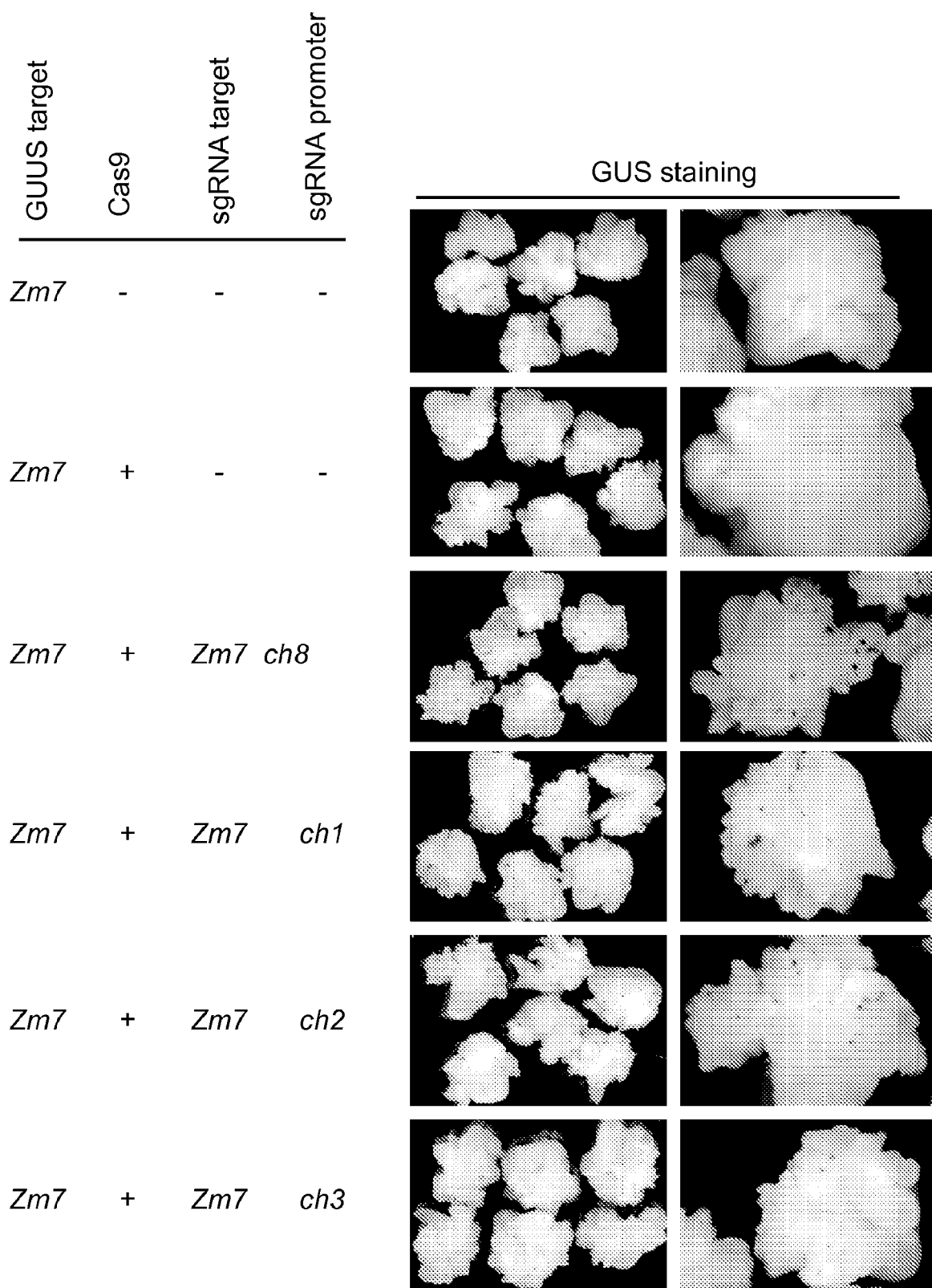
FIG. 3: GUS activities detected in corn callus after co-bombardment of a GUUS reporter construct together with CRISPR constructs designed for introducing a double-stranded break (DSB) at the Zm7 genomic target site.
Figure 4:
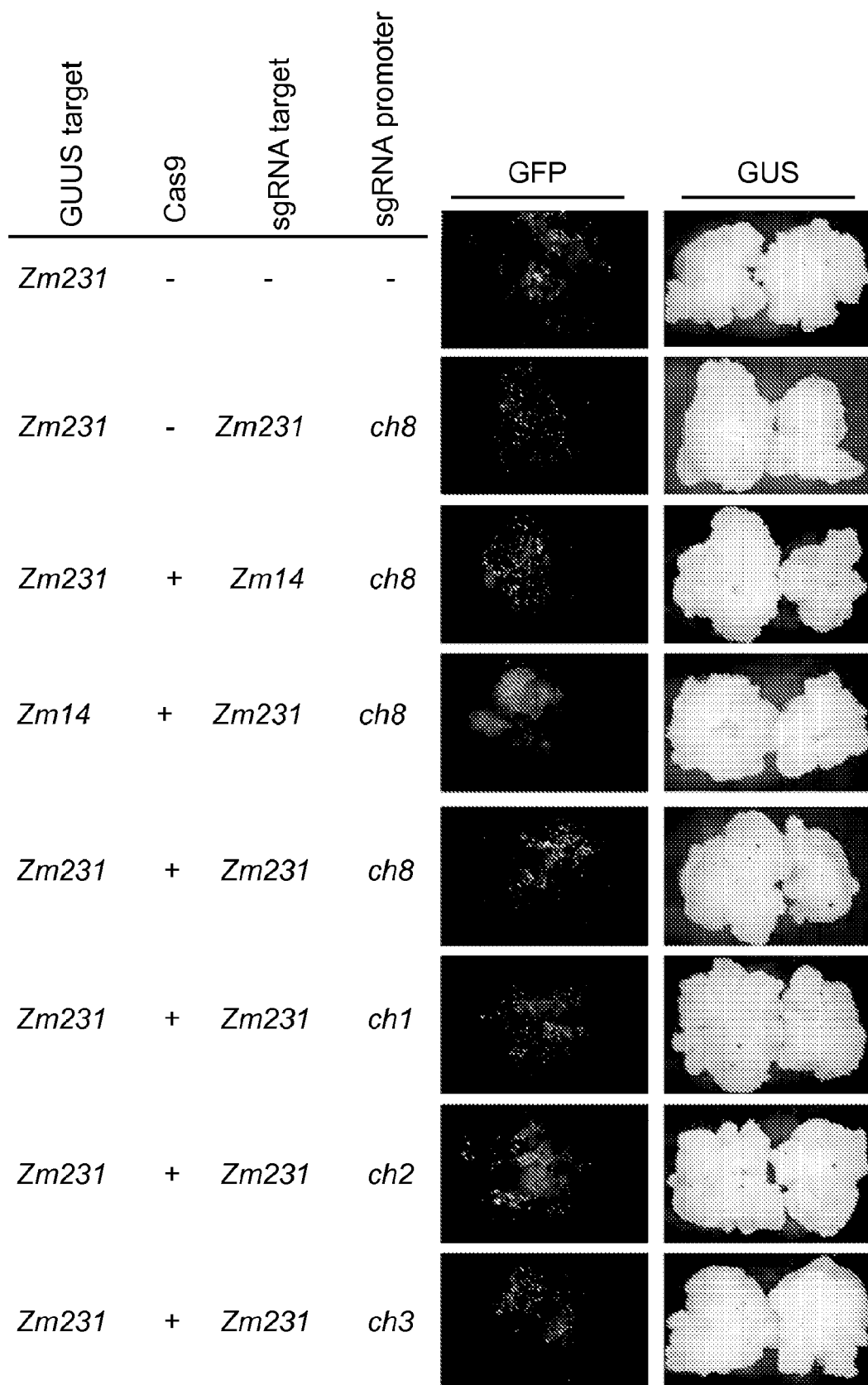
FIG. 4: GUS activity detected in corn callus after co-bombardment of a GUUS reporter construct together with CRISPR constructs designed for introducing a DSB at the Zm231 genomic target site. A different genomic target and single-guide RNA (sgRNA) spacer sequence, Zm14, were used as negative control. Also shown are fluorescence microscopy images of representative calli which were co-bombarded with a green fluorescent protein (GFP) expression vector with the GUUS reporter construct, Cas9 expression vector and vectors containing the various sgRNA cassettes.

If CRISPR-mediated Cas9 endonuclease activity occurs at the protospacer site in the modified reporter gene construct, then GUS activity is detected as blue foci using histochemical staining and X-Gluc (FIGS. 3 and 4).

Separate expression cassettes were designed to contain one of four corn U6 promoters (from chromosomes 1, 2, 3, and 8) driving expression of a sgRNA containing a spacer sequence complementary to the protospacer of the corn Zm7 genomic target site (FIG. 3). To prepare samples for the expression assay, 0.6 µM gold particles were coated with 0.6 pmol of one of the Zm7-sgRNA constructs and 0.3 pmol of each of the other constructs (Cas9 expression cassette and the Zm7-modified reporter construct (GU-Zm7-US)). Once the coated gold particles were prepared, ¼ of the mixture was used for bombardment of 3-day old immature corn embryos using standard protocols. More than 50 immature corn calli were bombarded for each set of constructs evaluated, and staining was done 5 days post-bombardment. Following staining, photographs of representative calli (overview of several calli and a close-up view of a single callus) were taken (FIG. 3). The modified reporter construct GU-Zm7-US was designed to contain the Zm7 genomic target site (SEQ ID NO:22), and the sgRNA was designed to contain a copy of the Zm7 spacer (SEQ ID NO:23). The Zm7-sgRNA spacer was incorporated into expression cassettes with one of the four 397 bp corn U6 promoters from chromosome 1 (SEQ ID NO:30), chromosome 2 (SEQ ID NO:32), chromosome 3 (SEQ ID NO:34), or chromosome 8 (SEQ ID NO:36). Negative controls used in the transformation included the modified reporter construct GU-Zm7-US with the Zm7 genomic target site and: (1) lacking both the Cas9 endonuclease expression cassette and the Zm7-sgRNA expression cassette; or (2) lacking just the Zm7-sgRNA expression cassette (FIG. 3). For both of these controls no blue sectors were detected, indicating no CRISPR-mediated cleavage of the modified reporter construct had occurred. The results from evaluation of the four different 397 bp corn U6 promoters in driving expression of the Zm7-sgRNA cassette showed that while all four 397 bp corn U6 promoters worked (i.e., blue sectors detected in the calli), the efficacy of the different promoters varied (as evidenced by the size and number of blue sectors in the calli). The U6 promoter from corn chromosome 8 showed the most efficacy, followed by the U6 promoter from chromosome 1. The U6 promoters from chromosomes 2 and 3 showed similar efficacy to each other (Chr 8>Chr 1>Chr2≈Chr3).

The specificity of the CRISPR/Cas9 system in this corn expression system was evaluated by testing mismatches between the protospacer sequence within the genomic target site in the modified GUUS reporter gene construct and the spacer sequence included in the varying sgRNA constructs (FIG. 4). As in the experiment described above, 0.6 µM gold particles were coated with one or more constructs; 0.3 pmol of the individual modified GUUS reporter construct (GUUS target), 0.16 pmol of the Cas9 endonuclease expression cassette, 0.3 pmol of the individual sgRNA cassettes, and 0.03 pmol of a transformation control construct expressing green fluorescent protein (GFP) (FIG. 4). Once the coated gold particles were prepared, ¼ of the mixture was used for bombardment of 3-day old immature corn embryos using standard protocols. More than 50 immature corn calli were bombarded for each set of constructs evaluated. Tissue was maintained in culture for 3 days post-bombardment. Determination of GFP expression by fluorescence microscopy was done on day 1 and again on day 3 to validate uniform bombardment and transformation. After the fluorescence microscopy on day 3, the calli were processed for X-Gluc staining and fluorescent and light micrographs of representative calli were taken (FIG. 4). The fluorescent staining for all calli indicated good transformation.

Negative controls used in the transformation included the modified reporter construct GU-Zm231-US with the Zm231 genomic target site (1) lacking both the Cas9 endonuclease expression cassette and any sgRNA expression cassette; or (2) having a Zm231-sgRNA expression cassette with a corn U6 promoter from chromosome 8, but lacking the Cas9 endonuclease expression cassette (FIG. 4). Both of these controls showed no blue sectors detected with X-Gluc staining, indicating no CRISPR-mediated cleavage of the modified reporter construct had occurred (FIG. 4).

The specificity of the CRISPR/Cas9 system was also evaluated using controls including a mismatch between the protospacer site in the modified GUUS reporter construct and the sgRNA spacer sequence. Specifically, the mismatch was between the modified reporter construct GU-Zm231-US with the Zm231 genomic target site and (1) the sgRNA expression cassette with the Zm14 spacer and a corn U6 promoter from chromosome 8; or (2) the sgRNA expression cassette with the Zm231 spacer sequence and a corn U6 promoter from chromosome 8 (FIG. 4).

Finally, the 397 bp corn U6 promoters (chromosome 1, 2, 3, and 8) were each used to generate sgRNA expression cassettes with the Zm231 genomic target site. These were each co-transformed with the modified reporter construct GU-Zm231-US made with the Zm231 genomic target site. Results indicated that when the sgRNA spacer sequence and the genomic target site of the reporter construct were mismatched, there was very little GUS activity detected. By contrast, when the sgRNA spacer sequence and the genomic target site of the reporter construct were matched, many large blue foci were detected (FIG. 4). The U6 promoter from corn chromosome 8 may have higher efficacy (based on the assumption that efficacy correlates to blue foci which were more numerous, larger in size, and darker in staining intensity), followed by the U6 promoter from corn chromosome 1. The U6 promoters from corn chromosomes 2 and 3 showed similar efficacy to each other (Chr 8>Chr 1>Chr2≈Chr3).

The sgRNA driven by the U6 promoter from corn chromosome 8 consistently showed high activity. These findings suggest that different corn U6 promoters have differing activities, and further highlights the usefulness of the U6 promoter derived from corn chromosome 8 in the CRISPR/Cas system of targeted genome modification.

Example 5

Blunt-End Oligonucleotide Integration

The CRISPR/Cas9 system was evaluated for targeting efficacy of insertion of a blunt-end double-stranded DNA fragment into one of three genomic target sites, identified as Zm_L70a (SEQ ID NO:47), Zm_L70c (SEQ ID NO:59), and Zm_L70d (SEQ ID NO:61) within the corn genome. Each of these three genomic target sites is unique in the corn genome. If the CRISPR components are capable of endonuclease activity and introduce a double strand break (DSB) in the protospacer of the selected genomic target site, then the endogenous corn non-homologous end-joining DNA repair system will insert the blunt-end double-stranded DNA fragment into the DSB.

Figure 5A:
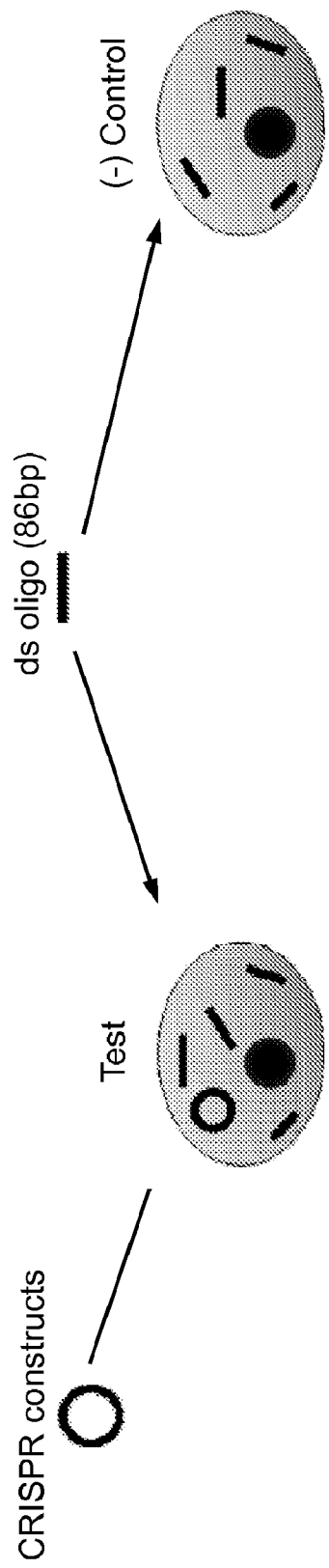
FIGS. 5A-5E: Illustrations of (FIG. 5A) oligonucleotide integration assay.
Figure 5B:
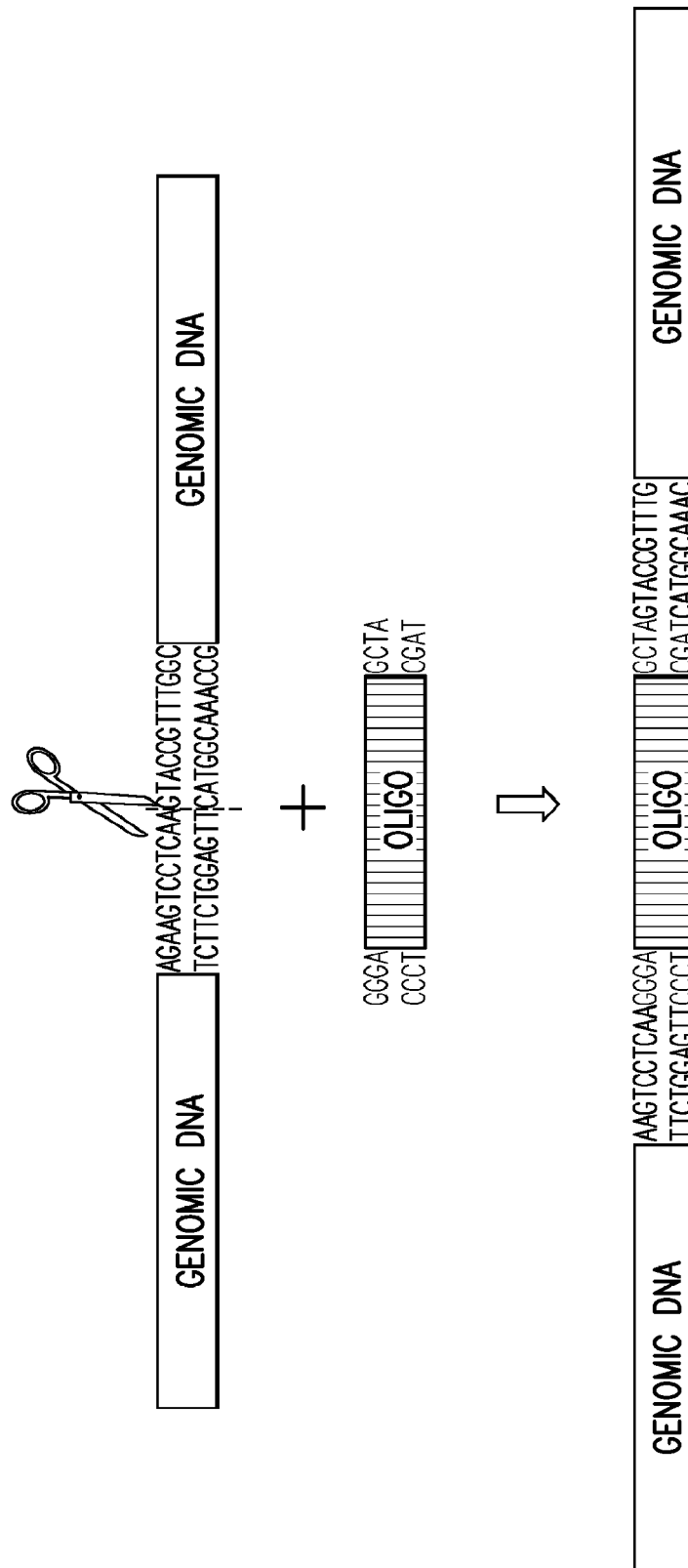
Figure 5C:
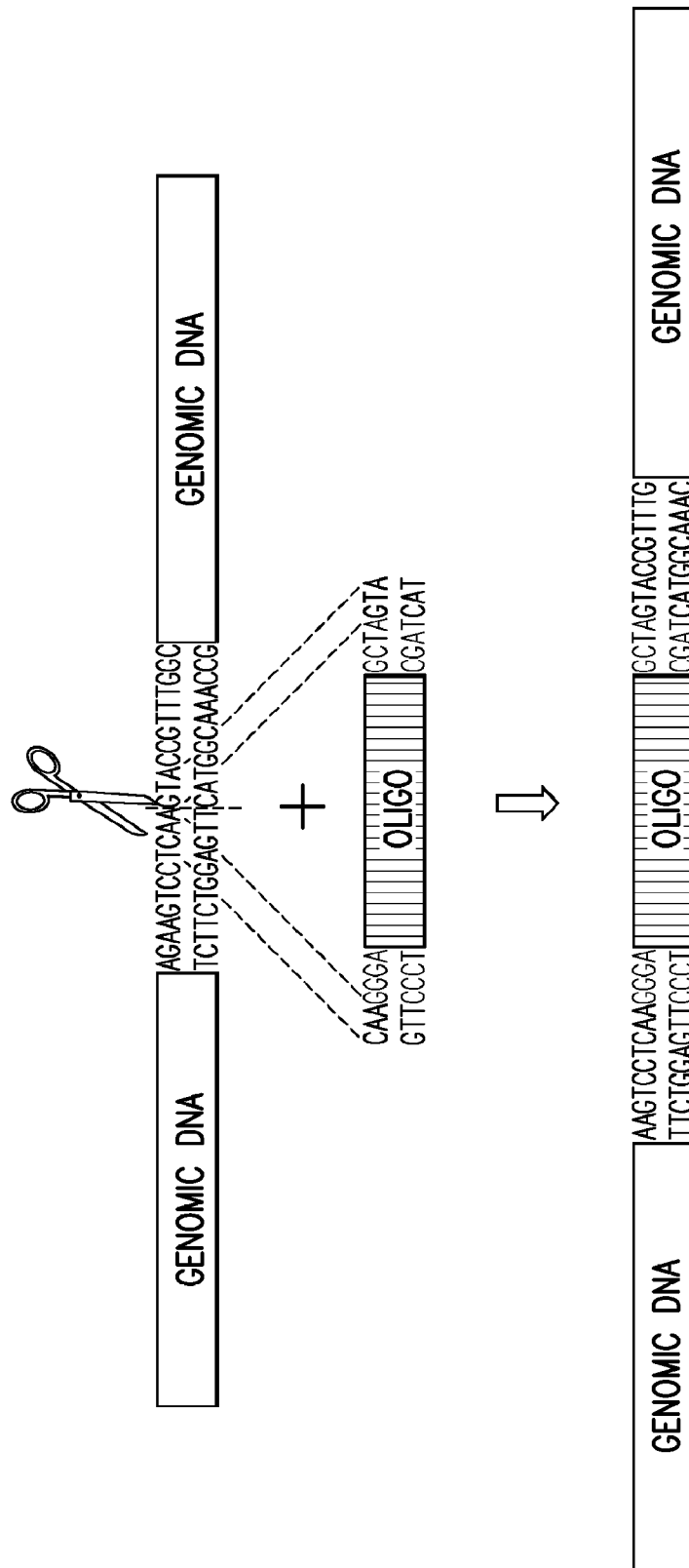

Complementary oligonucleotides were pre-annealed to form blunt-ended double-stranded DNA fragments, and these were co-transformed with CRISPR constructs into corn protoplasts (FIG. 5A). The oligonucleotide pairs were designed to either (1) not contain microhomology regions (see FIG. 5B), or (2) contain on each end (5' and 3') a 3 bp microhomology to the corresponding 5' and 3' flanking sequence at the cut site of the protospacer in the genomic target site (FIG. 5C). The microhomology sequences may promote blunt-end double-strand DNA fragment integrations through a mechanism of microhomology-driven non-homologous end-joining at the genomic target site. The two sequences of the oligonucleotide pair without microhomology sequence were SEQ ID NO:45 and SEQ ID NO:46. The three pairs of oligonucleotides, each containing microhomology to their respective genomic target site, were annealed in pairwise combinations of the following oligonucleotides: (1) SEQ ID NO:62 and SEQ ID NO:63 (microhomology to Zm_L70a); (2) SEQ ID NO:64 and SEQ ID NO:65 (microhomology to Zm_L70c); and (3) SEQ ID NO:66 and SEQ ID NO:67 (microhomology to Zm_L70d) to form blunt-end double-strand DNA fragments.

For these blunt-end double-strand DNA fragment integration assays, the CRISPR constructs used included the Cas9 endonuclease expression cassette described above, and one of three sgRNA expression cassettes. The three sgRNA expression cassettes were each driven by the 397 bp version of the U6 promoter from corn chromosome 8 (SEQ ID NO:7) and contained the spacer sequence corresponding to the genomic target sites: Zm_L70a (SEQ ID NO:48), Zm_L70c (SEQ ID NO:58), and Zm_L70d (SEQ ID NO:60). Differing combinations of the CRISPR components and oligonucleotides for these assays were mixed as follows: 0.6 pmol of the Cas9 expression cassette, 1.6 pmol of one of the sgRNA expression cassettes, and 35 pmol of the pre-annealed, oligonucleotide pair, and, using a standard PEG-mediated protocol, transformed into aliquots of corn leaf protoplast suspensions containing about 320,000 cells. Two days later, corn protoplasts were harvested and analyzed for insertion of the blunt-end double-strand DNA fragment into the particular L70 genomic target site targeted by the unique sgRNA selected in each case (Table 4). The negative control was the omission of the Cas9 expression cassette during the corn protoplast transformation.

To detect the insertion of the blunt-end double strand DNA fragment into the corn chromosome, DNA was extracted and high-throughput thermal amplification (PCR) was done with multiple pairs of primers (Table 5). As the blunt-end double strand DNA fragment may insert into the CRISPR cleaved chromosomal DNA in either orientation, primers were designed to one strand of the blunt-end double strand DNA fragment and to both flanking genomic regions, with each primer pair spanning the junction of the insertion site. The PCR amplicons were separated on a fragment analysis platform (ABI3730 DNA analyzer) from Life Technologies (Grand Island, NY). This platform, which is more sensitive than gel-based electrophoresis methods and has single-bp resolution, confirmed whether the amplicons originated from the template of interest and whether they were specific to the experimental treatment conditions.

TABLE 4

DNA and RNA sequences of *Streptococcus pyogenes* sgRNA containing spacer sequences complementary to the protospacer sequence of the corn genomic target sites L70a, L70c, L70d.

| SEQ ID NO. | | Genomic |
|---|---|---|
| DNA | RNA | target site |
| 82 | 85 | Zm_L70a |
| 83 | 86 | Zm_L70c |
| 84 | 87 | Zm_L70d |

Figure 5D:
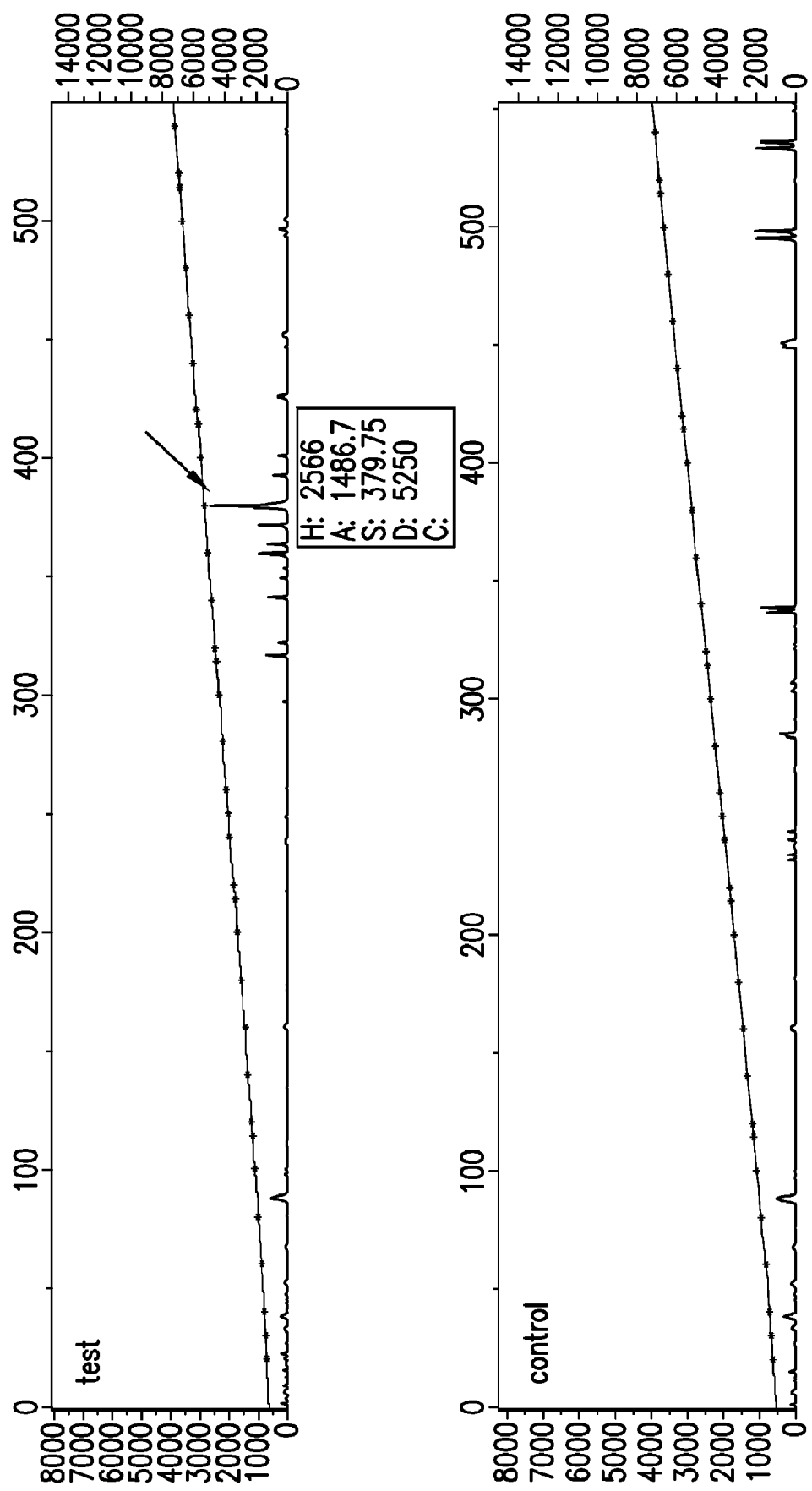

One representative fragment analysis profile is shown in FIG. 5D (Experiment T3, Table 5). Amplification of DNA extracted from corn protoplasts transformed with Cas9, sgRNA containing spacer sequences complementary to the protospacer sequence of the Zm_L70c corn genomic target site (SEQ ID NO:83), and the blunt-end double-stranded DNA fragment without microhomology, using primers at the Zm_L70c genomic target site (SEQ ID NO:49, primer specific for the inserted blunt-end double-strand DNA fragment, and SEQ ID NO:55, primer specific for flanking genomic DNA) revealed a major peak of the expected size and several additional peaks of similar sizes (arrow) (FIG. 5D, top panel). By contrast, no amplification products were seen from DNA extracted from the negative control transformations (FIG. 5D, bottom panel). This PCR profile was consistent with double-stranded breaks repaired erroneously by non-homologous end-joining, resulting in introduction of short indels at the site of repair.

Figure 5E:
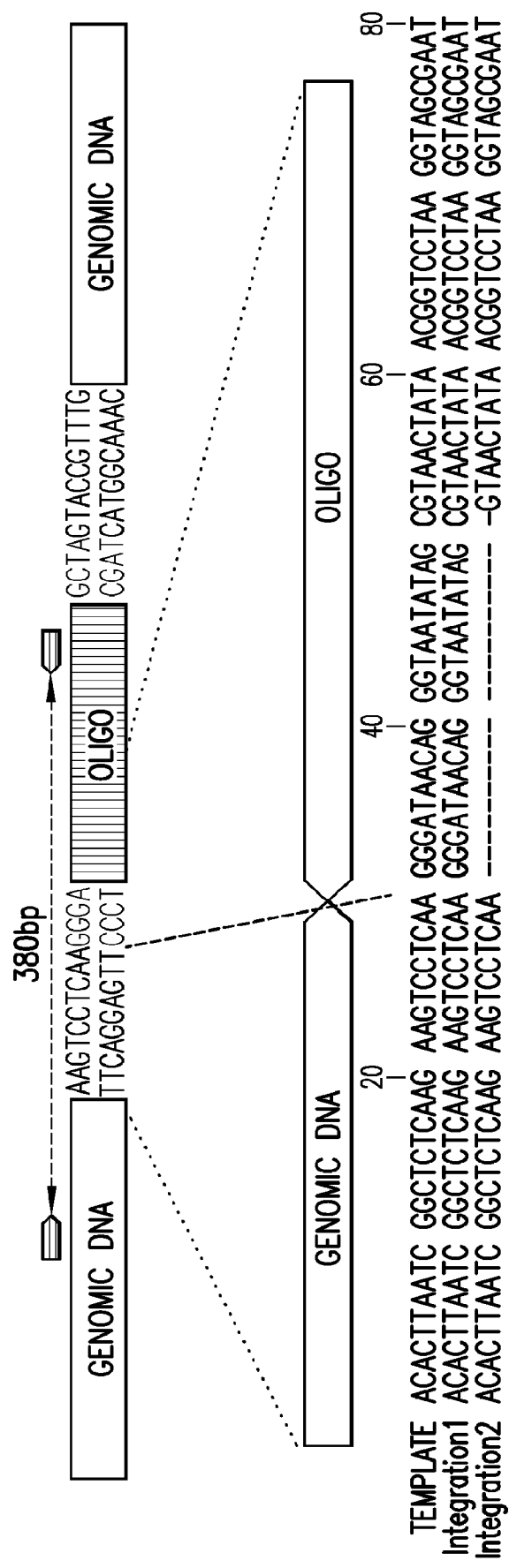

To confirm that the blunt-end double-strand DNA fragment was incorporated at the genomic target site, the PCR amplicons were cloned and sequenced (Table 5). Negative controls lacking Cas9 proteins did not produce PCR products. Seven of the ten experiments showed the expected pattern: a positive PCR product of the expected size for the test samples, and no PCR product for control samples. The seven experiments showing a positive PCR product included experiments demonstrating integrations occurring for both blunt-end double-strand DNA fragments with and without microhomology. Experiments T1 and T7 failed to detect targeted integrations in either test or control samples. PCR products from six of the experiments were cloned and sequenced, confirming the expected DNA fragment-chromosome junctions for blunt-end double-strand DNA fragment integration. Sequencing results showed the presence of both full-length and truncated DNA fragments (indels) present at the site of blunt-end double-strand DNA fragment integration (see, e.g., FIG. 5E, Experiment T1). Sequences were consistent with the fragment analysis (FIG. 5D) and demonstrated that CRISPR/Cas9 can target native, sequence-specific, chromosomal loci for cleavage in corn protoplasts. These results also demonstrated successful blunt-end double-strand DNA fragment integration with and without regions of microhomology.

TABLE 5

| | | Blunt-end oligonucleotide insertion assay. | | | | | | |
|---|---|---|---|---|---|---|---|---|
| Experiment | Treatments | Genomic protospacer/target site | Microhomology | Orientation | Primer pairs (SEQ ID NOs) | Expected amplicon size (bp) | Expected amplicon | Sequenced amplicon |
| T1 | test | L70a | − | + | 50/49 | 408 | − | − |
| | (−) control | L70a | − | + | 50/49 | N/A | − | − |
| T2 | test | L70a | − | − | 51/49 | 324 | + | + |
| | (−) control | L70a | − | − | 51/49 | N/A | − | − |
| T3 | test | L70c | − | + | 55/49 | 384 | + | + |
| | (−) control | L70c | − | + | 55/49 | N/A | − | − |
| T4 | test | L70c | − | − | 54/49 | 411 | + | + |
| | (−) control | L70c | − | − | 54/49 | N/A | − | − |
| T5 | test | L70c | + | + | 55/49 | 384 | + | + |
| | (−) control | L70c | + | + | 55/49 | N/A | − | − |
| T6 | test | L70c | + | − | 54/49 | 411 | + | − |
| | (−) control | L70c | + | − | 54/49 | N/A | − | − |
| T7 | test | L70d | − | + | 56/49 | 359 | − | − |
| | (−) control | L70d | − | + | 56/49 | N/A | − | − |
| T8 | test | L70d | − | − | 57/49 | 356 | + | + |
| | (−) control | L70d | − | − | 57/49 | N/A | − | − |
| T9 | test | L70d | + | + | 56/49 | 359 | + | + |
| | (−) control | L70d | + | + | 56/49 | N/A | − | − |
| T10 | test | L70d | + | − | 57/49 | 356 | + | − |
| | (−) control | L70d | + | − | 57/49 | N/A | * | − |

Where * = sample contaminated.

Example 6

Targeted Genome Modification with CRISPR/Cas9 Complex Genes from *Streptococcus thermophilus*

It may be desirable to accomplish CRISPR-mediated genome modification of some plants (e.g., crop plants) with CRISPR complex genes derived from *Streptococcus thermophilus* instead of *S. pyogenes*. The inventors have developed an expression cassette encoding a codon-optimized nucleotide sequence with two nuclear localization signals (NLS) (SEQ ID NO:136) of the Cas9 protein from *S.*

Figure 6:
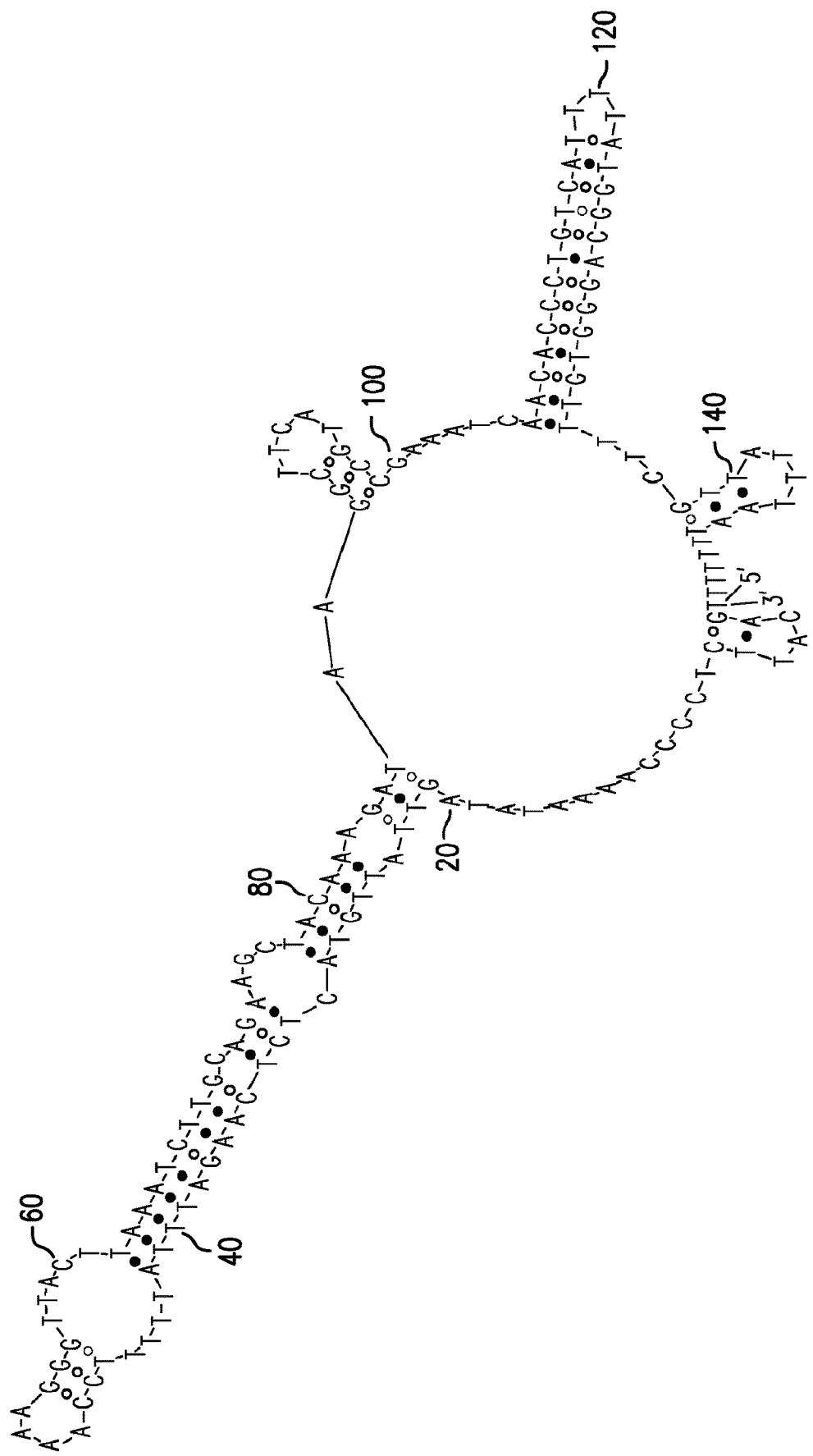
FIG. 6: Illustration of a sgRNA including a spacer sequence complementary to a native corn genomic target site and an artificial loop (5'-CCAAAAGG-3'; SEQ ID NO:105) and its predicted secondary structure designed for *Streptococcus thermophilus* Cas9-mediated targeting (SEQ ID NO:110).

*thermophilus* (SEQ ID NO:69). The StCas9 was designed to encode both an N-terminal and a C-terminal nuclear-localization signal (NLS) (SEQ ID NO:120) at amino acid position 2-11 and 1133-1142 (SEQ ID NO:135). Additionally, the DNA expression cassette (SEQ ID NO:136) included an intron at nucleotide position 507-695. A series of unique *S. thermophilus* single-guide RNAs (sgRNA) have been designed. The *S. thermophilus* sgRNA was designed to link the native *S. thermophilus* crRNA and tracrRNA with a stem loop (5'-CCAAAAGG-3'; SEQ ID NO:105), and to contain the spacer sequence complementary to the protospacer of the corn genomic target sites selected from Zm_L70e (SEQ ID NO:72), Zm_L70f (SEQ ID:73), Zm_L70g (SEQ ID NO:74), or Zm_L70h (SEQ ID NO:75). The seven nucleotides at the 3' end of each of these genomic target sites represent the *S. thermophilus*-specific protospacer adjacent motif (PAM, 5'-NNAGAAW-3'; SEQ ID NO:106). FIG. 6 shows the predicted secondary structure of this *S. thermophilus* sgRNA (SEQ ID NO:70) with a copy of the spacer sequence (SEQ ID NO:71) complementary to the protospacer sequence of the corn Zm_L70h genomic target site (SEQ ID NO:75) and stem-loop linker (5'-CCAAAAGG-3'; SEQ ID NO:105). Table 6 lists the corresponding SEQ ID NOs for the DNA and RNA sequences encoding *S. thermophilus* sgRNAs containing spacer sequences complementary to the protospacer sequence of the corn genomic target sites Zm_L70e, Zm_L70f, Zm_L70g, and Zm_L70h.

TABLE 6

DNA and RNA sequences of *Streptococcus thermophilus* sgRNA containing spacer sequences complementary to the protospacer sequence of the corn genomic target sites Zm_L70e, Zm_L70f, Zm_L70g, and Zm_L70h.

| SEQ ID NO. | | Genomic |
|---|---|---|
| DNA | RNA | target site |
| 107 | 111 | Zm_L70e |
| 108 | 112 | Zm_L70f |
| 109 | 113 | Zm_L70g |
| 110 | 114 | Zm_L70h |

The assay for *S. thermophilus* Cas9 mediated genome modification was essentially as described in example 5. Specifically, 320,000 corn protoplasts were transfected with 0.8 pmol *S. thermophilus* Cas9 (SEQ ID NO:136) expression construct, and 1.6 pmol of one of the sgRNA expression constructs driven by the 397 bp version of the U6 promoter from corn chromosome 8 (SEQ ID NO:7) containing the spacer sequence corresponding to the genomic target sites: sgRNA construct for site L70e (SEQ ID NO:107), sgRNA construct for site L70f (SEQ ID NO:108, and sgRNA construct for site L70g (SEQ ID NO:109), and 50 pmol of a pre-annealed blunt-end double-strand DNA fragment encoded by SEQ ID NO:115 and SEQ ID NO:116. To test for transformation efficiency, 2.5 ug of a construct encoding green fluorescent protein (GFP) was included. At the time of harvesting, an aliquot of the transfected protoplasts was collected to calculate transfection frequency on the PE Operetta® Imaging System (PerkinElmer, Waltham, MA) which calculates the ratio of GFP positive cells per total cells. Omission of the StCas9 expression cassette during the corn protoplast transformation served as the negative control. Protoplasts were harvested 48 hours post transfection and analyzed for insertion of the blunt-end double-strand DNA fragment into the L70e, or L70f, or L70g genomic target site by quantitative, high-throughput PCR analysis using a BioRad QX200™ Droplet Digital™ PCR (ddPCR™) system (BioRad, Hercules, CA) and TaqMan® probes. To determine the percent targeted integration rate, one set of TaqMan primers and probes was used with the ddPCR system to detect the template copy number of a junction of the inserted blunt-end double-strand DNA fragment at the chromosomal target site. The junction specific primers and probe for corn chromosomal sites L70e, L70f, L70g, and L70h are indicated in Table 7. To normalize the amount of DNA in the transfected protoplast aliquot, the ddPCR system was used with a second set of TaqMan primers and a probe (primers encoded by SEQ ID NO:132 and SEQ ID NO:134; probe encoded by SEQ ID NO:133) to determine the template copy number of a site unique in the corn genome and outside of the target site. The calculation for the percent targeted integration rate was the target site specific template copy number divided by the corn genome specific template copy number divided by the transformation frequency as determined by GFP-positive vs. total cell counts using the PE Operetta® Imaging System (PerkinElmer, Waltham, MA). The data points presented in the graph were determined by averaging four biological replicates. The results are presented in FIG. 15 and show that the percent integration rate for each of the sites L70e, L70f, and L70g was higher than the corresponding control.

PCR amplicons corresponding to targeted junctions from the protoplast experiments were sequenced to confirm the integration of the blunt-end double-strand DNA fragments into the selected target sites. FIG. 15B shows an alignment of the expected integration of the blunt-end, double-strand DNA fragment at the L70f target site (SEQ ID NO:144) and one example of target site integration (SEQ ID NO:145) with deletion of some of the sequence of the DNA fragment. Although these sequencing results show indels, the results confirm that the DNA fragment was integrated at the L70f target site.

TABLE 7

SEQ ID NOs for primers and probes for PCR amplification of junction at corn chromosomal target sites with inserted DNA fragment.

| Site | SEQ ID NO: of Genomic specific primer | SEQ ID NO: of Probe | SEQ ID NO: of Inserted DNA specific primer |
|---|---|---|---|
| L70e | 139 | 138 | 137 |
| L70f | 140 | 138 | 137 |
| L70g | 141 | 138 | 137 |
| L70h | 142 | 138 | 137 |

Example 7

Targeting Multiple Unique Genomic Sites by sgRNA Multiplexing

A key advantage of the CRISPR system, as compared to other genome engineering platforms, is that multiple sgRNAs directed to separate and unique genomic target sites can be delivered as individual components to effect targeting.

Figure 7A:
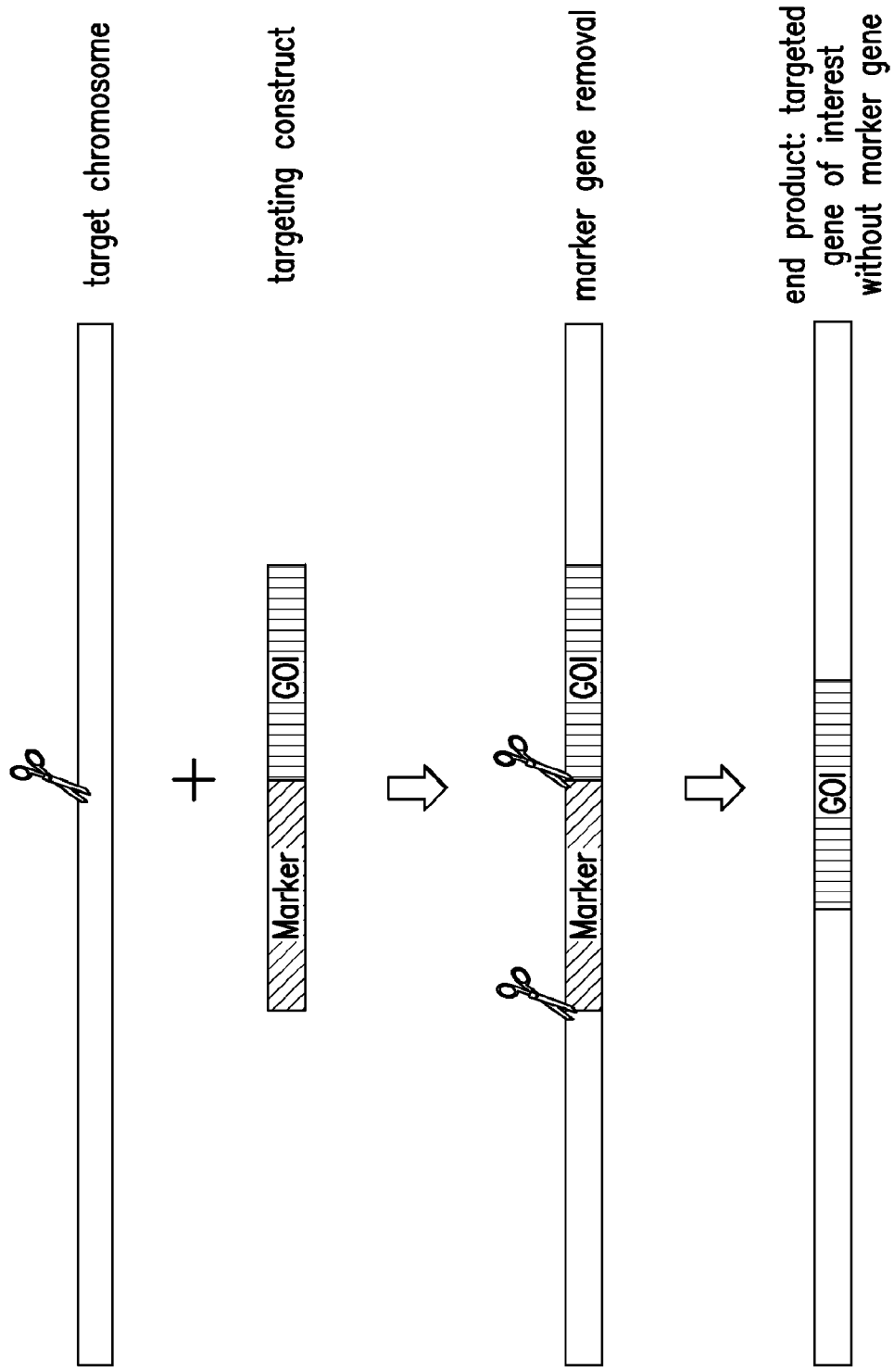
FIGS. 7A-7B: Illustrations of (FIG. 7A) selectable marker gene removal by multiplex CRISPR activity following targeted integration of the gene of interest (GOI)

Alternatively, multiple sgRNAs directed to separate and unique genomic target sites can be multiplexed (i.e., stacked) in a single expression vector to effect targeting. An example of an application that can require multiple targeted endonucleolytic cleavages includes marker-gene removal from a transgenic event (FIG. 7A). The CRISPR system can be used to remove the selectable marker from the transgenic insert, leaving behind the gene of interest.

Figure 7B:
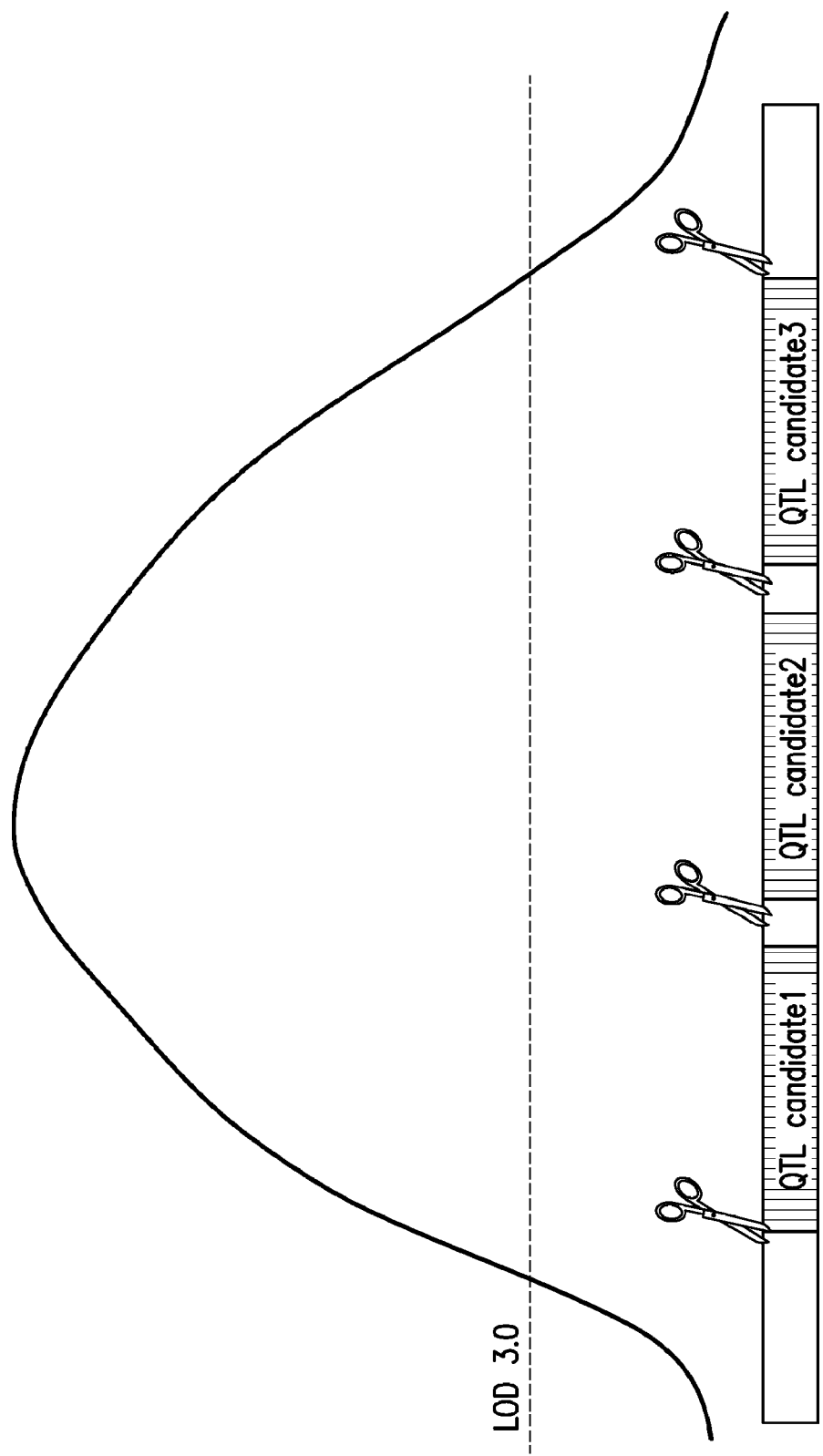

Another example of an application in which such a CRISPR/Cas system can be useful is when there is a requirement for multiple targeted endonucleolytic cleavages, such as when the identification of causal genes behind a quantitative trait is hampered by lack of meiotic recombinations in the QTL regions that would separate the gene candidates from each other. This can be circumvented by transformation with several CRISPR constructs targeting the genes of interests simultaneously. These constructs would either knock out the gene candidates by frame shift mutations or remove them by deletion. Such transformations can also lead to random combinations of intact and mutant loci that would allow for identification of casual genes (FIG. 7B).

Example 8

Integration Rates as a Function of Blunt-End DNA Fragment Concentration and Time The corn protoplast system essentially as described in Example 5 was used to determine the optimal concentration of blunt-end double-strand DNA fragment to be included in the assay mixture to achieve the highest percentage targeting integration rate. For these assays the expression construct encoding the S. pyogenes Cas9 was modified to include an intron from position 469-657 in the coding region (SEQ ID NO:119). Additionally, the protein sequence (SEQ ID NO:118) contained two NLS sequences (SEQ ID NO:120), one at the amino-terminal end (amino acids 2 to 11 of SEQ ID NO:118) and one at the carboxy-terminal end (amino acids 1379 to 1388 of SEQ ID NO:118).

Figure 8:
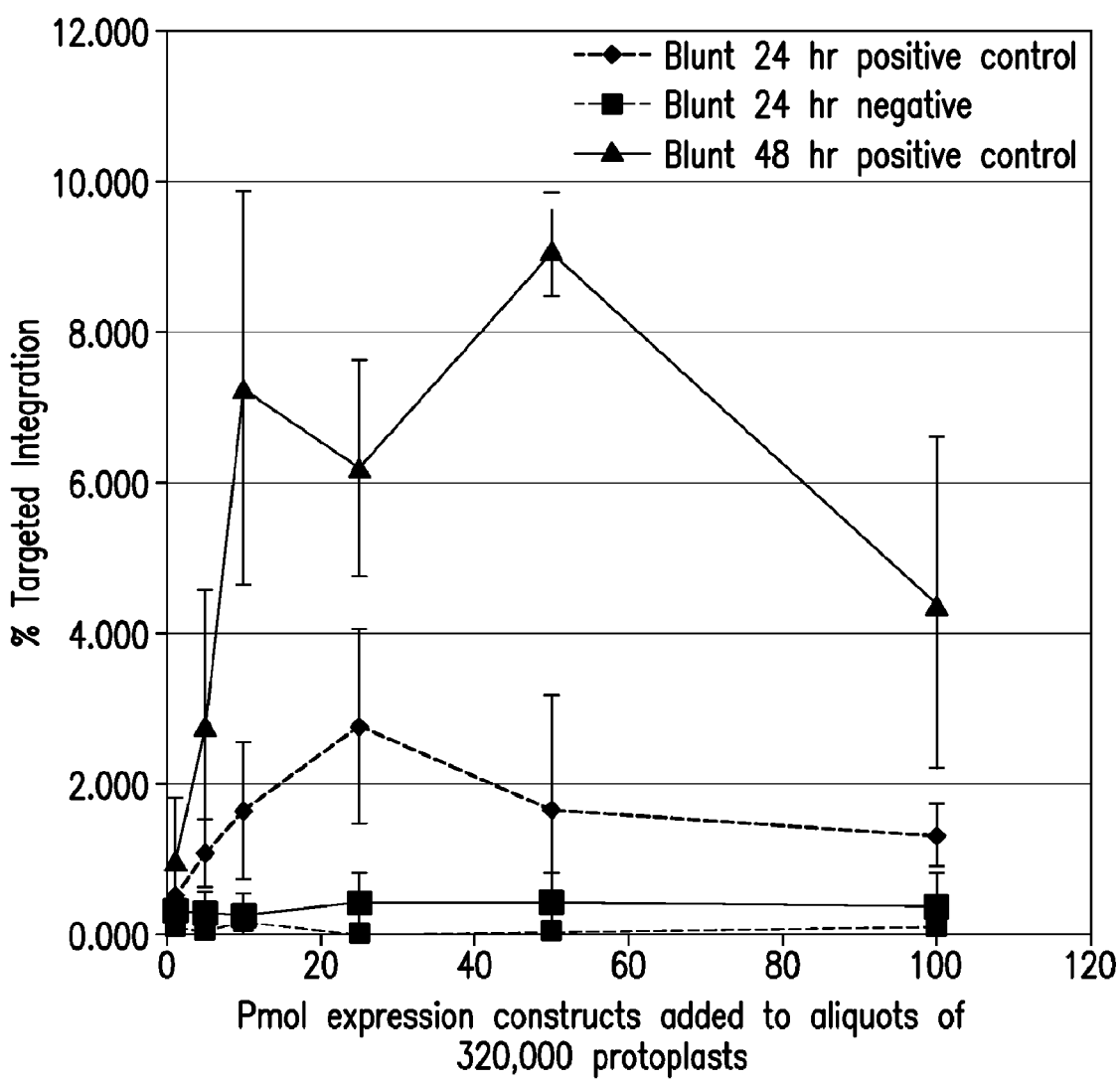
FIG. 8. Graphical presentation of data showing percentage targeted integration rates (Y-axis) detected at 24 and 48 hours post-transformation of corn protoplasts using CRISPR constructs targeting a native chromosomal target (Zm7) in corn and a titration of the pmol of blunt-end, double-stranded DNA fragment added to the transfection mixture (X-axis). The negative controls were run without added Cas9 expression constructs.

For the assay, 320,000 corn protoplasts were transfected with 0.8 pmol S. pyogenes Cas9 (SEQ ID NO:119) expression construct, and 1.6 pmol of sgRNA expression construct driven by the 397 bp version of the U6 promoter from corn chromosome 8 (SEQ ID NO:7) containing the spacer sequence corresponding to the genomic target sites: Zm7 (SEQ ID NO:23), and a pre-annealed blunt-end double-strand DNA fragment (SEQ ID NO:115 and SEQ ID NO:116) at 1, 5, 10, 25, 50, and 100 pmol. For transformation efficiency, 2.5 ug of a construct encoding green fluorescent protein (GFP) was included and the number of GFP positive protoplasts per 320,000 corn protoplasts was determined. Omission of the Cas9 expression cassette during the corn protoplast transformation served as the negative control. Protoplasts were harvested at 24 hours and 48 hours post transfection and analyzed for insertion of the blunt-end double-strand DNA fragment into the Zm7 genomic target site by quantitative, high-throughput PCR analysis using a BioRad QX200™ Droplet Digital™ PCR (ddPCR™) system (BioRad, Hercules, CA) and Taqman® probes. To determine the percent targeted integration rate, one set of Taqman primers (represented by SEQ ID NO:137 and SEQ ID NO:143) and a probe (represented by SEQ ID NO:138) was used with the ddPCR system to detect the template copy number of a junction of the inserted blunt-end double-strand DNA fragment at the chromosomal Zm7 target site. To normalize the amount of DNA in the transfected protoplast aliquot, the ddPCR system was used with a second set of Taqman primers and a probe (primers encoded by SEQ ID NO:132 and SEQ ID NO:134; probe encoded by SEQ ID NO:133) to determine the template copy number of a site unique in the corn genome and outside of the target site. The calculation for the percent targeted integration rate was the target site specific template copy number divided by the corn genome specific template copy number divided by the transformation frequency as determined by GFP-positive vs. total cell counts using the PE Operetta Imaging System (PerkinElmer, Waltham, MA). The data points presented in the graph were determined by averaging four biological replicates. The results are presented in FIG. 8 and show that the peak for percentage targeted integration rate was obtained with 50 pmol of the blunt-end, double-strand DNA fragment and incubation for 48 hours.

Example 9

Integration Rates as a Function of Cas9 Endonuclease Concentration

Figure 9:
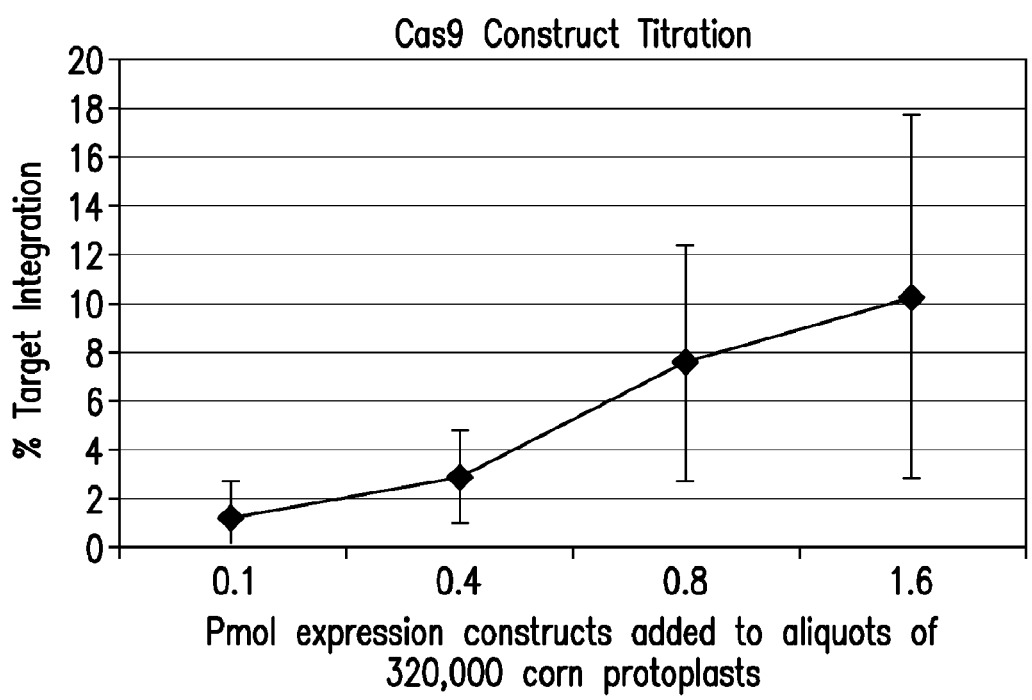
FIG. 9. Graphical presentation of the integration rate (Y-axis) as a function of the amount (in pmol) of SpCas9 expression construct added to transfection mixture of corn protoplasts (X-axis).

The corn protoplast system essentially as described in Example 8 was used to establish the optimal concentration of expression constructs encoding S. pyogenes Cas9 included in the protoplast transfection mixture to achieve the highest percentage targeted integration rate with the blunt-end double-strand DNA fragments. For these assays the expression construct encoding the modified S. pyogenes Cas9 was as described in Example 8. For the assay, 320,000 corn protoplasts were transfected with 0.1 pmol or 0.4 pmol or 0.8 pmol or 1.6 pmol of the S. pyogenes Cas9 (SEQ ID NO:119) expression construct, and 1.6 pmol of sgRNA expression construct driven by the 397 bp version of the U6 promoter from corn chromosome 8 (SEQ ID NO:7) containing the spacer sequence corresponding to the genomic target site Zm7 (SEQ ID NO:23), 50 pmol of pre-annealed blunt-end double-strand DNA fragment (SEQ ID NO:115 and SEQ ID NO:116), and a construct encoding GFP. The corn protoplasts were harvested 48 hours post-transfection and the percentage targeted integration was assessed as described in Example 8 using the ddPCR system and Taqman probes. The results of the analysis of the Cas9 expression construct titration are presented in FIG. 9 showing a linear increase in percentage targeted integration rate over the full-range of pmol of expression construct concentration tested.

Example 10

Sequence Confirmation of Insertion of Blunt-End Double-Strand DNA Fragments

PCR amplicons corresponding to targeted junctions from the protoplast experiments detailed in Example 5 and Example 8 were sequenced to confirm the integration of the blunt-end double-strand DNA fragments into the selected target site, Zm7 or L70c.

Figure 10A:
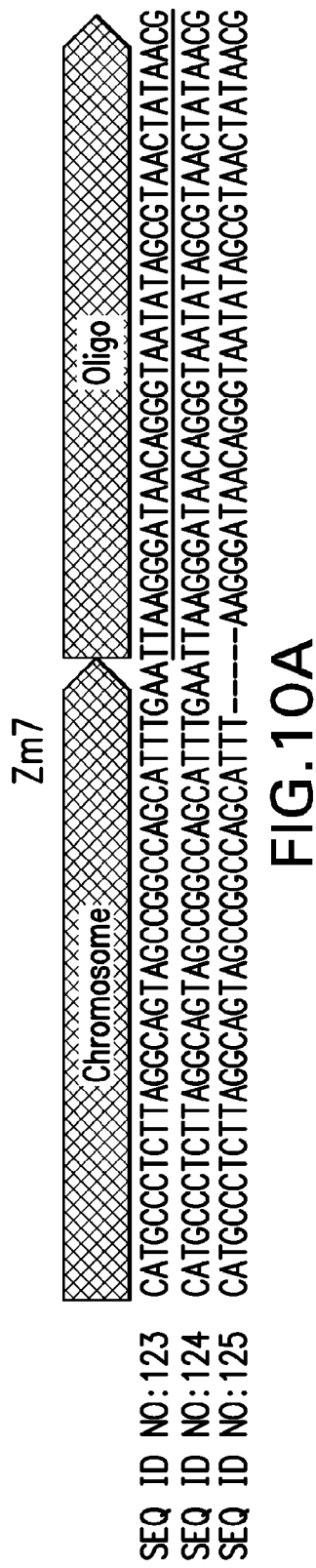
FIGS. 10A-10C. Sequence confirmation for targeted integrations of blunt-end, double-strand DNA fragments into chromosomes of corn protoplasts transformed with CRISPR/Cas9 and sgRNA expression constructs. For all panels FIGS. 10A, 10B, 10C, the top sequence is the expected sequence of one junction of the target site and the blunt-end double-strand DNA fragment (underlined sequence) included in the experiment.

For the corn chromosome site Zm7 targeted by CRISPR/Cas9 constructs and with blunt-end double-strand DNA fragment formed by annealed oligonucleotides encoded by SEQ ID NO:115 and SEQ ID NO:116 (see Example 8), PCR amplicons were agarose-gel purified and sequenced. The expected sequence is presented as SEQ ID NO:123, as shown in FIG. 10A. The results from the sequencing show at least one event with a base-pair perfect insertion of the blunt-end double-strand DNA fragment into the target site (SEQ ID NO:124). The results also show events with short deletions in either the chromosome or the DNA insert side of the junction, as indicated with SEQ ID NO:125 (see FIG. 10A).

Figure 10B:
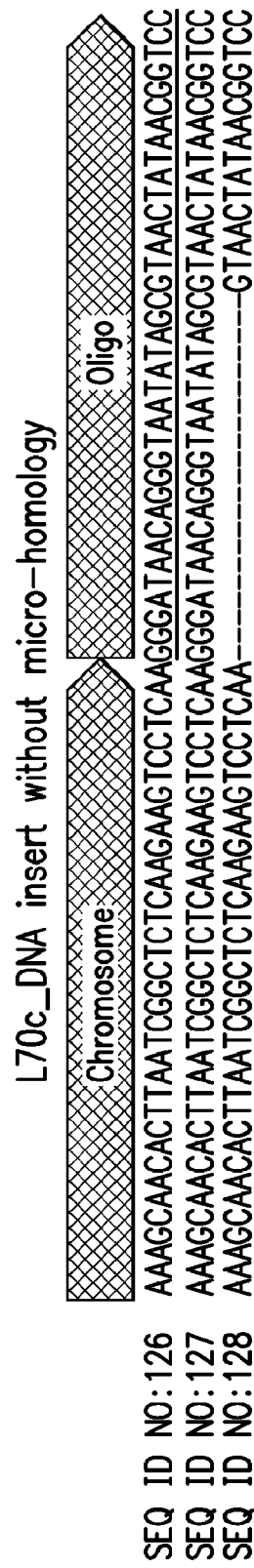

For the corn chromosome site L70c targeted by CRISPR/Cas9 constructs and with blunt-end double-strand DNA fragment without micro-homology sequences formed by annealed oligonucleotides encoded by SEQ ID NO:45 and SEQ ID NO:46 (see Example 5), PCR amplicons were agarose-gel purified and sequenced. The expected sequence is presented as SEQ ID NO:126, as shown in FIG. 10B. The results from the sequencing show at least one event that was detected with a base-pair perfect insertion of the blunt-end double-strand DNA fragment into the target site (SEQ ID NO:127). The results also show an example of events with short deletions in either the chromosome or the DNA insert side of the junction, as indicated with SEQ ID NO:128 (see FIG. 10B).

Figure 10C:
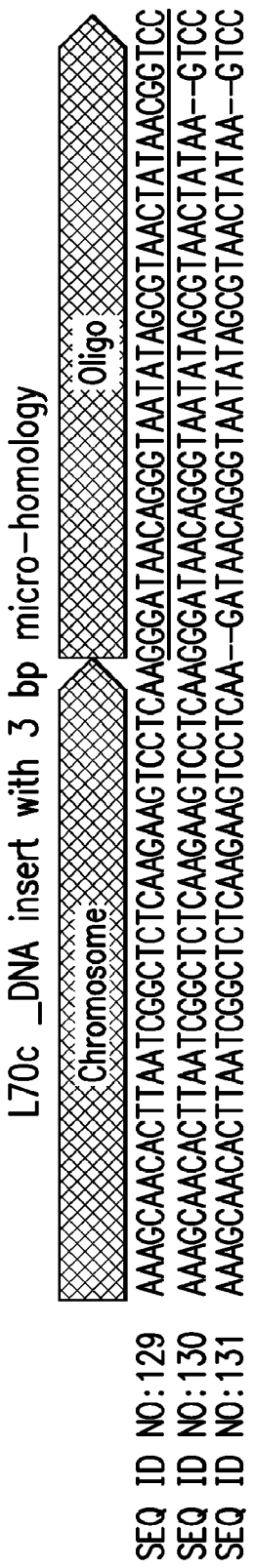

For the corn chromosome site L70c targeted by CRISPR/Cas9 constructs and with blunt-end double-strand DNA fragment with 3 bp micro-homology sequences at each end of the DNA fragment formed by annealed oligonucleotides encoded by SEQ ID NO:121 and SEQ ID NO:122 (see Example 5), PCR amplicons were agarose-gel purified and sequenced. The expected sequence is presented as SEQ ID NO:129, as shown in FIG. 10C. The results from the sequencing show at least one event that was detected with a base-pair perfect insertion at the junction of the blunt-end double-strand DNA fragment into the target site (SEQ ID NO:130). The results also show an example of events with short deletions in either the chromosome or the DNA insert side of the junction (SEQ ID NO:131) and/or in the DNA insert itself (SEQ ID NO:130 and SEQ ID NO:131), as indicated (see FIG. 10C).

These results indicate that blunt-end double-strand DNA fragments are incorporated into a double-strand break (DSB) at a target site created by a CRISPR/Cas9 system. The DNA fragments are incorporated by non-homologous end joining (NHEJ), an error-prone DNA repair mechanism that heals most somatic double-strand breaks in nature. Consistent with the endogenous NHEJ repair mechanism, the results show that blunt-end double-strand DNA fragments were incorporated with short deletions at the DSB created with CRISPR/Cas9 components, as illustrated by comparing SEQ ID NO:123 and SEQ ID NO:125 (FIG. 10A), and by comparing SEQ ID NO:126 and SEQ ID NO:128 (FIG. 10B), and by comparing SEQ ID NO:129 and SEQ ID NO:131 (FIG. 10C) (with this last pair there was also a 2 bp deletion internal to the inserted DNA fragment). Blunt-end double-strand DNA fragments were incorporated in a base-pair perfect manner at the DSB created with CRISPR/Cas9 components, as illustrated by comparing SEQ ID NO:123 and SEQ ID NO:124 (FIG. 10A), and by comparing SEQ ID NO:126 and SEQ ID NO:127 (FIG. 10B), and by comparing SEQ ID NO:129 and SEQ ID NO:130 (FIG. 10C) (though in this last pair there was a 2 bp deletion internal to the inserted DNA fragment).

Example 11

Integration Rates as a Function of TALEN Endonuclease Concentration

The corn protoplast system essentially as described in Example 8 was used to establish the optimal concentration of expression constructs encoding a pair of TALEN endonucleases needed in the transfection mixture to achieve the highest percentage targeting integration rate of blunt-end double-strand DNA fragments.

Figure 11:
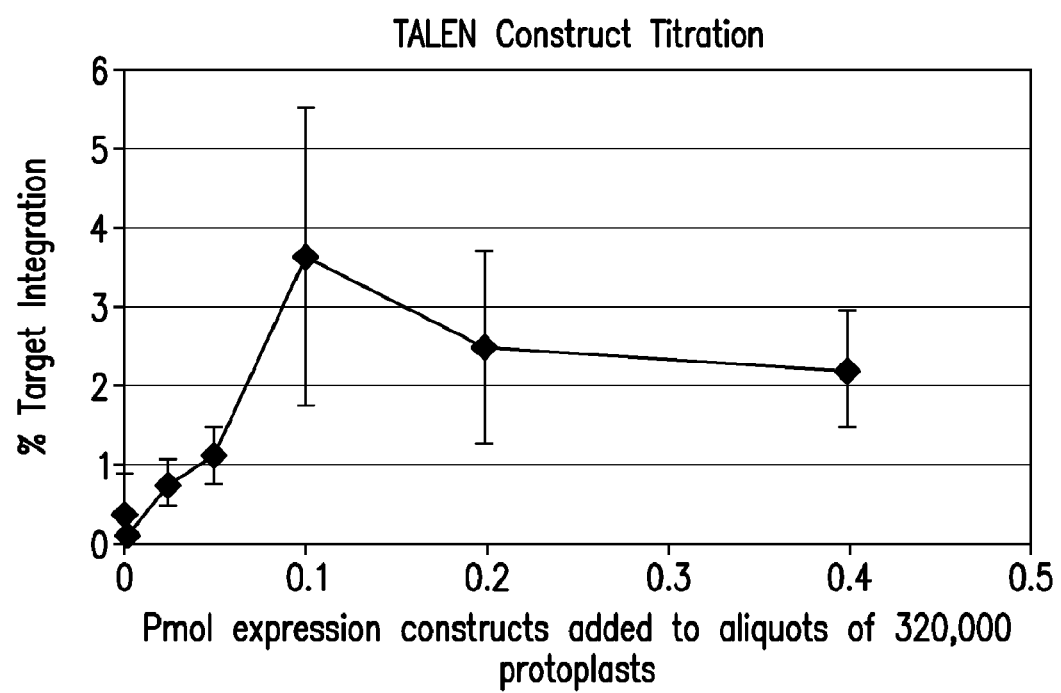
FIG. 11. Graphical presentation of the integration rate (Y-axis) as a function of the amount (in pmol) of TALEN expression constructs targeting corn chromosome site L70.4 which were added to transfection mixture of corn protoplasts (X-axis).

For these assays a pair of expression constructs with TALEN encoding cassettes was tested. The targeting site in the corn chromosome for the TALEN pair was L70.4. For the TALEN assay 0, 0.01, 0.02, 0.05, 0.1, 0.2 and 0.4 pmol of each of the constructs containing the TALEN encoding cassettes was used in the corn protoplast transformation. Also included was 50 pmol of pre-annealed blunt-end double-strand DNA fragment (SEQ ID NO:115 and SEQ ID NO:116) and 2.5 ug of the GFP encoding construct. The corn protoplasts were harvested 48 hours post-transfection and the percentage targeted integration was assessed by high-throughput PCR analysis essentially as described in previous examples. The results of the analysis of the TALEN expression construct titration are presented in FIG. 11 showing that the percentage targeted integration rate plateaus at about 0.1 pmol of each of the TALEN expression constructs included in the transfection reaction.

Example 12

Targeted Integration by Homologous Recombination—CRISPR/Cas9

Genome modification by targeted integration of a desired introduced DNA sequence will occur at sites of double strand breaks (DSB) in a chromosome. The integration of the DNA sequence is mediated by mechanisms of non-homologous end-joining (NHEJ) or homologous recombination using DNA repair mechanisms of the host cell. DSBs at specific sites in the host cell genome can be achieved using an endonuclease such as an engineered meganuclease, an engineered TALEN or a CRISPR/Cas9 system.

Figure 12B:
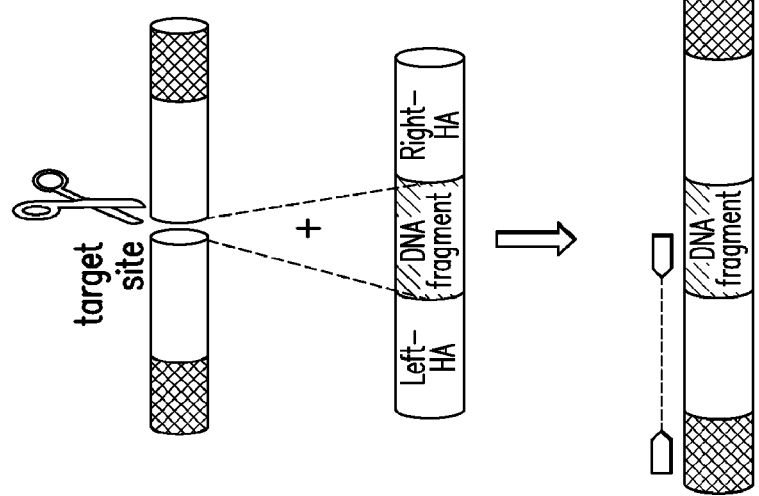
FIGS. 12A-12B. Schematic representation of NHEJ and HR-mediated targeted integration and PCR primer positions for high through-put screening. Targeted integration of a DNA fragment by non-homologous end-joining (NHEJ) is presented in FIG. 12A and targeted integration of a DNA fragment by homologous recombination (HR) is presented in FIG. 12B.
Figure 12A:
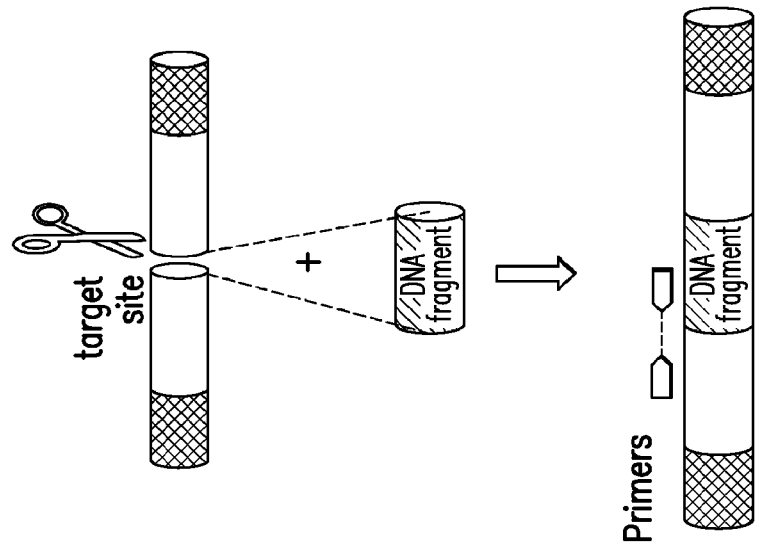

A schematic representation of a high through-put (HTP) testing method of NHEJ and HR-mediated targeted integration is presented in FIG. 12. Targeted integration of a DNA fragment by non-homologous end-joining (NHEJ) is presented in FIG. 12A and targeted integration of a DNA fragment by homologous recombination (HR) is presented in FIG. 12B. For HR, a recombinant DNA construct containing a cassette with the DNA fragment flanked with left- and right-homology arms (Left-HA and Right-HA, respectively) is introduced into the host cell. Following either NHEJ or HR targeted integration, HTP PCR analysis with primers (indicated by the short pair of arrows in FIGS. 12A and 12B) designed to detect a targeted event where one primer is internal to the inserted DNA fragment and a second primer is located in the flanking chromosomal region.

The corn protoplast system as described in the above examples was used to determine homologous recombination (HR) mediated targeted integration rates. The target site Zm7 was targeted by a CRISPR/Cas9 nuclease and the sgRNA for targeting the corn Zm7 site, as described in Example 8. In addition to the constructs encoding the CRISPR/Cas9 and sgRNA cassettes, a construct containing a cassette for homologous recombination cassette was included at either 4 ug concentration or 6 ug concentration. As described above, a construct encoding GFP was also transfected and the percentage of GFP positive cells was used in the calculation of the targeted integration rate. The controls did not contain the construct encoding the SpCas9 endonuclease.

Figure 13A:
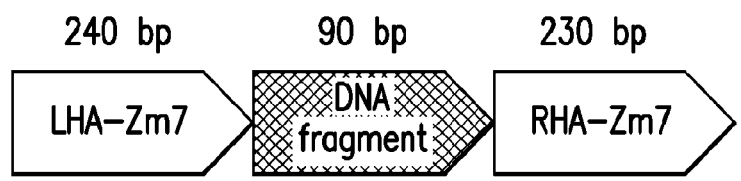
FIGS. 13A-13B. Schematic representation of the constructs used for homologous integration. The blunt-end DNA arrow indicates the 90 bp sequence corresponding to the 90 bp blunt-end, double-strand DNA fragment used for NHEJ assays, LHA refers to left-homology arm, RHA refers to right-homology arm, Zm7 refers to the target site Zm7 targeted by a CRISPR/Cas9+sgRNA. The length in bp of each of the homology arms is indicated.
Figure 13B:
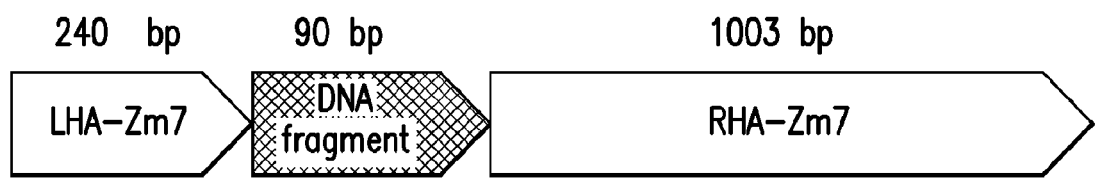

The recombinant DNA constructs containing cassettes for homologous recombination were designed to have the 90 bp sequence corresponding to the 90 bp blunt-end, double-strand DNA fragment used for NHEJ assays (encoded by sequences SEQ ID NO:115 and SEQ ID NO:116) flanked by left and right homology arms (HA). The left-HA is designed based on the sequence flanking the 5'-side of the site for the double-strand break (DSB) for targeted integration. The right-HA is designed as the sequencing flanking the 3'-side of the site for the double-strand break (DSB) for targeted integration. For the Zm7 site the left-HA was 240 bp in length, and two separate right-HA sequences were included, one of 230 bp and one of 1003 bp in length (see FIGS. 13A and 13B, respectively).

Protoplasts were transfected and harvested 48 hours later and analyzed for integration by high through-put PCR with one primer designed for the region of the DNA fragment sequence (encoded by the sequences SEQ ID NO:115 and SEQ ID NO:116) and one primer in the chromosomal region flanking the left homology arm. The size of the expected PCR amplicon with successful HR using the Zm7 targeting constructs (FIGS. 13A and 13B) was 411 bp. In conventional quantitative PCR (qPCR), amplicons longer than about 160 bp cannot be quantitatively measured, and thus, are not recommended to be used. The current experiment clearly demonstrated that significantly longer PCR amplicons can also be used in the ddPCR system, which opens up a host of new opportunities in quantitative biology.

Figure 15A:
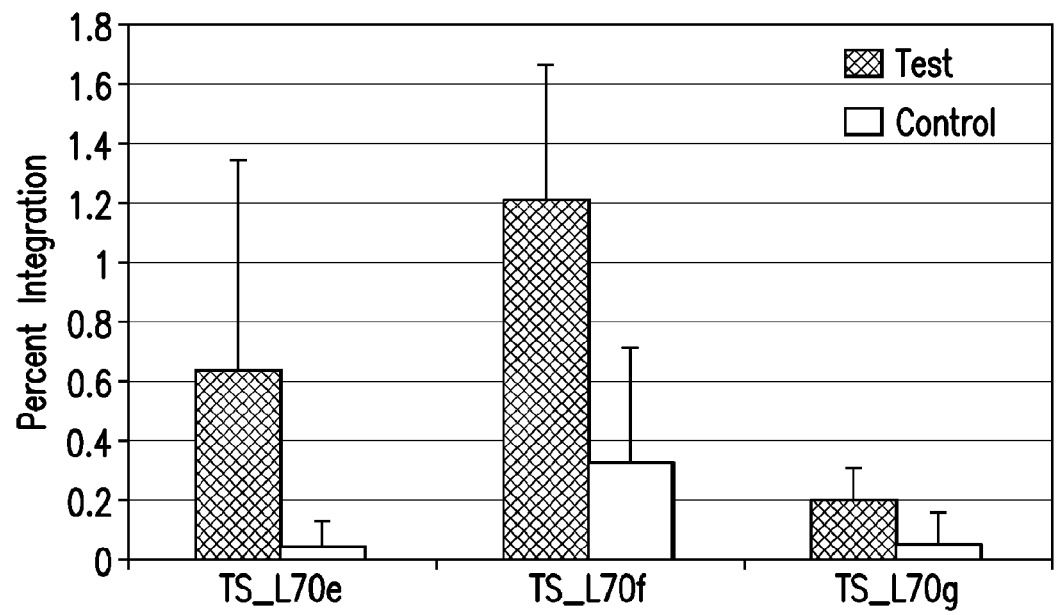
FIGS. 15A-15B.
Figure 15B:

The HR-mediated recombination rate for the corn chromosomal site Zm7 are presented in Table 8 and FIG. 15. When the left-HA and the right-HA were 240 bp and 230 bp, respectively, and the construct with the homology arm cassette was at a concentration of 4 ug or 6 ug, there was not a statistically significant difference in the percentage integration rate between the test sample and the control. When the left-HA was 240 bp and the right-HA was 1003 bp (indicated by SL in Table 8), and the construct with the homology arm cassette was at a concentration of 4 ug there was not a statistically significant difference in the percentage integration rate between the test sample and the control. In contrast, when the left-HA was 240 bp and the right-HA was 1003 bp (indicated by SL in Table 8), and the construct with the homology arm cassette was at a concentration of 6 ug there was a statistically significant (p<0.05) difference in the percentage integration rate between the test sample and the control. This result shows that targeted integration can be achieved by the mechanism of HR at sites of DSB which are targeted by CRISPR/Cas9 system in a corn genome.

TABLE 8

HR-mediated integration rates in corn protoplasts with DSB mediated by a CRISPR/Cas9 system at the chromosomal site Zm7.

|  | Mean | | Std Dev | |
| --- | --- | --- | --- | --- |
|  | Test | Control | Test | Control |
| Zm7 + SS + 4 ug | 0.88346 | 0.15936 | 0.83999 | 0.17658 |
| Zm7 + SS + 6 ugl | 1.20057 | 0.15936 | 0.92889 | 0.17658 |
| Zm7 + SL + 4 ug | 1.297183 | 0.98692 | 0.791837 | 0.86133 |
| Zm7 + SL + 6 ug** | 2.32094 | 0.98692 | 1.35951 | 0.86133 |

**Test was statistically higher (p < 0.05) than the corresponding control based on a student's t-test.

Example 13

Targeted Integration by Homologous Recombination—TALEN

The corn protoplast system as described in the above examples was used to determine homologous recombination (HR) mediated targeted integration rates. The target site L70.4 was targeted by a pair of recombinant DNA constructs encoding a TALEN pair directed to target the corn L70.4 site, as described in Example 11. In addition to the constructs encoding the TALEN cassettes, a construct containing a cassette for homologous recombination cassette was included at either 4 ug concentration or 6 ug concentration. As described above, a construct encoding GFP was also transfected and the percentage of GFP positive cells was used in the calculation of the targeted integration rate. The controls did not contain the constructs encoding the TALENs.

Figure 14A:
FIGS. 14A-14B. Schematic representation of the constructs used for homologous integration. In the figure, blunt-end DNA arrow indicates the 90 bp sequence corresponding to the 90 bp blunt-end, double-strand DNA fragment used for NHEJ assays, LHA refers to left-homology arm, RHA refers to right-homology arm, L70.4 refers to the target site L70.4 in the corn chromosome targeted by a TALEN pair. The length in bp of each of the homology arms is indicated.
Figure 14B:
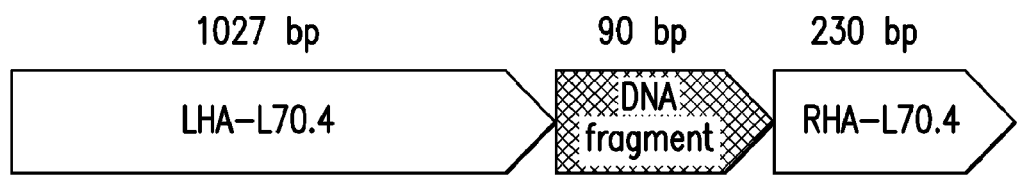

The recombinant DNA constructs containing cassettes for homologous recombination were designed to have the 90 bp sequence corresponding to the 90 bp blunt-end, double-strand DNA fragment used for NHEJ assays (encoded by sequences SEQ ID NO:115 and SEQ ID NO:116) flanked by left and right homology arms (HA). The left-HA is designed based on the sequence flanking the 5'-side of the site for the double-strand break (DSB) for targeted integration. The right-HA is designed as the sequencing flanking the 3'-side of the site for the double-strand break (DSB) for targeted integration. For the L70.4 site the right-HA was 230 bp in length, and two separate left-HA sequences were included, one of 230 bp and one of 1027 bp in length (see FIGS. 14A and 14B, respectively).

Protoplasts were transfected and harvested 48 hours later and analyzed for integration by quantitative, high through-put PCR using the ddPCR system and Taqman probes with one primer designed for the region of the DNA fragment sequence (encoded by the sequences SEQ ID NO:115 and SEQ ID NO:116) and one primer in the chromosomal region flanking the left homologous arm. The size of the expected PCR amplicon with successful HR using the L70.4 targeting construct of FIG. 14A was 383 bp. The size of the expected PCR amplicon with successful HR using the L70.4 targeting construct of FIG. 14B was 1208 bp.

The HR-mediated recombination rate for the corn chromosomal site L70.4 with two separate template DNA constructs is presented in Table 9. When the left-HA and the right-HA were both 230 bp (indicated by SS in Table 9), and the construct with the homology arm cassette was at a concentration of 4 ug there was a statistically significant (p<0.05) difference in the percentage integration rate between the test sample and the control. When the left-HA and the right-HA were both 230 bp (indicated by SS in Table 9), and the construct with the homology arm cassette was at a concentration of 6 ug there was not a statistically significant difference in the percentage integration rate between the test sample and the control. When the left-HA was 1027 bp and the right-HA was 230 bp (indicated by LS in Table 9), and the construct with the homology arm cassette was at a concentration of 4 ug or 6 ug there was not a statistically significant difference in the percentage integration rate between the test sample and the control. This result shows that targeted integration can be achieved by the mechanism of HR at sites of DSB which are targeted by TALENs directed to a specific site in a corn genome.

TABLE 9

HR-mediated Integration Rates in corn protoplasts with DSB mediated by TALENs at the chromosomal site L70.4.

| | Mean | | Std Dev | |
|---|---|---|---|---|
| | Test | Control | Test | Control |
| L70.4 + SS + 4 ug** | 1.54833 | 0.12181 | 1.48997 | 0.14504 |
| L70.4 + SS + 6 ug | 0.28395 | 0.12181 | 0.20174 | 0.14504 |
| L70.4 + LS + 4 ug | 0.163347 | 0.38048 | 0.282926 | 0.67502 |
| L70.4 + LS + 6 ug | 0.51467 | 0.38048 | 0.23052 | 0.67502 |

**Test was statistically higher (p < 0.05) than the corresponding control based on a student's t-test.

Example 14

Targeting in Corn Genome with Chimeric U6 Promoters

Chimeric U6 promoters were determined to be effective at driving expression of sgRNA constructs and resulting in targeted integration of double-strand, blunt-end DNA fragments at preselected sites in corn chromosomes. These experiments were conducted using the quantitative chromosome cutting assay in corn protoplast assay as described in example 5 and example 6. The U6 promoters incorporated into the sgRNA constructs were: a) the 397 bp corn chromosome 8 U6 promoter encoded by SEQ ID NO:7, b) the 397 bp ch1:ch8 chimeric U6 promoter encoded by SEQ ID NO:18, b) the 397 bp ch8:ch1 chimeric U6 promoter encoded by SEQ ID NO:19, and c) the 397 bp ch8:ch2:ch1:ch8 chimeric U6 promoter encoded by SEQ ID NO:20. The corn chromosomal target sites were L70a, L70c, and L70d, as described in example 5. The CRISPR/Cas9 system employed an expression cassette with the *S. pyogenes* Cas9 modified to contain two NLS sequences and an intron and encoded by SEQ ID NO:119. The double-strand, blunt-end DNA fragment was encoded by SEQ ID NO:115 and SEQ ID NO:116.

In one assay, 48 hours post transfection of the corn protoplasts with the CRISPR/Cas9 system components, the quantitative assay was done with TaqMan probes. The results (see FIG. 16A) indicate that the targeted integration rate at target site L70a with the sgRNA construct containing the ch8 U6 promoter or the sgRNA construct containing the chimeric ch1:ch8 U6 promoter resulted in about the equivalent percent target integration rate. The targeted integration rate at target site L70c, the sgRNA construct containing the chimeric ch8:ch1 U6 promoter resulted in about double the target integration rate compared to sgRNA construct containing the ch8 U6 promoter. The targeted integration rate at target site L70d, the sgRNA construct containing the ch8 U6 promoter had higher targeted integration rate compared to the sgRNA construct containing the chimeric ch8:ch2:ch1:ch8 U6 promoter.

In another assay, 48 hours post transfection of the corn protoplasts with the CRISPR/Cas9 system components, the quantitative assay was done with EvaGreen® (BioRad, Hercules, CA) intercalating dye. The results (see FIG. 16B) indicate that the targeted integration rate with the sgRNA construct containing the ch8 U6 promoter was nearly the same as the targeted integration rate at target site L70a with the sgRNA construct containing the chimeric ch1:ch8 U6 promoter, and at target site L70c with the sgRNA construct containing the chimeric ch8:ch1 U6 promoter, and at target site L70d with the sgRNA construct containing the chimeric ch8:ch2:ch1:ch8 U6 promoter. These data indicate that the targeted integration rate detected by the EvaGreen intercalating dye was about ten-fold higher compared to the targeted integration rates detected using MGB TaqMan probes. This discrepancy is mostly due to differences in the chemistries of the assays. The TaqMan assay uses just two primers and an internal probe, of which one of the primers and the probe are located on the inserted DNA fragment sequence. Unfortunately, the double-strand, blunt-end DNA fragment used in the transfection often undergo degradation by endogenous exonucleases in the protoplasts, and this results in DNA fragment integrations with truncated sites where the TaqMan probe binds. These truncated integration events are not detectable by the TaqMan assay. On the other hand, the binding site for the TaqMan primer located within the inserted DNA fragment sequence is located more internally in the inserted DNA fragment and remains intact even in most truncated inserted DNA fragments. Since the assay with the intercalating Evagreen dye does not require the internal probe, and only the TaqMan primers, this assay is not affected by oligo degradations and thus can detect many more integrations than the TaqMan assay. Otherwise, the two methods of measuring the percent targeted integration showed similar patterns at the three chromosomal target sites and the three different chimeric U6 promoters driving sgRNA expression.

Figure 16A:
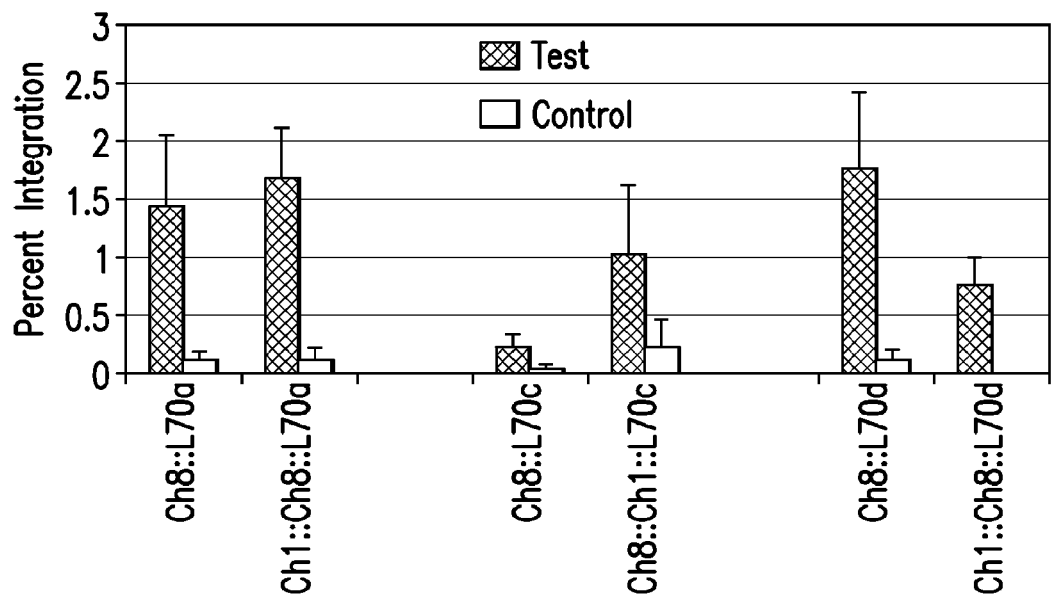
FIGS. 16A-16B.
Figure 16B:
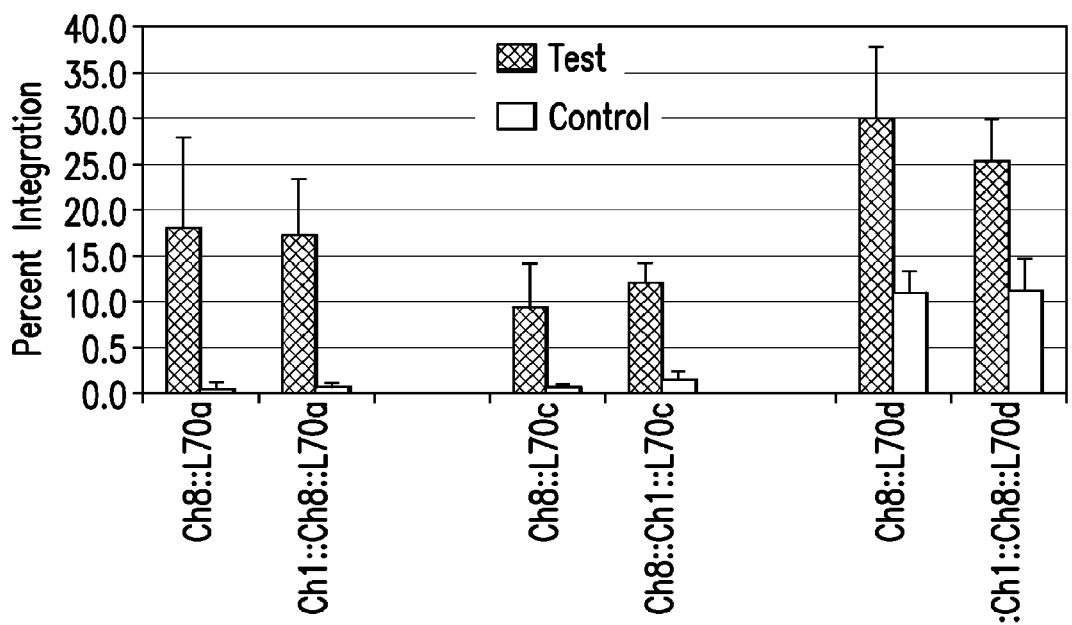

These results show that targeted integration rate at corn chromosomal site L70c when the sgRNA construct contains the Ch8::Ch1 chimeric promoter was slightly, to significantly higher compared to targeted integration rate when the sgRNA construct contains the ch8 U6 promoter (FIGS. 16A and 16B). These results also show that the targeted integration rate at corn chromosomal site L70a when the sgRNA construct contains the Ch1::Ch8 chimeric promoter is about equivalent compared to targeted integration rate when the sgRNA construct contains the ch8 U6 promoter (FIGS. 16A and 16B). Finally, these results show that the targeted integration rate at corn chromosomal site L70d when the sgRNA construct contains the ch8:ch2:ch1:ch8 chimeric promoter was lower compared to the targeted integration rate when the sgRNA construct contains the ch8 U6 promoter (FIGS. 16A and 16B). In conclusion, at least two of the three chimeric promoters were as good as, or better than, the best non-chimeric promoter in corn. These will have utility in multiplex targeting experiments, where the diversity of expression elements is indispensable.

Example 15

Targeted Mutation in Tomato Invertase Inhibitor

The CRISPR/Cas9 system was used to knock out the apoplastic invertase inhibitor gene of tomato (INVINH1) by introducing targeted frameshift point mutations following imperfect repair of the targeted double-strand breaks by NHEJ. In an earlier study, knock-down of this gene by RNAi showed elevated fruit sugar content and increased seed weight (Jin et al. *Plant Cell* 21:2072-2089, 2009). Reducing or eliminating the invertase inhibitor activity by either targeted mutagenesis or RNA interference is useful to improve yield and/or quality traits in other crop species too (Braun et al. *J Exp Bot* 65: 1713-1735, 2014).

For these experiments tomato protoplasts were transfected with an expression construct containing a cassette encoding the SpCas9 with one NLS at the C-terminus (SEQ ID NO:28), and one expression construct encoding an sgRNA cassette where expression was driven by one of 4 separate tomato U6 promoters: promoter 1 encoded by SEQ ID NO:146 (which is a fragment of SEQ ID NO:10), promoter 2 encoded by SEQ ID NO:147 (which is a fragment of SEQ ID NO:11), promoter 3 encoded by SEQ ID NO:148 (which is a fragment of SEQ ID NO:9), or promoter 4 encoded by SEQ ID NO:149. The sgRNA were targeted to an invertase inhibitor site (site 1) without a Sm1I site or to a site (labeled site 2) in the invertase inhibitor gene with a Sm1I restriction endonuclease site. The site 2 sgRNA is encoded by SEQ ID NO:150. The CRISPR/Cas9 cleavage site within target site 2 contains a Sm1I restriction endonuclease site. Upon CRISPR/Cas9 induced double-strand break at target site 2, the NHEJ repair will result in indels at this site, thus effectively removing the Sm1I restriction endonuclease site. This mutation of the Sm1I site was leveraged during the screening for targeted events by amplifying a 380 bp amplicon (SEQ ID NO:159) and subjecting the PCR amplicon to digestion with Sm1I. If the Sm1I site was not mutated, then the amplicon would be digested into two fragments of 181 bp and 199 bp. If the Sm1I site was mutated, then the PCR amplicon would not be digested. This PCR scheme is illustrated in FIG. 17A.

Tomato protoplasts were transfected with the CRISPR/Cas9 system targeting the tomato invertase inhibitor and harvested 48 hours later and genomic DNA extracted. Negative control for the CRISPR/Cas9 system was omission of the expression construct encoding the Cas9 endonuclease. A negative control for the target site was use of a sgRNA to target site 1, and it is not expected that the Sm1I site will be mutated with this sgRNA. PCR amplification was done with primers SEQ ID NO:157 and SEQ ID NO:158 and the resulting PCR amplicons were either undigested or digested with Sm1I. The reactions were run on agarose gels and the results are shown in FIG. 17B. The negative controls of sgRNA to target site 1 and the omission of Cas9 endonuclease resulted only in PCR amplicons with the Sm1I site intact. When the sgRNA was for target site 2, the Sm1I site was mutated when the sgRNA cassette contained tomato U6 promoter 1, or tomato U6 promoter 2, or tomato U6 promoter 3, as evidenced by the full-length PCR amplicons (see FIG. 17B, arrows showing amplicons without a Sm1I site). The sgRNA construct targeting site 2 and with U6 promoter 4 apparently did not show targeting.

To confirm that the PCR amplicons without a Sm1I site were indeed due to CRISPR/Cas9 induced NHEJ mutation, these apparent mutated amplicons were gel-purified and pooled, and then they were sequenced. The multiple sequence alignment in FIG. 17C shows that these PCR amplicons without a Sm1I site were from the target site 2 of the tomato invertase inhibitor and contained indels, consistent with CRISPR/Cas9 induced mutation. Specifically, in the multiple sequence alignment, SEQ ID NO:151 represents a region of the PCR amplicon (SEQ ID NO:159) without a mutation. SEQ ID NOs:152 and 153 illustrate indels where there was a 1 bp insertion at the cleavage site. SEQ ID NO:154 illustrates an indel with a 3 bp deletion at the cleavage site. SEQ ID NO:155 illustrates an indel with a 4 bp deletion at the cleavage site. SEQ ID NO:156 illustrates an indel with a 6 bp deletion at the cleavage site. In conclusion, these results indicate that the CRISPR/Cas9 system using tomato U6 promoter 1 (SEQ ID NO:146), or tomato U6 promoter 2 (SEQ ID NO:147), or tomato U6 promoter 3 (SEQ ID NO:148) to drive sgRNA induces mutation at the tomato invertase inhibitor gene target site 2.

Example 16

Promoters to Drive sgRNA Expression

To identify and select additional promoters which would be useful to drive expression of sgRNAs from expression cassettes introduced into dicots and monocots, RNA polymerase II (Pol II) and RNA polymerase III (Pol III) promoters (SEQ ID NOs:160-201 and SEQ ID NOs:247-283) were identified by comparing the sequence encoding U6, U3, U5, U2 and 7SL small nuclear RNA (snRNA) against soy and corn genomes using BLAST (see Table 10). From regions of this bioinformatic alignment, 200 or more nucleotides immediately upstream of the 5' end of the coding region of the respective snRNA was used for testing as putative promoters for driving expression of sgRNA from expression cassettes introduced into plant cells.

TABLE 10

SEQ ID NO of putative promoter sequence upstream of the snRNA genes and source (tomato or soy or corn).

| Promoter SEQ ID NO: | snRNA | Promoter Source | Promoter + GUS + Terminator SEQ ID NO | Terminator |
|---|---|---|---|---|
| 148 | Promoter 3 | tomato | 202 | poly(T)7 |
| 160 | SoyU6a | soy | 203 | poly(T)7 |
| 161 | SoyU6c | soy | 204 | poly(T)7 |
| 162 | SoyU6d | soy | 205 | poly(T)7 |
| 163 | SoyU6e | soy | 206 | poly(T)7 |
| 164 | SoyU6f | soy | 207 | poly(T)7 |
| 165 | SoyU6g | soy | 208 | poly(T)7 |
| 166 | SoyU6i | soy | 209 | poly(T)7 |
| 167 | U3a | soy | 210 | poly(T)7 |
| 168 | U3b | soy | 211 | poly(T)7 |
| 169 | U3c | soy | 212 | poly(T)7 |
| 170 | U3d | soy | 213 | poly(T)7 |
| 171 | U3e | soy | 214 | poly(T)7 |
| 172 | 7SL_CR13 | soy | 215 | poly(T)7 |
| 173 | 7SL_CR14 | soy | 216 | poly(T)7 |
| 174 | 7SL_CR10 | soy | 217 | poly(T)7 |
| 175 | 7SLCR01 | corn | 218 | poly(T)7 |
| 176 | 7SLCR07 | corn | 219 | poly(T)7 |
| 177 | 7SLCR09 | corn | 220 | poly(T)7 |
| 178 | U3CR02 | corn | 221 | poly(T)7 |
| 179 | U3CR10 | corn | 222 | poly(T)7 |
| 180 | U3CR08 | corn | 223 | poly(T)7 |
| 181 | U3CR08b | corn | 224 | poly(T)7 |
| 182 | U3CR05 | corn | 225 | poly(T)7 |

TABLE 10-continued

SEQ ID NO of putative promoter sequence upstream of the snRNA genes and source (tomato or soy or corn).

| Promoter SEQ ID NO: | snRNA | Promoter Source | Promoter + GUS + Terminator SEQ ID NO | Terminator |
|---|---|---|---|---|
| 183 | U2snRNA_P | corn | 226 | SEQ ID NO 237 |
| 184 | U2snRNA_I | corn | 227 | SEQ ID NO 237 |
| 185 | U2snRNA_B | corn | 228 | SEQ ID NO 237 |
| 186 | U2snRNA_G | corn | 229 | SEQ ID NO 237 |
| 187 | U2snRNA_A | corn | 230 | SEQ ID NO 237 |
| 188 | U5snRNA_A | corn | 231 | SEQ ID NO 237 |
| 189 | U5snRNA_C | corn | 232 | SEQ ID NO 237 |
| 190 | U5snRNA_D | corn | 233 | SEQ ID NO 237 |
| 191 | U5snRNA_E | corn | 234 | SEQ ID NO 237 |
| 192 | U2snRNA_C | corn | — | — |
| 193 | U2snRNA_D | corn | — | — |
| 194 | U2snRNA_E | corn | — | — |
| 195 | U2snRNA_F | corn | — | — |
| 196 | U2snRNA_H | corn | — | — |
| 197 | U2snRNA_K | corn | — | — |
| 198 | U2snRNA_L | corn | — | — |
| 199 | U2snRNA_M | corn | — | — |
| 200 | U6Chr08 | corn | 235 | poly(T)7 |
| 201 | U6Chr01 | corn | 236 | poly(T)7 |
| 247 | U2CR01a | Soy | — | — |
| 248 | U2CR01b | Soy | — | — |
| 249 | U2CR02 | Soy | — | — |
| 250 | U2CR03 | Soy | — | — |
| 251 | U2CR04 | Soy | — | — |
| 252 | U2CR05a | Soy | — | — |
| 253 | U2CR05b | Soy | — | — |
| 254 | U2CR06a | Soy | — | — |
| 255 | U2CR06b | Soy | — | — |
| 256 | U2CR06v | Soy | — | — |
| 257 | U2CR07 | Soy | — | — |
| 258 | U2CR08a | Soy | — | — |
| 259 | U2CR08b | Soy | — | — |
| 260 | U2CR08c | Soy | — | — |
| 261 | U2CR10a | Soy | — | — |
| 262 | U2CR10b | Soy | — | — |
| 263 | U2CR10c | Soy | — | — |
| 264 | U2CR13 | Soy | — | — |
| 265 | U2CR14 | Soy | — | — |
| 266 | U2CR15 | Soy | — | — |
| 267 | U2CR17a | Soy | — | — |
| 268 | U2CR17b | Soy | — | — |
| 269 | U2CR17c | Soy | — | — |
| 270 | U2CR17d | Soy | — | — |
| 271 | U2CR17e | Soy | — | — |
| 272 | U2CR17f | Soy | — | — |
| 273 | U2CR19a | Soy | — | — |
| 274 | U2CR19b | Soy | — | — |
| 275 | U2CR20 | Soy | — | — |
| 276 | U5CR07 | Soy | — | — |
| 277 | U5CR10 | Soy | — | — |
| 278 | U5CR10 | Soy | — | — |
| 279 | U5CR15 | Soy | — | — |
| 280 | U5CR19 | Soy | — | — |
| 281 | U5CR20a | Soy | — | — |
| 282 | U5CR20b | Soy | — | — |
| 283 | SoyU6b | Soy | — | — |

Example 17

Normalized RNA Transcript Level Assay

To assess the efficacy of the promoters listed in Table 10 to drive expression of sgRNAs, a series of constructs were generated which contained a cassette encoding one of the putative promoters (SEQ ID NO:154, and SEQ ID NOs: 160-201) operably linked to a 221 bp fragment of a beta-glucuronidase (GUS) open reading frame and either a poly (T)7 terminator for Pol III promoters (7SL, U6, and U3) or the sequence 5'-ACAATTCAAAACAAGTTTTAT-3' (SEQ ID NO:237) for the pol II U2 and U5 promoters (Table 10). The recombinant constructs (0.5 pmol) containing the promoter-GUS fragment fusions were transfected into soy cotyledon protoplasts (SEQ ID NO:202-217 or corn leaf protoplasts (SEQ ID NO: 218-236) along with 300 ng of a plasmid serving as a transformation control encoding Renilla Luciferase (RLUC) expressed using the CaMV promoter. The transfected protoplasts were harvested 18 hours after transfection and the RNA levels were measured via TaqMan assays using a probe and primers complementary to the GUS fragment. Internal controls used to normalized the TaqMan assay included (1) an 18S primer pair/probe set to control for RNA concentration and (2) RLUC luminescence as a transformation control.

Figure 18A:
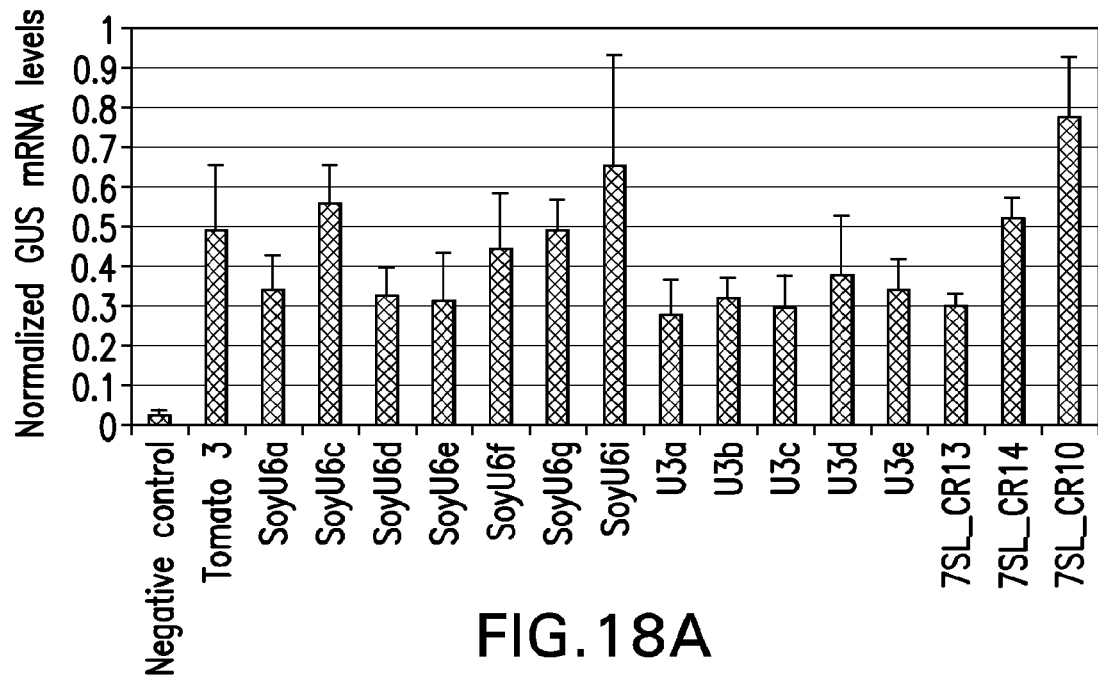
FIGS. 18A-18B.
Figure 18B:
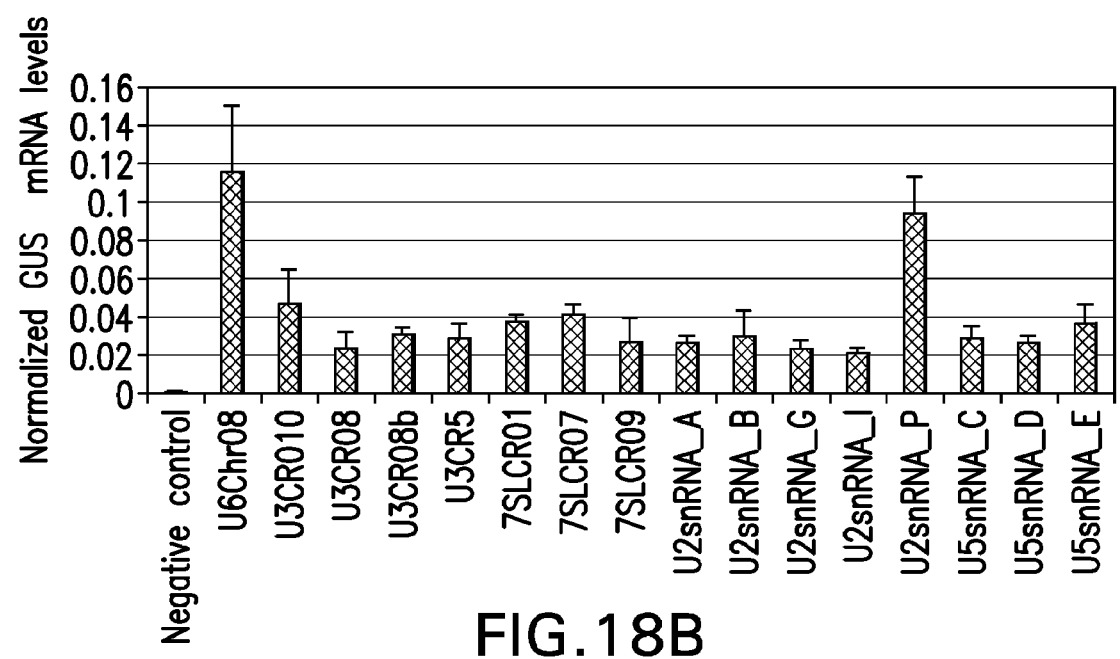

In soy cotyledon protoplasts, all promoters tested resulted in significantly higher normalized levels of GUS mRNA than the control (no GUS construct) (One-way ANOVA student t-test p value<0.05) (FIG. 18A). The lowest level of normalized GUS mRNA was with construct (SEQ ID NO:210) containing the U3a promoter (SEQ ID NO:167). The highest level of normalized GUS mRNA was with construct (SEQ ID NO:210) containing the 7SL_CR10 promoter (SEQ ID NO:174). The level of normalized GUS mRNA with all promoters tested with this assay ranged from 11-31 times higher expression levels that the no DNA negative control. No one class of promoters (U6, U3, or 7SL) performed better than the other, although the U3 promoters were generally in the lower range of expression observed in the experiment. U3 promoters have been successfully used by Liang et al. (*J. Genetics and Genomics* 41:63-68, 2014) to drive sgRNAs in corn. Thus, although these data indicate that the U3 promoters may be lower than U6 or 7SL, they are still viable candidates to drive sgRNA expression in soy. These data suggest that any of the U6, U3, or 7SL promoters identified here would be good candidates for making recombinant expression constructs to drive expression of sgRNA in plant cells. In corn leaf protoplast, all promoters tested resulted in significantly higher normalized levels of GUS mRNA compared to the control (One-way ANOVA student t-test p value<0.05) with values ranging from 26 fold to 141 fold higher expression than the negative control (FIG. 18B). The U6Chr08 promoter construct (SEQ ID NO:235) resulted in the highest normalized levels of GUS mRNA expression, and U2snRNA_I promoter construct (SEQ ID NO:227) resulted in the lowest, with approximately a 5.5-fold difference in normalized levels of GUS mRNA expression between them. The U2snRNA_P promoter construct (SEQ ID NO:226) also stood out as having high normalized levels of GUS mRNA expression. All the remaining promoters were within the same relative range having less than 2 fold difference between them (FIG. 18B). These data suggest that any of the U6, U3, 7S1, U2, or U5, promoters identified here would be good candidates for making recombinant expression constructs to drive expression of sgRNA in plant cells.

Example 18

GUS Expression Assay for sgRNA Expression

To determine how the difference in sgRNA expression levels impact Cas9 activity, an assay was used that relied on activating transcription from a minimal promoter upstream of the GUS open reading frame in a reporter construct transfected into corn leaf protoplasts. For this assay, a Cas9 nuclease from *S. thermophilus* was mutated at amino acid positions D9A and H599A of the native protein sequence, effectively creating a Cas9 without endonuclease cleavage activity (also referred to as a 'dead Cas9'). Additionally, this dead Cas9 was modified to encode one NLS domain (SEQ ID NO:120) at amino acid positions 2-11 of SEQ ID NO:239 and an activation domain from a TALE protein from amino acid positions 1135-1471 of SEQ ID NO:239. The polynucleotide sequence of the dead Cas9, represented by SEQ ID NO:238, included an intron at positions 507-695. A reporter construct was constructed where the uidA (GUS) reporter gene was driven by a minimal CaMV promoter with three adjacent sgRNA binding sites (SEQ ID NO:240) at nucleotide positions 80-98, 117-135, and 154-172 of the sequence SEQ ID NO:246. Also constructed were a set of sgRNA (based on the sgRNA of Cong et al. 2013 Science 339:819) expression constructs that consisted of the one of the promoters from each class of snRNA genes, namely U6, 7SL, U2, U5, and U3 (Table 11) and which would target the dead Cas9-TALE-AD to one or more of the sgRNA binding sites of the GUS reporter construct. The U6 and 7SL promoters normally initiate transcription on a G, and the U2, U5 and U3 promoters normally initiate transcription on an A. To ensure proper transcription initiation of the sgRNA, for constructs with either a U6 or 7SL promoter, a G was inserted between the promoter and spacer sequence. For constructs with a U2, U5 or U3 promoter, an A was inserted between the promoter and spacer sequence. When the dead Cas9-TALE-AD and sgRNA complex binds the GUS reporter construct, the TALE activation domain functions as a transcription factor activating the minimal CaMV promoter resulting in higher expression of the GUS transcript, and ultimately higher levels of GUS protein expression.

TABLE 11

SEQ ID NO corresponding to sgRNA expression constructs

| Promoter + sgRNA SEQ ID NO: | Promoter | Promoter SEQ ID NO: |
|---|---|---|
| 241 | U6Chr08 | 200 |
| 242 | 7SLCR07 | 176 |
| 243 | U2snRNA_I | 184 |
| 244 | U5snRNA_E | 191 |
| 245 | U3CR08b | 181 |

Figure 19:
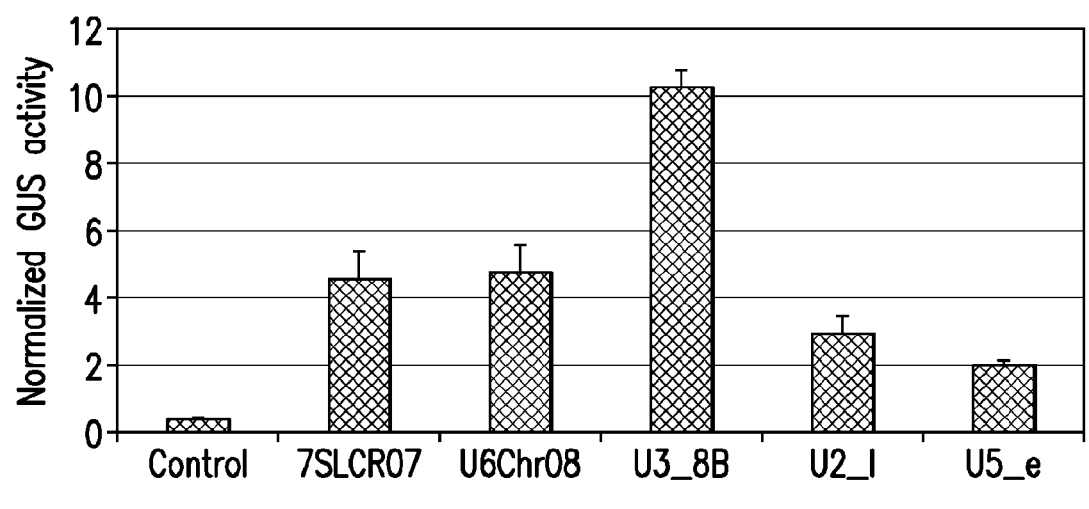
FIG. 19. Graphical representation of data from normalized GUS expression levels from corn leaf protoplast assays with, a recombinant expression constructs encoding 1) a GUS expression construct 2) a dead Cas9-TALE-AD expression construct, and 3) recombinant sgRNA expression constructs with 7SL, U6, U3, U2, or U5 promoters.

For the assay, corn leaf protoplasts were transfected with 0.8 pmol of dead Cas9-TALE-AD expression cassette, 0.5 pmol of the GUS expression cassette, 1.6 pmol of one of the sgRNA expression cassettes, 650 ng of Luciferase expression cassette, and 300 ng of Renilla Luciferase (RLUC) expression cassette. The transfected protoplasts were harvested 18 hours later and GUS activity was measured using the 4-methylumbelliferyl-beta-D-glucuronide (MUG, Sigma, St. Louis, MO) fluorimetric assay, and luciferase and RLUC activity was measured and used as control to normalize relative to transfection controls. The activity of GUS is a readout of the how often the dead Cas9-TALE-AD binds to the reporter plasmid. Each class of snRNA promoter driving sgRNA gave higher normalized GUS activity compared to the control (FIG. 19). The U3CR08b (U3_8B in FIG. 19) promoter resulted in the highest normalized GUS activity of about 10× over control. The two promoters 7SLCR07 and U6Chr08 both gave about the same normalized GUS activity of about 4× over control. The two promoters U2snRNA_I (Us_I in FIG. 19) and U5snRNA_E (U5_e in FIG. 19) were each at or slightly above 2× over control for normalized GUS activity. These results indicate that the 7SL, U6, U3, U2, and U5 snRNA promoters may be good to excellent candidates for use in sgRNA expression constructs for CRISPR/Cas9 system useful in genome modification.

The differences in normalized GUS expression observed using the dead Cas9-TALE-AD assay do not mirror the normalized GUS mRNA levels shown in the corn leaf protoplast assay detailed in Example 17.

What is claimed is:

1. A recombinant DNA construct comprising a 7SL promoter; operably linked to:
   (i) a sequence encoding a single-guide RNA (sgRNA), or
   (ii) a sequence specifying a non-coding RNA;
   and wherein the sequence of said 7SL promotor comprises SEQ ID NO:174; or a fragment thereof, wherein the fragment is at least 140 bp in length, wherein the 7SL promotor or fragment thereof and the sgRNA or non-coding RNA come from different sources.

2. The recombinant DNA construct of claim 1, further comprising a transcription termination sequence.

3. The recombinant DNA construct of claim 1, further comprising a sequence encoding a promoter operably linked to a sequence encoding a clustered, regularly interspaced, short palindromic repeats (CRISPR)-associated Cas endonuclease gene product.

4. The recombinant DNA construct of claim 3, wherein the Cas endonuclease gene product is further operably linked to a nuclear localization sequence (NLS).

5. The recombinant DNA construct of claim 3, wherein the sequence encoding said Cas endonuclease is selected from the group consisting of SEQ ID NO:27, SEQ ID NO:68, and SEQ ID NO:97, SEQ ID NO:119, and SEQ ID NO:136.

6. The recombinant DNA construct of claim 1, wherein the non-coding RNA is selected from the group consisting of: a microRNA (miRNA), a miRNA precursor, a small interfering RNA (siRNA), a small RNA (22-26 nt in length) and precursor encoding same, a heterochromatic siRNA (hc-siRNA), a Piwi-interacting RNA (piRNA), a hairpin double strand RNA (hairpin dsRNA), a trans-acting siRNA (ta-siRNA), and a naturally occurring antisense siRNA (nat-siRNA).

7. A cell comprising the recombinant DNA construct of claim 1.

8. The cell of claim 7, wherein the cell is a plant cell.

9. A method of introducing a double-strand break in the genome of a cell, comprising introducing in said cell:
   a) at least one recombinant DNA construct of claim 1; and
   b) a second recombinant DNA construct comprising a sequence encoding a promoter operably linked to a sequence encoding a clustered, regularly interspaced, short palindromic repeats (CRISPR)-associated Cas endonuclease gene product operably linked to a nuclear localization sequence (NLS).

10. The method of claim 9, wherein the sequence encoding said Cas endonuclease is selected from the group consisting of SEQ ID NO:27, SEQ ID NO:68, and SEQ ID NO:97, SEQ ID NO:119, and SEQ ID NO:136.

11. A method of introducing a double-strand break in the genome of a cell, comprising introducing to said cell at least one recombinant DNA construct of claim 3.

12. The method of claim 11, wherein the sequence encoding the Cas endonuclease is selected from the group consisting of SEQ ID NO:27, SEQ ID NO:68, and SEQ ID NO:97, SEQ ID NO:119, and SEQ ID NO:136.

13. A method of genome modification comprising:
   a) introducing a double-strand break in the genome of a plant cell by the method according to claim 9; and
   b) introducing into said plant cell a recombinant blunt-end double-strand DNA fragment,
wherein said recombinant blunt-end double-strand DNA fragment is incorporated into said double strand break by endogenous DNA repair.

14. A method of genome modification comprising:
   a) introducing a double-strand break in the genome of a plant cell by the method according to claim 11; and
   b) introducing into said plant cell a recombinant blunt-end double-strand DNA fragment,
wherein said recombinant blunt-end double-strand DNA fragment is incorporated into said double strand break by endogenous DNA repair.

* * * * *